United States Patent
Ahn et al.

(10) Patent No.: US 11,394,000 B2
(45) Date of Patent: *Jul. 19, 2022

(54) ELECTRON BUFFERING MATERIALS, ELECTRON TRANSPORT MATERIALS AND ORGANIC ELECTROLUMINESCENT DEVICE COMPRISING THE SAME

(71) Applicant: Rohm and Haas Electronic Materials Korea Ltd., Cheonan (KR)

(72) Inventors: Hee-Choon Ahn, Gyeonggi-do (KR); Sang-Hee Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 245 days.

This patent is subject to a terminal disclaimer.

(21) Appl. No.: 15/770,215

(22) PCT Filed: Oct. 17, 2016

(86) PCT No.: PCT/KR2016/011648
§ 371 (c)(1),
(2) Date: Apr. 23, 2018

(87) PCT Pub. No.: WO2017/073942
PCT Pub. Date: May 4, 2017

(65) Prior Publication Data
US 2018/0323397 A1 Nov. 8, 2018

(30) Foreign Application Priority Data

Oct. 30, 2015 (KR) .................. 10-2015-0152004
Sep. 1, 2016 (KR) .................. 10-2016-0112625

(51) Int. Cl.
*H01L 51/50* (2006.01)
*C07D 413/14* (2006.01)
(Continued)

(52) U.S. Cl.
CPC ........ *H01L 51/5072* (2013.01); *C07D 277/60* (2013.01); *C07D 403/04* (2013.01);
(Continued)

(58) Field of Classification Search
CPC .... C07D 403/00–14; C07D 413/00–14; C07D 417/00–14; H01L 51/5072–5096
See application file for complete search history.

(56) References Cited

U.S. PATENT DOCUMENTS 3,279,918 A   10/1966   Cassiers et al.
8,883,323 B2  11/2014   Kawamura et al.
(Continued)

FOREIGN PATENT DOCUMENTS

CN   104447566 A  *  3/2015
CN   104650041 A  *  5/2015
(Continued)

OTHER PUBLICATIONS

Machine Translation of JP 2001023777 A.*
(Continued)

*Primary Examiner* — William E Mcclain
(74) *Attorney, Agent, or Firm* — G. Creston Campbell

(57) ABSTRACT

The present disclosure relates to an electron buffering material, and an organic electroluminescent device comprising a first electrode, a second electrode facing the first electrode, a light-emitting layer between the first electrode and the second electrode, and an electron transport zone and an electron buffering layer between the light-emitting layer and the second electrode. The organic electroluminescent device comprising the electron buffering material of the present disclosure has low driving voltage, excellent luminous efficiency, and long lifespan.

11 Claims, 1 Drawing Sheet

(51) Int. Cl.

| | | |
|---|---|---|
| *C07D 413/04* | (2006.01) | |
| *C07D 413/12* | (2006.01) | |
| *C07D 417/04* | (2006.01) | |
| *C07D 403/10* | (2006.01) | |
| *C07D 513/04* | (2006.01) | |
| *C07D 498/14* | (2006.01) | |
| *C07D 417/14* | (2006.01) | |
| *C07D 413/10* | (2006.01) | |
| *C07D 403/04* | (2006.01) | |
| *C07D 417/10* | (2006.01) | |
| *C07D 277/60* | (2006.01) | |
| *C07D 487/04* | (2006.01) | |
| *C07D 495/14* | (2006.01) | |
| *H01L 51/00* | (2006.01) | |
| *C09K 11/06* | (2006.01) | |

(52) U.S. Cl.
CPC ......... *C07D 403/10* (2013.01); *C07D 413/04* (2013.01); *C07D 413/10* (2013.01); *C07D 413/12* (2013.01); *C07D 413/14* (2013.01); *C07D 417/04* (2013.01); *C07D 417/10* (2013.01); *C07D 417/14* (2013.01); *C07D 487/04* (2013.01); *C07D 495/14* (2013.01); *C07D 498/14* (2013.01); *C07D 513/04* (2013.01); *C09K 11/06* (2013.01); *H01L 51/006* (2013.01); *H01L 51/0052* (2013.01); *H01L 51/0054* (2013.01); *H01L 51/0058* (2013.01); *H01L 51/0059* (2013.01); *H01L 51/0061* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/0081* (2013.01); *H01L 51/5004* (2013.01); *H01L 51/5012* (2013.01); *H01L 51/5056* (2013.01); *H01L 51/5096* (2013.01); *H01L 51/508* (2013.01); *H01L 51/5076* (2013.01)

(56) References Cited

U.S. PATENT DOCUMENTS

| | | |
|---|---|---|
| 9,246,108 B2 | 1/2016 | Ober et al. |
| 2004/0230084 A1 | 11/2004 | Yagi |
| 2005/0230665 A1* | 10/2005 | Thompson .......... H01L 51/0067 252/500 |
| 2006/0029828 A1 | 2/2006 | Kanno et al. |
| 2009/0009067 A1* | 1/2009 | Nishimura .......... H01L 51/0052 313/504 |
| 2009/0286772 A1 | 11/2009 | Chau et al. |
| 2012/0168731 A1 | 7/2012 | Schildknecht et al. |
| 2012/0313091 A1* | 12/2012 | Kang .................. C07D 498/14 257/40 |
| 2018/0208837 A1 | 7/2018 | Ahn et al. |

FOREIGN PATENT DOCUMENTS

| | | | |
|---|---|---|---|
| CN | 104987309 A | * | 10/2015 |
| JP | 2000323278 A | * | 11/2000 |
| JP | 2001023777 A | | 1/2001 |

OTHER PUBLICATIONS

Machine Translation of JP-2000323278-A.*
International search report for corresponding Application No. PCT/KR2016/011648 dated Feb. 1, 2017.
Awad et al, "Darzens reactions with quinonoid systems. Spiro oxirana-2,2'-Chrysenes from chrysenequinone, and chryso-oxazoles from chrysenequinone imine or chrysenequinone monoxime", Journal f. prakt. Chemie, 1978, pp. 986-990, vol. 320, issue 6.
Awad.et al, "Chrysenoxazoles", J. Am. Chem. Soc., 1955, pp. 1013-1014, vol. 77.
Search Report for Chinese Patent Application No. 201680061858.6; dated Oct. 17, 2016.

\* cited by examiner

[Fig. 1]
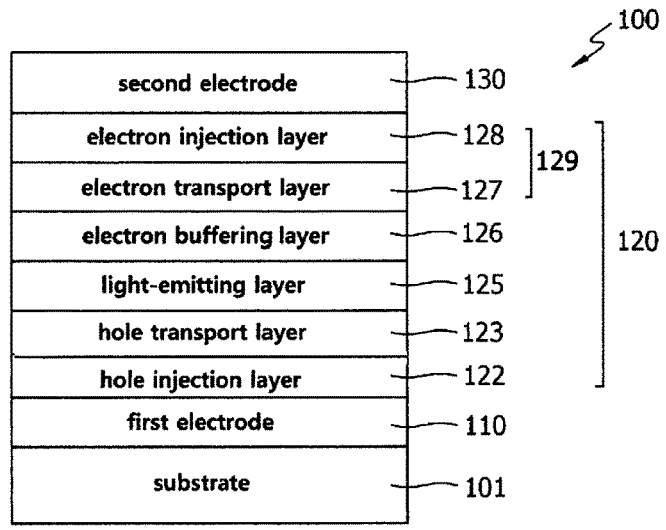
[Fig. 2]
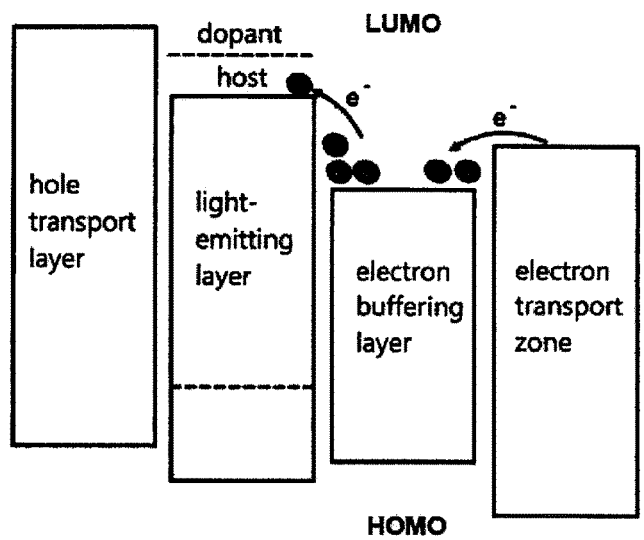
[Fig. 3]
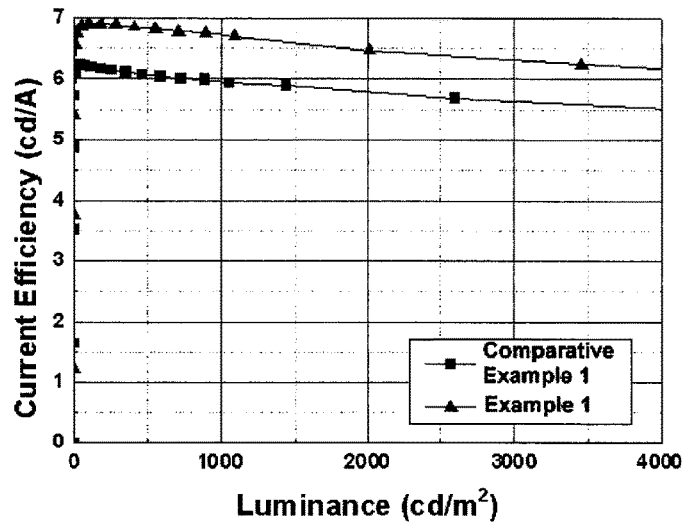

ELECTRON BUFFERING MATERIALS, ELECTRON TRANSPORT MATERIALS AND ORGANIC ELECTROLUMINESCENT DEVICE COMPRISING THE SAME

TECHNICAL FIELD

The present disclosure relates to an electron buffering material, an electron transport material and an organic electroluminescent device comprising the same.

BACKGROUND ART

An organic electroluminescent device (OLED) emitting green light was first proposed by Tang et al. of Eastman Kodak in 1987, which employs a double layer of TPD/Alq$_3$, composed of a light-emitting layer and a charge transport layer. Afterward, an organic electroluminescent device had been rapidly researched, and has now become commercialized. At present, a phosphorescent material, which has excellent luminous efficiency, is mainly used for a panel of an organic electroluminescent device. An organic electroluminescent device emitting red or green light has been successfully commercialized by using a phosphorous material. However, a phosphorous material for emitting blue light has the following disadvantages, which are blocking realization of full color display: roll-off is reduced at high current due to loss of excessively formed excitons, thereby deteriorating performances; the blue-emitting phosphorescent material itself has a problem in long term stability of lifespan; and color purity is rapidly decreasing by lapse of time.

A fluorescent material has been used, but has several problems. First, when exposed to high-temperature during a panel production process, a current feature can be changed, which can cause a change in luminance. Furthermore, due to a structural characteristic, an interface feature between a light-emitting layer and an electron injection layer can deteriorate, which can cause a decrease of luminance. In addition, a fluorescent material provides lower efficiencies than a phosphorescent material. Accordingly, there have been attempts to improve efficiencies by developing a specific fluorescent material such as a combination of an anthracene-based host and a pyrene-based dopant. However, the proposed combination makes holes become greatly trapped, which can cause light-emitting sites in a light-emitting layer to shift to the side close to a hole transport layer, thereby light being emitted at an interface. The light-emission at an interface decreases lifespan of a device, and efficiencies are not satisfactory.

It is not easy to solve the aforementioned problems of a fluorescent material by improvement of a light-emitting material itself. Accordingly, recently, there has been research to solve the problems, which includes improvement of a charge transport material to change a charge transport feature, and development of an optimized device structure.

Korean Patent Application Laying-Open No. 10-2012-0092550 discloses an organic electroluminescent device in which a blocking layer is interposed between an electron injection layer and a light-emitting layer, wherein the blocking layer comprises an aromatic heterocyclic derivative comprising an azine ring. However, this Korean patent reference fails to disclose an organic electroluminescent device employing a compound having a phenanthrothiazole skeleton in an electron buffering layer or an electron transport layer.

Japanese patent no. 4947909 discloses a blue fluorescent light-emitting device comprising an electron buffering layer, wherein electrons are efficiently injected to the light-emitting layer compared to Alq$_3$ by inserting the electron buffering layer, and mobility is controlled to lower the driving voltage and enhance lifespan by preventing degradation of the light-emitting interface. However, in this Japanese reference, groups of the electron buffering materials are limited to Alq$_3$ derivatives, and it is desired to restrict electron mobility. Thus the improvement in efficiency and lifespan is limited.

Korean Patent Application Laying-Open No. 2014-0086861 discloses an organic electroluminescent device comprising an electron transfer layer containing quinoline-benzoxazole derivatives. However, this Korean patent reference fails to disclose the compounds having a phenanthrothiazole skeleton, and according to this Korean patent reference, the optimization of an organic electroluminescent device comprising an electron buffering layer or an electron transport layer is limited.

Japanese Patent Application Laying-Open No. 2001-23777 discloses an organic electroluminescent device comprising a compound having a phenanthrene skeleton wherein a five-membered nitrogen-containing heteroaryl is fused to the benzene ring positioned in the middle of the phenanthrene skeleton, as a host material. However, the organic electroluminescent device comprising the compound disclosed in this Japanese patent reference still needs improvement in driving voltage, current efficiency and lifespan, even though the organic electroluminescent device shows good blue color purity.

DISCLOSURE OF INVENTION

Technical Problem

The objective of the present disclosure is to provide an organic electroluminescent device having low driving voltage, excellent luminous efficiency, and long lifespan.

Solution to Problem

The present inventors found that the objective above can be achieved by an electron buffering material or an electron transport material comprising a compound represented by the following formula 1.

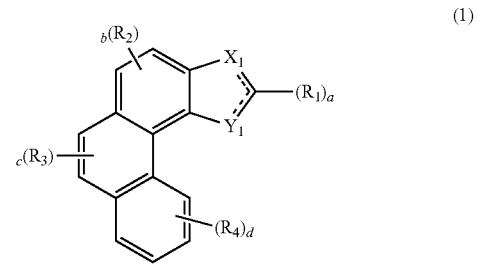

wherein,
$X_1$ represents —N=, —NR$_7$—, —O— or —S—;
$Y_1$ represents —N=, —NR$_8$—, —O— or —S—; where $X_1$ is —N=, $Y_1$ is —NR$_8$—, —O— or —S—; where $X_1$ is —NR$_7$—, $Y_1$ is —N; the case that both of $X_1$ and $Y_1$ are —O— or —S—, and the case that one of $X_1$ and $Y_1$ is —O—, and the other is —S— are excluded;

$R_1$ represents a substituted or unsubstituted (C6-C30)aryl, or a substituted or unsubstituted (3 to 30-membered)heteroaryl;

$R_2$ to $R_4$, $R_7$ and $R_8$, each independently, represent hydrogen, deuterium, a halogen, a cyano, a substituted or unsubstituted (C1-C30)alkyl, a substituted or unsubstituted (C6-C30)aryl, a substituted or unsubstituted (3 to 30-membered) heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino, or may be linked to an adjacent substituent(s) to form a substituted or unsubstituted (C3-C30), mono- or polycyclic, alicyclic or aromatic ring, whose carbon atom(s) may be replaced with at least one heteroatom selected from nitrogen, oxygen, and sulfur;

a represents an integer of 1; b and c, each independently, represent an integer of 1 or 2; d represents an integer of 1 to 4; and the heteroaryl contains at least one heteroatom selected from B, N, O, S, Si and P.

Advantageous Effects of Invention

By using the electron buffering material or the electron transport material according to the present disclosure, an electron injection is controlled, and the interfacial characteristic between the light-emitting layer and the electron injection layer is improved, and so it is possible to manufacture an organic electroluminescent device having excellent luminous efficiency. Usually, the presence of the electron buffering layer between the light-emitting layer and the electron transport zone disturbs electron current and results in an increase in driving voltage and a reduction in efficiency. However, by using the electroluminescent compound of the present disclosure, an organic electroluminescent device can have low driving voltage, excellent luminous efficiency such as current efficiency and power efficiency, and emission of colors with high purity, through the improvement in rapid electron injection characteristic and interfacial characteristic due to intermolecular stacking and interaction characteristics.

Furthermore, by using a combination of the electron buffering material and the electron transport material, an organic electroluminescent device can have low driving voltage, excellent luminous efficiency, and long lifespan.

BRIEF DESCRIPTION OF DRAWINGS

FIG. 1 is a schematic sectional view illustrating a structure of an organic electroluminescent device according to one embodiment of the present disclosure;

FIG. 2 is a schematic sectional view illustrating an energy band diagram among a hole transport layer, a light-emitting layer, an electron buffering layer, and an electron transport zone of an organic electroluminescent device according to one embodiment of the present disclosure; and FIG. 3 is a graph illustrating a current efficiency versus a luminance of organic electroluminescent devices of Example 1 and Comparative Example 1.

MODE FOR THE INVENTION

Hereinafter, the present disclosure will be described in detail. However, the following description is intended to explain the invention, and is not meant in any way to restrict the scope of the invention.

The present disclosure relates to an electron buffering material comprising a compound represented by the following formula 1, an electron transport material comprising a compound represented by the following formula 1, and an organic electroluminescent device comprising the electron buffering material or the electron transport material.

The compound of formula 1 may be represented by any one of the following formulae 2 to 4.

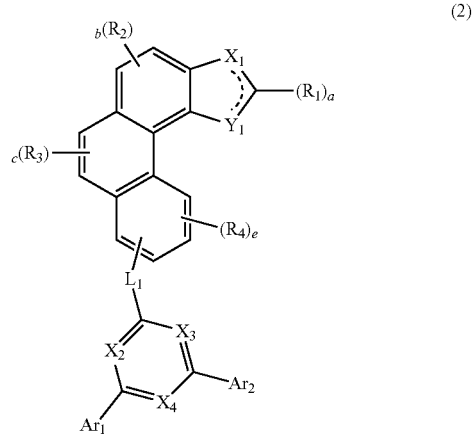

(2)

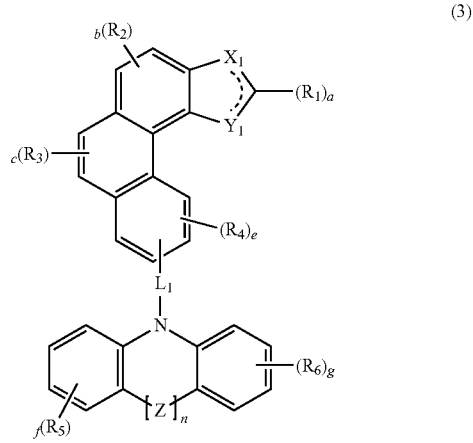

(3)

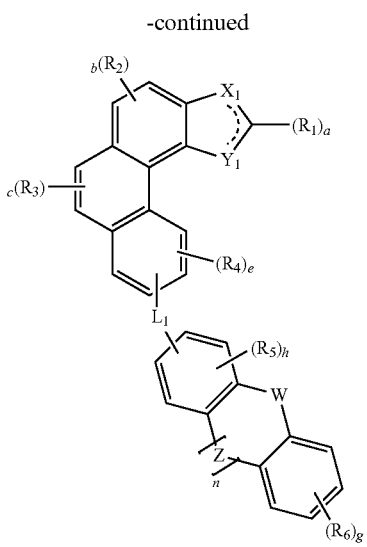

(4)

wherein,

R₁ may represent a substituted or unsubstituted (C6-C30) aryl, or a substituted or unsubstituted (3- to 30-membered) heteroaryl, preferably a substituted or unsubstituted (C6-C30)aryl, or a substituted (5- to 25-membered)heteroaryl, and more preferably a substituted or unsubstituted (C6-C30) aryl, or a substituted (5- to 20-membered)heteroaryl, and may include an unsubstituted phenyl, an unsubstituted biphenyl, an unsubstituted naphthyl, a fluorenyl substituted with a methyl, a benzofluorenyl substituted with a methyl, a carbazolyl substituted with a phenyl, a benzocarbazolyl substituted with a phenyl, an indolocarbazolyl substituted with a phenyl, an unsubstituted dibenzofuranyl, an unsubstituted dibenzothiophenyl, spiro[fluorene-fluorene], or spiro[fluorene-benzofluorene].

In formulae 1 to 4, R₂ to R₉, each independently, may represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent(s) to form a substituted or unsubstituted (C3-C30), mono- or polycyclic, alicyclic or aromatic ring whose carbon atom(s) may be replaced with at least one heteroatom selected from nitrogen, oxygen, and sulfur; preferably, each independently, may represent hydrogen, a substituted or unsubstituted (C6-C25)aryl, a substituted or unsubstituted (5-25 membered)heteroaryl, or a substituted or unsubstituted mono- or di-(C6-C25)arylamino; or may be linked to an adjacent substituent(s) to form a substituted or unsubstituted (C5-C25), mono- or polycyclic, alicyclic or aromatic ring whose carbon atom(s) may be replaced with at least one heteroatom selected from nitrogen, oxygen, and sulfur; more preferably, each independently, may represent hydrogen, a substituted or unsubstituted (C6-C20)aryl, a substituted or unsubstituted (5-25 membered)heteroaryl, or a substituted or unsubstituted di(C6-C18)arylamino; or may be linked to an adjacent substituent(s) to form a substituted or unsubstituted (C3-C25), mono- or polycyclic, alicyclic or aromatic ring whose carbon atom(s) may be replaced with at least one heteroatom selected from nitrogen and sulfur; the heteroaryl may contain at least one heteroatom selected from B, N, O, S, Si and P. For example, R₂ to R₄, each independently, may be selected from the group consisting of hydrogen, a substituted phenyl, a substituted triazinyl, a substituted pyrimidinyl, a substituted or unsubstituted carbazolyl, a substituted benzocarbazolyl, an unsubstituted dibenzocarbazolyl, and a substituted or unsubstituted diphenylamino, or may be linked to an adjacent substituent(s) to form a substituted indene ring, or a substituted ben-zothiophene ring; and R₅ and R₆, each independently, may be selected from the group consisting of hydrogen, a substituted or unsubstituted phenyl, a substituted or unsubstituted carbazolyl, an unsubstituted benzocarbazolyl, and an unsubstituted dibenzocarbazolyl, or may be linked to an adjacent substituent(s) to form an unsubstituted benzene ring, an indole ring substituted with a phenyl, a benzoindole ring substituted with a phenyl, an indene ring substituted with a methyl, or a benzoindene ring substituted with a methyl.

In formulae 1 to 4, X₁ may represent —N=, —NR₇—, —O— or —S—; Y₁ may represent —N=, —NR₈—, —O— or —S—; where X₁ is —N=, Y₁ is —NR₈—, —O— or —S—; where X₁ is —NR₇—, Y₁ is —N; preferably, the case that both of X₁ and Y₁ are —O— or —S—, and the case that one of X₁ and Y₁ is —O—, and the other is —S— are excluded; R₇ and R₈, each independently, may represent an unsubstituted phenyl. Specifically, one of X₁ and Y₁ may represent —N=, the other may represent —O—, —S— or —NR₁₃— (wherein, R₁₃ may represent a substituted or unsubstituted (C6-C20)aryl).

In formulae 1 to 4, a may represent an integer of 1; and, b and c, each independently, may represent an integer of 1 or 2, and preferably an integer of 1.

In formula 1, d may represent preferably an integer of 1 or 2.

In formulae 2 to 4, L₁ may represent a single bond, a substituted or unsubstituted (C6-C30)arylene, or a substituted or unsubstituted (3-30 membered)heteroarylene; preferably a single bond, or a substituted or unsubstituted (C6-C18)arylene; more preferably a single bond, or an unsubstituted (C6-C12)arylene; and may include a single bond or an unsubstituted phenyl.

In formula 2, X₂ to X₄, each independently, may represent —N— or —CR₉—; preferably one or more of X₂ to X₄ may represent —N—; and more preferably two or more of X₂ to X₄ may represent —N—. Specifically, R₉ may represent hydrogen.

In formula 2, Ar₁ and Ar₂, each independently, may represent a substituted or unsubstituted (C6-C30)aryl, or a substituted or unsubstituted (3-30 membered)heteroaryl; preferably a substituted or unsubstituted (C6-C25)aryl, or a substituted or unsubstituted (3-25 membered)heteroaryl; more preferably an unsubstituted (C6-C20)aryl, or a substituted or unsubstituted (5-20 membered)heteroary; and may include an unsubstituted phenyl, an unsubstituted biphenyl, an unsubstituted naphthyl, an unsubstituted dibenzothiophenyl, a fluorenyl substituted with a methyl, a benzofluorenyl substituted with a methyl, a carbazolyl substituted with a phenyl, a benzocarbazolyl substituted with a phenyl, or an unsubstituted benzonaphthothiophenyl.

In formulae 2 to 4, e may represent an integer of 1 to 3, and preferably an integer of 1 or 2.

In formulae 3 and 4, Z may represent a single bond, or a substituted or unsubstituted (C1-C6)alkylene, and preferably a single bond.

In formula 3, n may represent an integer of 0 or 1; and f and g, each independently, may represent an integer of 1 to 4, and preferably an integer of 1 or 2.

In formula 4, n may represent an integer of 0 or 1, and preferably an integer of 1; g may represent an integer of 1 to 4, and preferably an integer of 1 or 2; and h may represent an integer of 1 to 3, and preferably an integer of 1 or 2.

In formula 4, W may represent —$NR_{10}$—, —O—, —S— or —$CR_{11}R_{12}$—, and preferably —$NR_{10}$—.

In formula 4, $R_{10}$ may represent a substituted or unsubstituted (C6-C30)aryl, or a substituted or unsubstituted (3-30 membered)heteroaryl, preferably a substituted or unsubstituted (C6-C20)aryl, and more preferably an unsubstituted (C6-C18)aryl, such as, an unsubstituted phenyl.

In formula 4, $R_{11}$ and $R_{12}$, each independently, may represent a substituted or unsubstituted (C1-C30)alkyl, a substituted or unsubstituted (C6-C30)aryl, or a substituted or unsubstituted (3-30 membered)heteroaryl, preferably a substituted or unsubstituted (C1-C20)alkyl, and more preferably an unsubstituted (C1-C15)alkyl, such as an unsubstituted methyl.

Herein, "(C1-C30)alkyl" indicates a linear or branched alkyl having 1 to 30, preferably 1 to 20, and more preferably 1 to 10 carbon atoms, and includes methyl, ethyl, n-propyl, isopropyl, n-butyl, isobutyl, tert-butyl, etc. "(C3-C30)cycloalkyl" indicates a mono- or polycyclic hydrocarbon having 3 to 30, preferably 3 to 20, and more preferably 3 to 7 carbon atoms and includes cyclopropyl, cyclobutyl, cyclopentyl, cyclohexyl, etc. Furthermore, "(C6-C30)aryl(ene)" indicates a monocyclic or fused ring derived from an aromatic hydrocarbon and having 6 to 30, preferably 6 to 20, and more preferably 6 to 15 ring backbone carbon atoms, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl etc. "(3- to 30-membered) heteroaryl(ene)" indicates an aryl group having 3 to 30, preferably 5 to 25 ring backbone atoms including at least one, preferably 1 to 4, heteroatom selected from the group consisting of B, N, O, S, Si, and P; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, ben-zoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenanthridinyl, benzodioxolyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. The substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or dialkylamino, the substituted mono- or diarylamino, the substituted alkylarylamino, and the substituted mono- or polycyclic, alicyclic or aromatic ring in $R_1$ to $R_{12}$, $L_1$, $Ar_1$, $Ar_2$ and Z of formulae 1 to 4 of the present disclosure, each independently, are at least one selected from the group consisting of deuterium, a halogen; a cyano; a carboxy; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl; a (C6-C30)aryl unsubstituted or substituted with a cyano, a (3- to 30-membered)heteroaryl or a mono- or di-(C6-C30)arylamino; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl; and preferably, each independently, are at least one selected from the group consisting of a (C1-C6)alkyl; a (C6-C25)aryl unsubstituted or substituted with a (5- to 25-membered)heteroaryl or di(C6-C25)arylamino; a (5- to 25-membered)heteroaryl unsubstituted or substituted with a (C6-C25)aryl; a mono- or di-(C6-C20)arylamino; and a (C1-C20)alkyl(C6-C25)aryl; or may be linked to an adjacent substituent(s) to form a substituted or unsubstituted (C5-C30), mono- or polycyclic, alicyclic or aromatic ring, whose carbon atom(s) may be replaced with at least one heteroatom selected from nitrogen, oxygen, and sulfur; and the substituent may include an unsubstituted methyl, a phenyl substituted or unsubstituted with a carbazolyl or di phenylamino, an unsubstituted biphenyl, an unsubstituted naphthyl, a fluorenyl substituted with a methyl, a benzofluorenyl substituted with a methyl, an unsubstituted dibenzothiophenyl, a carbazolyl unsubstituted or substituted with a phenyl, a benzocarbazolyl unsubstituted or substituted with a phenyl, an unsubstituted dibenzocarbazolyl, a pyrimidinyl substituted with a phenyl, an unsubstituted benzonaphthothiophenyl, or an unsubstituted di(C6-C12)arylamino; or may be linked to an adjacent substituent(s) to form an indole ring substituted with a phenyl, a benzoindole ring substituted with a phenyl, an unsubstituted benzene ring, a benzindene ring substituted with a methyl, or an indene ring substituted with a methyl.

Specifically, the compound of formula 1 includes the following, but is not limited thereto.

C-1
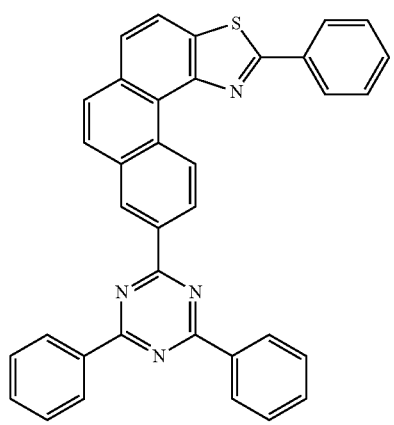
C-2
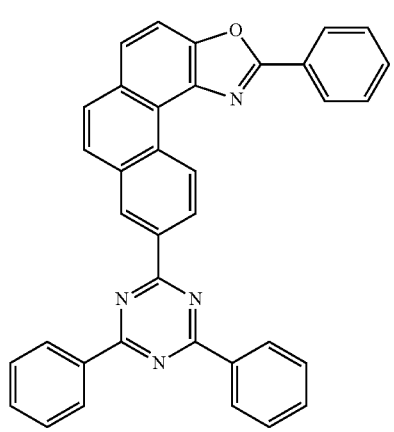
C-3
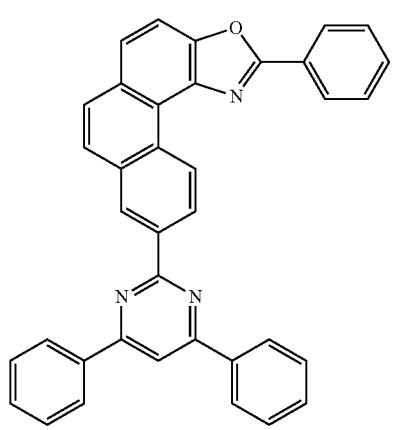
C-4
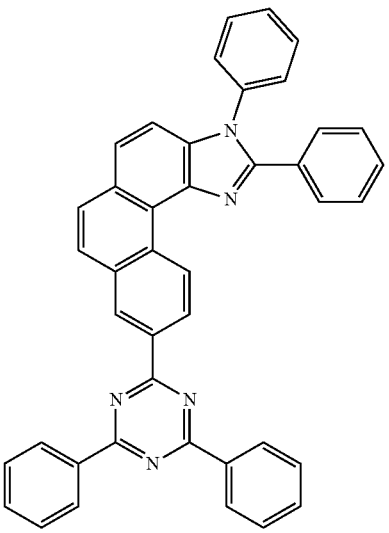
C-5
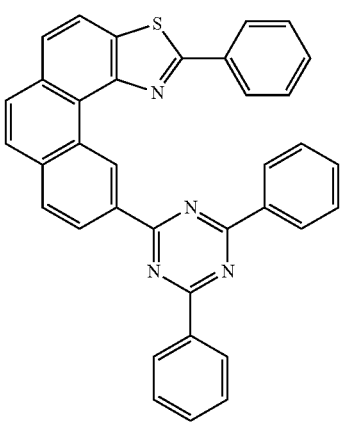
C-6
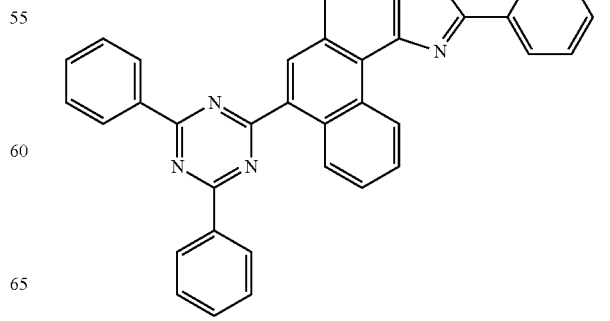

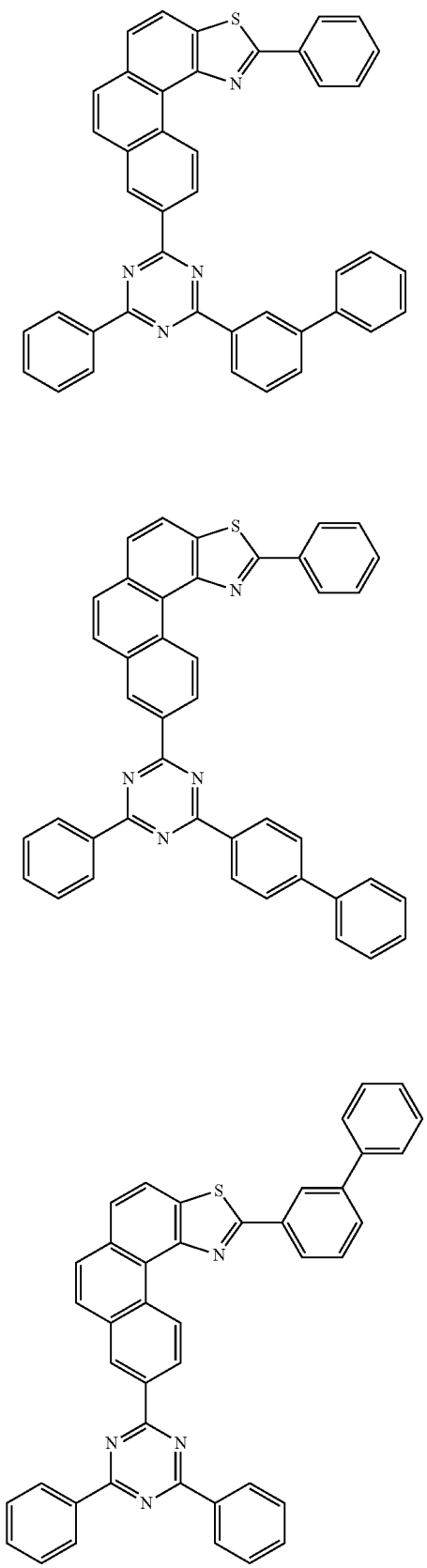
C-7
C-8
C-9
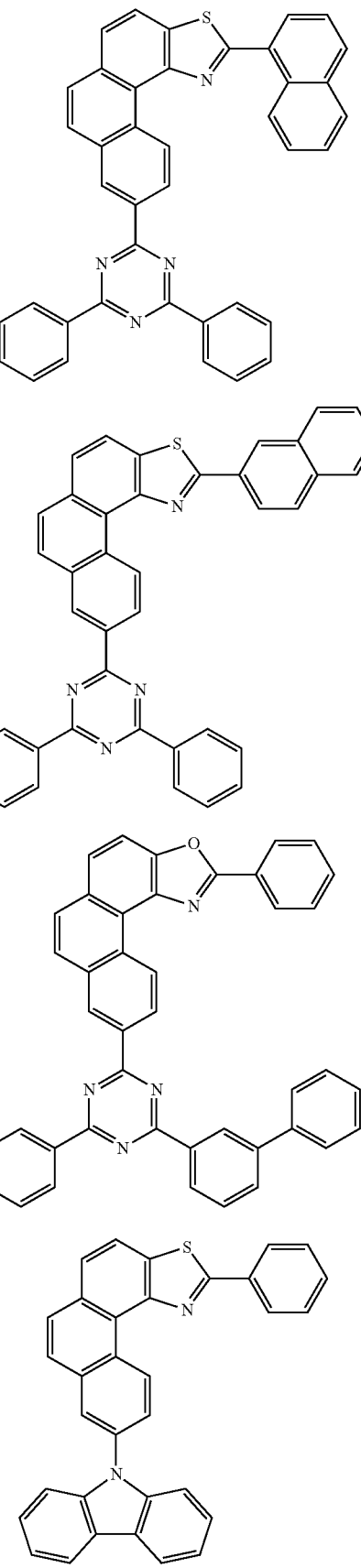
C-10
C-11
C-12
C-13

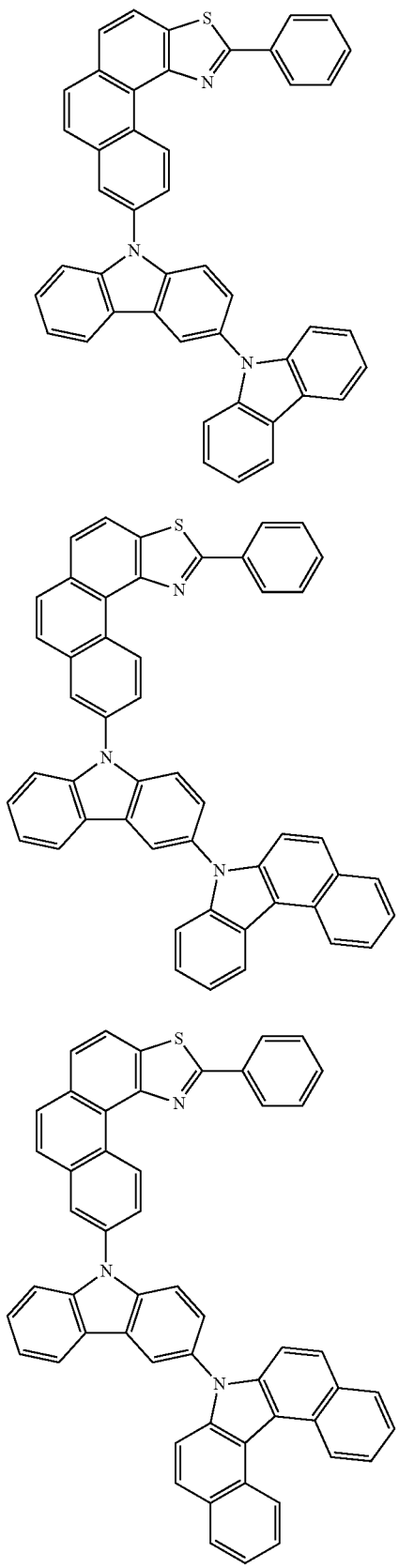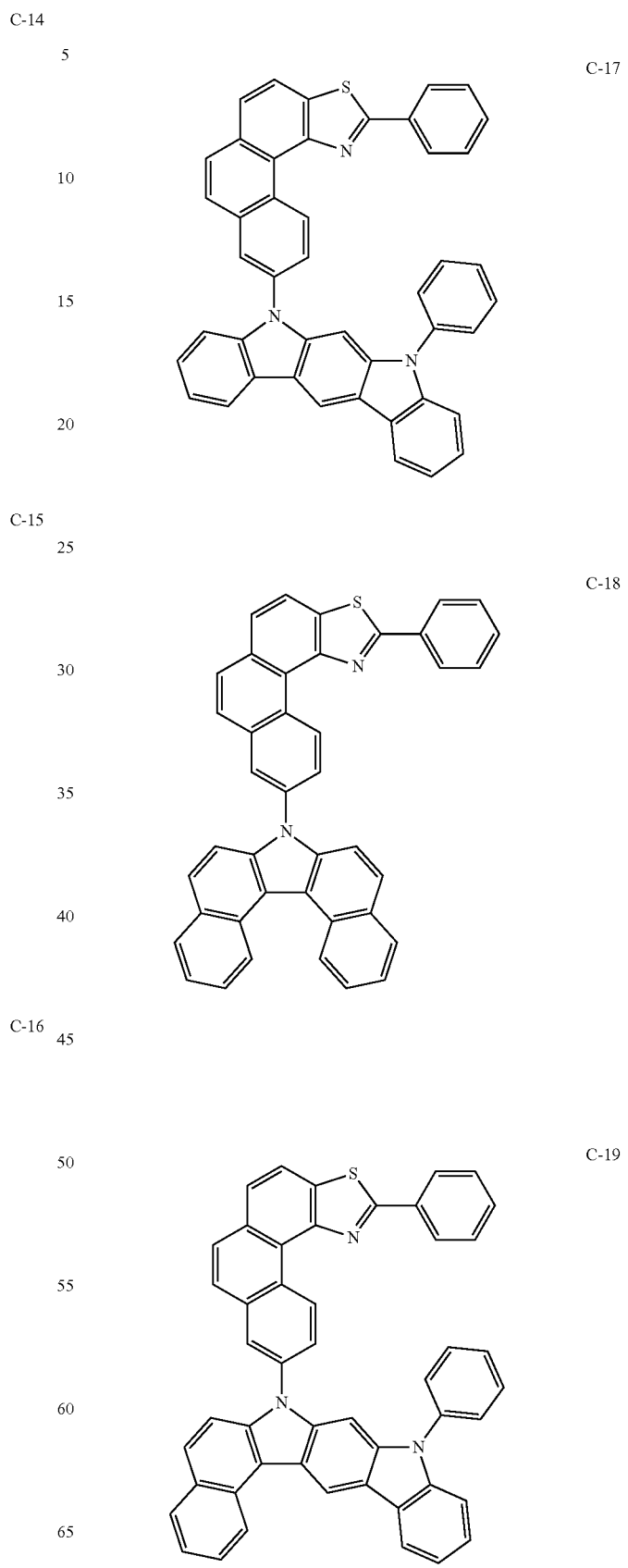

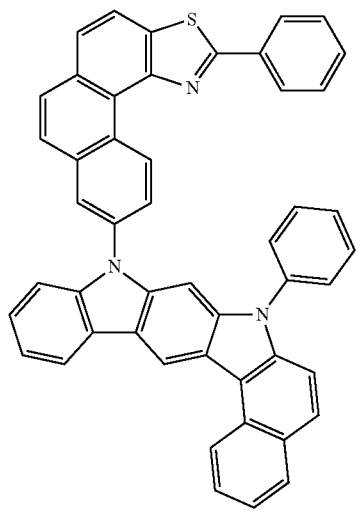
C-20
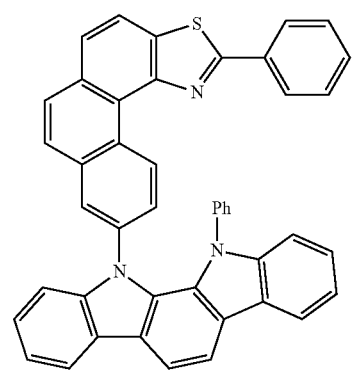
C-21
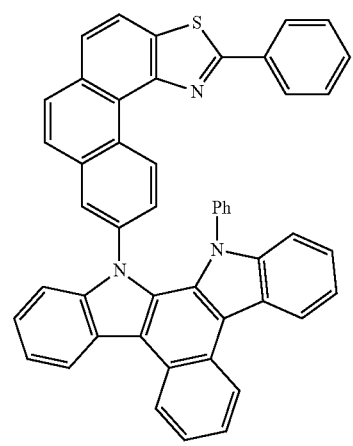
C-22
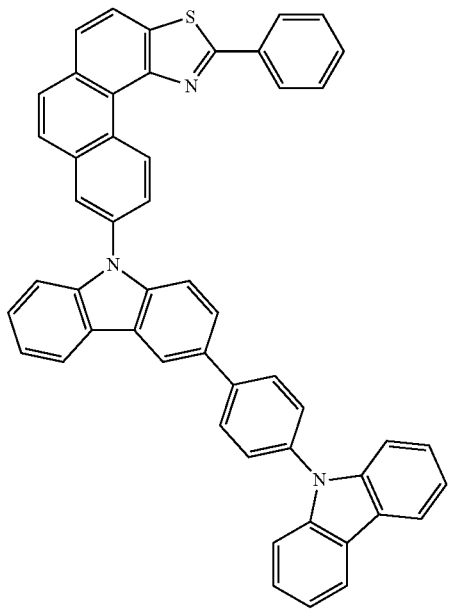
C-23
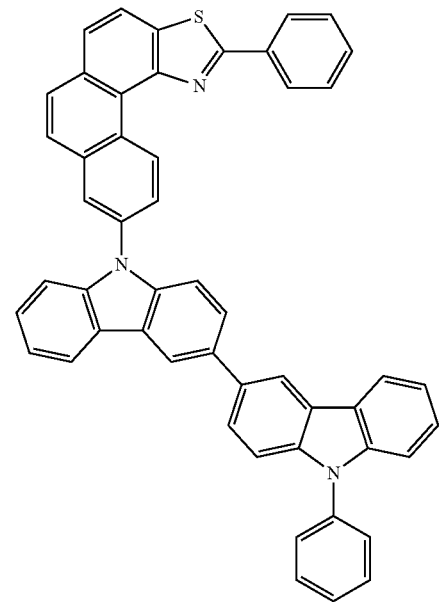
C-24

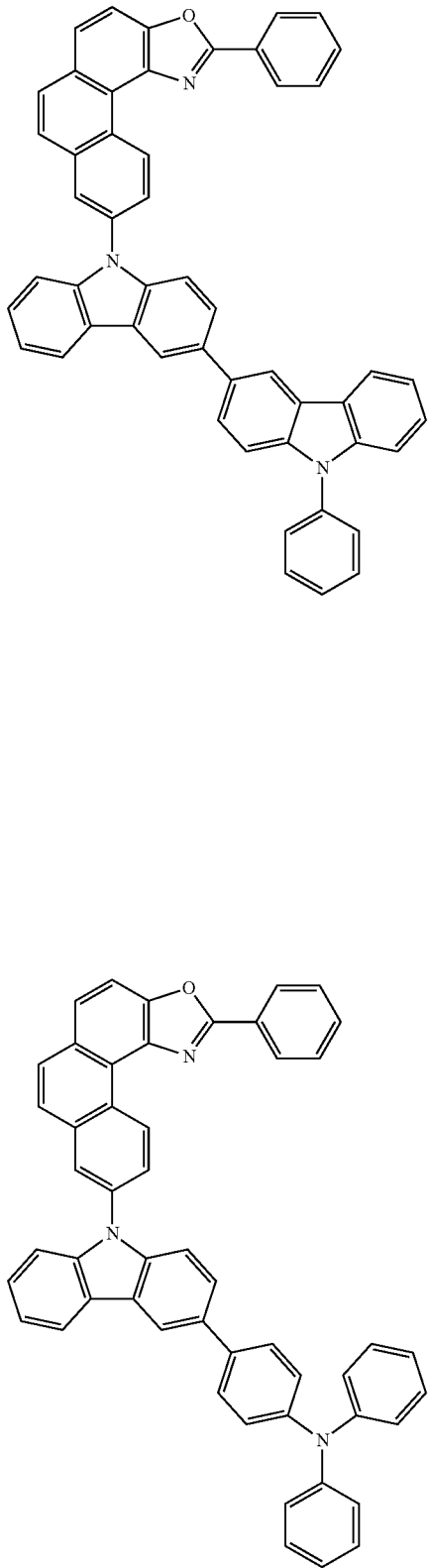
C-25
C-26
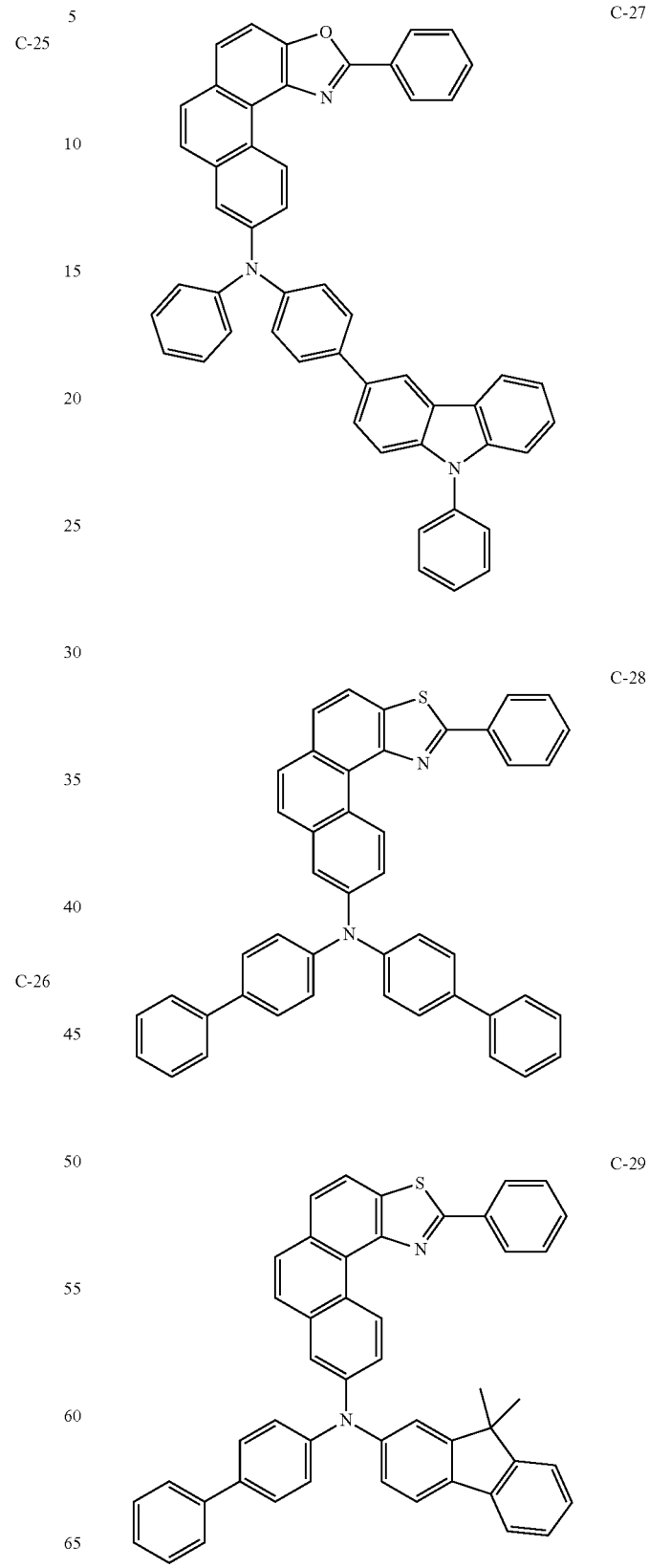
C-27
C-28
C-29

C-30
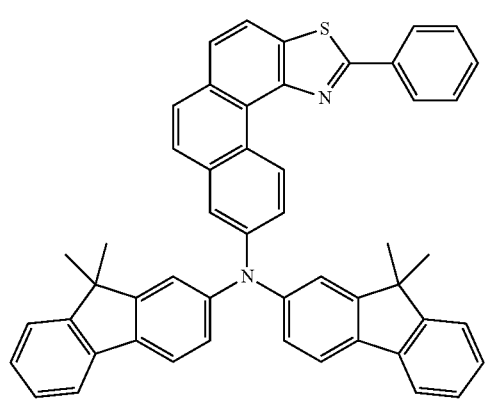
C-31
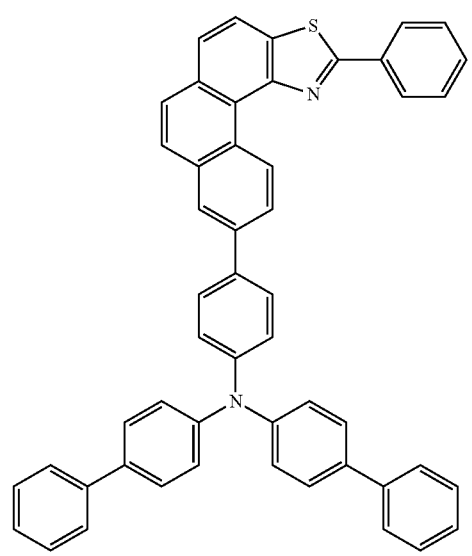
C-32
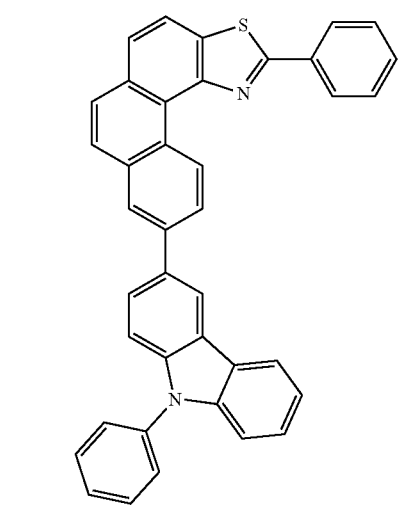
C-33
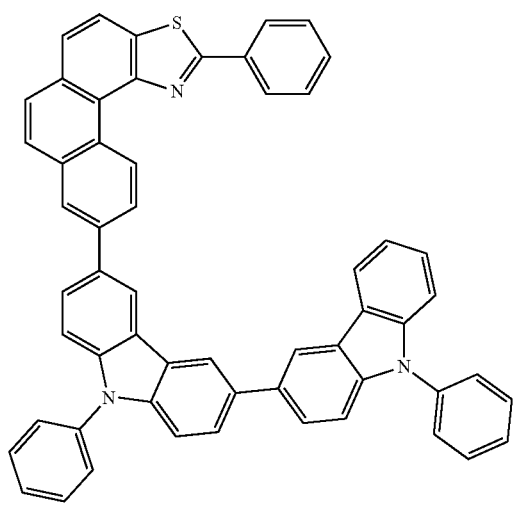
C-34
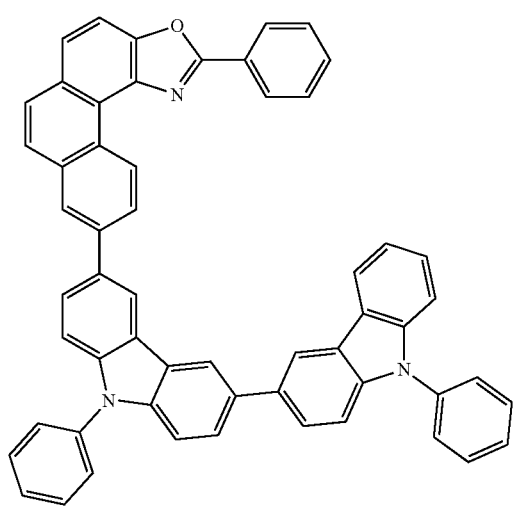
C-35
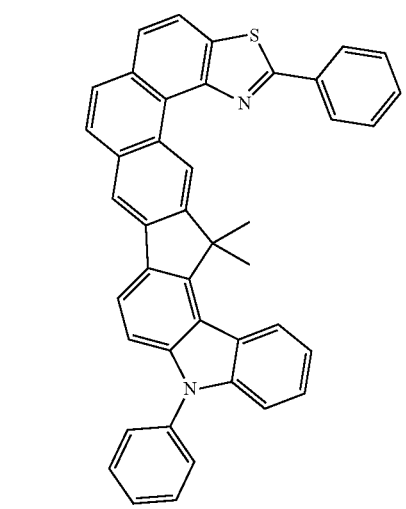

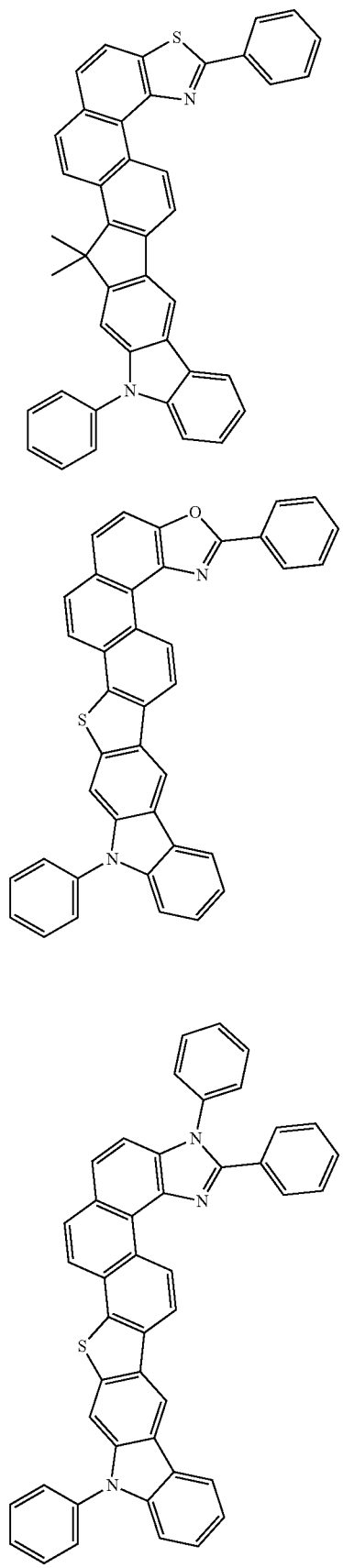
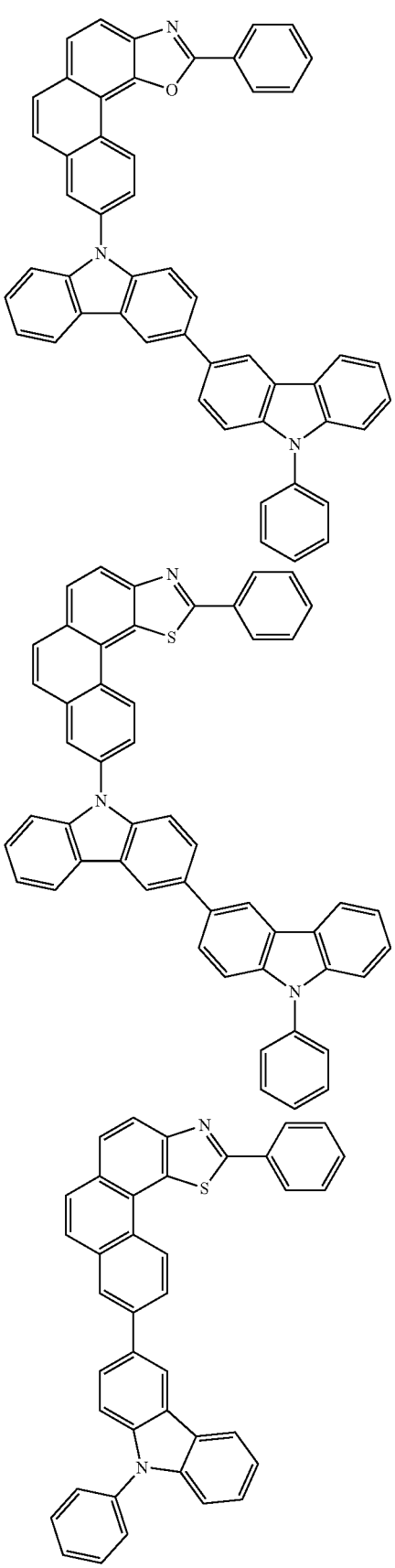

C-42 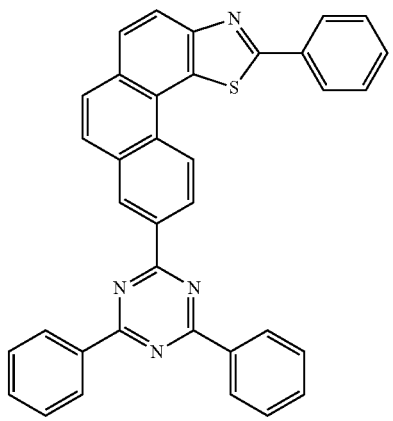
C-45 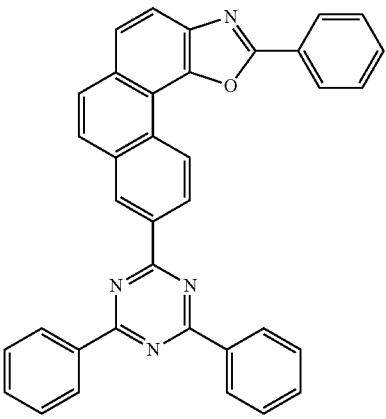
C-43 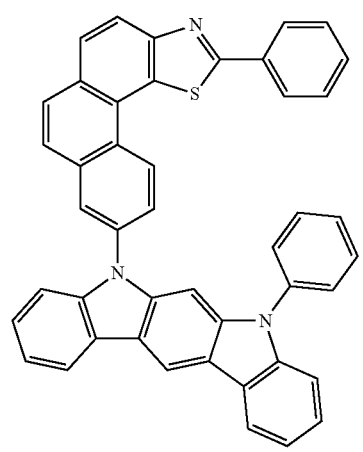
C-46 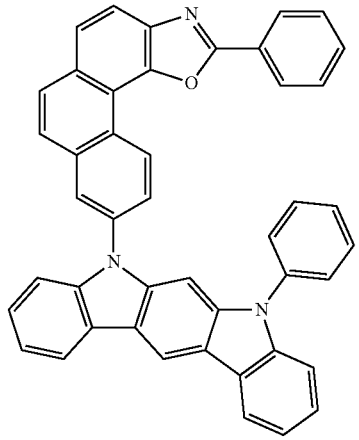
C-44 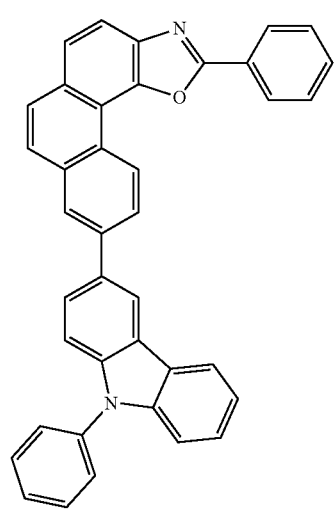
C-47 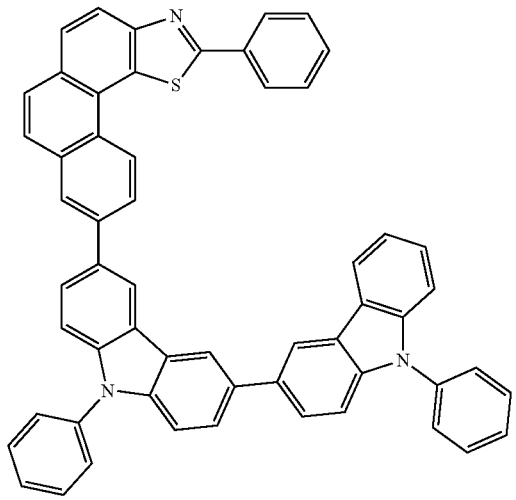

-continued
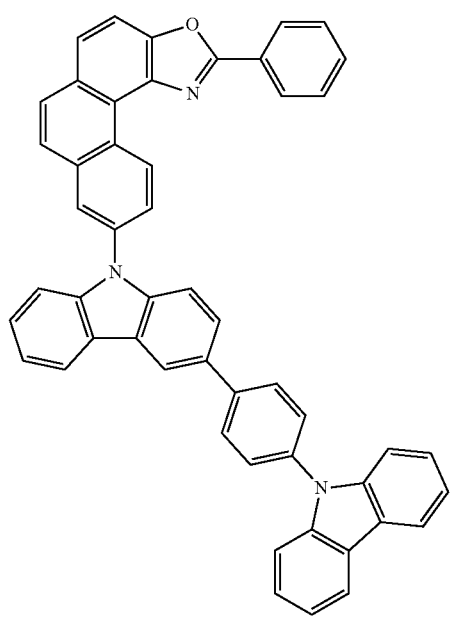
C-48
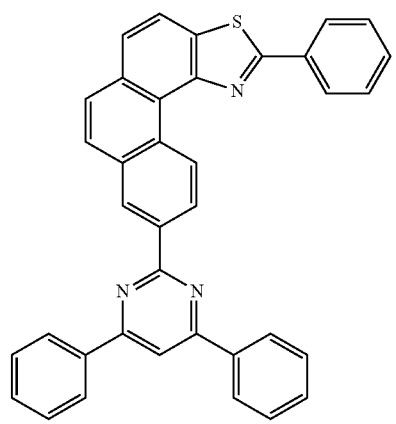
C-49
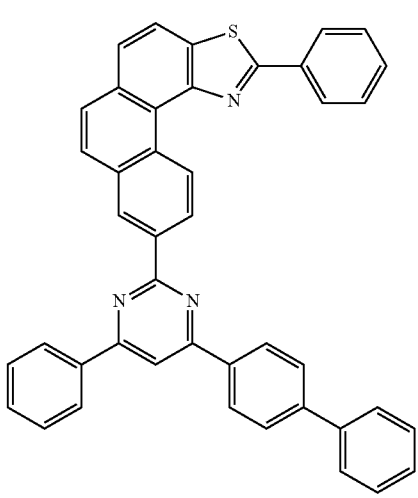
C-50
-continued
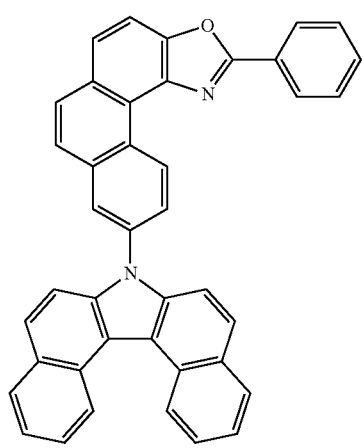
C-51
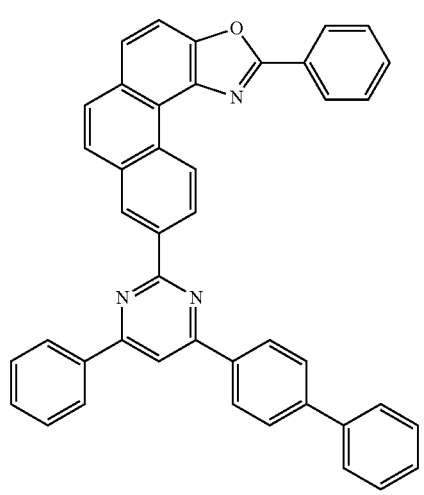
C-52
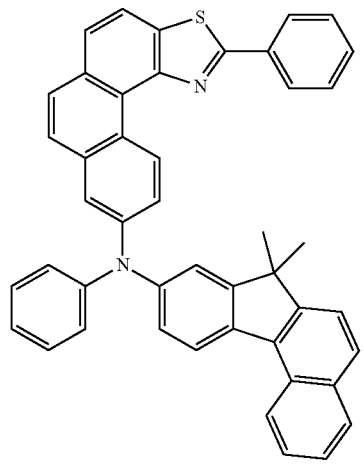
C-53

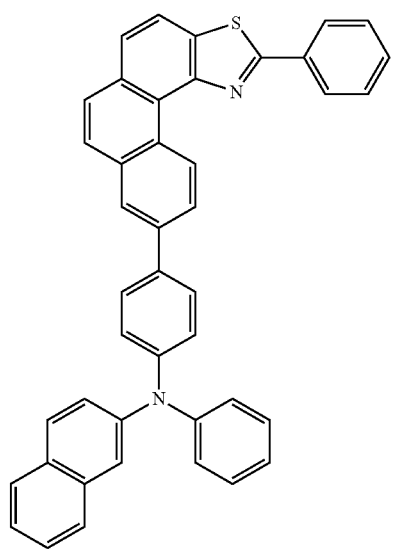
C-54
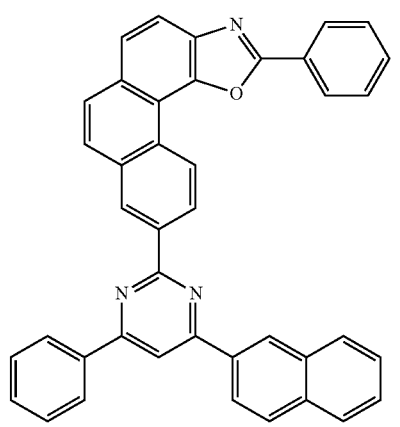
C-55
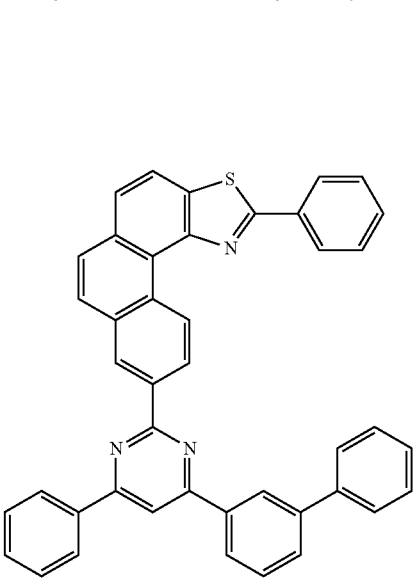
C-56
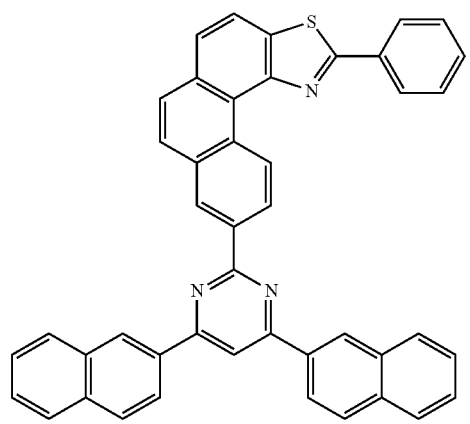
C-57
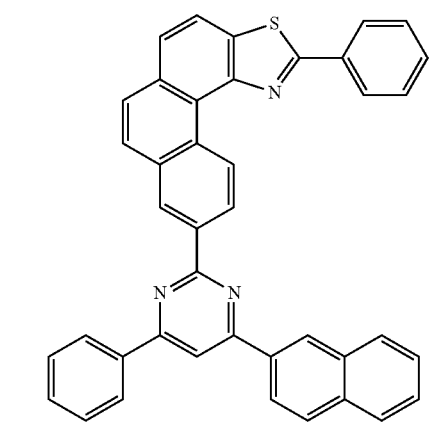
C-58
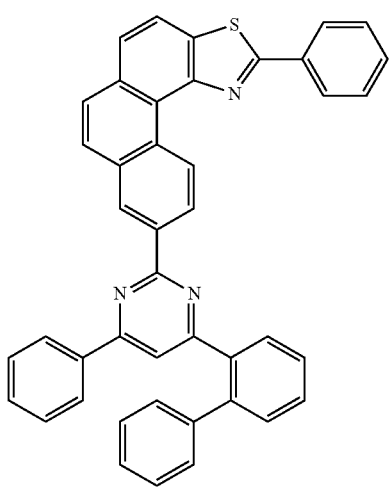
C-59

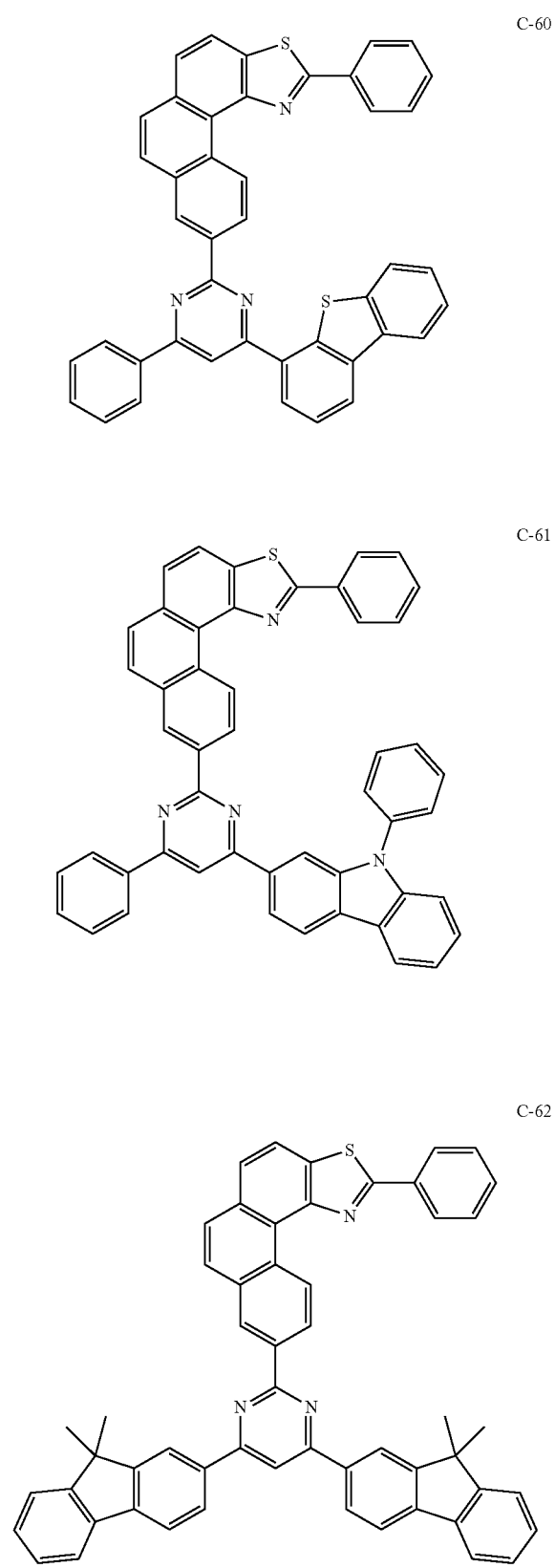

-continued
C-66
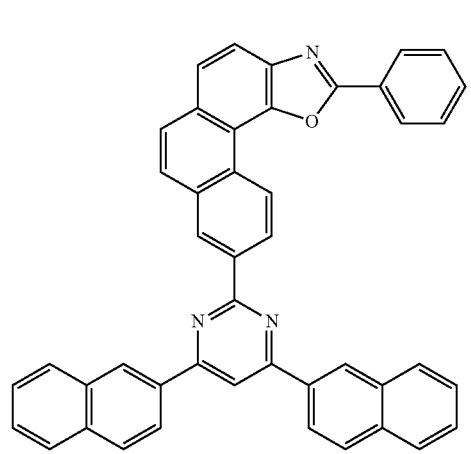
C-67
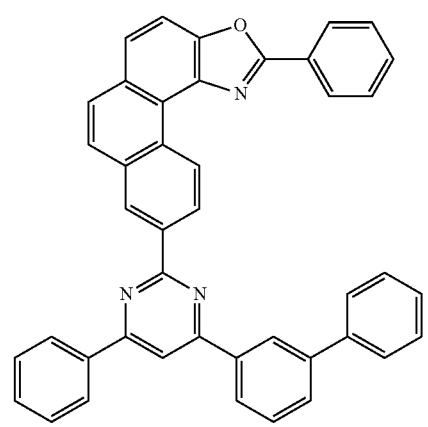
C-68
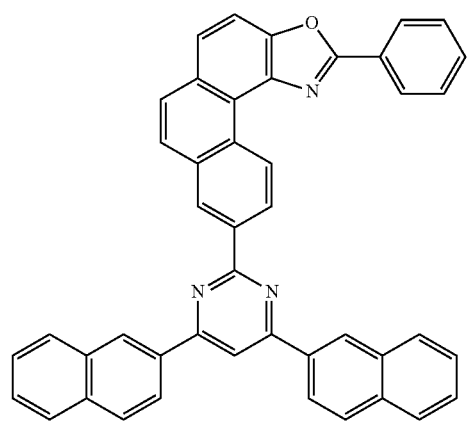
-continued
C-69
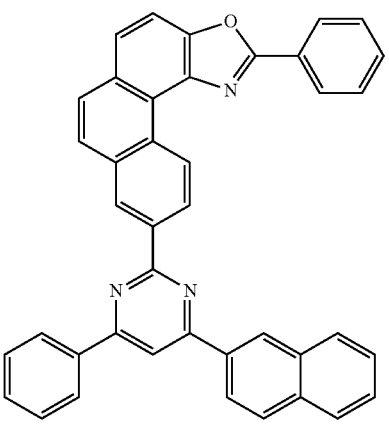
C-70
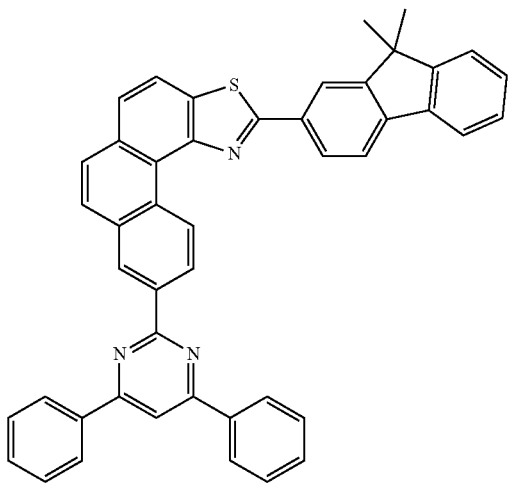
C-71
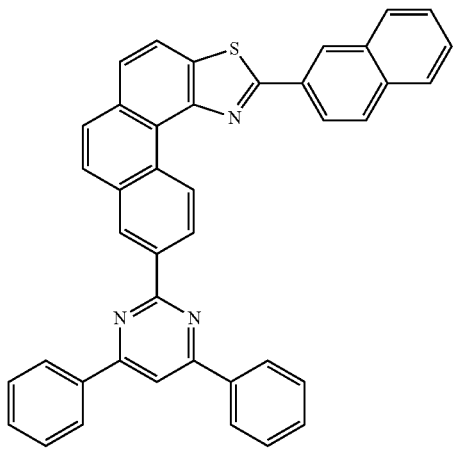

C-72
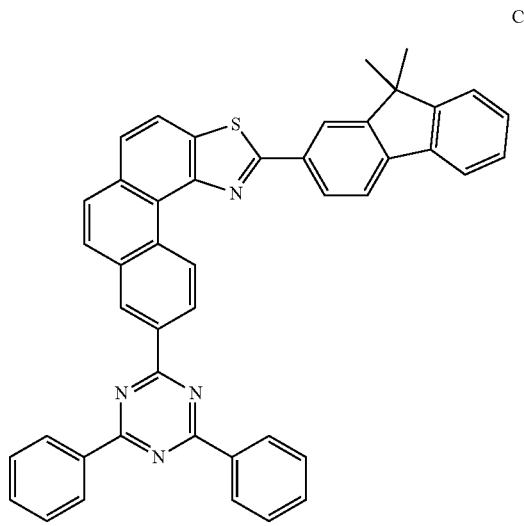
C-75
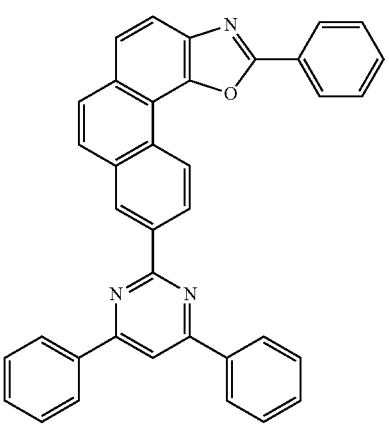
C-73
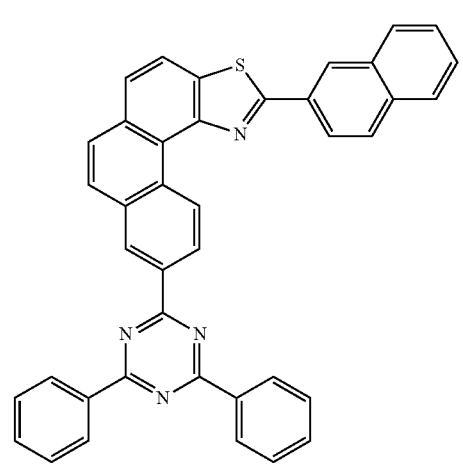
C-76
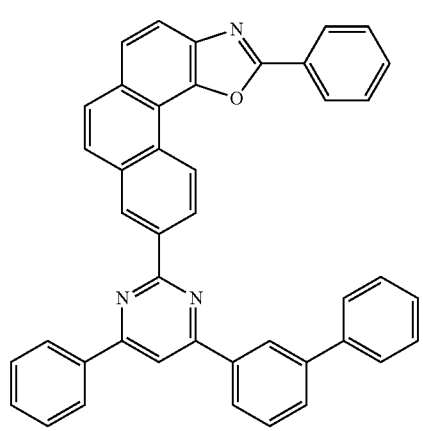
C-74
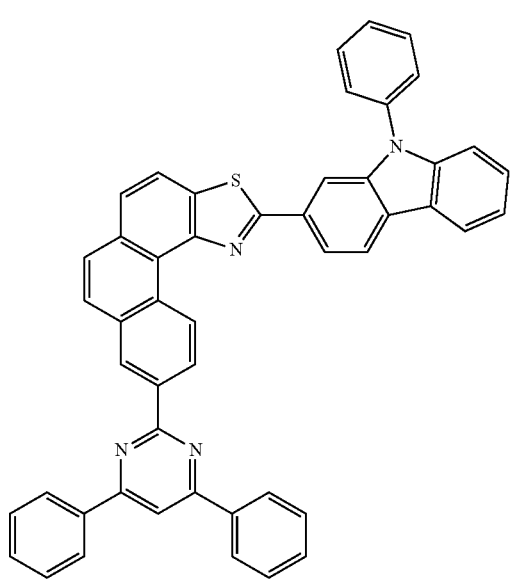
C-77
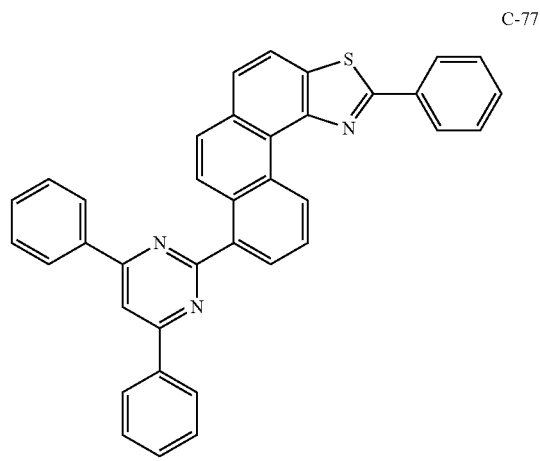

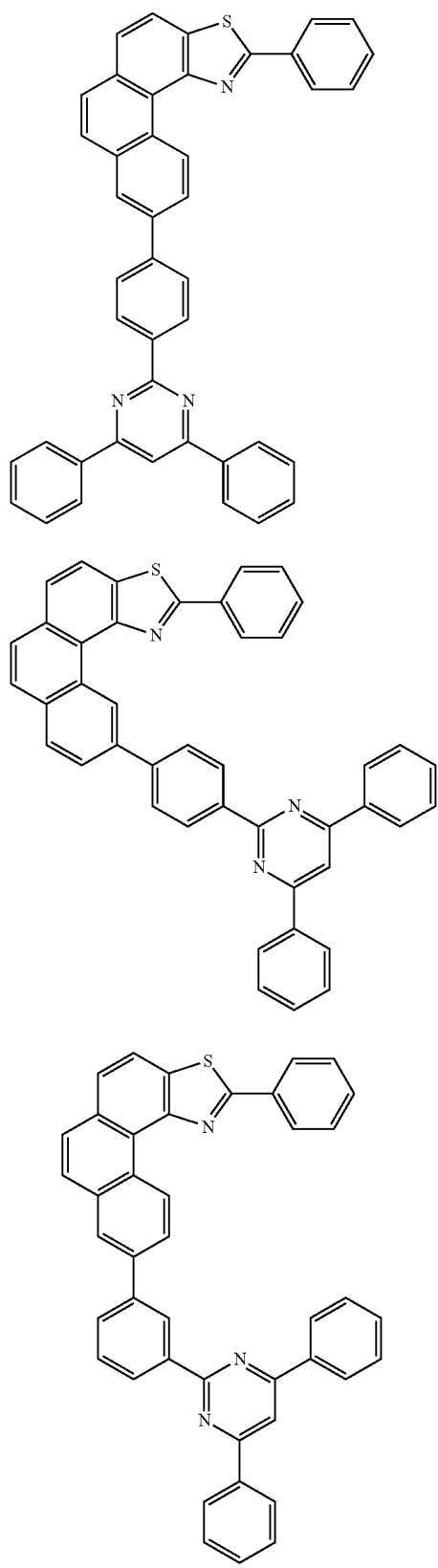
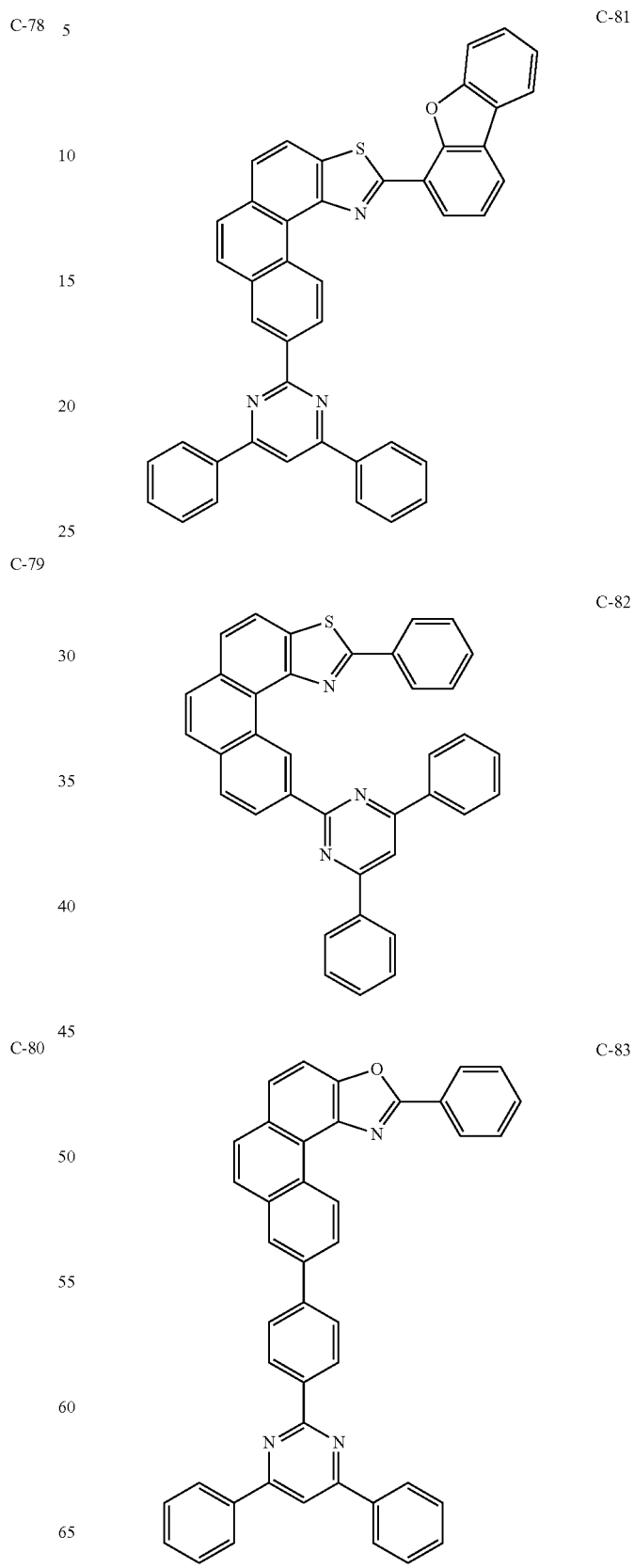

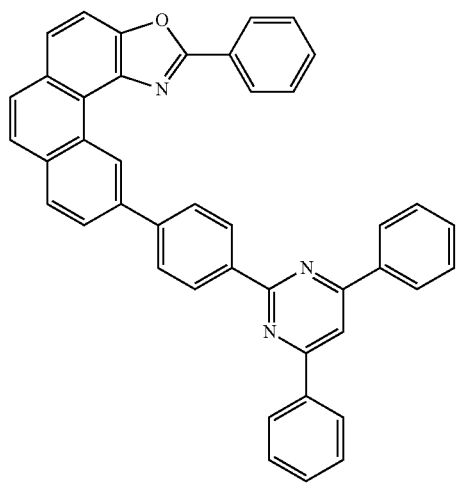
C-84
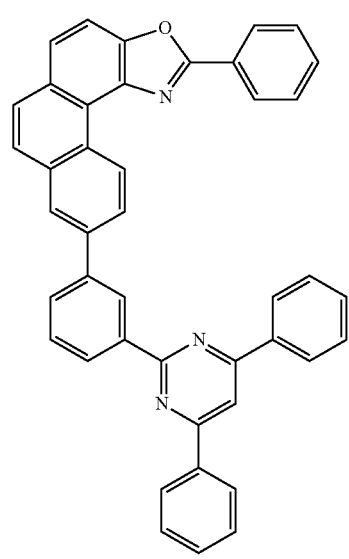
C-85
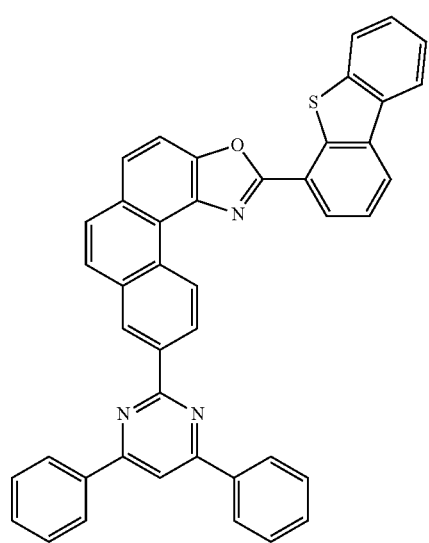
C-86
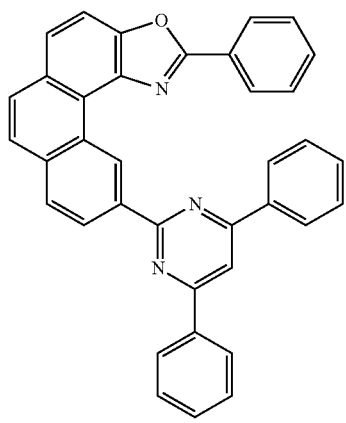
C-87
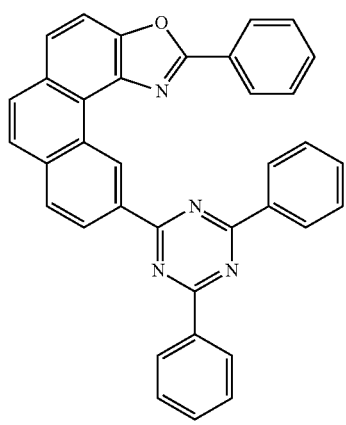
C-88
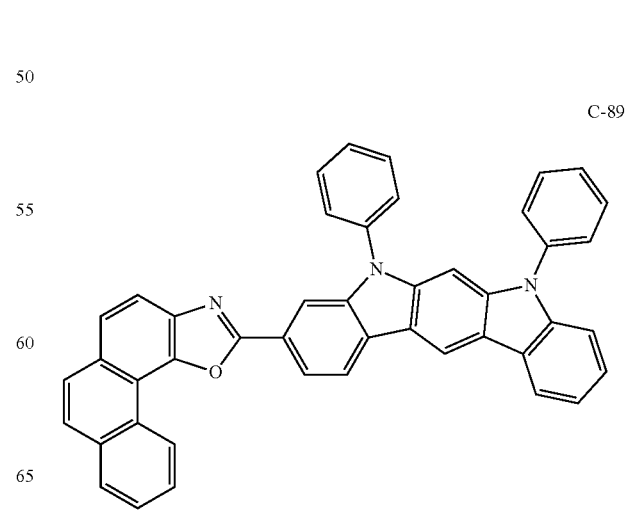
C-89

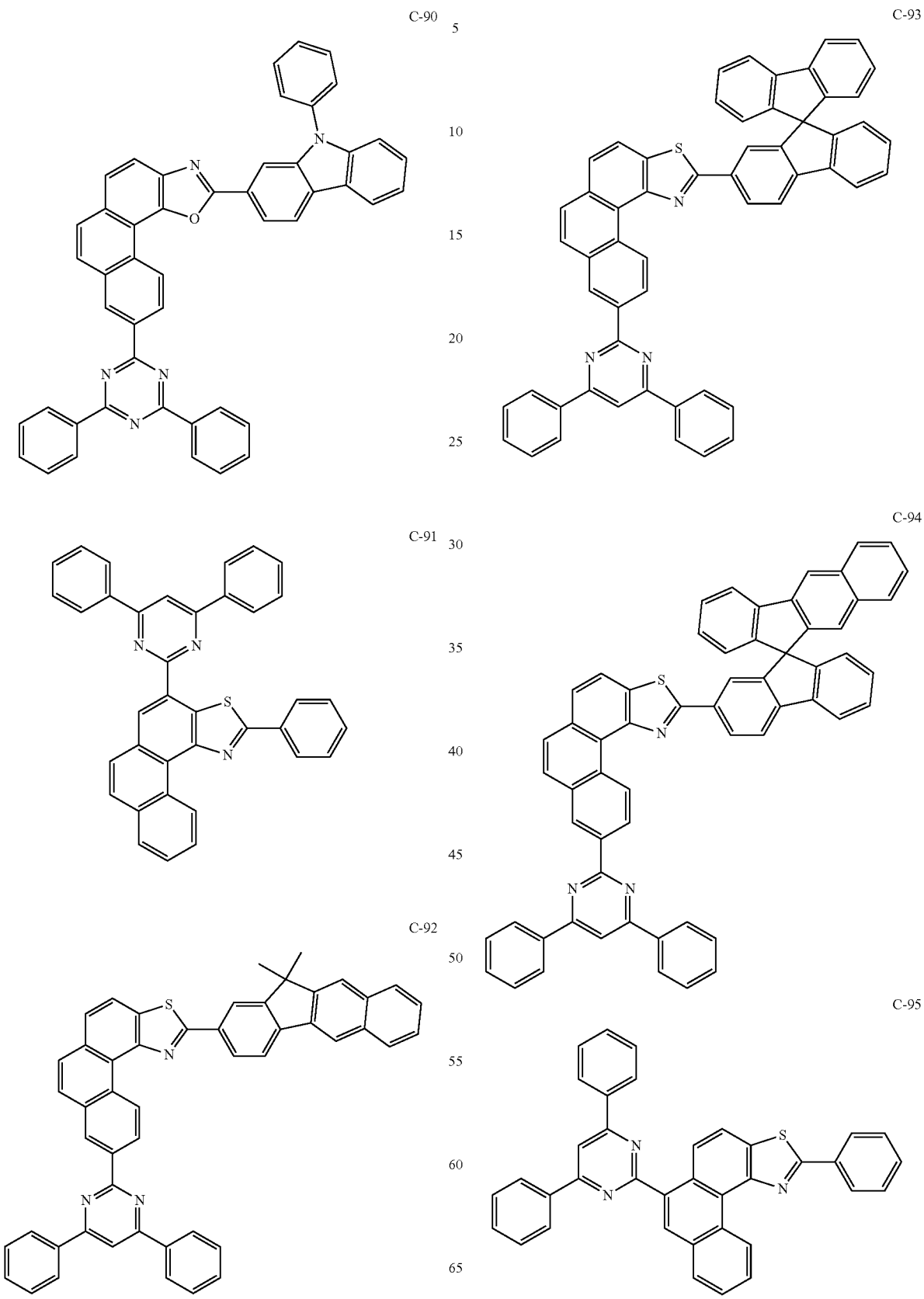

C-96
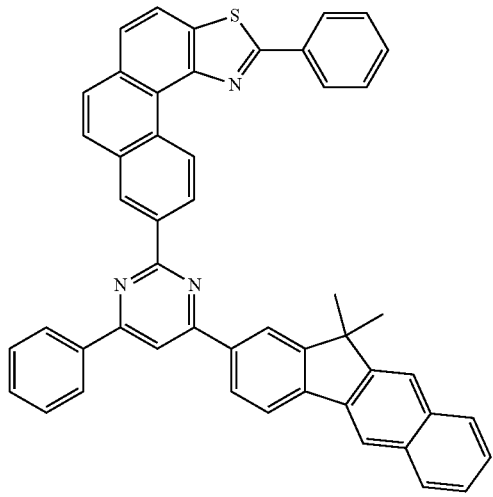
C-97
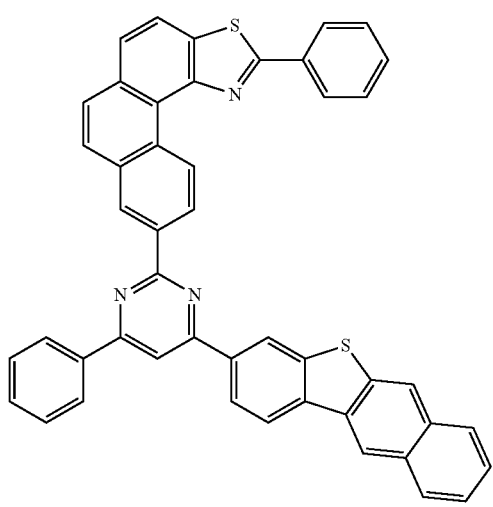
C-98
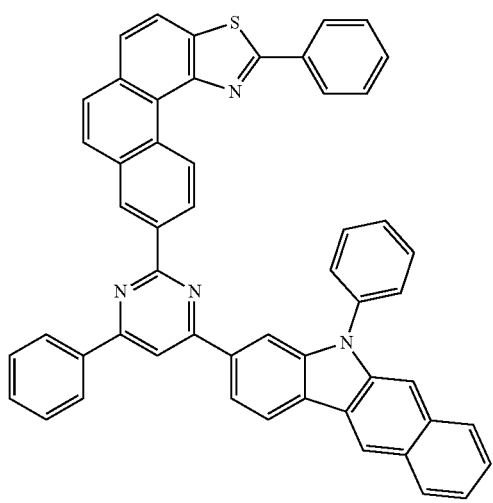
C-99
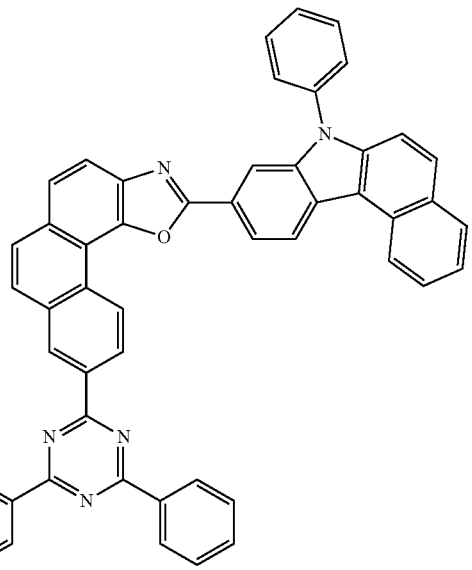
C-100
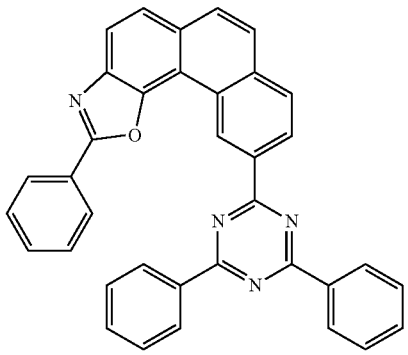
C-101
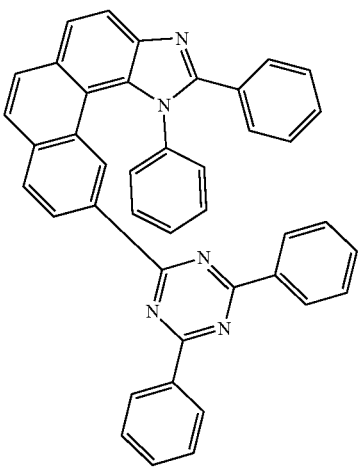

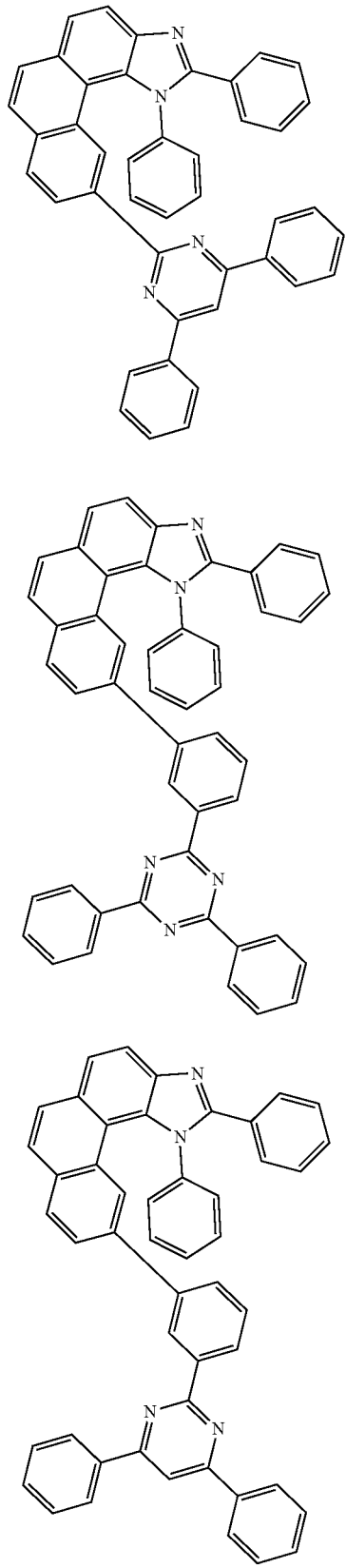
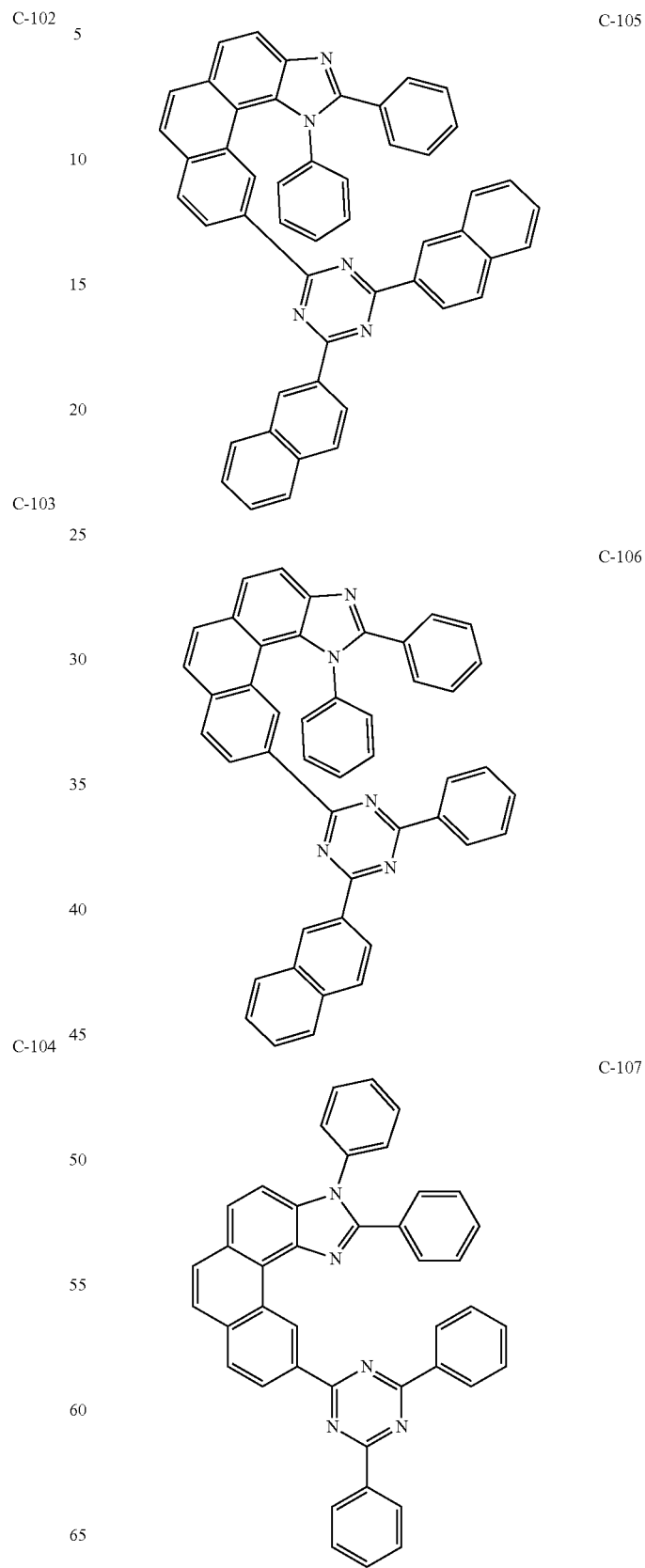

C-108
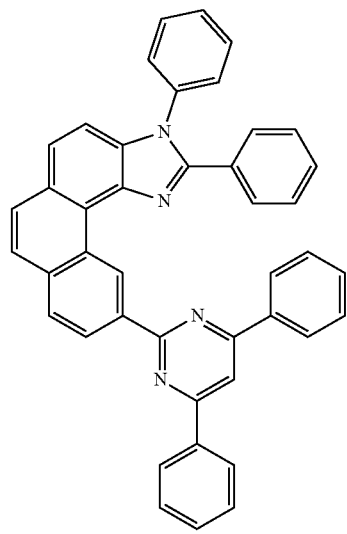
C-110
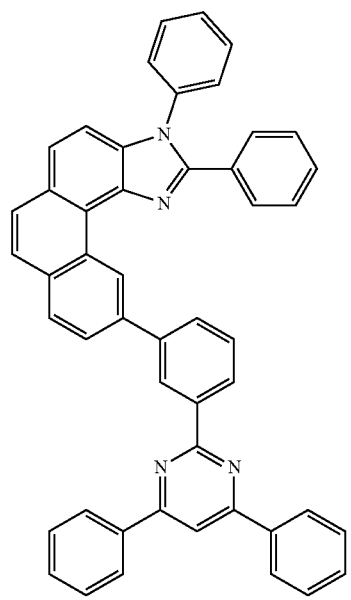
C-109
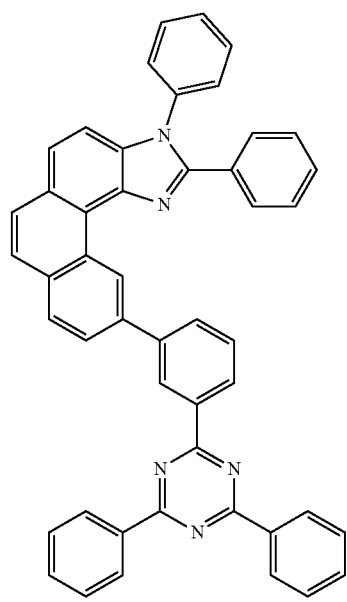
C-111
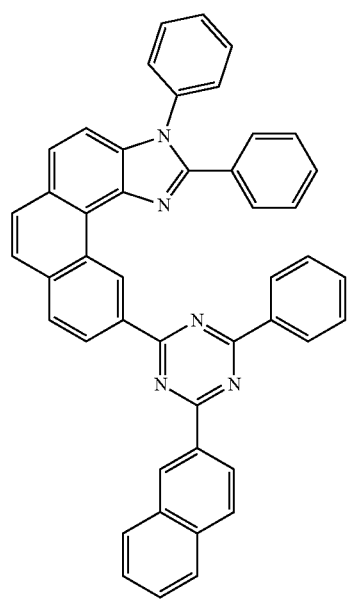

C-112
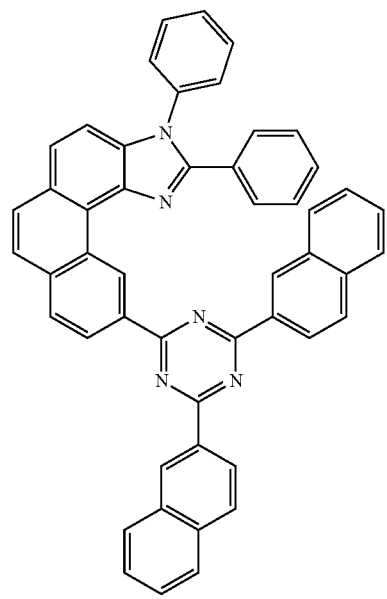
C-115
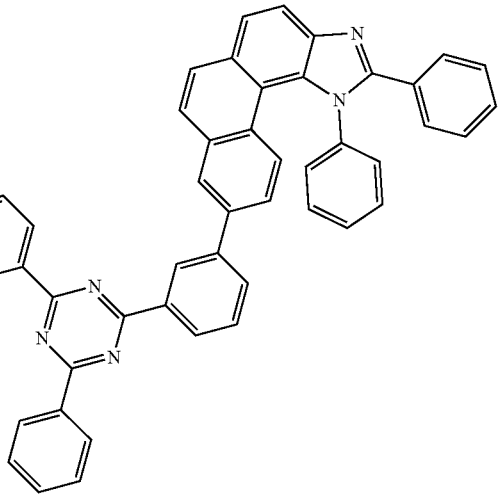
C-113
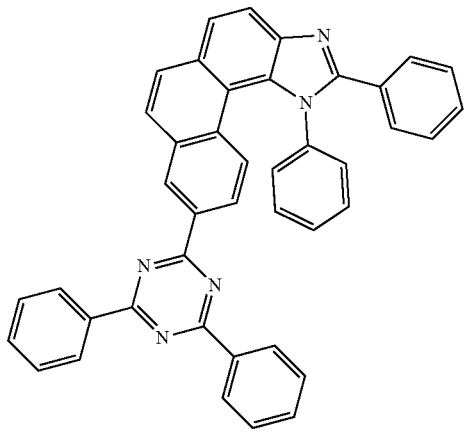
C-116
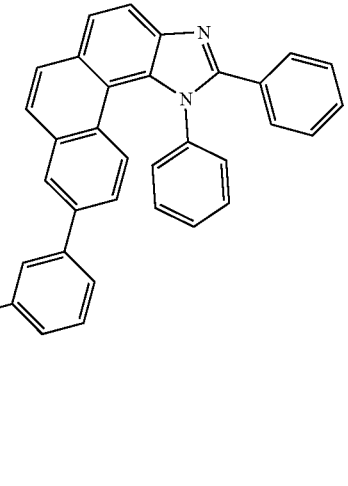
C-114
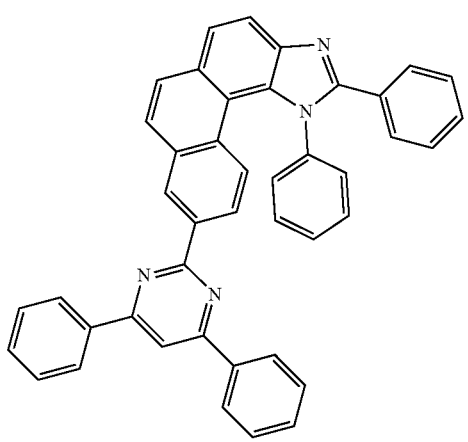
C-117

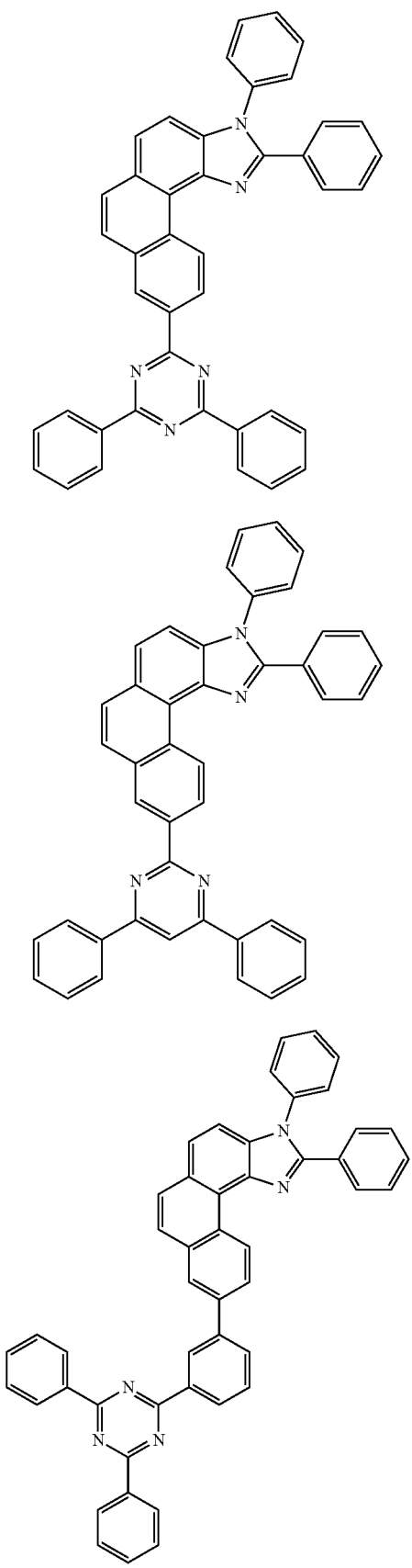
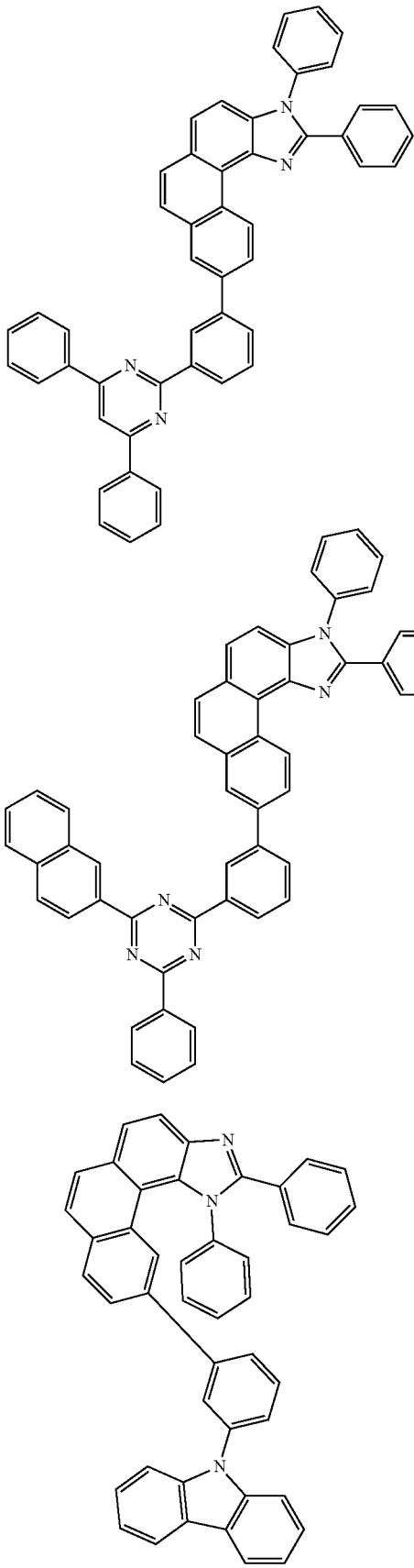

C-124
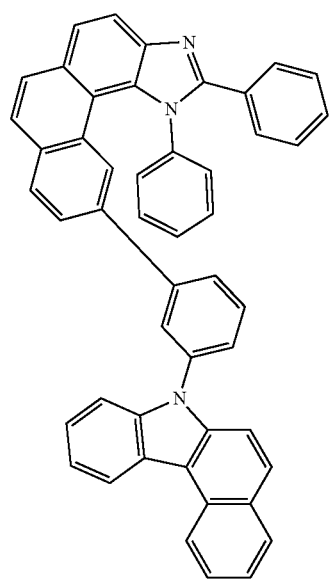
C-125
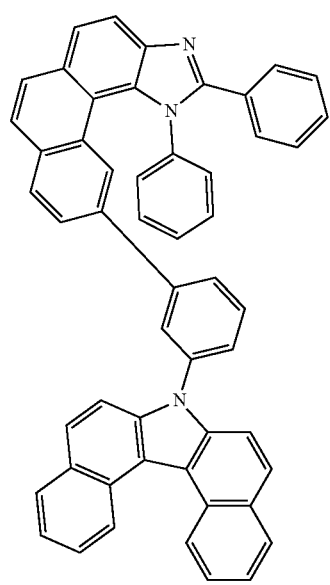
C-126
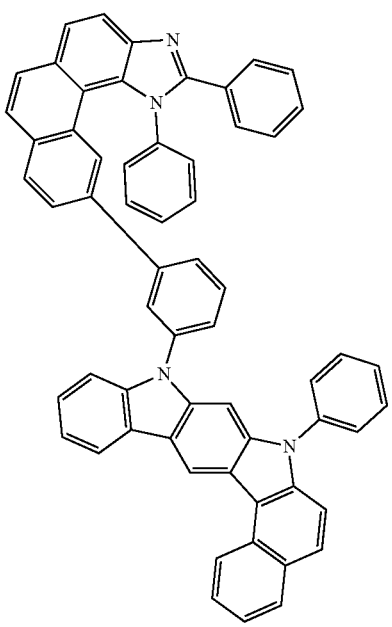
C-127
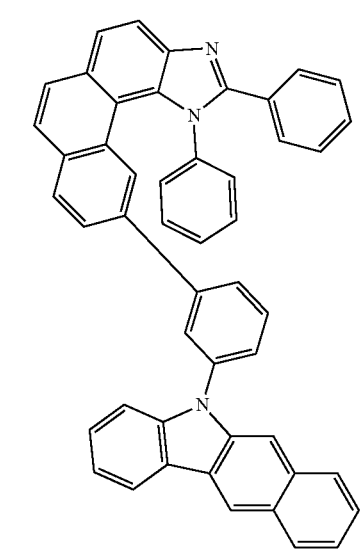
C-128
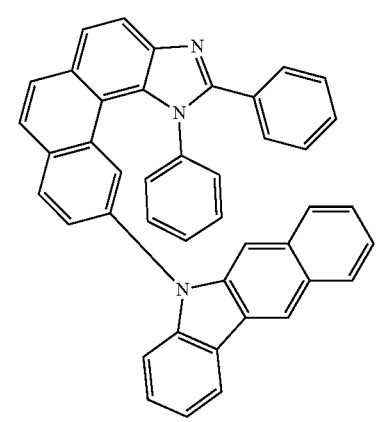

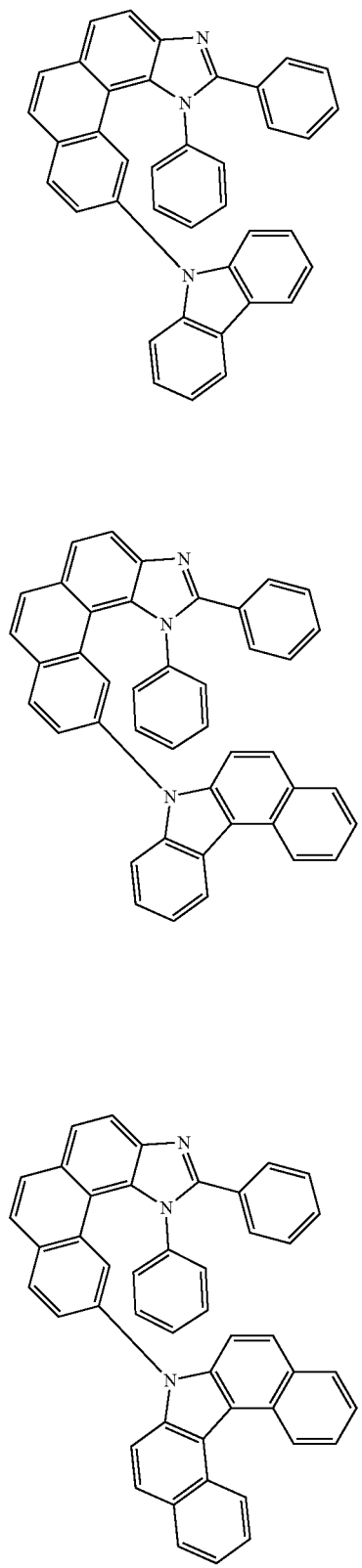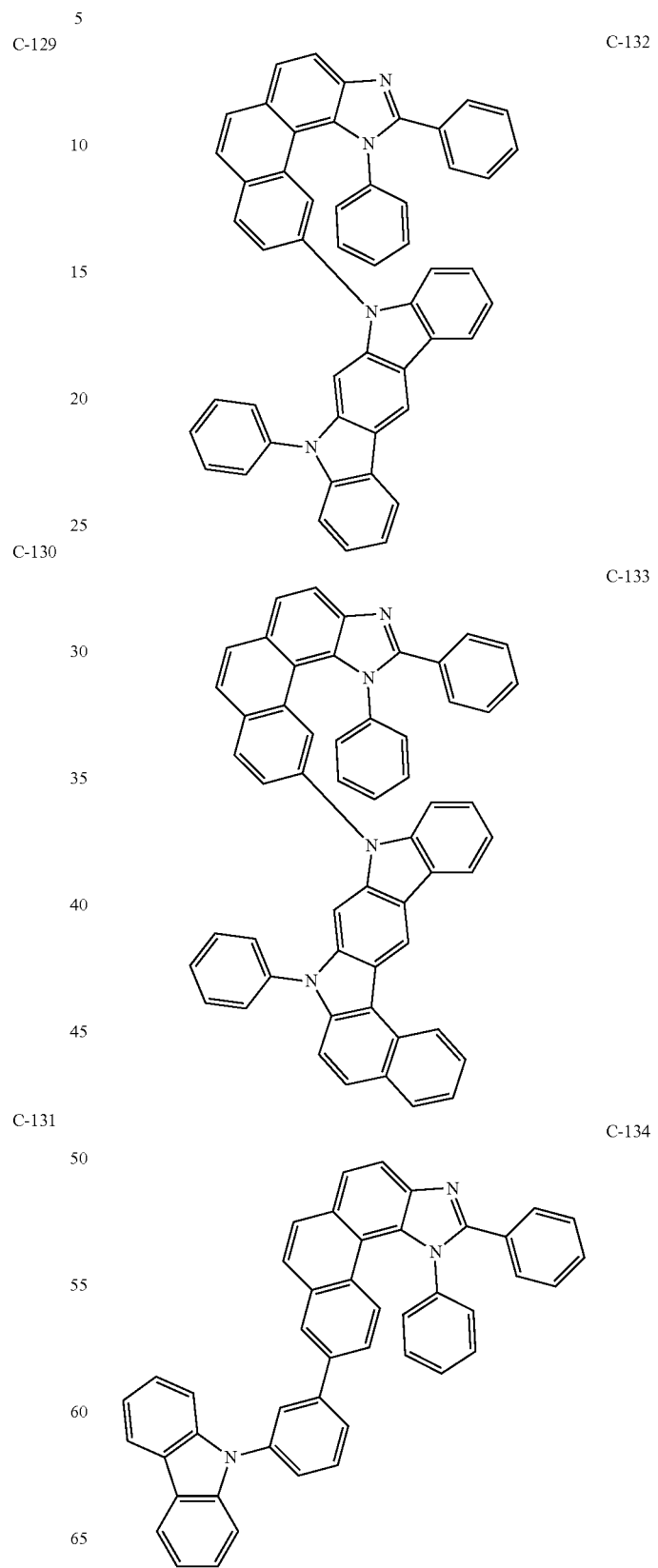

-continued
C-135
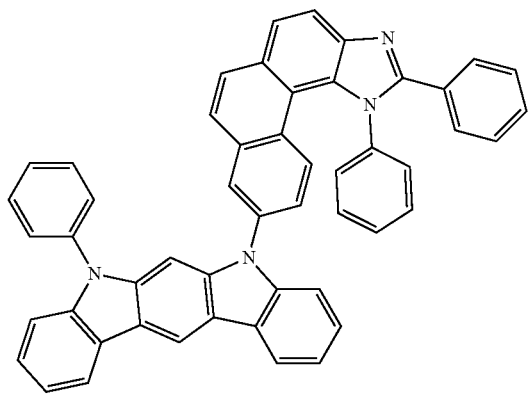
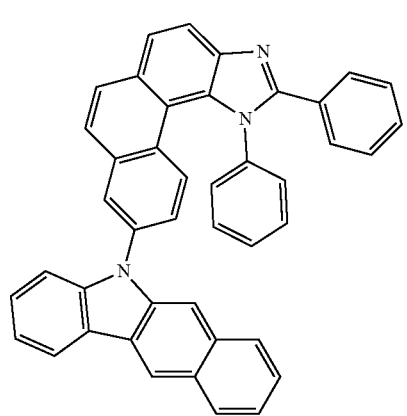
C-136
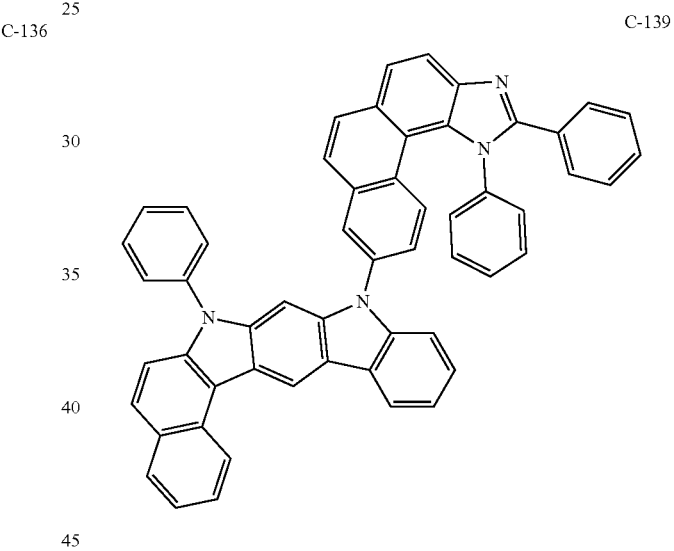
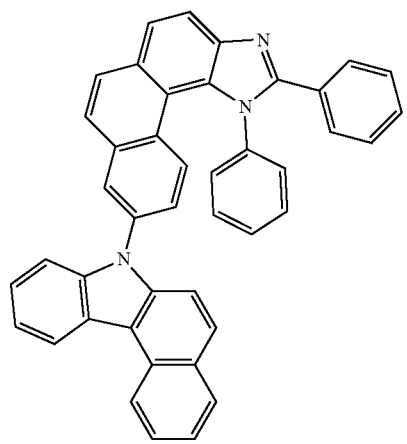
C-138
C-139
C-137
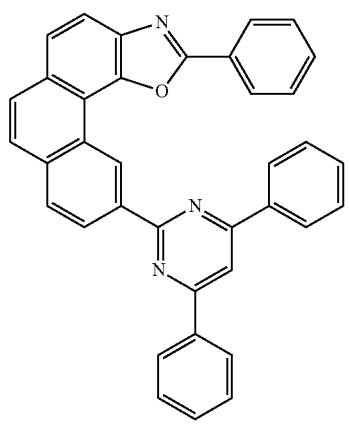
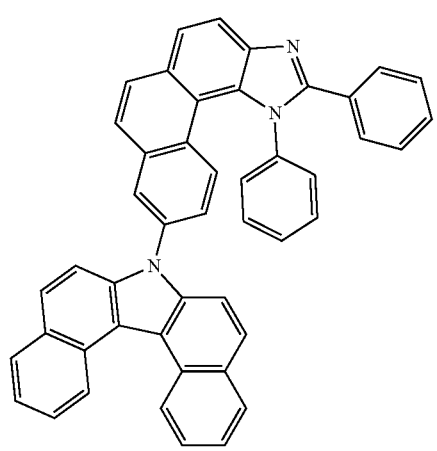
C-140

C-141

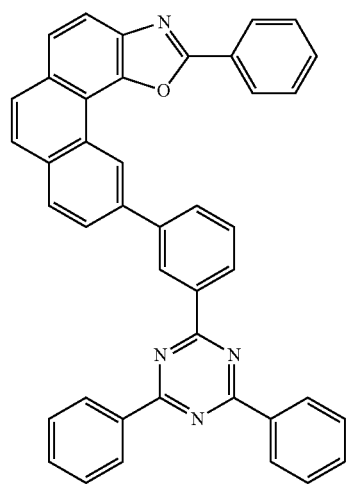

C-142

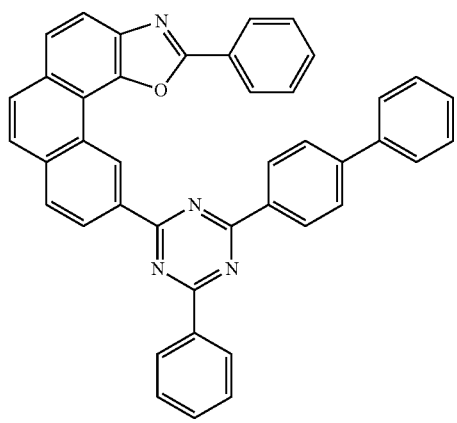

An organic electroluminescent device of the present disclosure may comprise a first electrode, a second electrode facing the first electrode, a light-emitting layer between the first electrode and the second electrode, and an electron transport zone between the light-emitting layer and the second electrode, wherein the electron transport zone may comprise the compound represented by formula 1 above. Furthermore, an organic electroluminescent device of the present disclosure may comprise a first electrode, a second electrode facing the first electrode, a light-emitting layer between the first electrode and the second electrode, and an electron transport zone and an electron buffering layer between the light-emitting layer and the second electrode, wherein the electron transport zone and/or the electron buffering layer comprises the compound represented by formula 1 above. An electron buffering layer may resolve the problem that when exposed to high-temperature during a panel production process, a current feature can be changed, which can cause a change in luminance. In this regard, for OLED having an electron buffering layer, the properties of a compound contained in such an electron buffering layer are critical so that the OLED has similar current characteristics to an OLED in which an electron buffering layer is not comprised and the OLED can have stability to the exposure to high-temperature.

The compounds represented by formula 1 above comprise phenanthrooxazole and phenanthrothiazole compounds which have high electronegativity and electron-rich groups as well as a fused structure between a phenanthrene and an oxazole or a phenanthrene and a thiazole providing a rigid characteristic. Thereby, the compounds represented by formula 1 above can provide easy intermolecular transition. Fuar-thermore, the build-up of such intermolecular stacking can provide easy horizontal molecular orientation, and then can provide rapid electron current characteristic. Accordingly, the compounds of the present disclosure can contribute greatly to provide low driving voltage and the improvement in efficiency and lifespan of an organic electroluminescent device. These device characteristics have large effects for stability to the exposure to a high-temperature during a panel production process and performance improvement.

According to one aspect of the present disclosure, an electron buffering material comprising the compound represented by formula 1 is provided. The electron buffering material indicates a material controlling an electron flow. Therefore, the electron buffering material may be, for example, a material which traps electrons, blocks electrons, or lowers an energy barrier between an electron transport zone and a light-emitting layer. Specifically, the electron buffering material may be for an organic electroluminescent device. In the organic electroluminescent device, the electron buffering material may be used for preparing an electron buffering layer, or may be incorporated to another area such as an electron transport zone or a light-emitting layer. The electron buffering layer may be formed between a light-emitting layer and an electron transport zone, or between an electron transport zone and a second electrode of an organic electroluminescent device. The electron buffering material may be a mixture or composition which may further comprise materials which are conventionally used for preparing an organic electroluminescent device.

Hereinafter, referring to FIG. 1, the structure of an organic electroluminescent device, and a method for preparing it will be described in detail.

FIG. 1 shows an organic electroluminescent device 100 comprising a substrate 101, a first electrode 110 formed on the substrate 101, an organic layer 120 formed on the first electrode 110, and a second electrode 130 formed on the organic layer 120 and facing the first electrode 110.

The organic layer 120 comprises a hole injection layer 122, a hole transport layer 123 formed on the hole injection layer 122, a light-emitting layer 125 formed on the hole transport layer 123, an electron buffering layer 126 formed on the light-emitting layer 125, and an electron transport zone 129 formed on the electron buffering layer 126; and the electron transport zone 129 comprises an electron transport layer 127 formed on the electron buffering layer 126, and an electron injection layer 128 formed on the electron transport layer 127. The hole injection layer 122, the hole transport layer 123, the light-emitting layer 125, the electron buffering layer 126, the electron transport layer 127, and the electron injection layer 128 may be a single layer, or may be composed of two or more layers.

The substrate 101 may be any conventional substrate for an organic electroluminescent device, such as a glass substrate, a plastic substrate, or a metal substrate.

The first electrode 110 may be an anode, and may be prepared with a high work-function material.

The hole injection layer 122 may be prepared with any hole injection material known in the art. The known material may include phthalocyanines such as copper ph-thalocyanine etc., MTDATA(4,4',4''-tris[(3-methylphenyl)phenylamino]triphenylamine), 2-TNATA(4,4',4''-tris[2-naphthyl(phenyl)amino]triphenylamine), $N^1,N^{1'}$-([1,1'- biphenyl]-4,4'-diyl)bis(N1-(naphthalen-1-yl)-N$^4$,N$^4$-diphenylbenzene-1,4-diamine), Pani/DBSA (polyaniline/dodecylbenzene sulphonic acid), PEDOT/PSS(poly(3,4-ethylenedioxythiophene)/poly(4-styrene sulfonate)), Pani/CSA (polyaniline/camphorsulfonic acid) or Pani/PSS (polyaniline)/poly(4-styrene sulfonate)) etc., but is not limited thereto.

Furthermore, the hole injection layer 122 may be formed of a compound represented by the following formula 200.

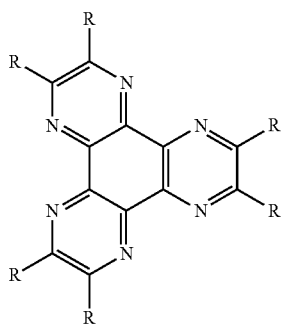

(200)

wherein R may be selected from the group consisting of a cyano(-CN), a nitro(-NO$_2$), a phenylsulfonyl(-SO$_2$(C$_6$H$_5$)), a cyano- or nitro-substituted (C2-C5) alkenyl, and a cyano- or nitro-substituted phenyl.

The compound of formula 200 has a characteristic to be crystallized. Thus, by using the compound, the hole injection layer 122 can have strength. The example of the compound of formula 200 includes HAT-CN (1,4,5,8,9,11-hexaazatriphenylene-hexacarbonitrile).

The hole transport layer 123 may be prepared with any hole transport material known in the art. The examples of the known material may include aromatic amine derivatives, particularly biphenyl diamine derivatives, such as TPD(N,N'-bis-(3-methylphenyl)-N,N'-diphenylbenzidine), N$^4$,N$^4$,N$^{4'}$,N$^{4'}$-tetra([1,1'-biphenyl]-4-yl)-[1,1'-biphenyl]-4,4'-diamine, and the compounds below, but are not limited thereto.

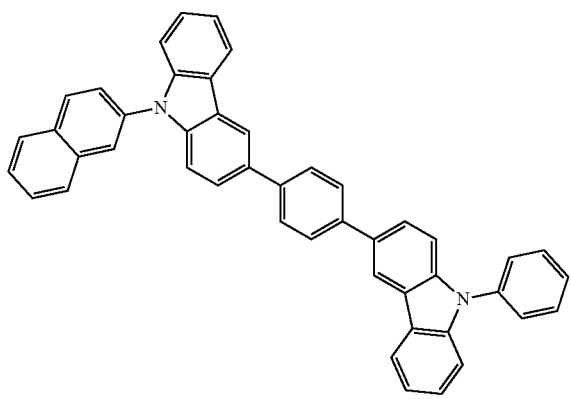

-continued

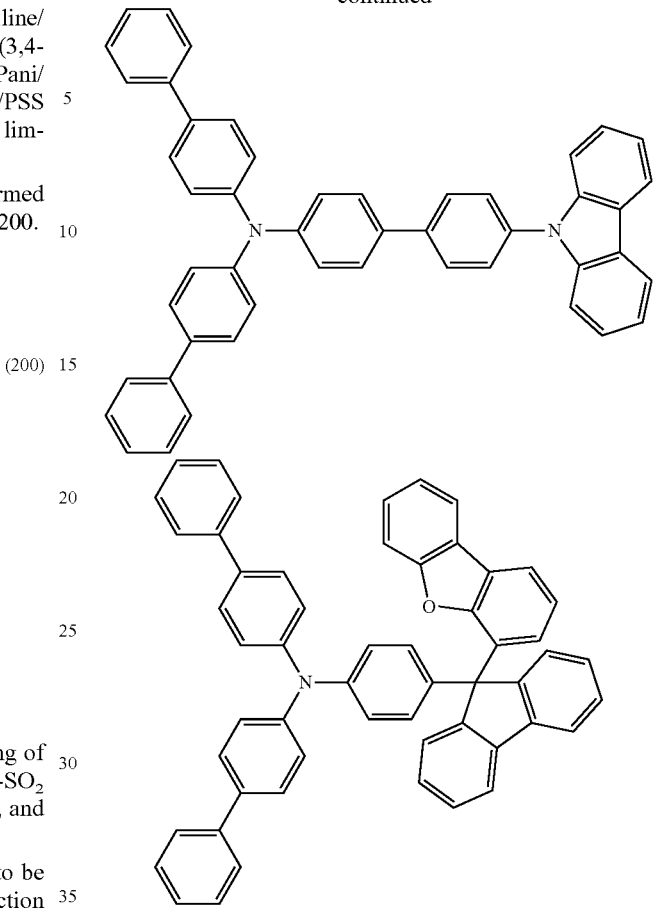

The light-emitting layer 125 may be prepared with a host compound and a dopant compound. The kinds of host compound and dopant compound to be used are not particularly limited, and may be selected from compounds known in the art. The examples of the host compound and the dopant compound will be described below. When the light-emitting layer 125 comprises a host and a dopant, the dopant can be doped in an amount of less than about 25 wt %, and preferably less than 17 wt %, based on the total amount of the dopant and host of the light-emitting layer. When the light emitting layer 125 is composed of two or more layers, each of the layers may be prepared to emit color different from one another. For example, the device may emit white light by preparing three light-emitting layers 125 which emit blue, red, and green colors, respectively. Furthermore, the device may include light-emitting layers which emit yellow or orange color, if necessary.

The electron buffering layer 126 may employ the compound of formula 1 of the present disclosure or other compounds for the electron buffer. The thickness of the electron buffering layer 126 is 1 nm or more, but is not particularly limited thereto. Specifically, the thickness of the electron buffering layer 126 may be in the range of from 2 nm to 200 nm. The electron buffering layer 126 may be formed on the light-emitting layer 125 by using known various methods such as vacuum deposition, wet film-forming methods, laser induced thermal imaging, etc. The electron buffering layer 126 may comprise a compound represented by the following formula 20.

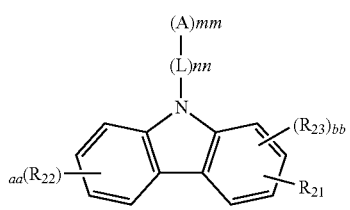

(20)

wherein

A represents a substituted or unsubstituted (5- to 30-membered)heteroaryl;

L represents a single bond, a substituted or unsubstituted (C6-C30)arylene, or a substituted or unsubstituted (5- to 30-membered)heteroarylene;

$R_{21}$ represents the following formula 20a or 20b:

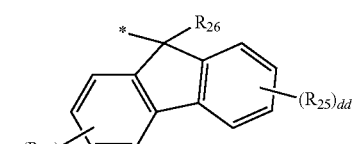

(20a)

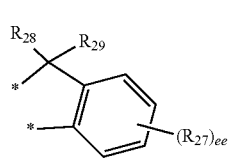

(20b)

$R_{22}$ represents hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, a substituted or unsubstituted (C1-C30)alkyl(C6-C30)arylamino, or the following formula 21; or may be fused with the carbazole backbone to form a substituted or unsubstituted benzocarbazole;

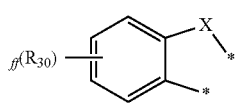

(21)

X represents O, S, $CR_{31}R_{32}$, $NR_{33}$ or $SiR_{33}R_{34}$;

$R_{23}$ represents hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$R_{24}$, $R_{25}$, $R_{27}$ and $R_{30}$, each independently, represent hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; or may be linked to an adjacent substituent(s) to form a substituted or unsubstituted (C3-C30), mono- or polycyclic, alicyclic or aromatic ring whose carbon atom(s) may be replaced with at least one heteroatom selected from nitrogen, oxygen, and sulfur;

$R_{26}$, $R_{28}$ and $R_{29}$, each independently, represent a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$R_{31}$ to $R_{34}$, each independently, represent a substituted or unsubstituted (C1-C30)alkyl, a substituted or unsubstituted (C6-C30)aryl, or a substituted or unsubstituted (5- to 30-membered)heteroaryl; or may be linked to an adjacent substituent(s) to form a substituted or unsubstituted (C3-C30), mono- or polycyclic, alicyclic or aromatic ring whose carbon atom(s) may be replaced with at least one heteroatom selected from nitrogen, oxygen, and sulfur;

aa, cc, dd, ee, and ff, each independently, represent an integer of 0 to 4; where aa, cc, dd, ee, or ff is an integer of 2 or more, each of $R_{22}$, $R_{24}$, $R_{25}$, $R_{27}$ or $R_{30}$ may be the same or different;

bb represents an integer of 0 to 3; where bb is an integer of 2 or more, each of $R_{23}$ may be the same or different;

nn represents an integer of 0 or 1; mm represents an integer of 1 or 2;

* represents a bonding site to the carbazole backbone; and the heteroaryl(ene) contains one or more hetero atoms selected from B, N, O, S, Si, and P.

In formula 20, A may represent preferably, a substituted or unsubstituted nitrogen-containing (5- to 30-membered)heteroaryl; and, more preferably, a substituted or unsubstituted nitrogen-containing (6- to 20-membered)heteroaryl. Specifically, A may represent a substituted or unsubstituted pyridyl, a substituted or unsubstituted pyrimidinyl, a substituted or unsubstituted triazinyl, a substituted or unsubstituted pyrazinyl, a substituted or unsubstituted quinolyl, a substituted or unsubstituted isoquinolyl, a substituted or unsubstituted quinolinyl, a substituted or unsubstituted quinazolinyl, a substituted or unsubstituted quinoxalinyl, or a substituted or unsubstituted naphthyridinyl; and more specifically, a substituted or unsubstituted pyridyl, a substituted or unsubstituted pyrimidinyl, a substituted or unsubstituted triazinyl, or a substituted or unsubstituted pyrazinyl.

In formula 20, L may represent preferably, a single bond or a substituted or unsubstituted (C6-C20)arylene; and more preferably, a single bond or an unsubstituted (C6-C18)

arylene. Specifically, L may represent a single bond, a substituted or unsubstituted phenyl, a substituted or unsubstituted naphthyl, a substituted or unsubstituted biphenyl, a substituted or unsubstituted terphenyl, a substituted or unsubstituted phenylnaphthyl, or a substituted or unsubstituted naphthylphenyl.

In formula 20, $R_{22}$ may represent preferably, hydrogen, deuterium, a substituted or unsubstituted (C6-C20)aryl, a substituted or unsubstituted (5- to 20-membered)heteroaryl, a substituted or unsubstituted mono- or di-(C6-C20)arylamino, or formula 21, or may be fused with the carbazole backbone to form a substituted or unsubstituted benzocarbazole. Specifically, $R_{22}$ may represent hydrogen, or a substituted or unsubstituted (C6-C20)aryl. More specifically, $R_{22}$ may represent hydrogen, a substituted or unsubstituted phenyl, a substituted or unsubstituted dibenzothiophenyl, a substituted or unsubstituted dibenzofuranyl, a substituted or unsubstituted carbazolyl, a substituted or unsubstituted diphenylamino, a substituted or unsubstituted fluorenyl, or formula 21, or may be fused with the carbazole backbone to form a substituted or unsubstituted benzocarbazole.

In formula 21, X may represent preferably, O, S, $CR_{31}R_{32}$, or $NR_{33}$. $R_{30}$ may represent preferably, hydrogen or a (C1-C20)alkyl. $R_{31}$ to $R_{34}$, each independently, may represent preferably, hydrogen, a substituted or unsubstituted (C1-C10)alkyl, a substituted or unsubstituted (C6-C20)aryl, or a substituted or unsubstituted (5- to 20-membered)heteroaryl; and specifically, hydrogen, a (C1-C6)alkyl, phenyl, naphthyl, or biphenyl.

In formula 20, $R_{23}$, $R_{24}$, $R_{25}$, and $R_{27}$, each independently, may represent preferably, hydrogen or a substituted or unsubstituted (C1-C20)alkyl. Specifically, $R_{23}$, $R_{24}$, $R_{25}$, and $R_{27}$ may represent hydrogen.

In formula 20, $R_{26}$, $R_{28}$, and $R_{29}$, each independently, may represent preferably, a substituted or unsubstituted (C1-C20)alkyl, a substituted or unsubstituted (C6-C20)aryl, or a substituted or unsubstituted (6- to 20-membered)heteroaryl; and more preferably, a substituted or unsubstituted (C6-C20)aryl. Specifically, $R_{26}$, $R_{28}$, and $R_{29}$, each independently, may represent a substituted or unsubstituted phenyl, a substituted or unsubstituted biphenyl, or a substituted or unsubstituted naphthyl.

Specifically, the compound of formula 20 includes the following, but is not limited thereto.

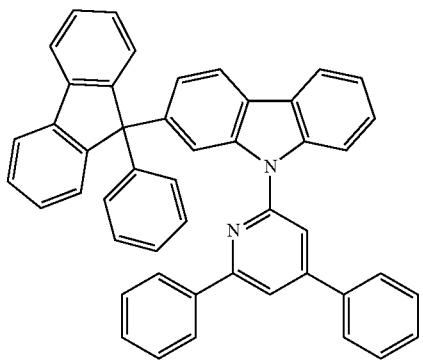

B-1

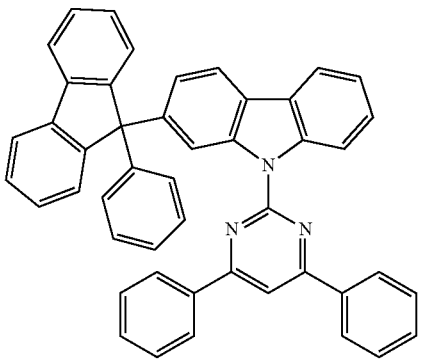

B-2

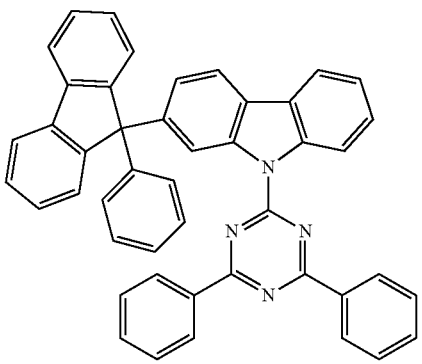

B-3

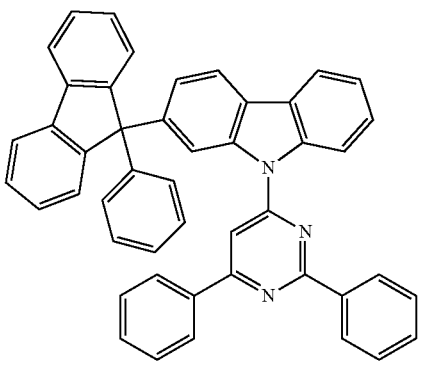

B-4

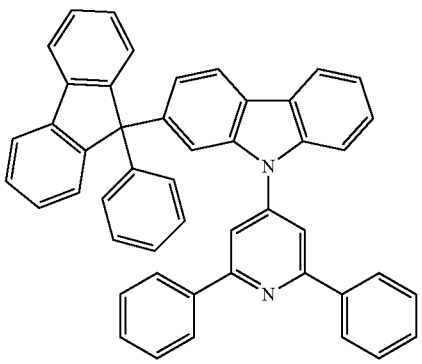

B-5

B-6
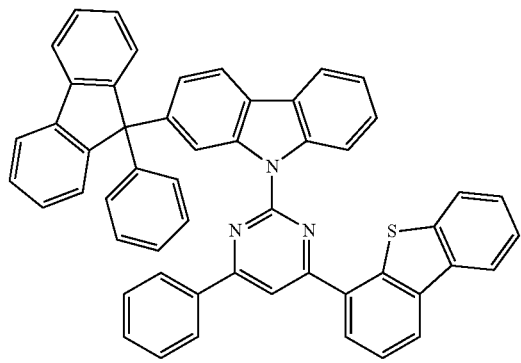
B-7
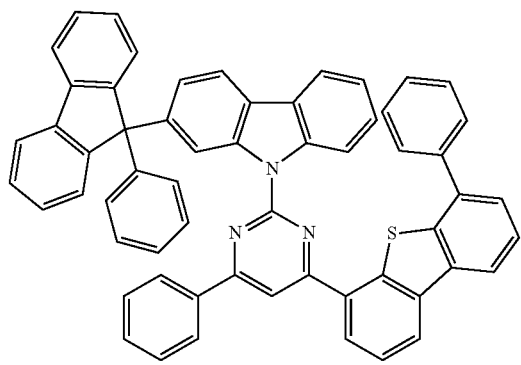
B-8
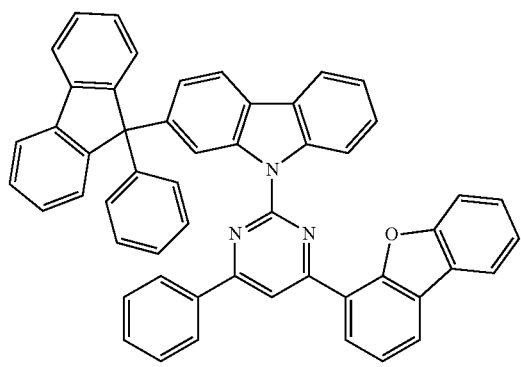
B-9
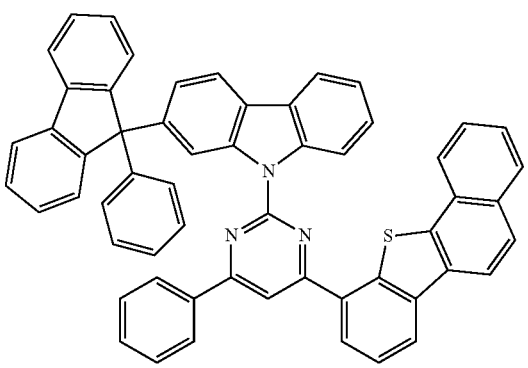
B-10
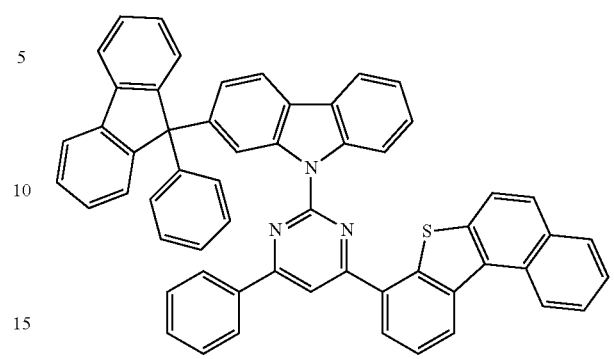
B-11
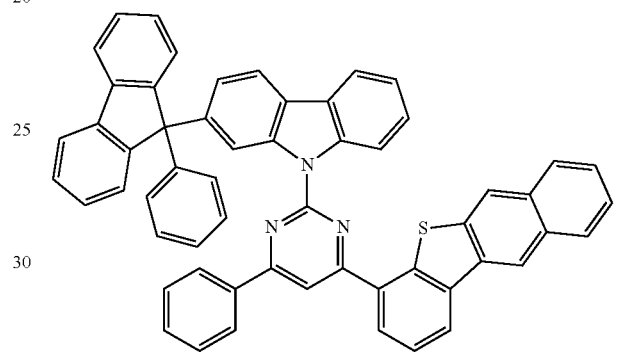
B-12

B-13
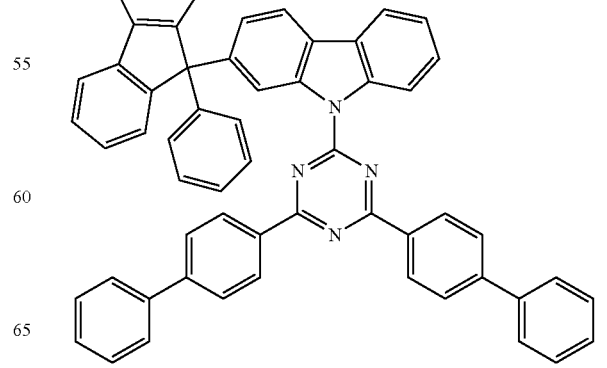

B-14
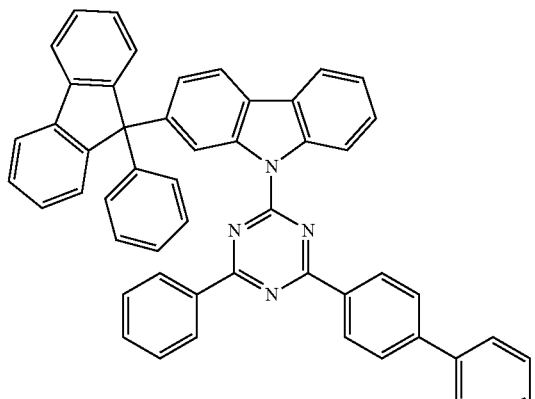
B-15
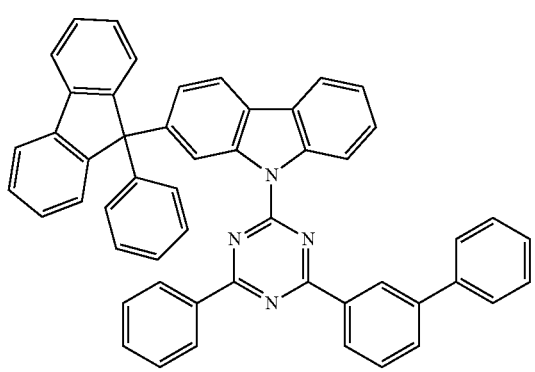
B-16
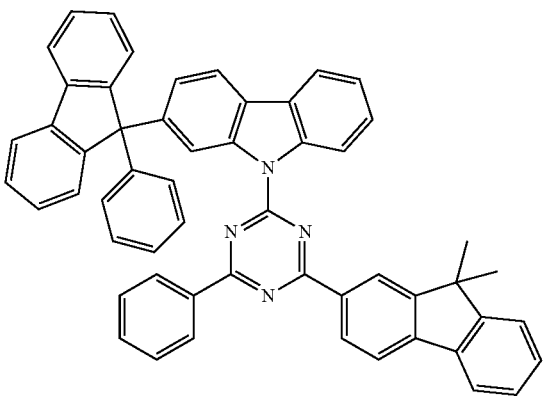
B-17
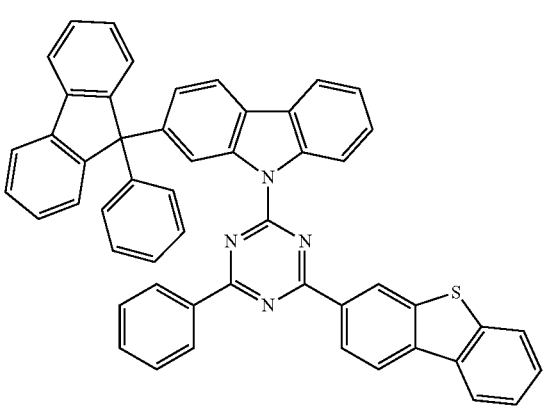
B-18
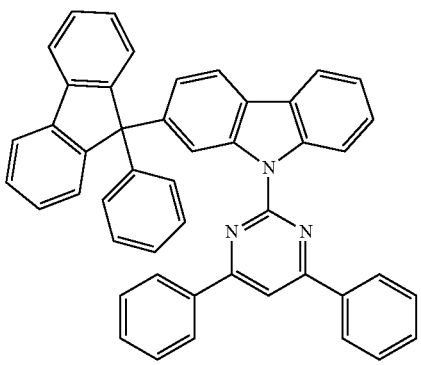
B-19
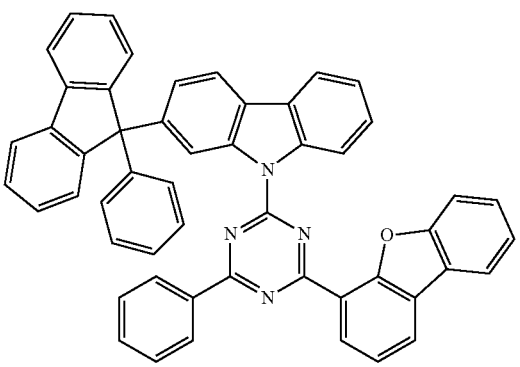
B-20
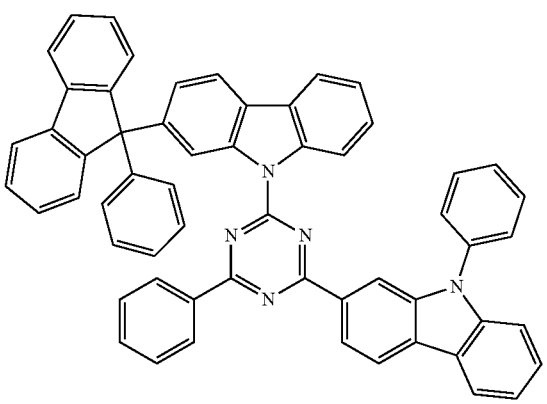
B-21
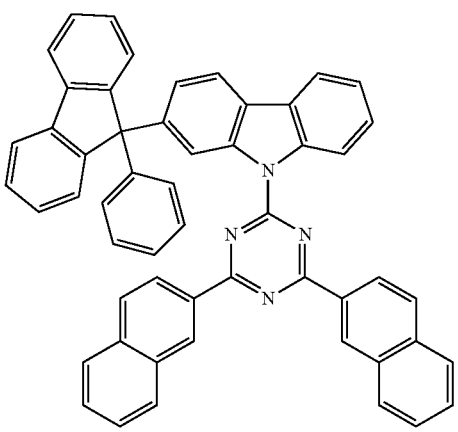

B-22
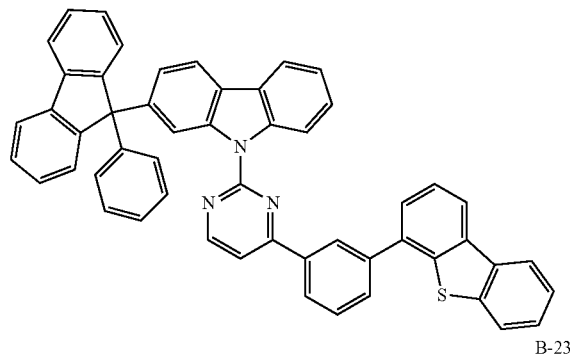
B-23
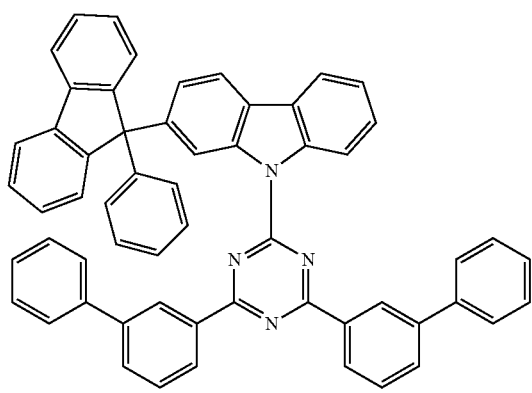
B-24
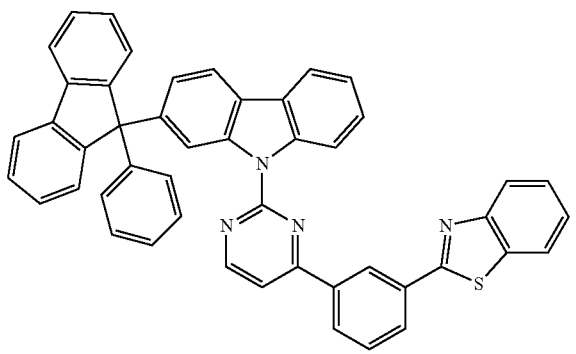
B-25
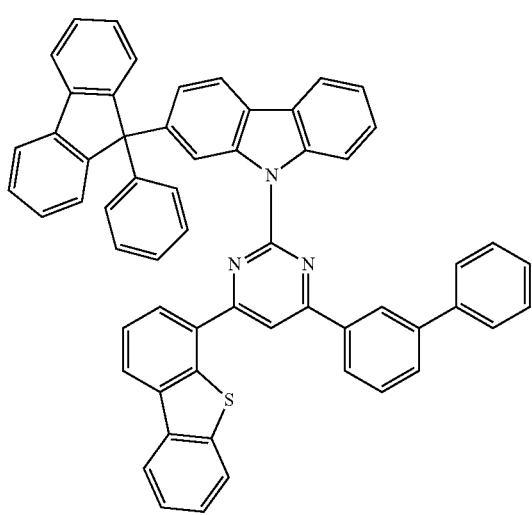
B-26
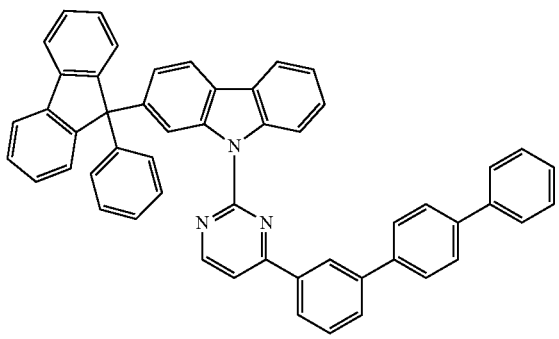
B-27
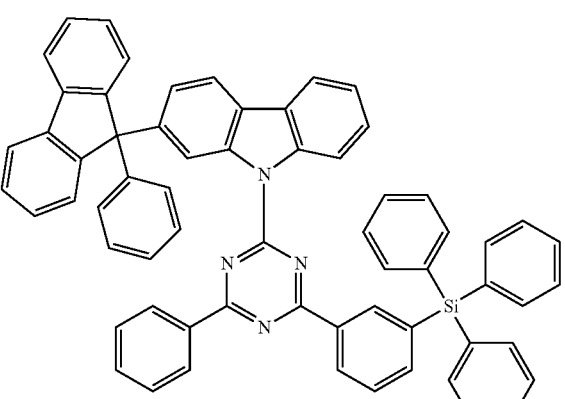
B-28
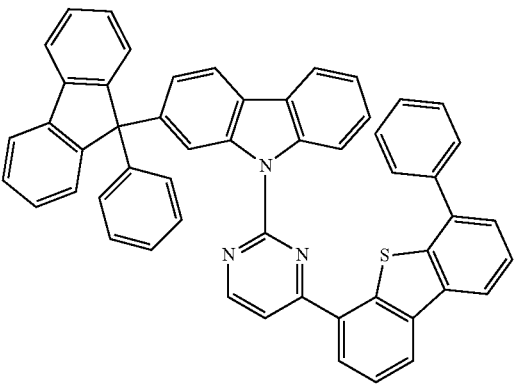
B-29
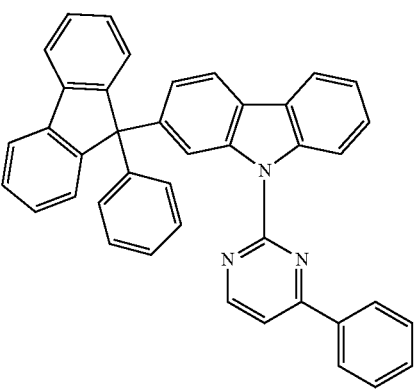

-continued
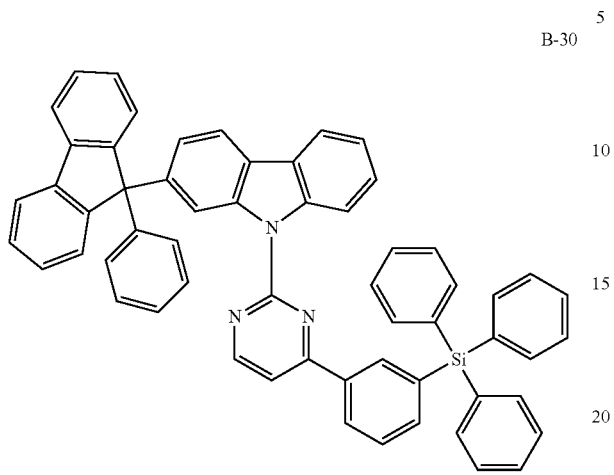
B-30
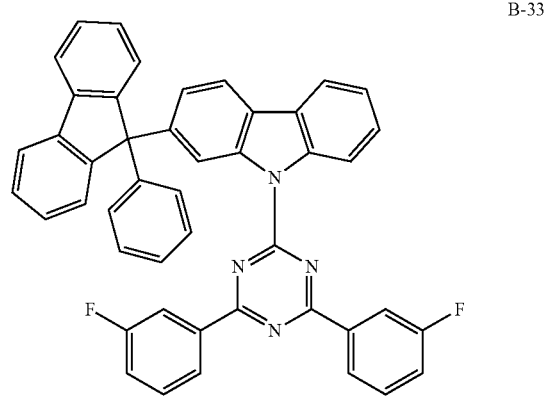
B-33
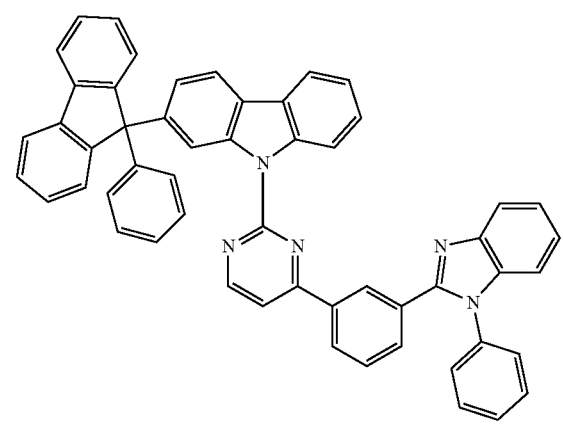
B-31
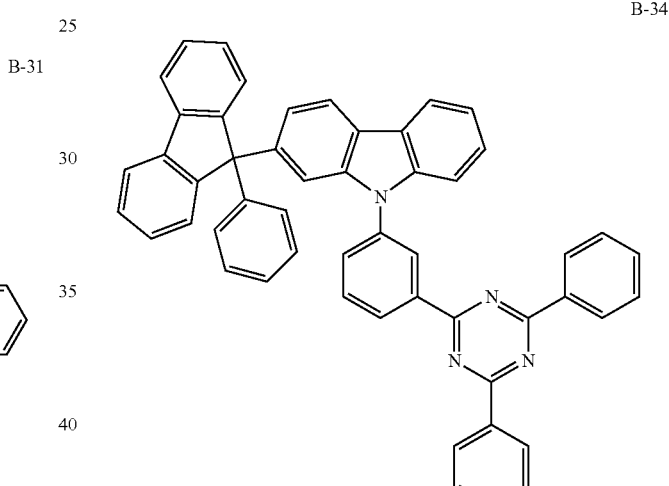
B-34
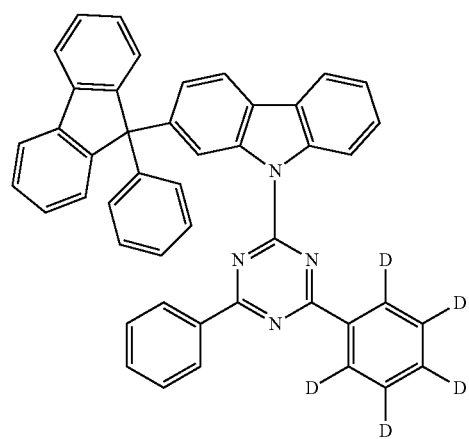
B-32
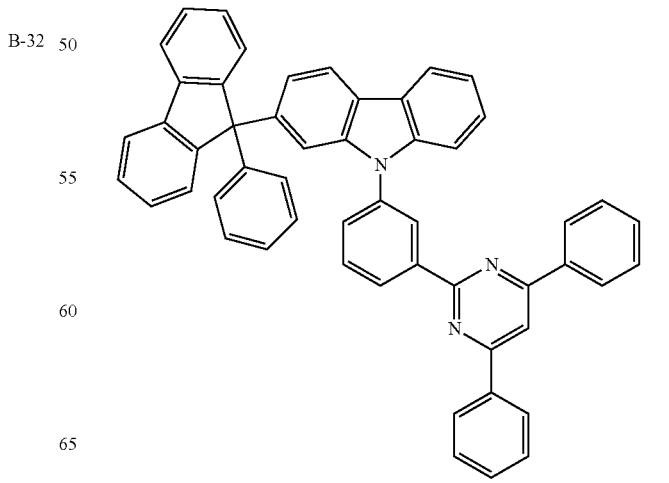
B-35

B-36
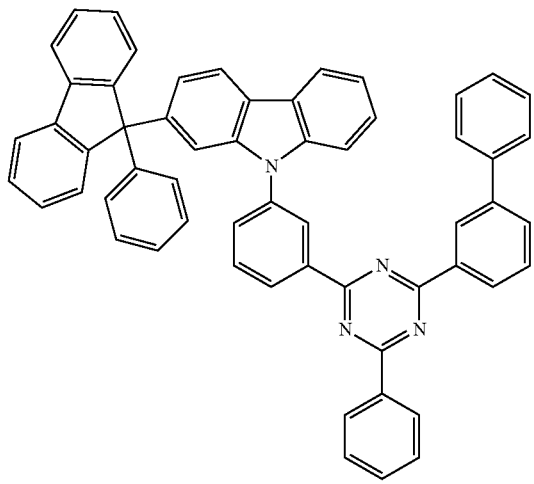
B-40
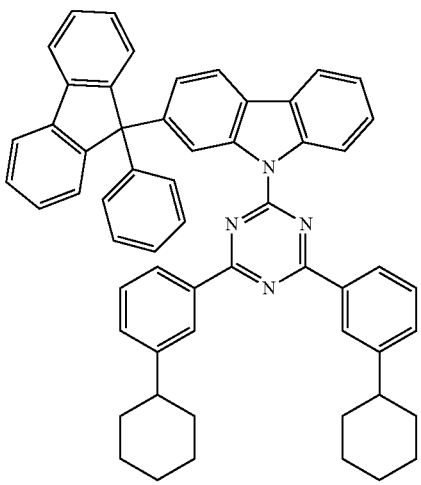
B-37
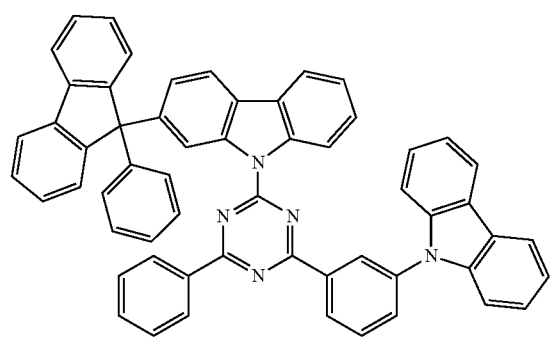
B-41
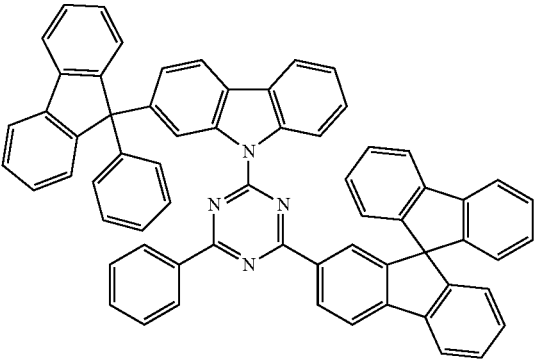
B-38
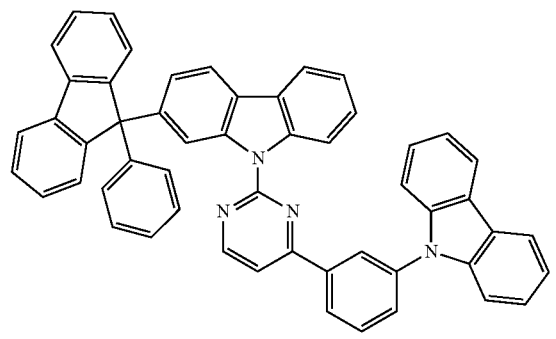
B-39
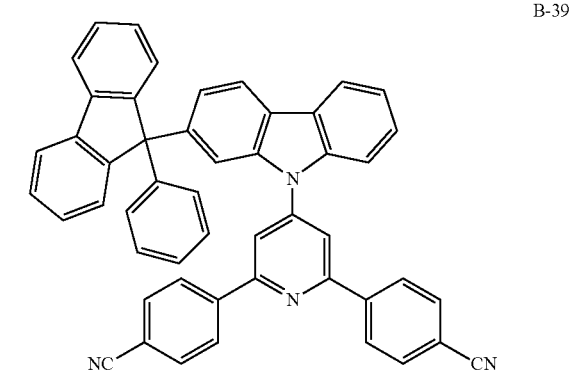
B-42
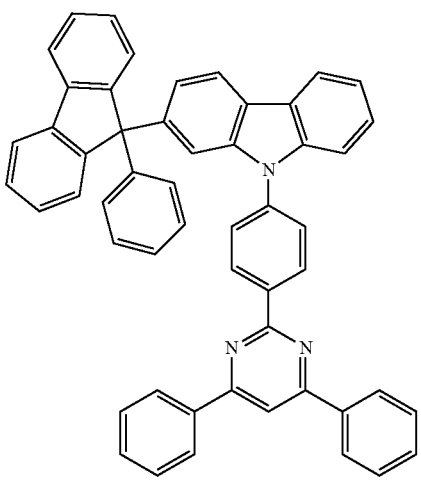

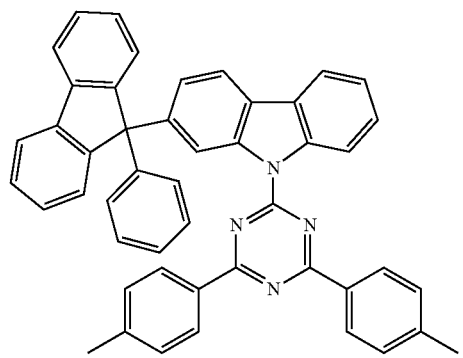
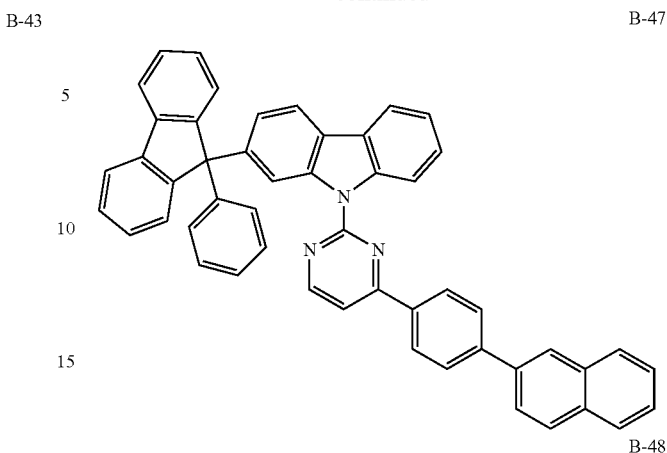

B-51
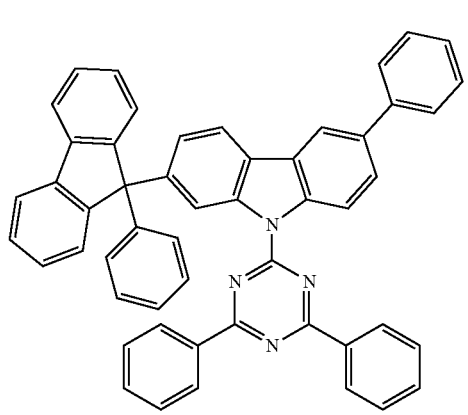
B-54
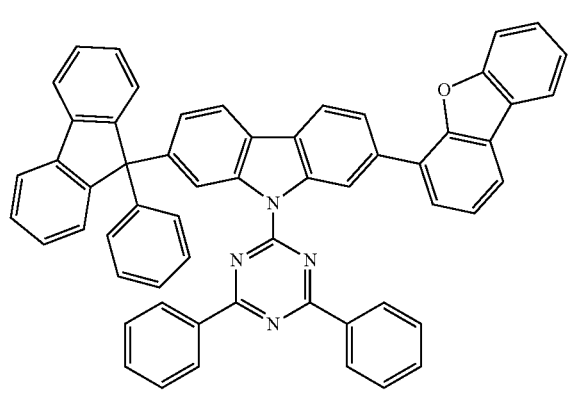
B-52
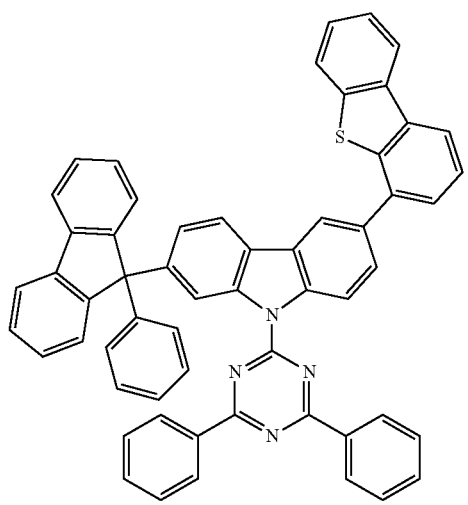
B-55
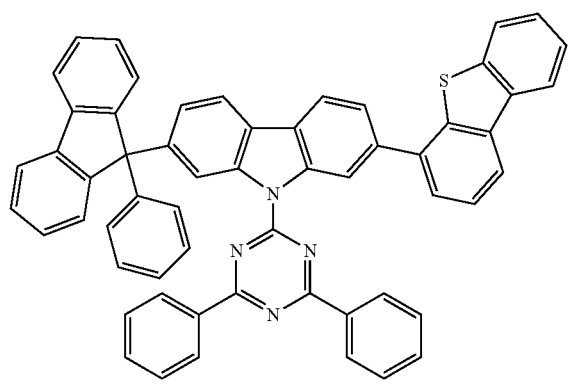
B-53
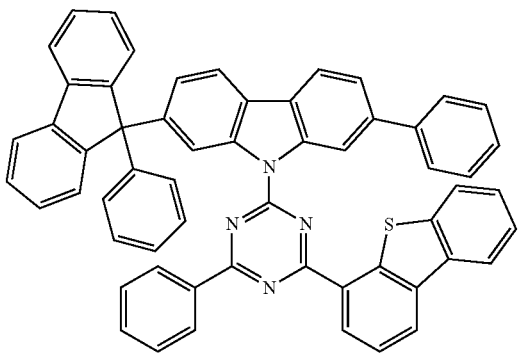
B-56
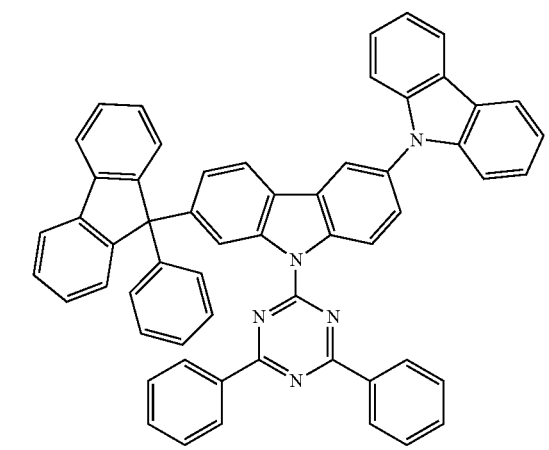

-continued
B-57
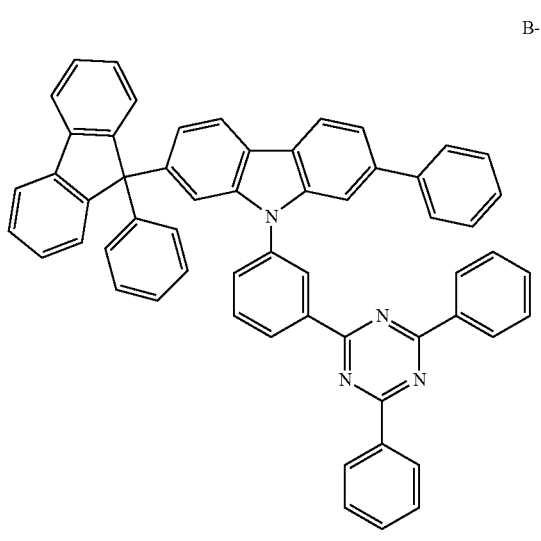
B-60
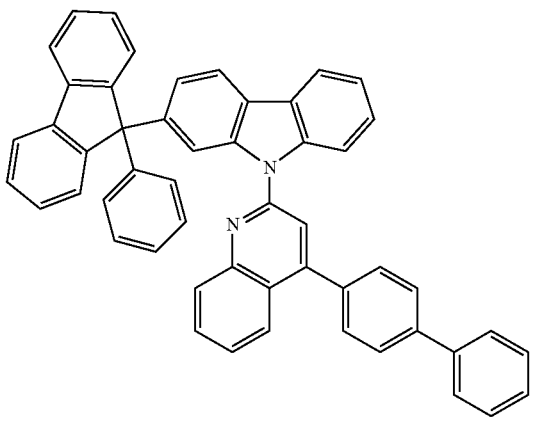
B-58
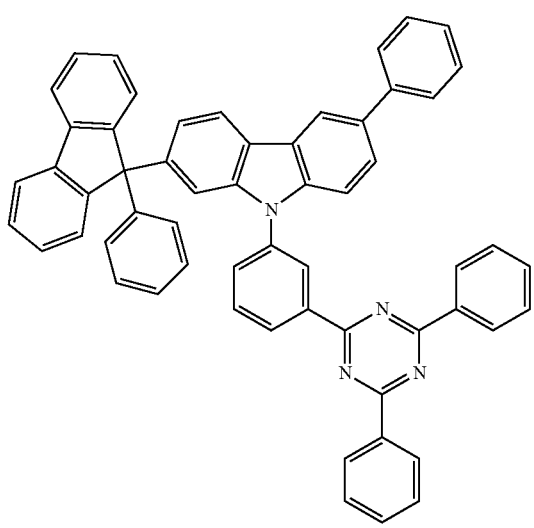
B-61
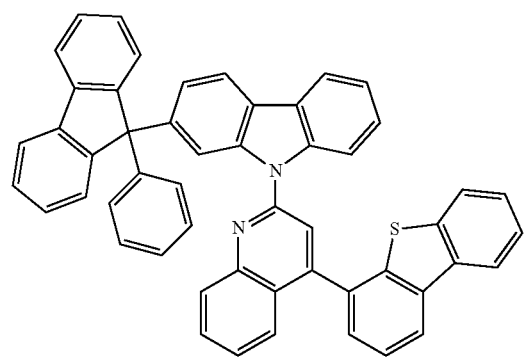
B-59
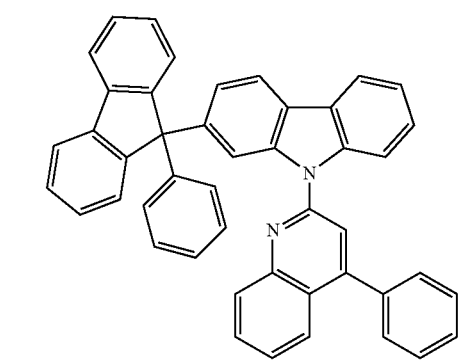
B-62
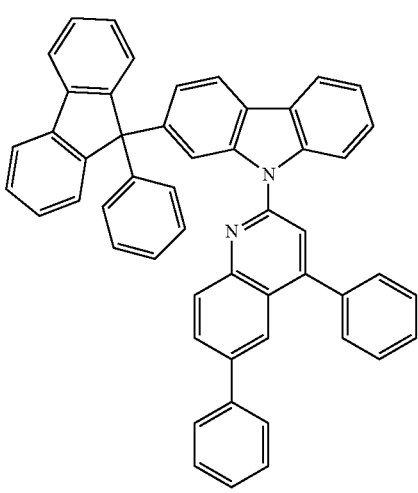

B-63
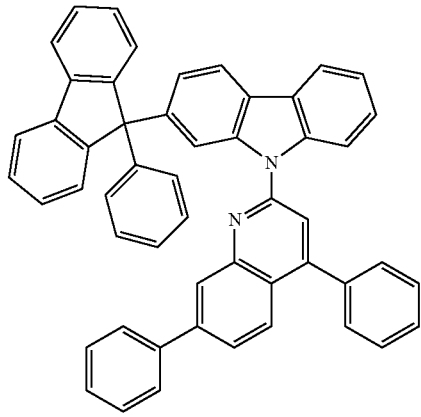
B-64
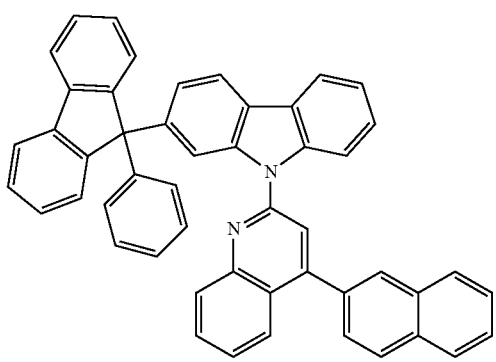
B-65
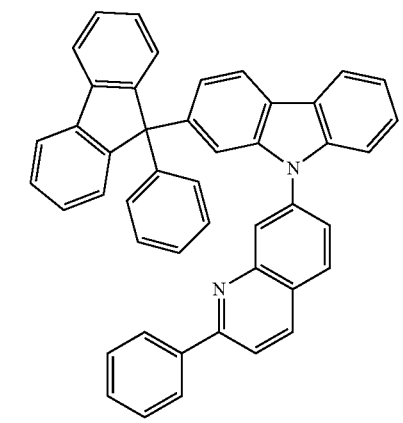
B-66
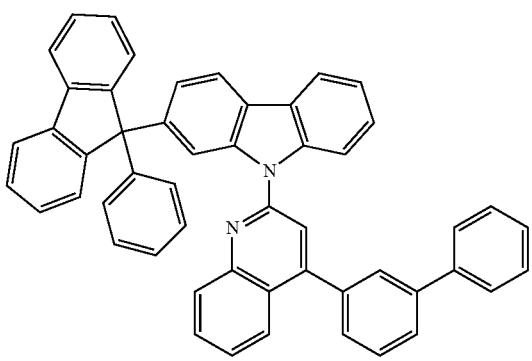
B-67
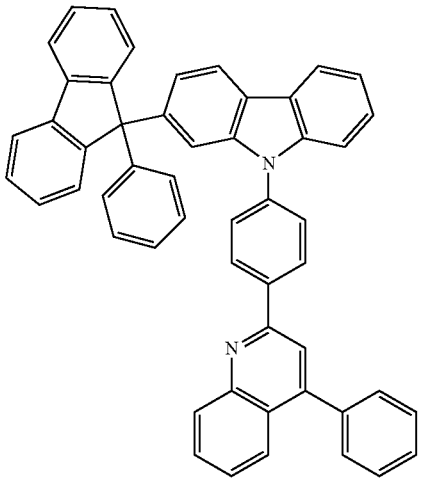
B-68
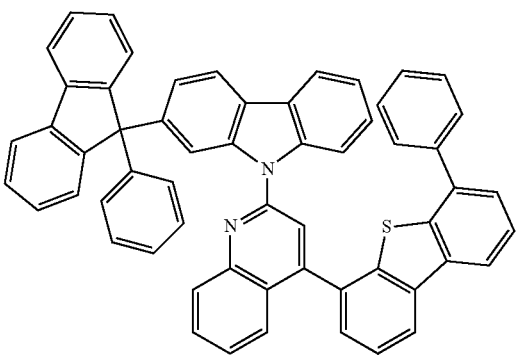
B-69
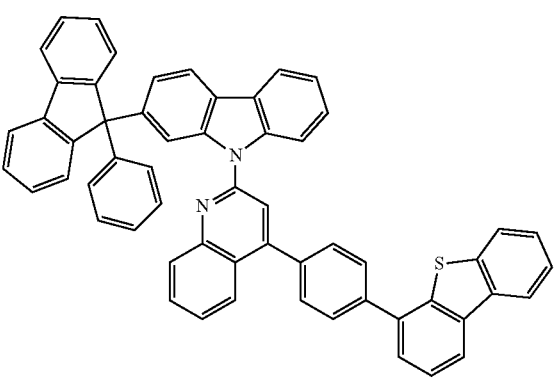
B-70
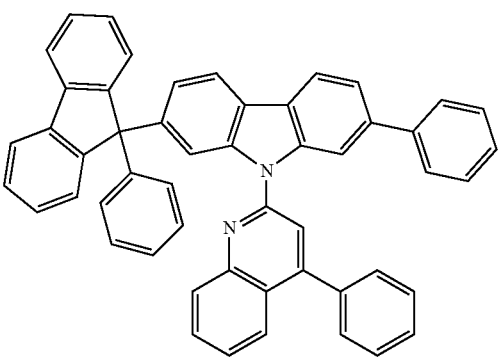

B-71
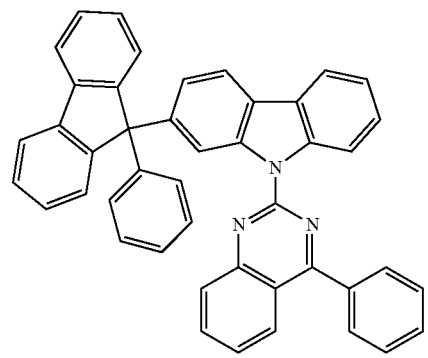
B-72
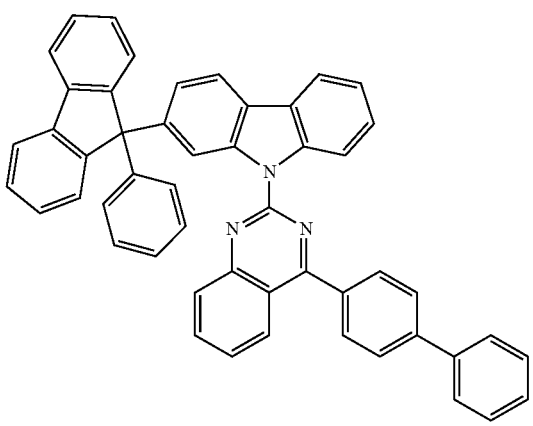
B-73
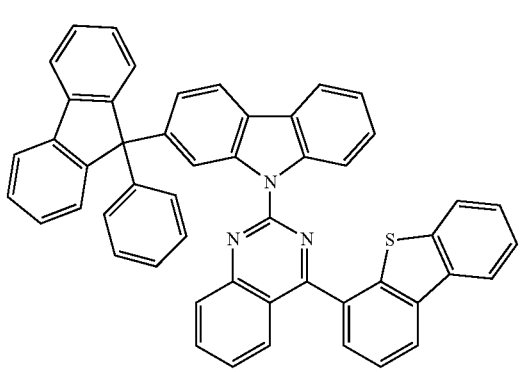
B-74
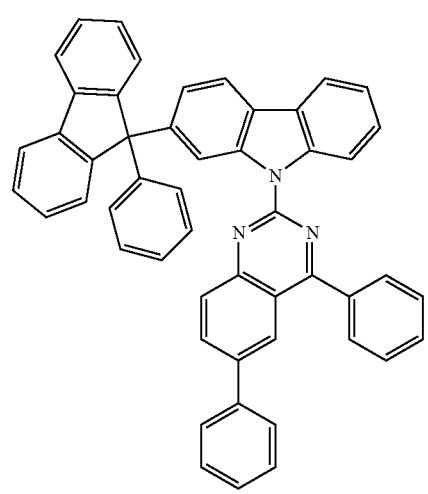
B-75
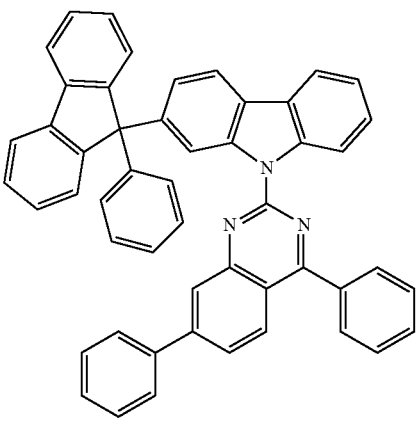
B-76
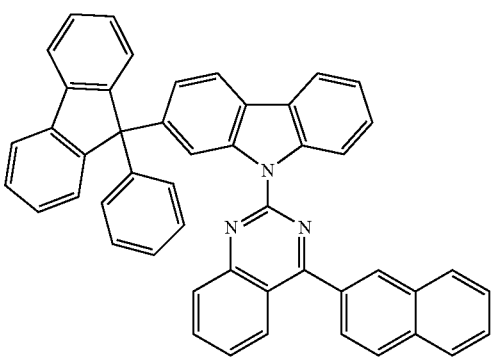
B-77
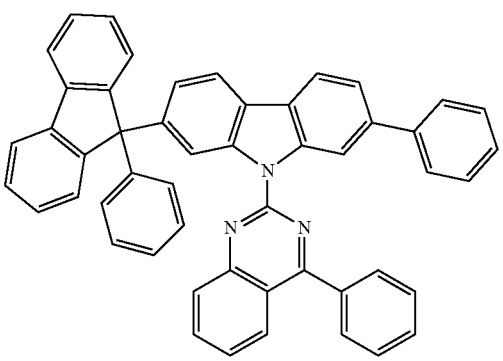
B-78
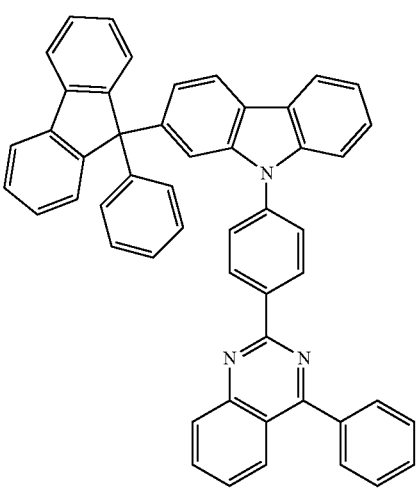

B-79
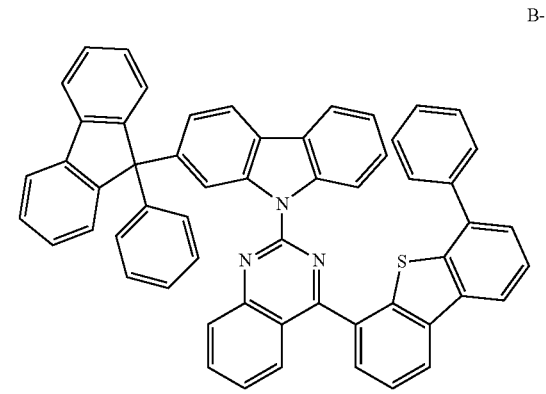
B-80
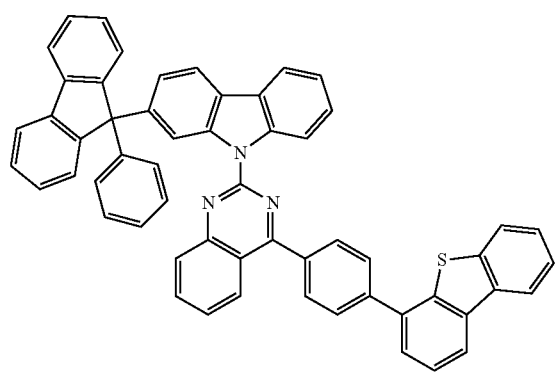
B-81
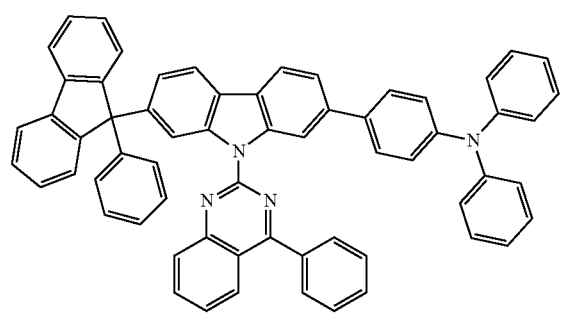
B-82
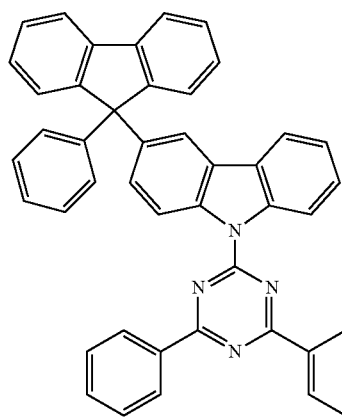
B-83
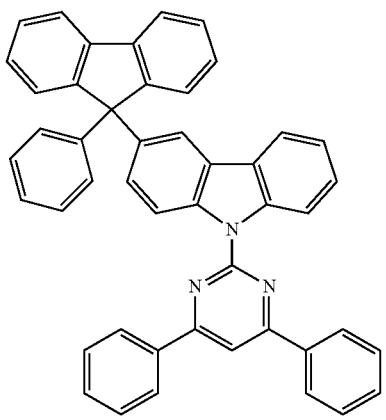
B-84
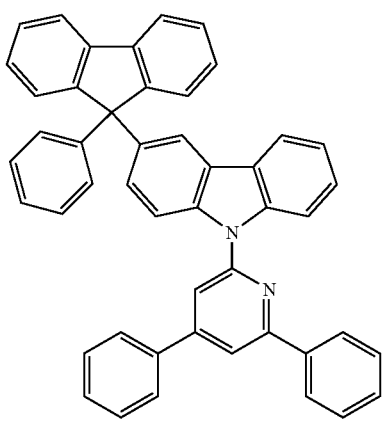
B-85
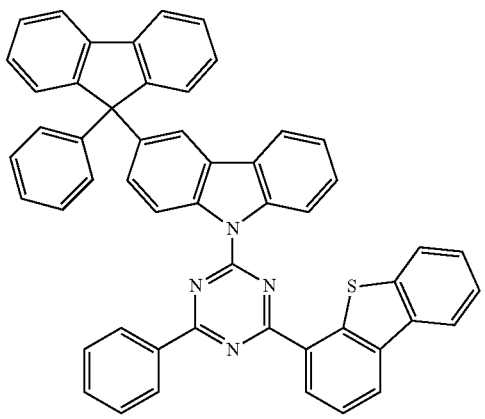

B-86
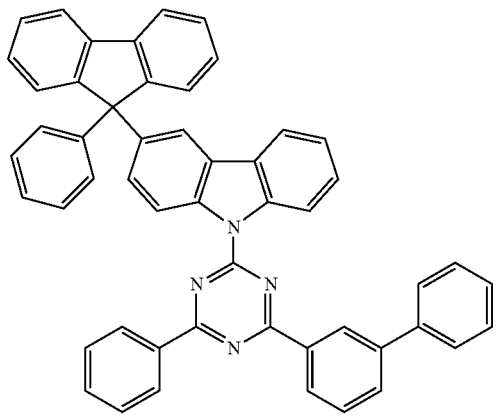
B-87
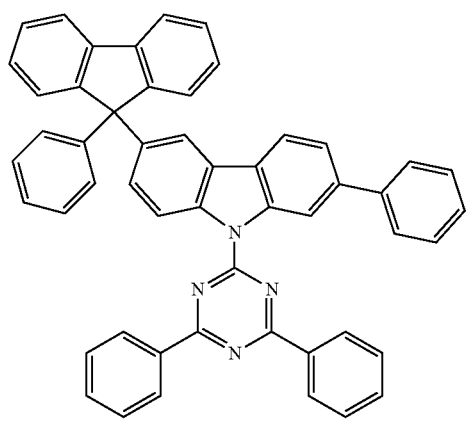
B-88
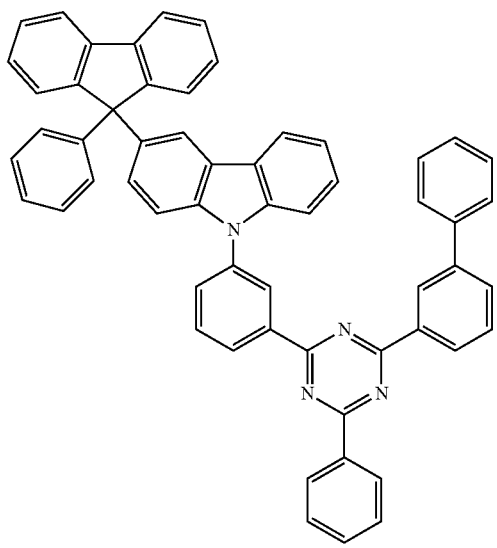
B-89
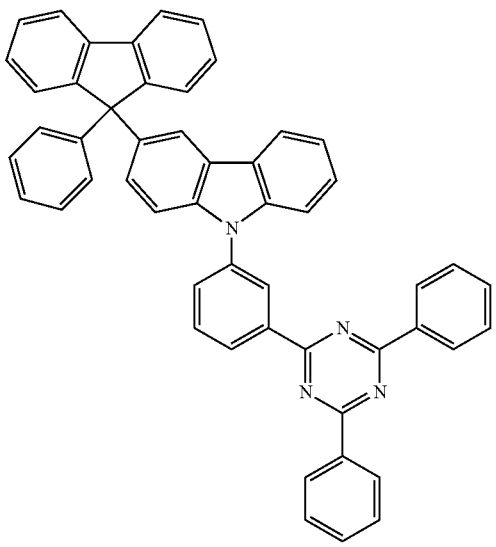
B-90
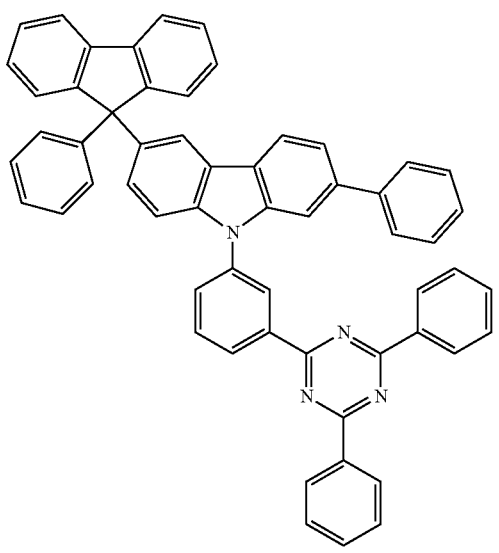
B-91
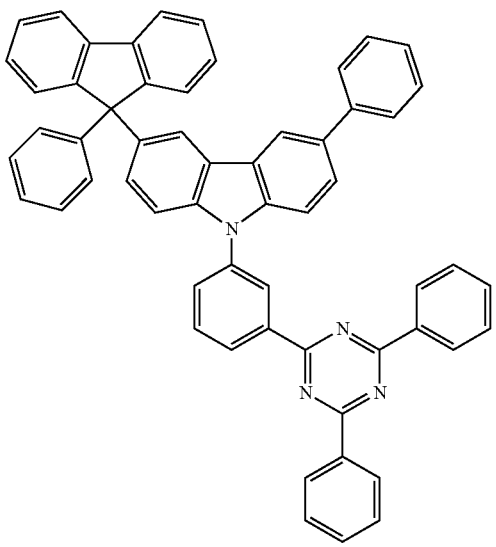

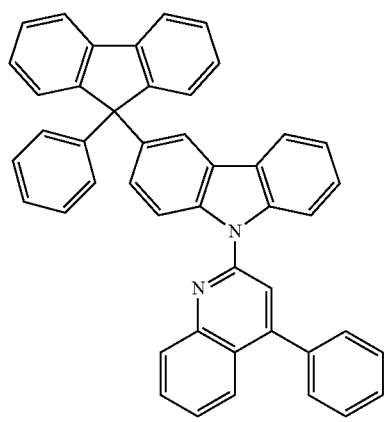
B-92
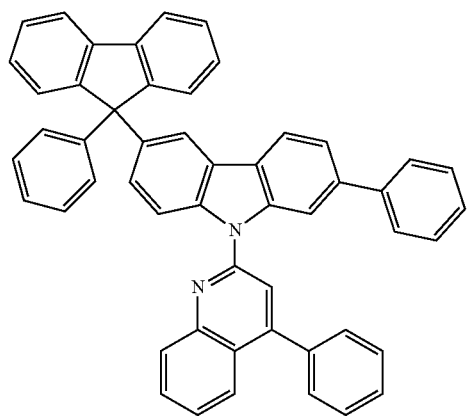
B-95
B-93
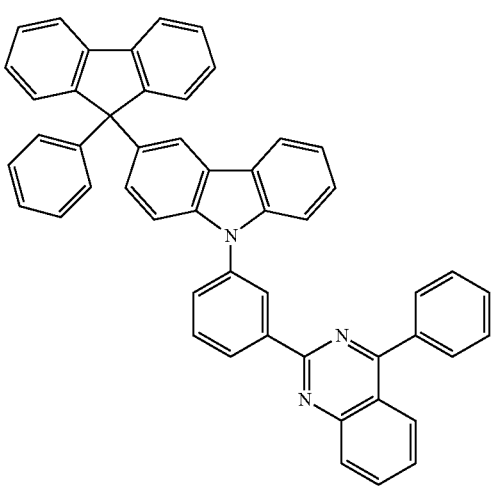
B-96
B-94
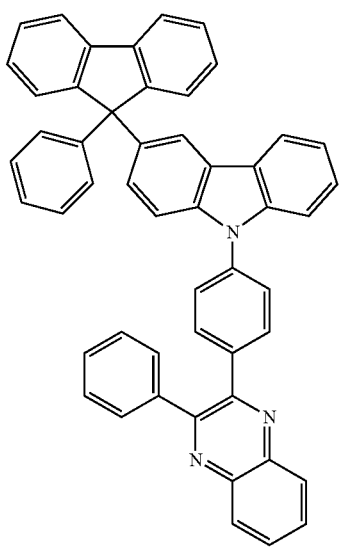
B-97

B-98
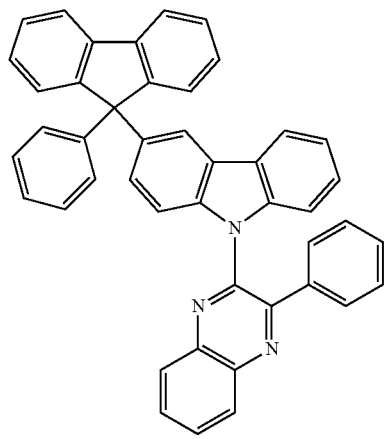
B-99
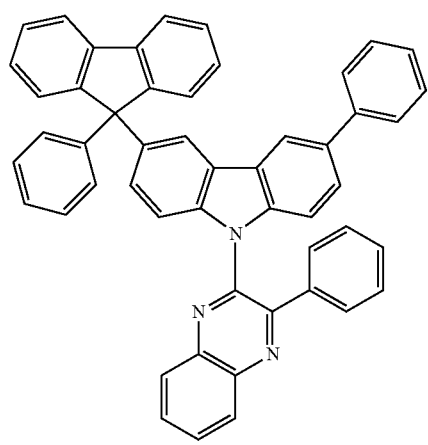
B-100
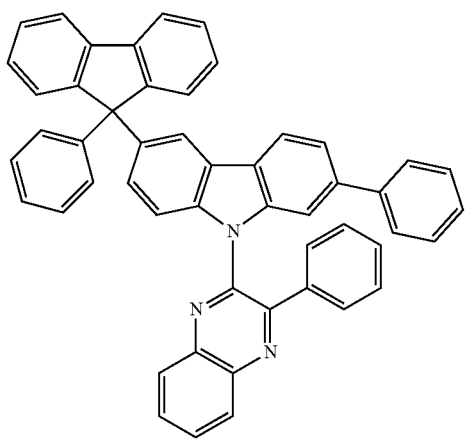
B-101
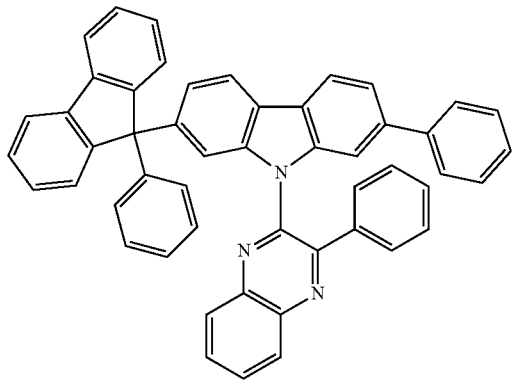
B-102
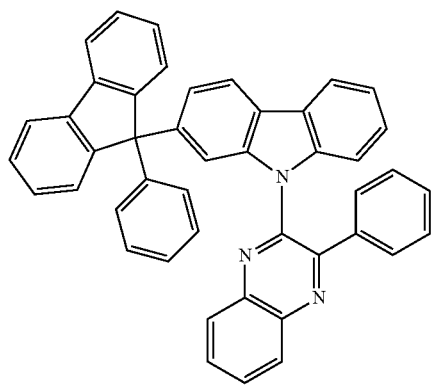
B-103
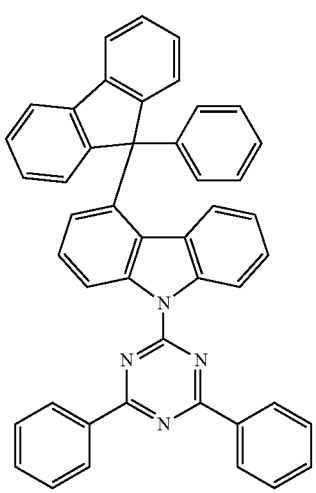

-continued
B-104
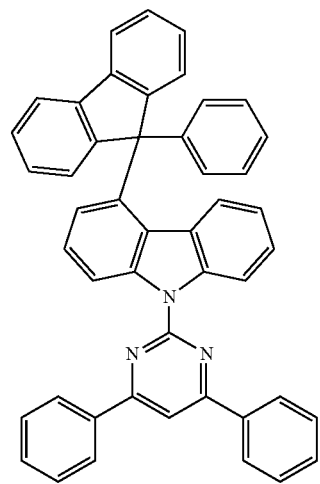
B-105
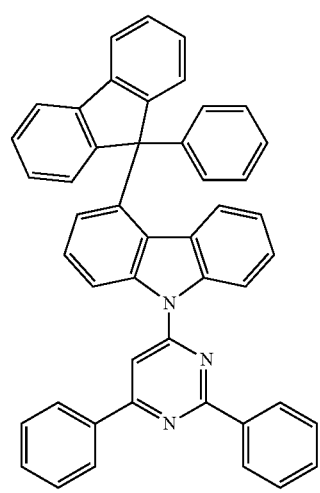
B-106
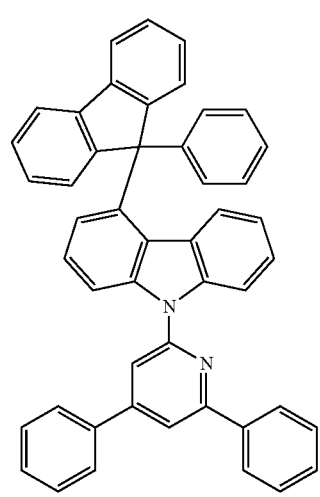
-continued
B-107
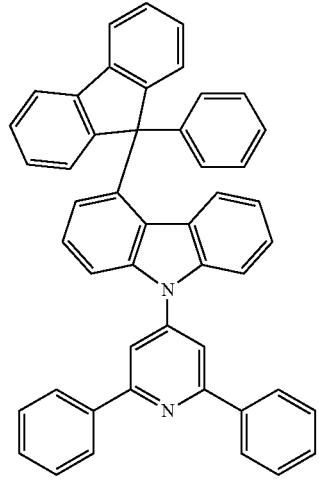
B-108
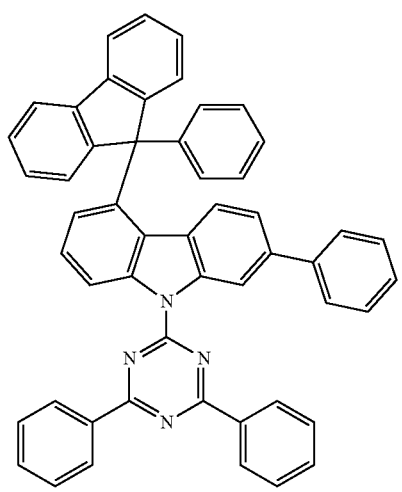
B-109
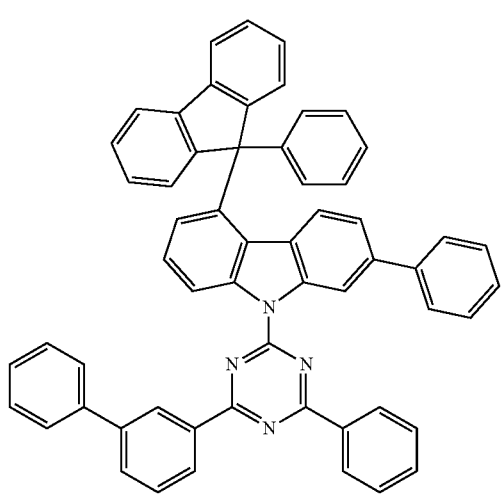

B-110
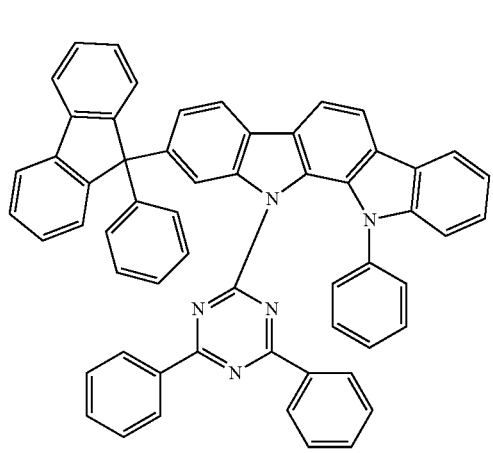
B-113
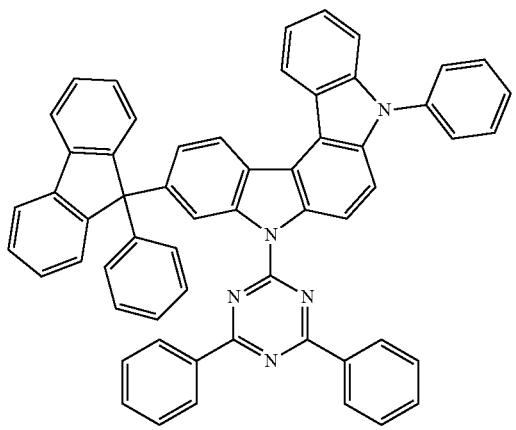
B-111
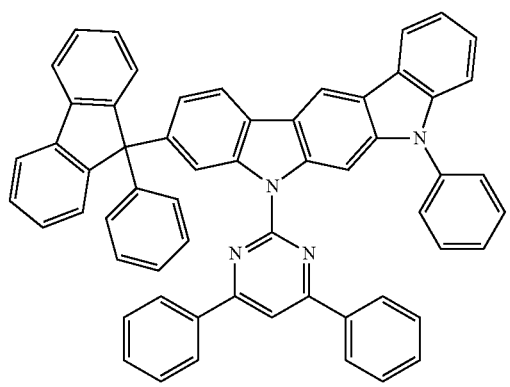
B-114
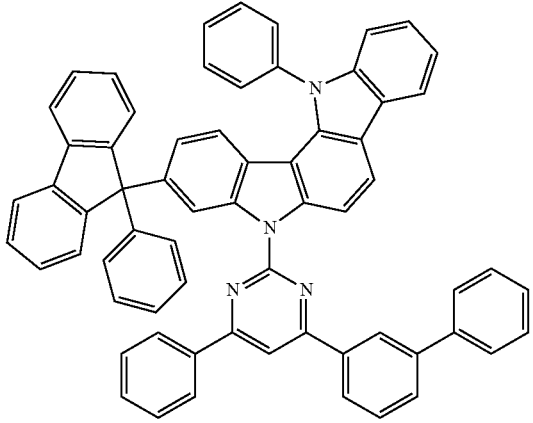
B-112
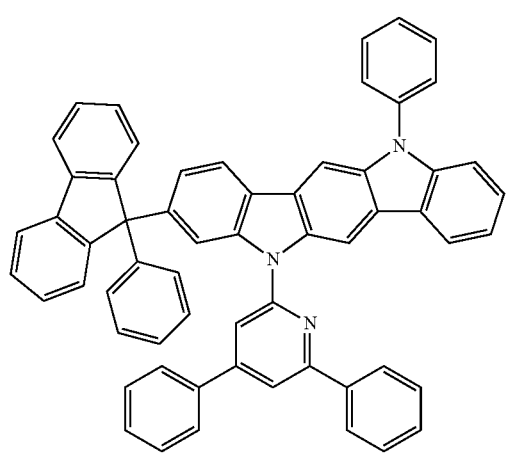
B-115
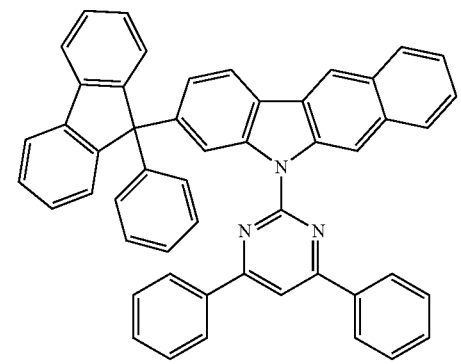

B-116
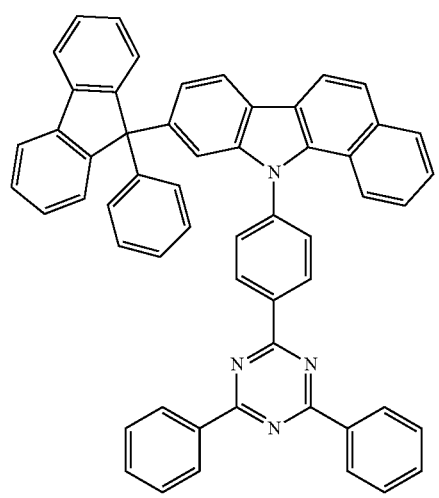
B-117
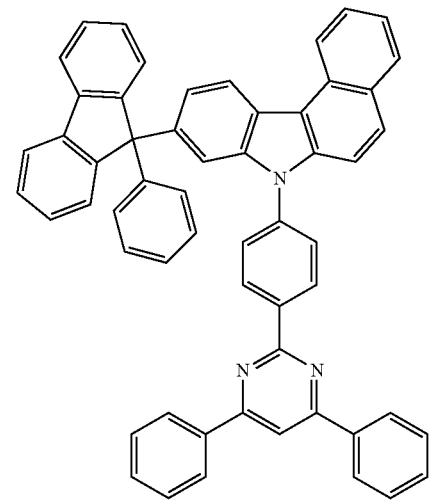
B-118
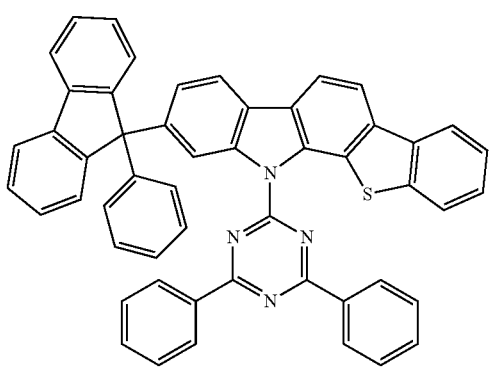
B-119
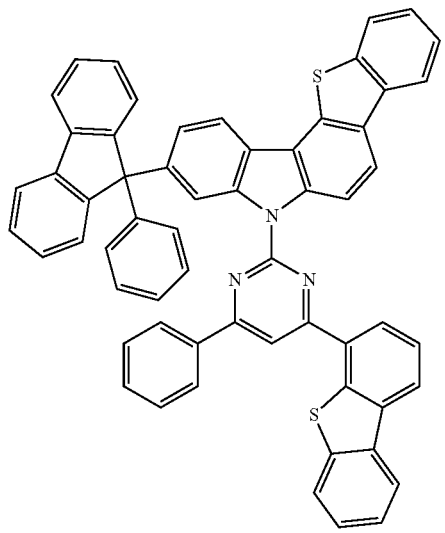
B-120
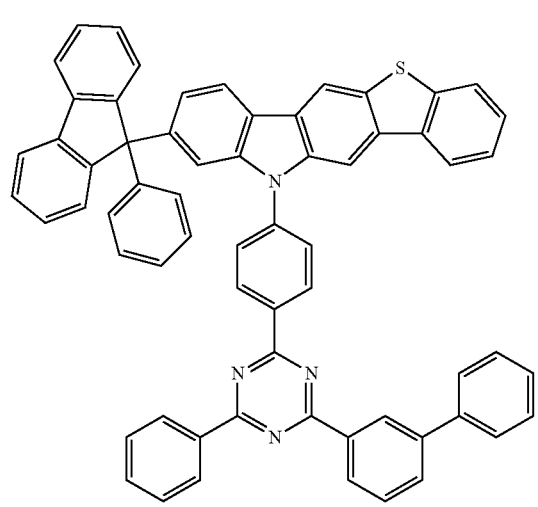
B-121
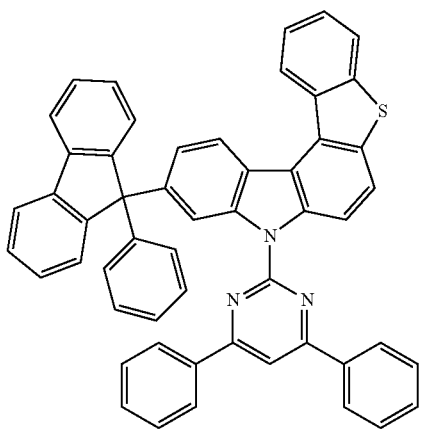

B-122
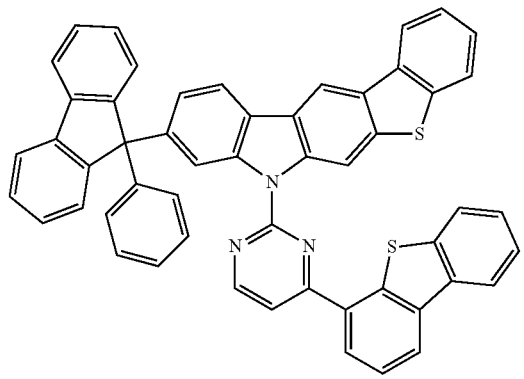
B-123
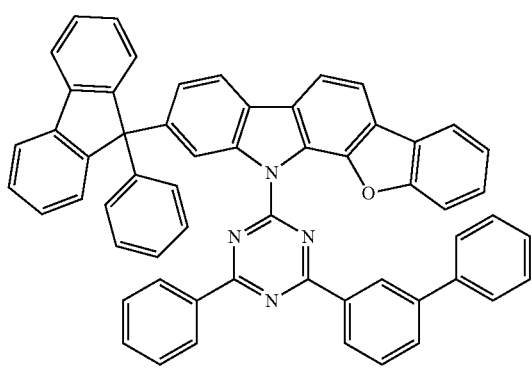
B-124
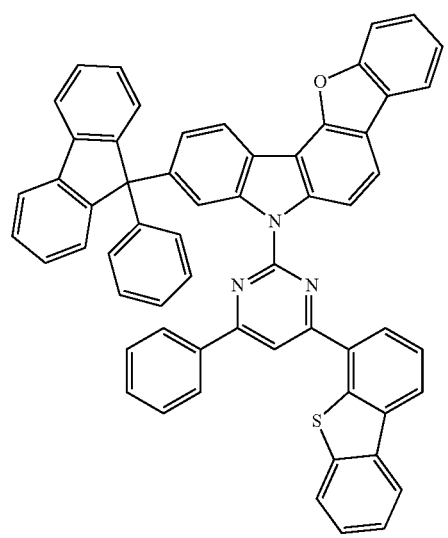
B-125
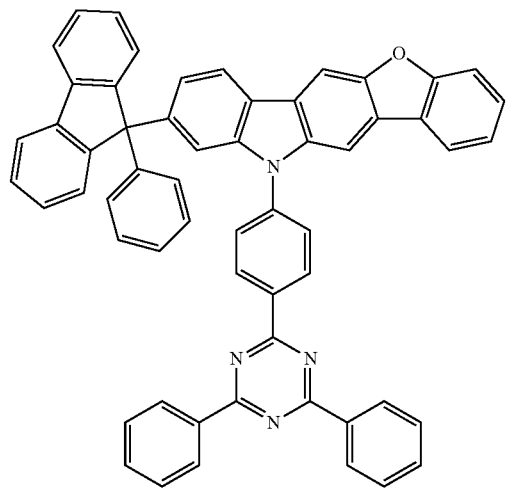
B-126
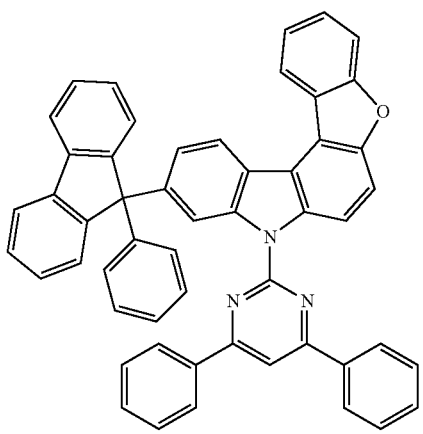
B-127
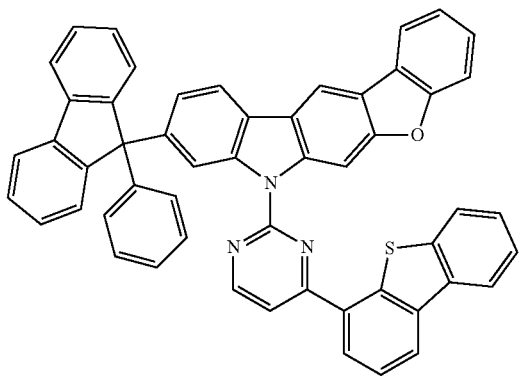

-continued
B-128
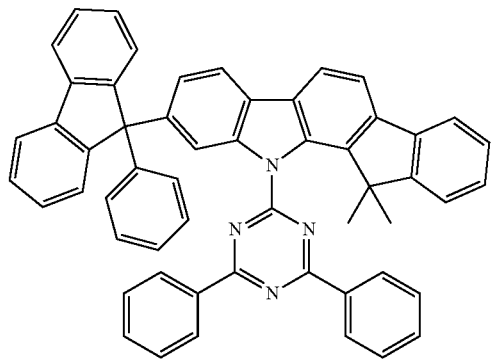
B-129
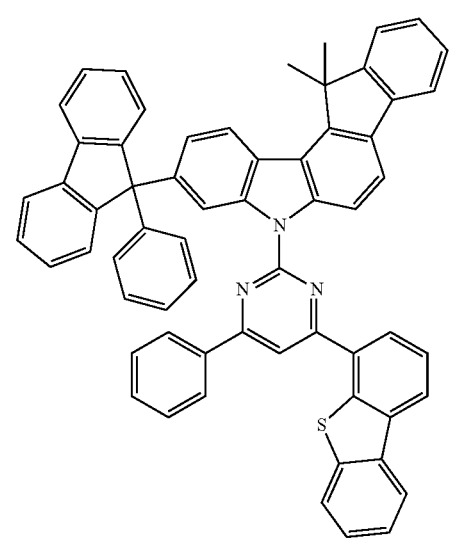
B-130
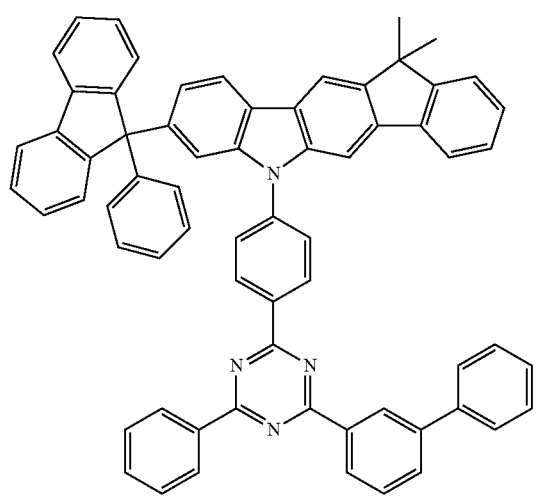
-continued
B-131
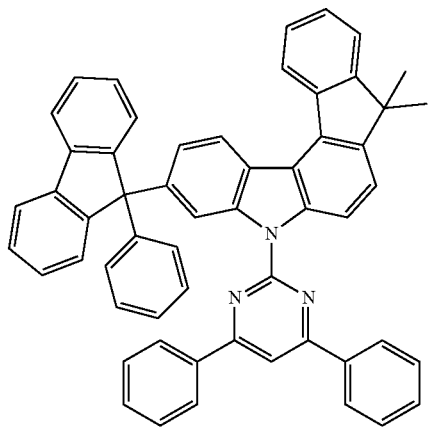
B-132
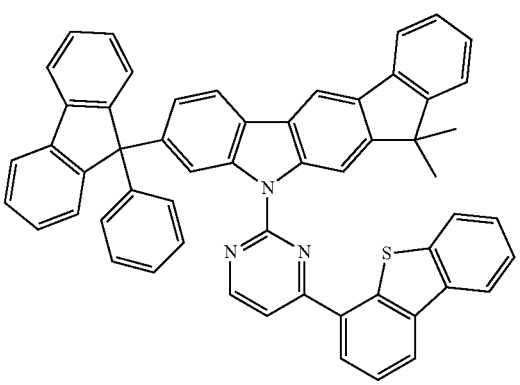
B-133
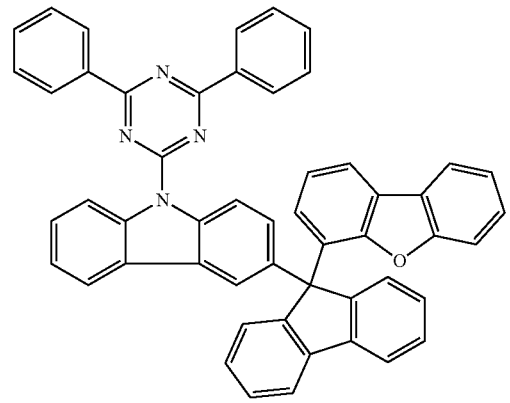
B-134
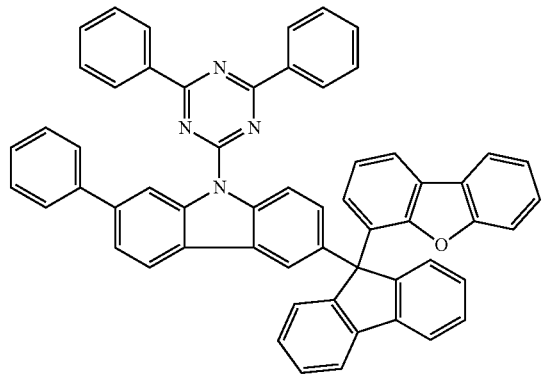

B-135
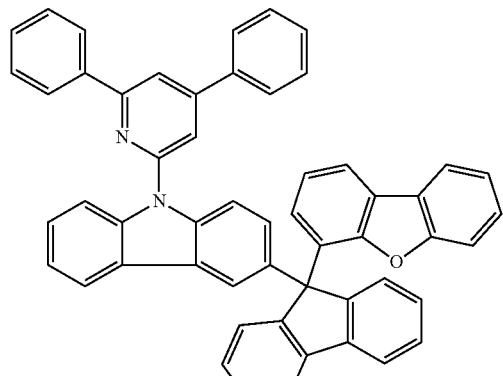
B-136
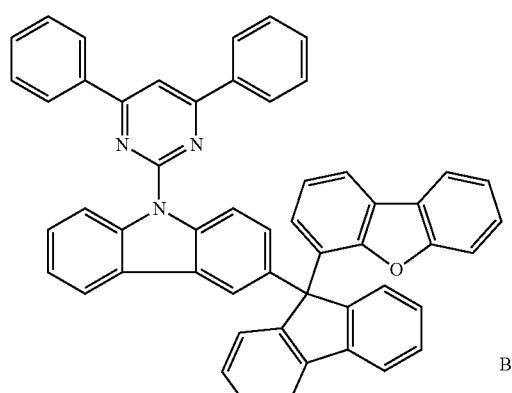
B-137
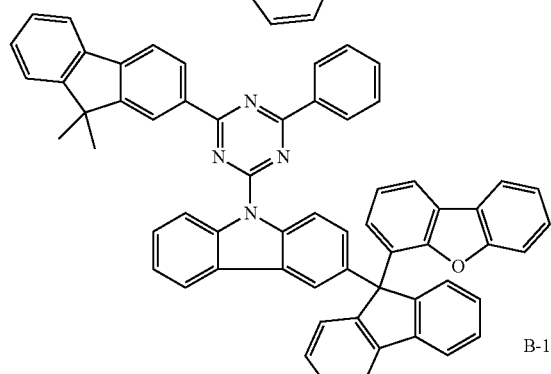
B-138
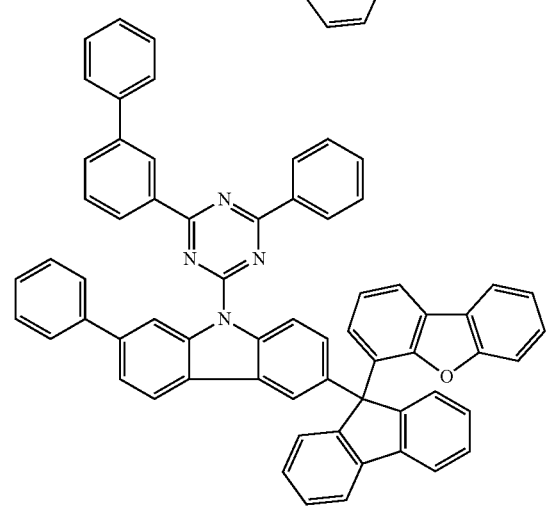
B-139
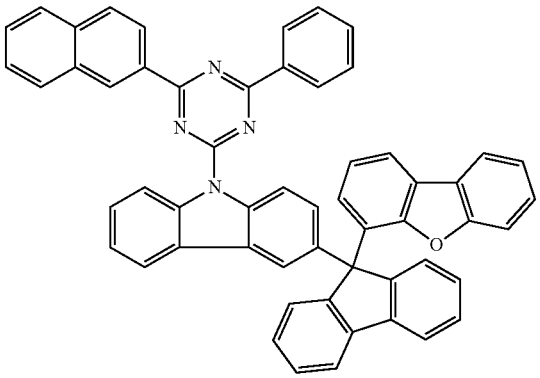
B-140
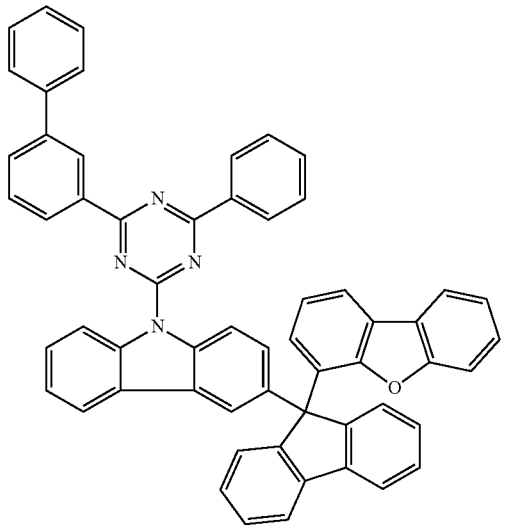
B-141
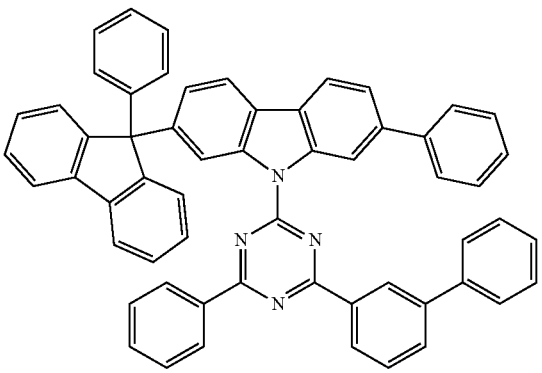

B-142
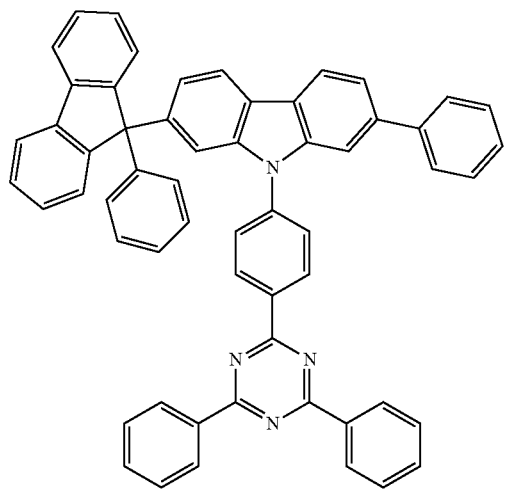
B-145
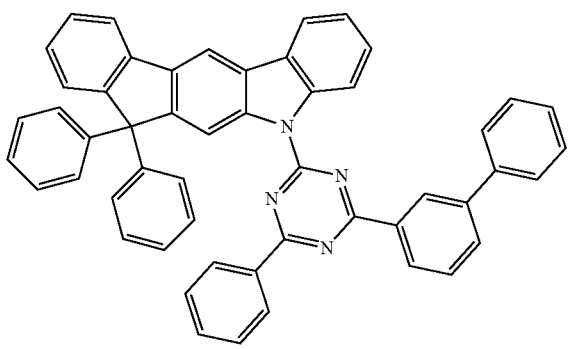
B-143
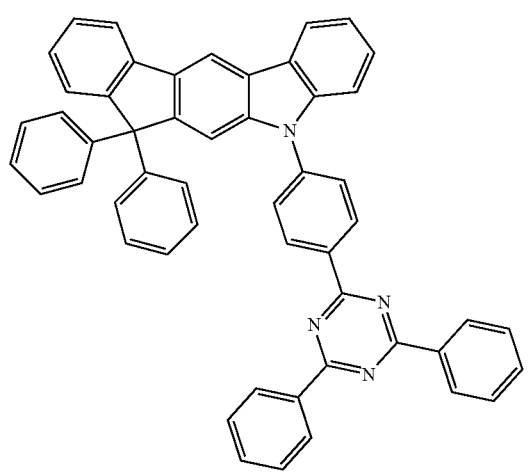
B-146
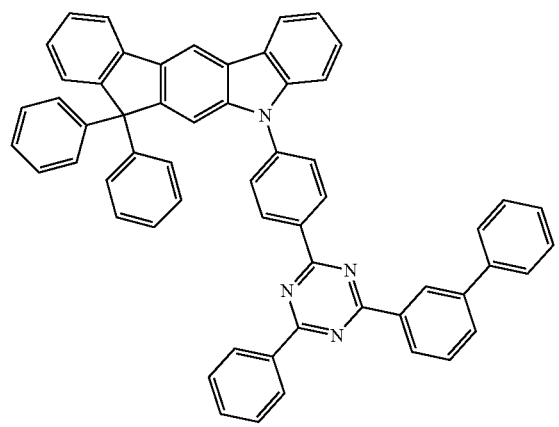
B-144
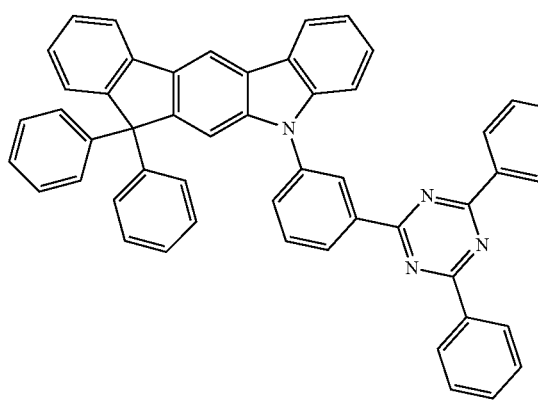
B-147
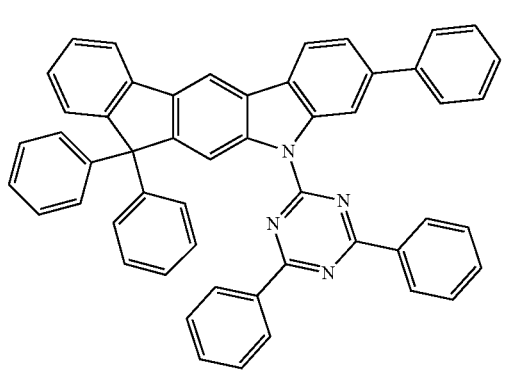

B-148

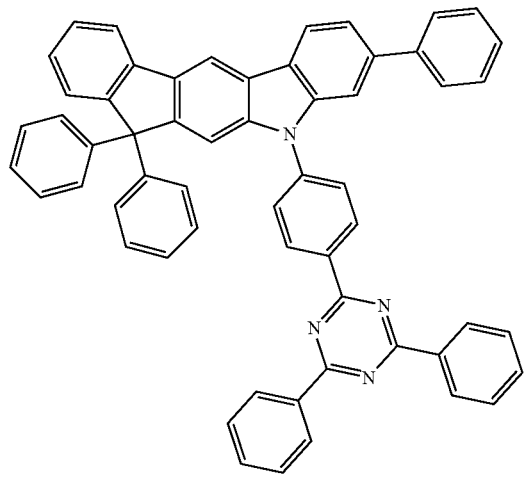

B-149

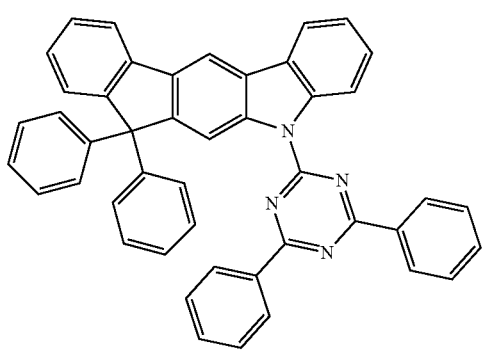

B-150

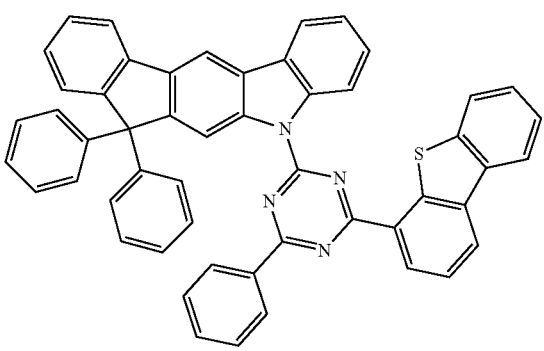

B-151

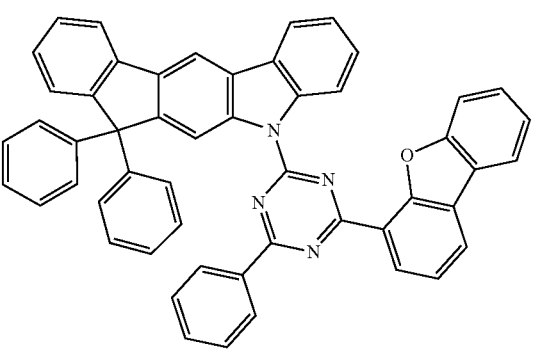

B-152

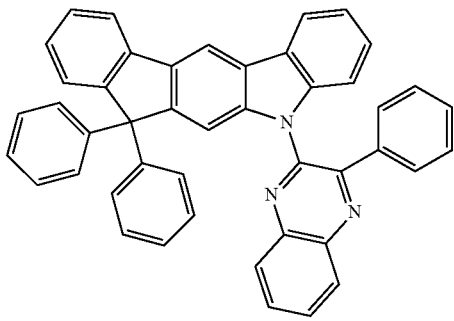

B-153

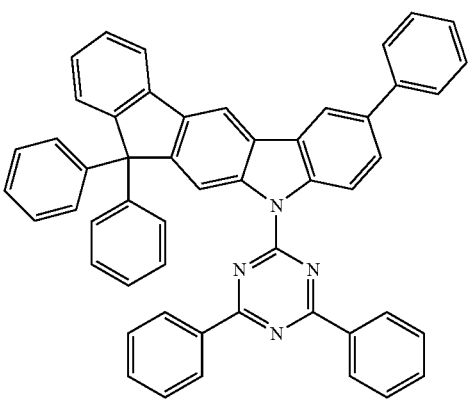

B-154

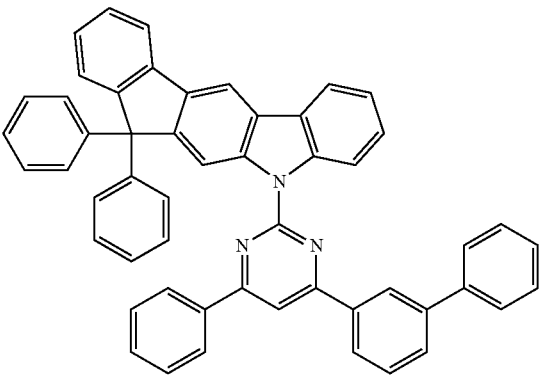

The electron transport zone 129 means a zone in which electrons are transported from the second electrode to the light-emitting layer. The electron transport zone 129 can comprise an electron transport compound, a reductive dopant, or a combination thereof. The electron transport compound can be at least one selected from a group comprising oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, and gallium complexes. The reductive dopant may be selected from alkali metals, alkali metal compounds, alkaline earth metals, rare-earth metals, and halides, oxides, and complexes thereof. Specifically, the reductive dopant includes lithium quinolate, sodium quinolate, cesium quinolate, potassium quinolate, LiF, NaCl, CsF, $Li_2O$, BaO, and $BaF_2$, but are not limited thereto. In addition, the electron transport zone 129 can comprise an electron transport layer 127, an electron injection layer 128, or both of them. The electron transport layer 127 and the electron injection layer 128 can each be composed of two or more layers. The electron transport layer 127 can comprise an electron transport material including the compound represented by formula 1, or the known electron transport material. The example of the known electron transport material may include the electron transport compounds above, but is not limited thereto. In addition, the electron transport layer 127 can further comprise the reductive dopant above.

The electron injection layer 128 may be prepared with any electron injection material known in the art, which includes lithium quinolate, sodium quinolate, cesium quinolate, potassium quinolate, LiF, NaCl, CsF, $Li_2O$, BaO, and $BaF_2$, but is not limited thereto.

The second electrode 130 may be a cathode, and may be prepared with a low work-function material.

The aforementioned description regarding the organic electroluminescent device shown in FIG. 1 is intended to explain one embodiment of the invention, and is not meant in any way to restrict the scope of the invention. The organic electroluminescent device can be constructed in another way. For example, any one optional component such as a hole injection layer may not be comprised in the organic electroluminescent device of FIG. 1, except for a light-emitting layer and an electron buffering layer. In addition, an optional component may be further comprised therein, which includes one or more of a hole blocking layer, an electron blocking layer, an impurity layer such as n-doping layer and p-doping layer, a hole auxiliary layer and an auxiliary light-emitting layer. The hole auxiliary layer or the auxiliary light-emitting layer is interposed between the hole transport layer and the light-emitting layer, and modulates hole mobility. The hole auxiliary layer or the auxiliary light-emitting layer has the effects to provide improved efficiency and lifespan of the organic electroluminescent device. The organic electroluminescent device may be a both side emission type in which a light-emitting layer is placed on each of both sides of the impurity layer. The two light-emitting layers on the impurity layer may emit different colors. The organic electroluminescent device may be a bottom emission type in which a first electrode is a transparent electrode and a second electrode is a reflective electrode. The organic electroluminescent device may be a top emission type in which a first electrode is a reflective electrode and a second electrode is a transparent electrode. The organic electroluminescent device may have an inverted type structure in which a cathode, an electron transport layer, a light-emitting layer, a hole transport layer, a hole injection layer, and an anode are sequentially stacked on a substrate.

FIG. 2 illustrates an energy band diagram among a hole transport layer, a light-emitting layer, an electron buffering layer, and an electron transport zone of an organic electroluminescent device according to one embodiment of the present disclosure.

In FIG. 2, a hole transport layer 123, a light-emitting layer 125, an electron buffering layer 126, and an electron transport zone 129 are sequentially stacked. Electrons (e-) injected from a cathode are transported to a light-emitting layer 125 through an electron transport zone 129 and an electron buffering layer 126.

By interposing the electron buffering layer between the light-emitting layer and the second electrode in the organic electroluminescent device comprising the first and second electrodes and the light-emitting layer, an electron injection can be controlled by electron affinity LUMO (lowest unoccupied molecular orbital) energy of the electron buffering layer.

LUMO ("Lowest Unoccupied Molecular Orbital") and HOMO ("Highest Occupied Molecular Orbital") have negative energy levels. However, for convenience, LUMO energy level and HOMO energy level are indicated by absolute values in the present disclosure. Thus, the comparison between the LUMO energy level and the HOMO energy level is conducted on the basis of their absolute values. In the present disclosure, the LUMO energy level and the HOMO energy level are calculated by Density Functional Theory (DFT).

In the OLED of the present disclosure, the LUMO energy level of the electron buffering layer may be higher than the LUMO energy level of the host compound. Specifically, the difference in LUMO energy levels between the electron buffering layer and the host compound may be 0.2 eV to 0.3 eV or less, and preferably about ±0.1 eV. For example, the LUMO energy levels of the electron buffering layer and the host compound may be about 1.8 eV and about 1.6 eV, respectively, and thus the difference in the LUMO energy level may be about 0.2 eV. Although a LUMO barrier between the host compound and the electron buffering layer can cause an increase in driving voltage, the compound of formula 1 comprised in the electron buffering layer may allow to form LUMO energy levels suitable for easy electron injection between the electron transport layer and the light-emitting layer. Therefore, the OLED of the present disclosure can have low driving voltage, high luminous efficiency, and long lifespan. Herein, specifically, the LUMO energy level of an electron buffering layer may indicate the LUMO energy level of the compound of formula 1 comprised in the electron buffering layer.

In the OLED of the present disclosure, the LUMO energy level of the electron buffering layer may be lower or higher than the LUMO energy level of the electron transport zone. For example, the LUMO energy levels of the electron buffering layer and the electron transport zone may be about 1.8 eV and about 1.9 eV, respectively, and thus the difference in LUMO energy level may be about 0.1 eV. Due to the LUMO energy level of the electron buffering layer, electrons can be easily injected into a light-emitting layer through the electron buffering layer. However, the LUMO energy level of the electron transport zone may be about 1.7 eV or more or about 1.9 eV or more. For example, the LUMO energy levels of the electron buffering layer and the electron transport zone may be about 1.7 eV and about 1.9 eV, respectively, and thus the difference in the LUMO energy level may be about 0.2 eV. As setforth above, the compound of the present disclosure comprised in the electron buffering layer can provide rapidness of electron current despite a barrier between an electron buffering layer and an electron transport zone.

Generally, LUMO energy level of the electron buffering layer may be in the middle between those of the host compound and the electron transport zone. For example, LUMO energy levels may have the following relationship: the electron transport zone>the electron buffering layer>the host compound. According to the aforementioned LUMO relationship, electrons can be suitably injected to a light-emitting layer through the electron buffering layer from the electron transport zone by cascade, and thus, an electron buffering layer comprising the compound of formula 1 can easily transport electrons to the light-emitting layer. Accordingly, the organic electroluminescent device of the present disclosure can have low driving voltage, high luminous efficiency, and long lifespan.

LUMO energy level can be easily measured by known various methods. Generally, cyclic voltammetry or ultraviolet photoelectron spectroscopy (UPS) may be used. Therefore, one skilled in the art can easily understand and determine the electron buffering layer, the host material, and the electron transport zone which satisfy the aforementioned relationship for LUMO energy levels, so that he/she can easily embody the electron buffering layer, the host material, and the electron transport zone of the present disclosure. HOMO energy level can be easily measured in the same manner as LUMO energy level.

The host compound to be used in the present disclosure may be a phosphorescent host compound or a fluorescent host compound. The kinds of host compound to be used are not particularly limited, and may be compounds having the aforementioned LUMO energy level and selected from compounds known in the art. Specifically, the host compound may be a fluorescent host compound. The fluorescent host compound may be an anthracene-based compound represented by the following formula 30.

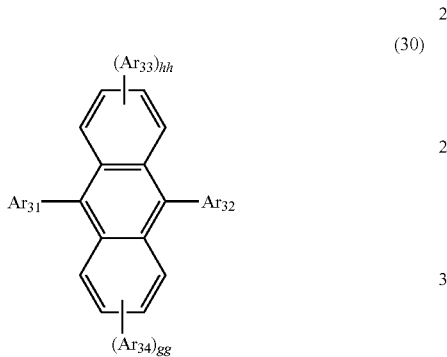

(30)

wherein $Ar_{31}$ and $Ar_{32}$, each independently, represent a substituted or unsubstituted (C6-C30)aryl, or a substituted or unsubstituted (5- to 30-membered) heteroaryl; $Ar_{33}$ and $Ar_{34}$, each independently, represent hydrogen, deuterium, a halogen, a cyano, a nitro, a hydroxy, a substituted or unsubstituted (C1-C30)alkyl, a substituted or unsubstituted (C6-C30)aryl, a substituted or unsubstituted (5- to 30-membered) heteroaryl, a substituted or unsubstituted (C3-C30) cycloalkyl, a substituted or unsubstituted (C1-C30)alkoxy, a substituted or unsubstituted (C1-C30)alkylsilyl, a substituted or unsubstituted (C6-C30)arylsilyl, a substituted or unsubstituted (C6-C30)aryl(C1-C30)alkylsilyl, or —$NR_{41}R_{42}$; $R_{41}$ and $R_{42}$, each independently, represent hydrogen, a substituted or unsubstituted (C6-C30)aryl, or a substituted or unsubstituted (5- to 30-membered) heteroaryl, or may be bonded to each other to form a (C3-C30), mono- or polycyclic, alicyclic or aromatic ring whose carbon atom(s) may be replaced with at least one heteroatom selected from nitrogen, oxygen, and sulfur; gg and hh, each independently, represent an integer of 1 to 4; and where gg or hh is an integer of 2 or more, each of $Ar_{33}$ or $Ar_{34}$ may be the same or different.

In formula 30, $Ar_{31}$ and $Ar_{32}$, each independently, may represent preferably, a substituted or unsubstituted (C6-C30) aryl. Specifically, $Ar_{31}$ and $Ar_{32}$, each independently, may represent a substituted or unsubstituted phenyl, a substituted or unsubstituted biphenyl, a substituted or unsubstituted naphthyl, a substituted or unsubstituted anthracenyl, a substituted or unsubstituted phenanthrenyl, a substituted or unsubstituted naphthacenyl, a substituted or unsubstituted fluoranthenyl, a substituted or unsubstituted pyrenyl, or a substituted or unsubstituted chrysenyl. In formula 30, $Ar_{33}$ and $Ar_{34}$, each independently, may represent preferably, hydrogen, a substituted or unsubstituted (C6-C21)aryl, a substituted or unsubstituted (5- to 21-membered) heteroaryl or —$NR_{41}R_{42}$.

Specifically, the compound of formula 30 includes the following, but is not limited thereto:

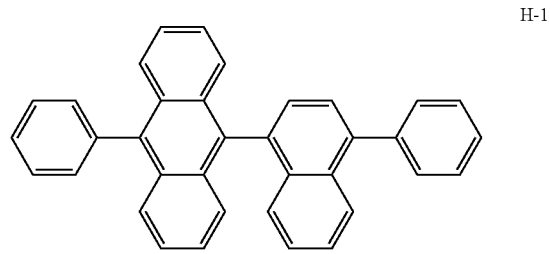

H-1

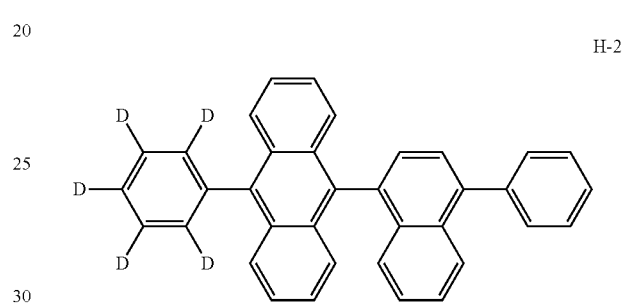

H-2

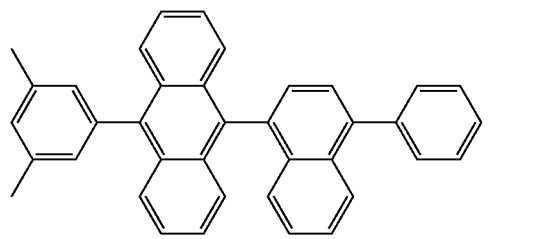

H-3

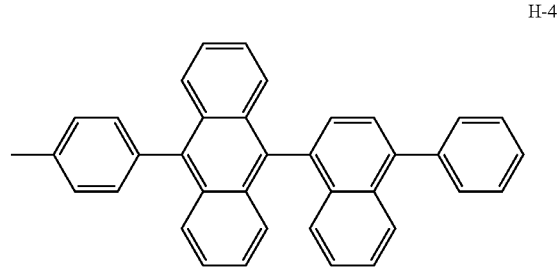

H-4

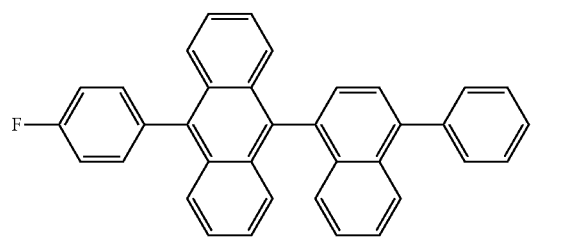

H-5

H-6
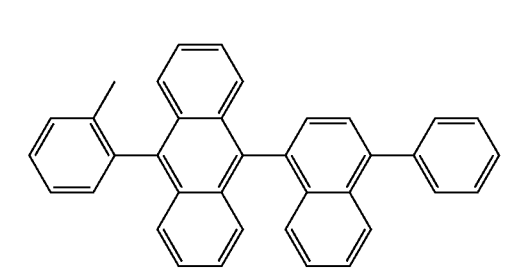
H-7
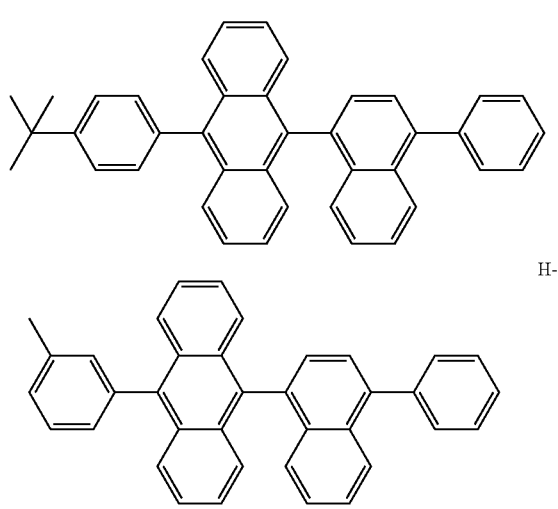
H-8
H-9
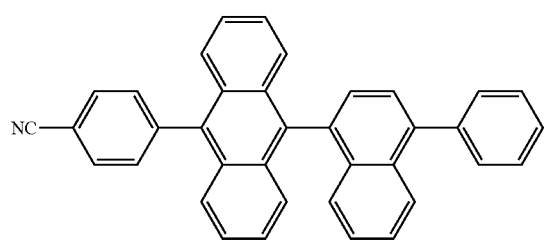
H-10
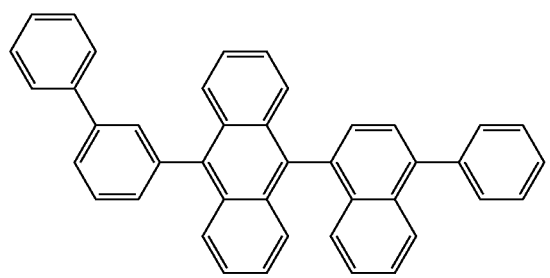
H-11
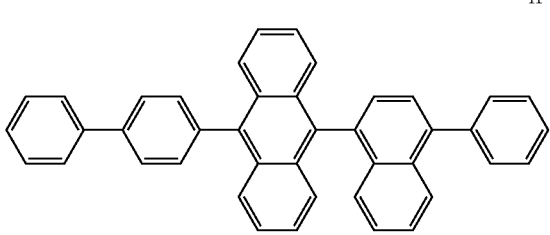
H-12
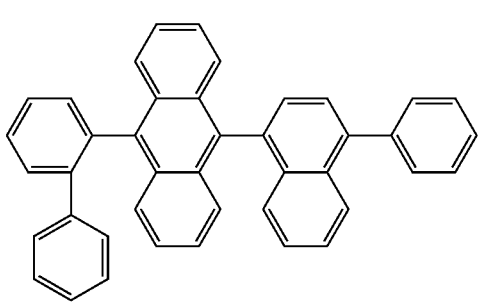
H-13
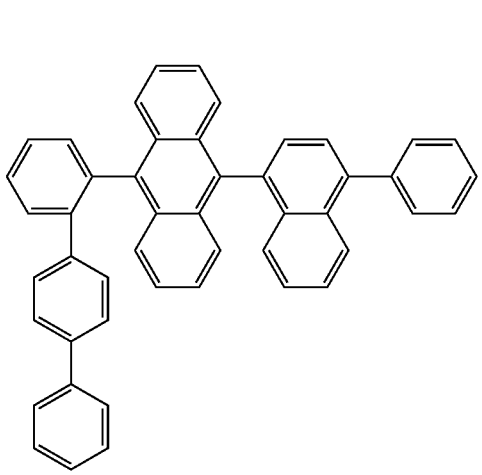
H-14
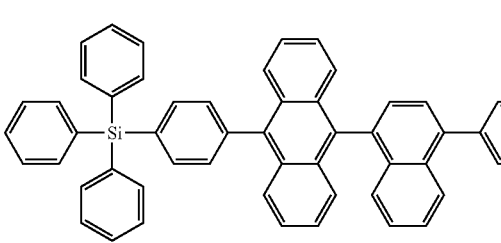
H-15
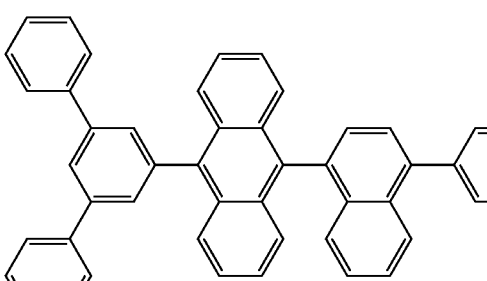
H-16
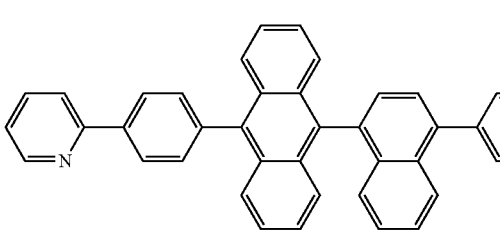

-continued
H-17
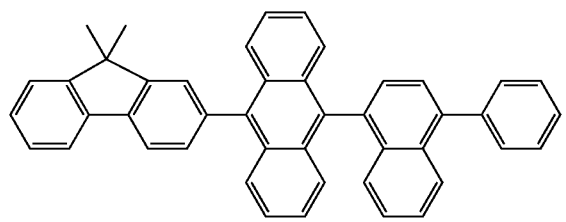
H-18
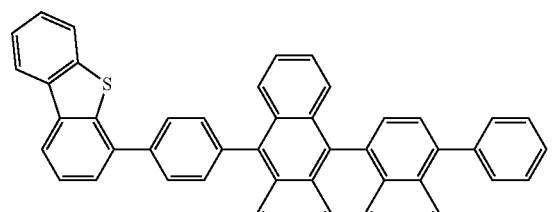
H-19
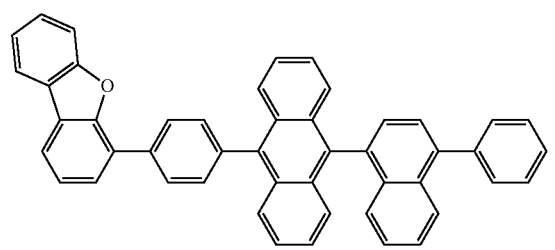
H-20
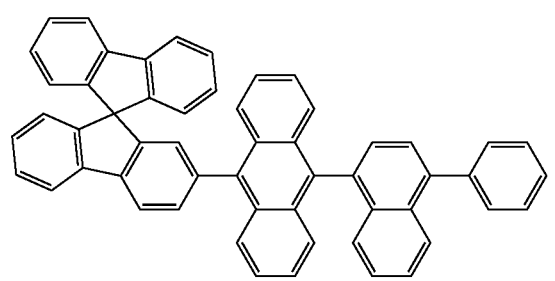
H-21
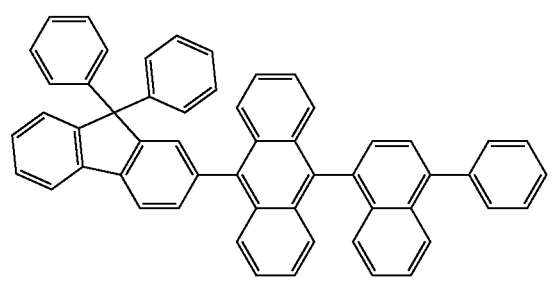
H-22
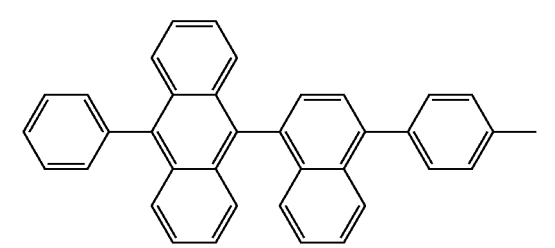
-continued
H-23
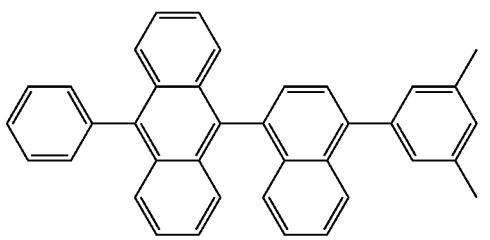
H-24
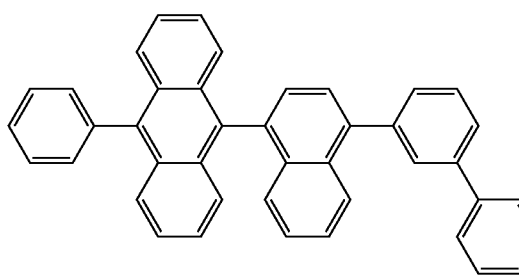
H-25
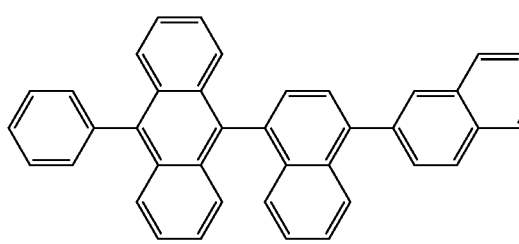
H-26
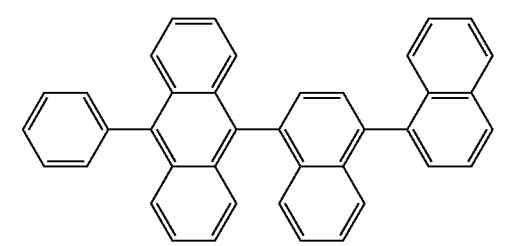
H-27
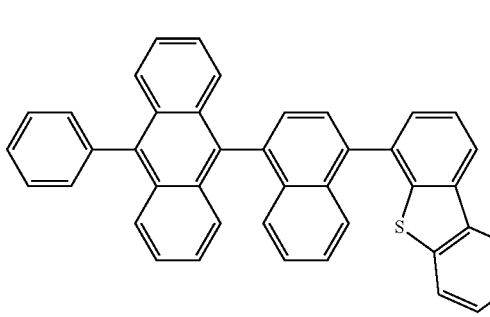

H-28
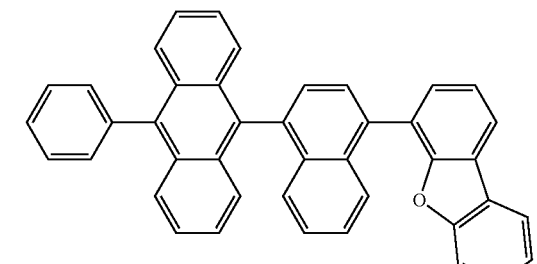
H-29
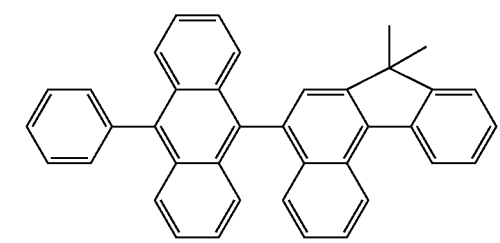
H-30
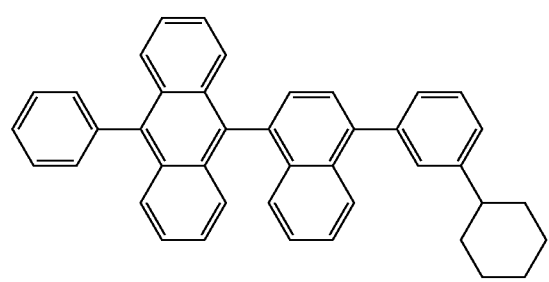
H-31
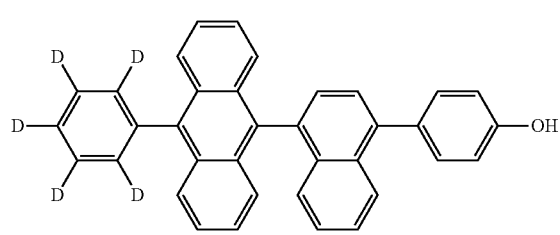
H-32
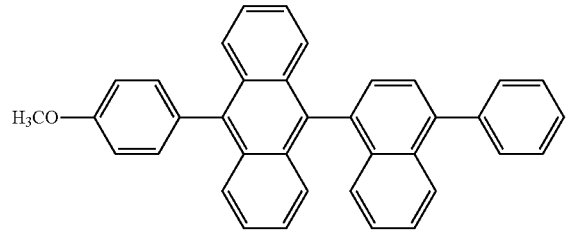
H-33
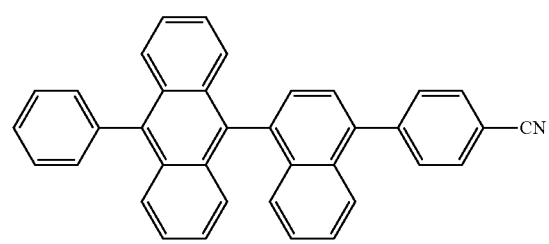
H-34
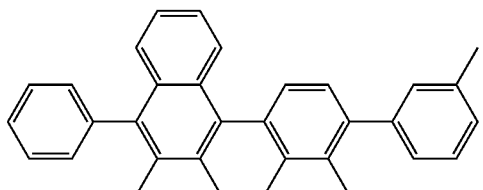
H-35
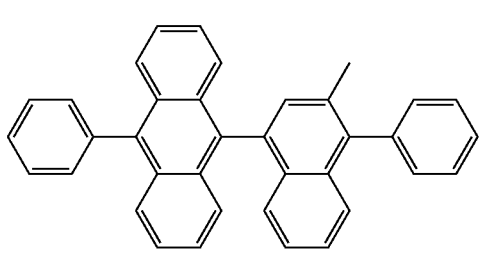
H-36
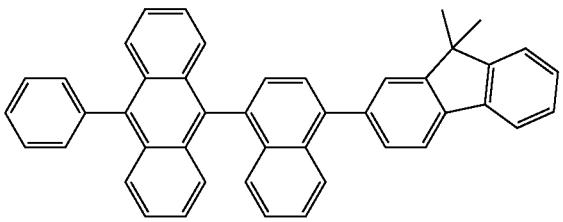
H-37
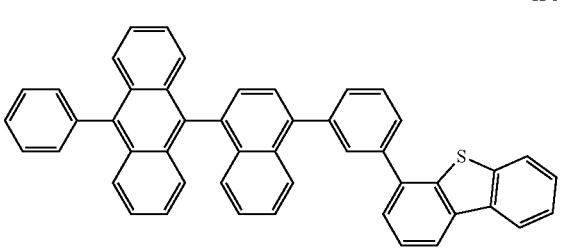
H-38
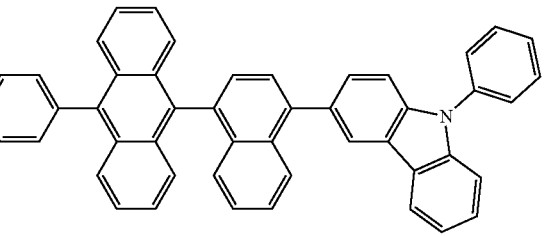
The dopant compound to be used in the present disclosure may be a phosphorescent dopant compound or a fluorescent dopant compound. Specifically, the dopant compound may be a fluorescent dopant compound. The fluorescent dopant compound may be a condensed polycyclic amine derivative represented by the following formula 40.
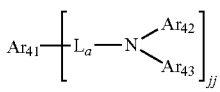 (40)

wherein Ar$_{41}$ represents a substituted or unsubstituted (C6-050)aryl or styryl; L$_d$ represents a single bond, a substituted or unsubstituted (C6-C30)arylene, or a substituted or unsubstituted (3- to 30-membered)heteroarylene; Ar$_{42}$ and Ar$_{43}$, each independently, represent hydrogen, deuterium, a halogen, a substituted or unsubstituted (C1-C30)alkyl, a substituted or unsubstituted (C6-C30)aryl, or a substituted or unsubstituted (3- to 30-membered)heteroaryl, or may be linked to an adjacent substituent(s) to form a (C3-C30), mono- or polycyclic, alicyclic or aromatic ring whose carbon atom(s) may be replaced with at least one heteroatom selected from nitrogen, oxygen, and sulfur; jj represents 1 or 2; and where jj is 2, each of

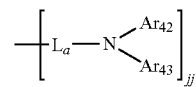

may be the same or different.

A preferable aryl for Ar$_{41}$ includes a substituted or unsubstituted phenyl, a substituted or unsubstituted fluorenyl, a substituted or unsubstituted anthryl, a substituted or unsubstituted pyrenyl, a substituted or unsubstituted chrysenyl, a substituted or unsubstituted benzofluorenyl, and spiro[fluoren-benzofluorene], etc.

Specifically, the compound of formula 40 includes the following, but is not limited thereto:

D-1
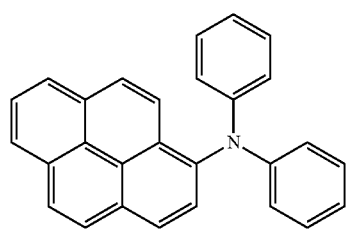

D-2
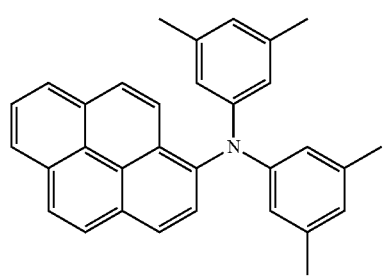

D-3
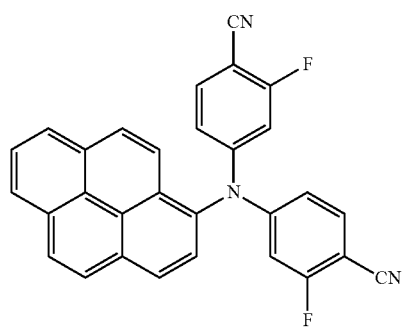

D-4
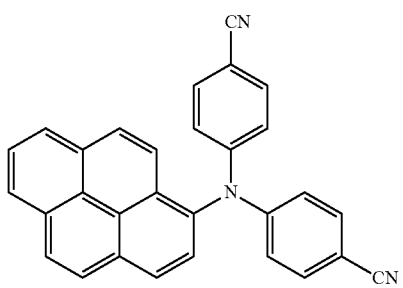

D-5
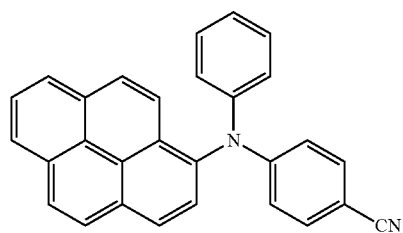

D-6
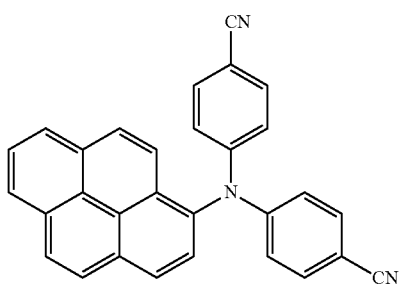

D-7
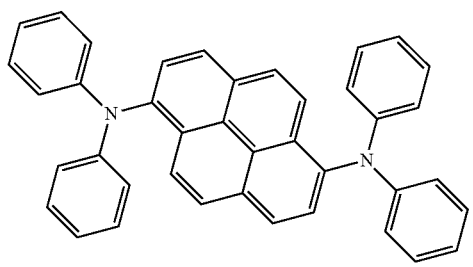

D-8
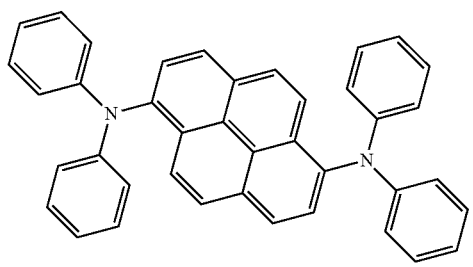

D-9
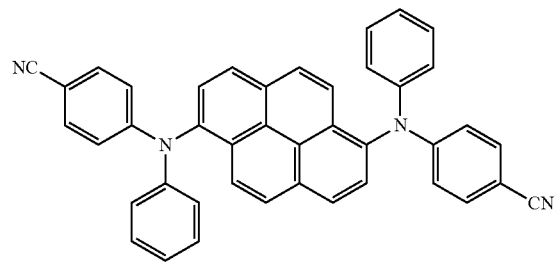
D-10
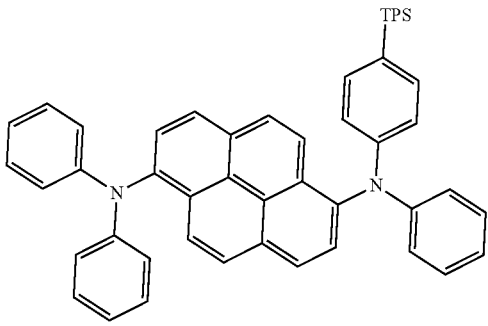
D-11
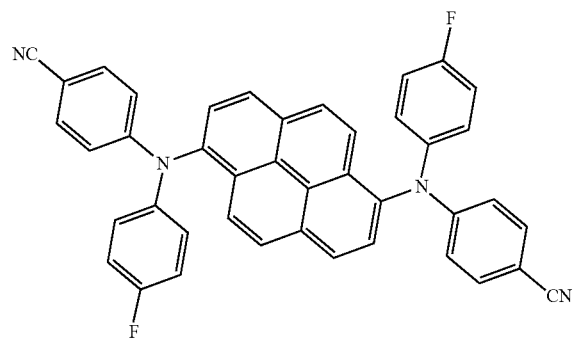
D-12
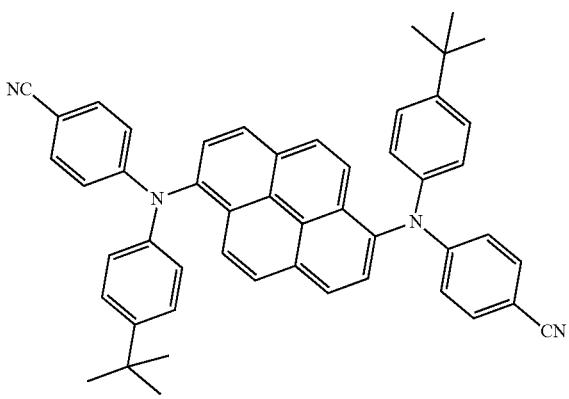
D-13
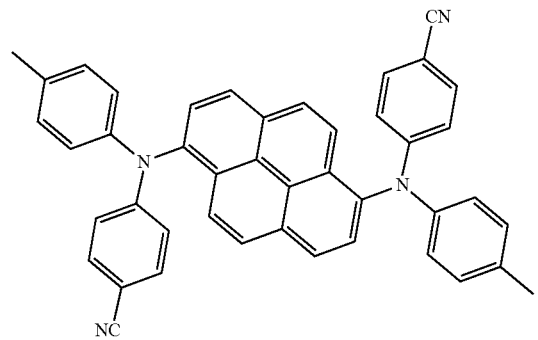
D-14
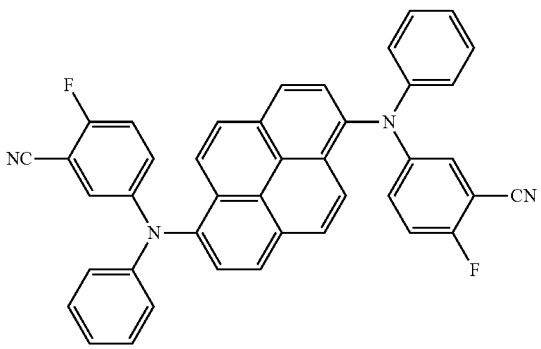
D-15
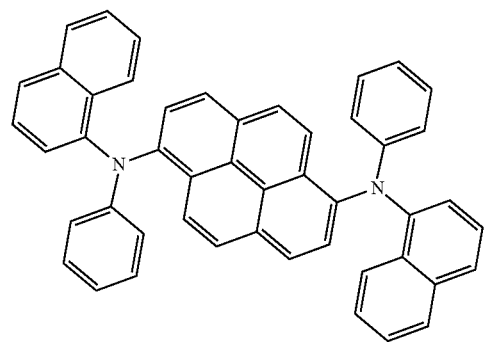
D-16
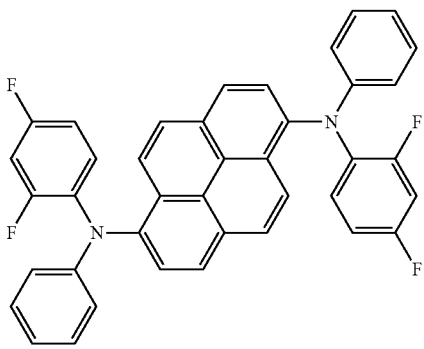

-continued
D-17
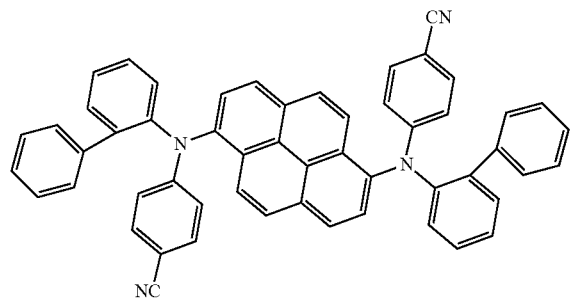
D-18
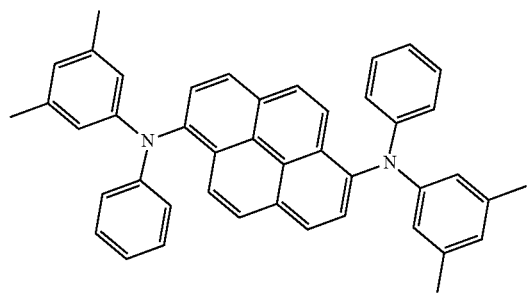
D-19
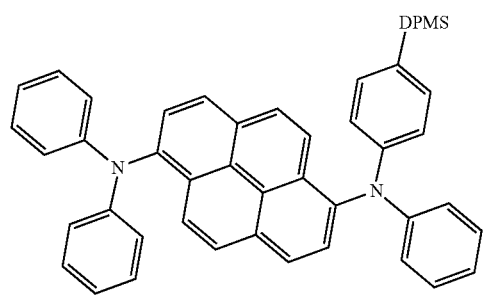
D-20
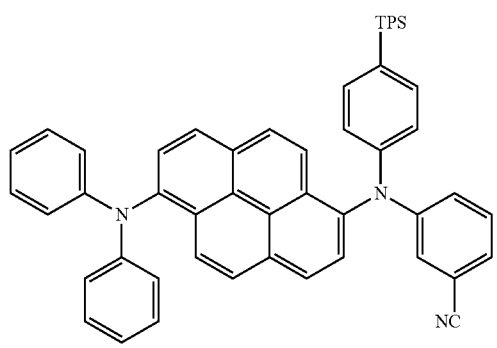
D-21
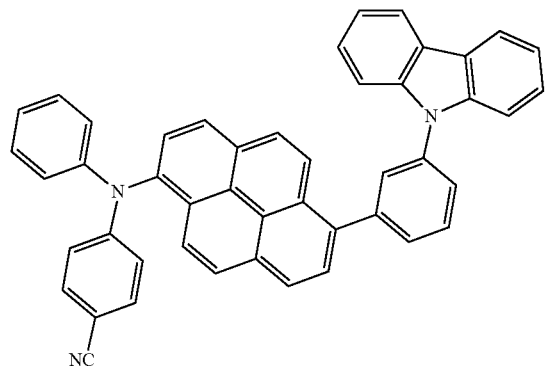
D-22
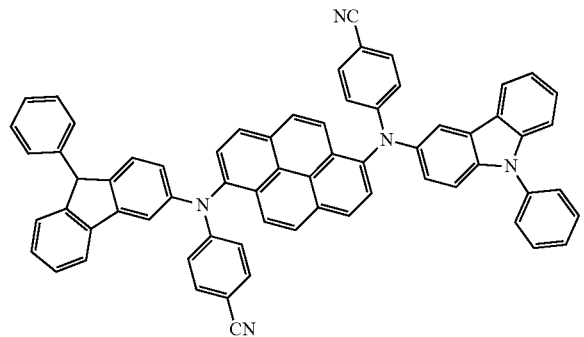
D-23
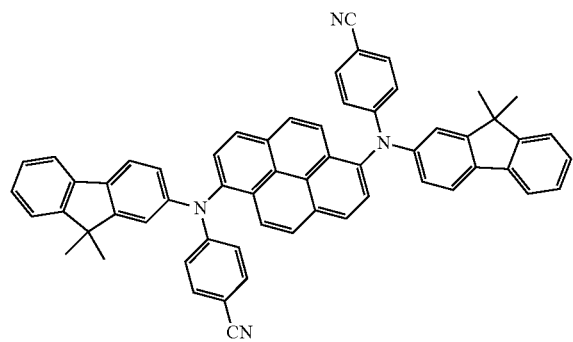
D-24
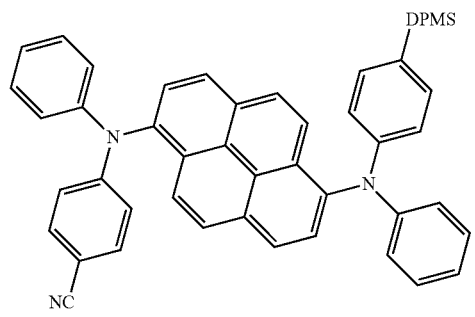

-continued
D-25
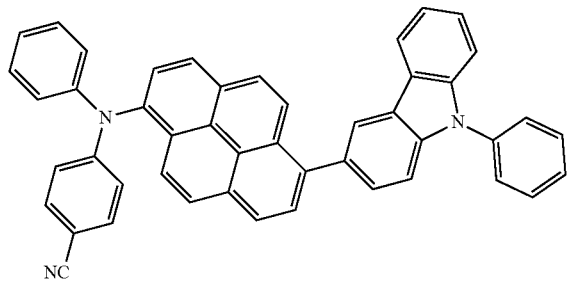
D-26
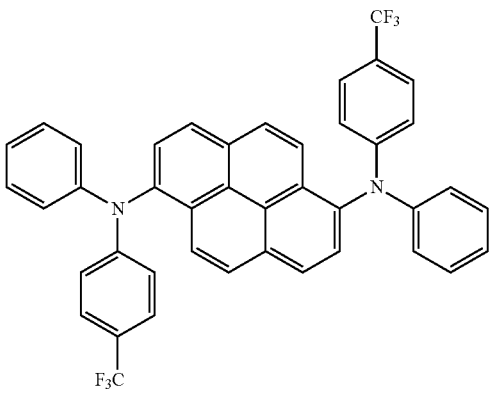
D-27
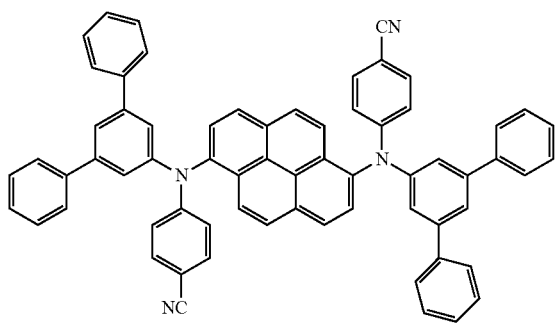
D-28
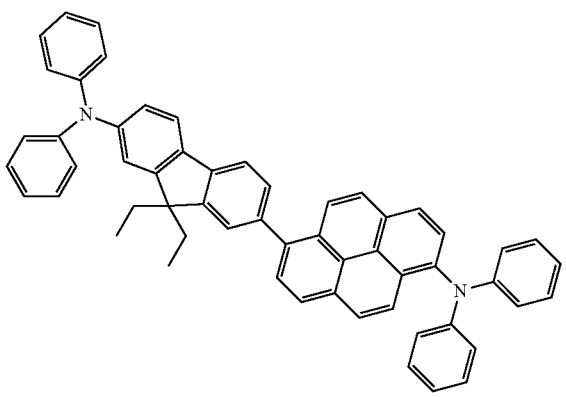
D-29
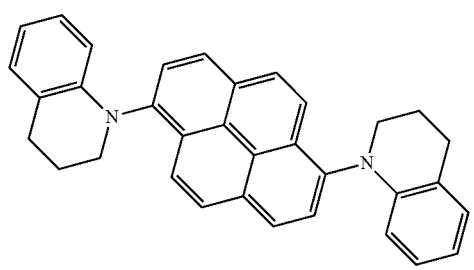
D-30
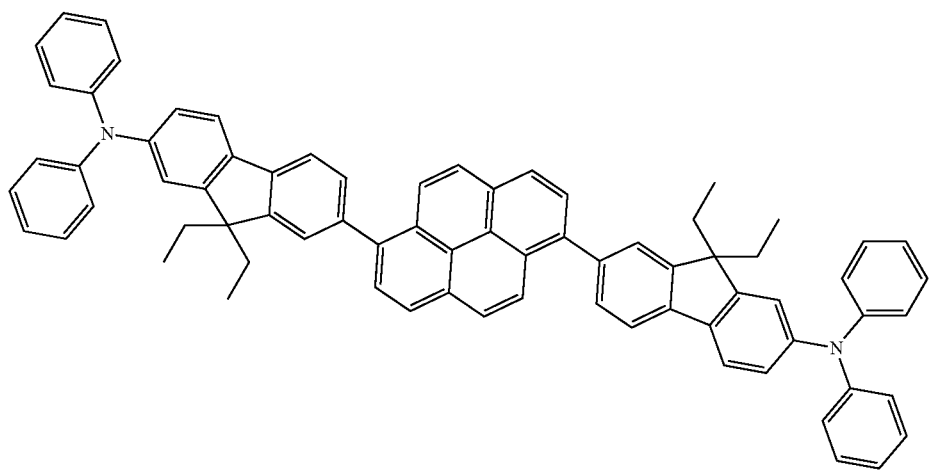

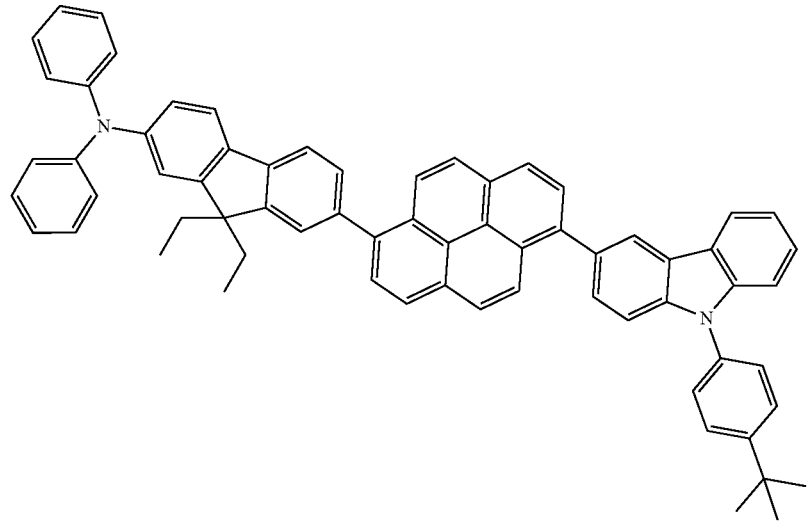
D-31
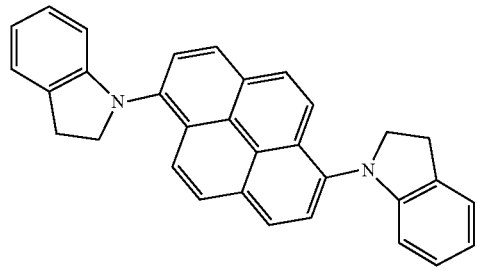
D-32
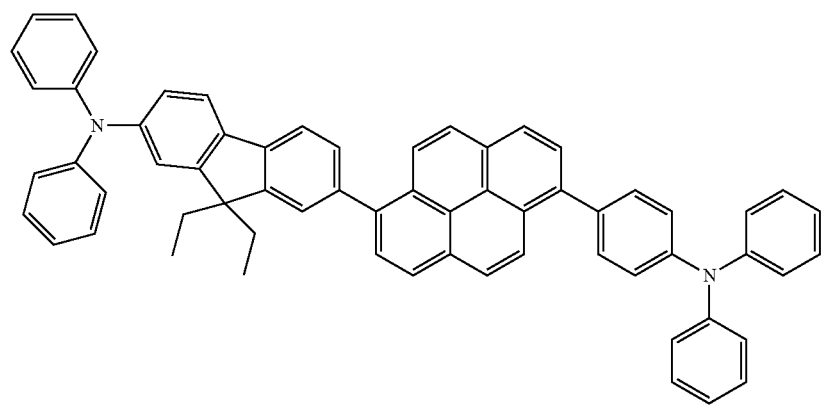
D-33

-continued
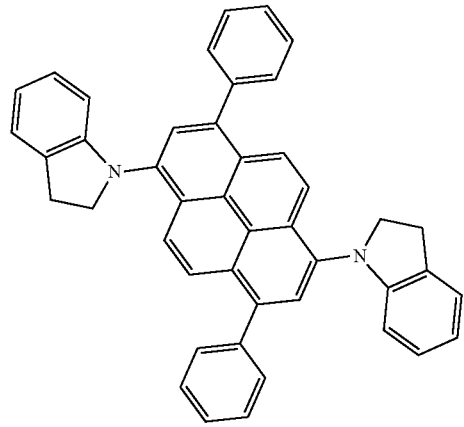
D-34
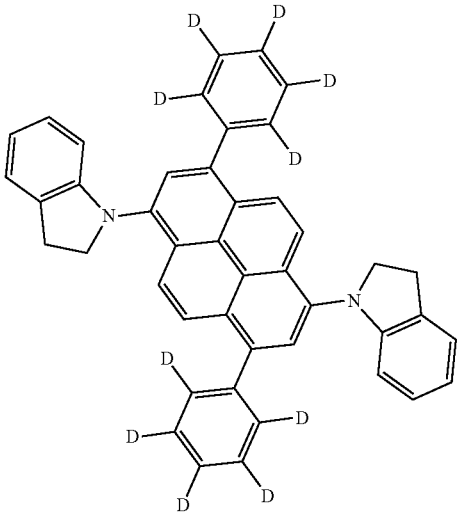
D-35
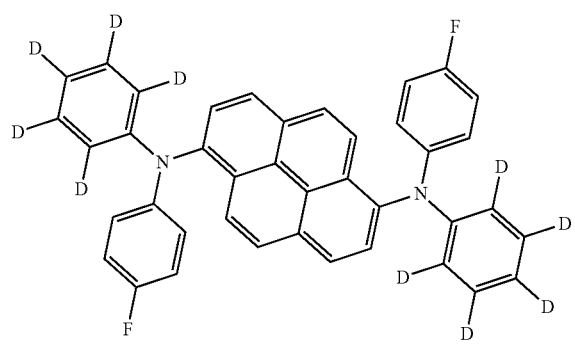
D-36
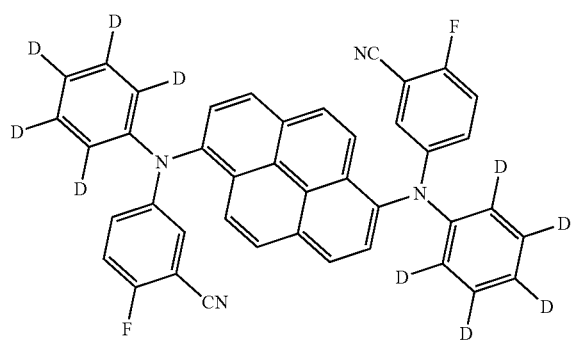
D-37
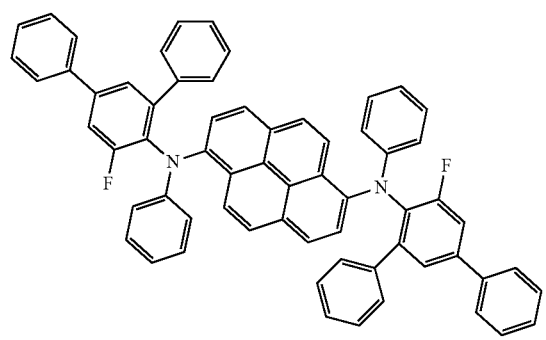
D-38
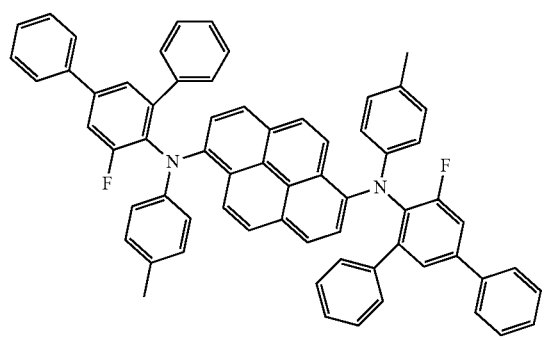
D-39
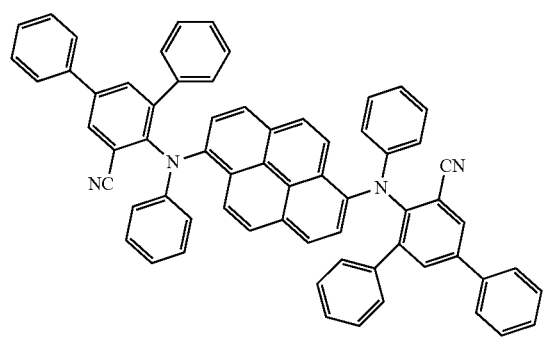
D-40
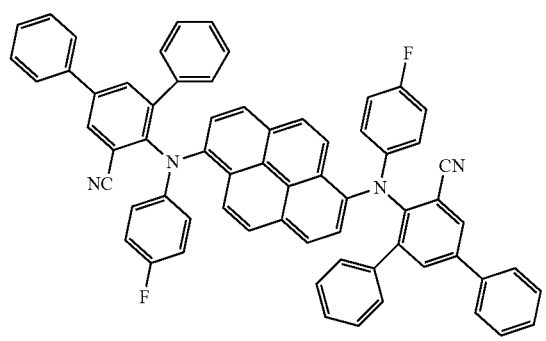
D-41

-continued
D-42
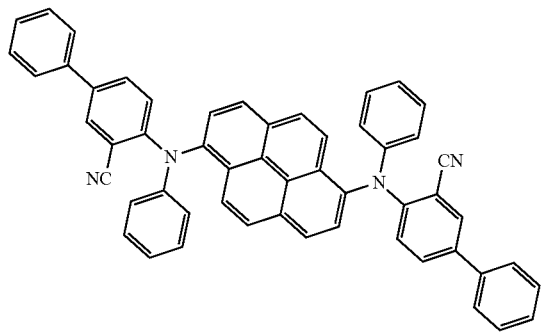
D-43
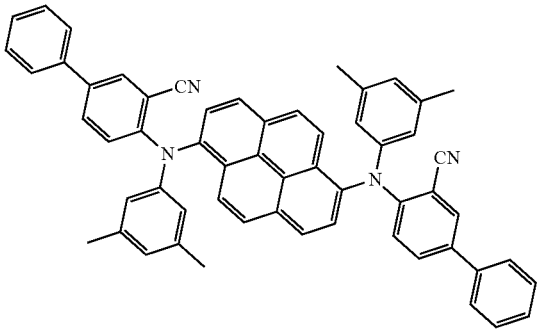
D-44
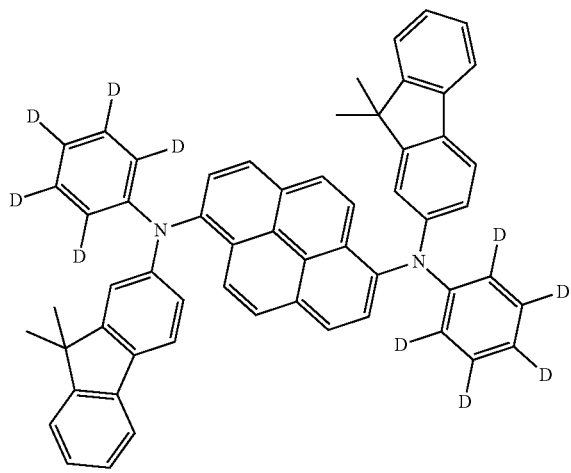
D-45
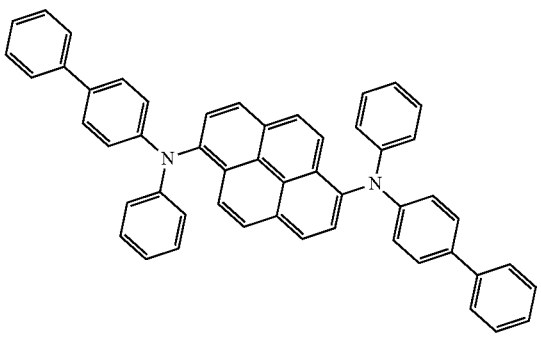
D-46
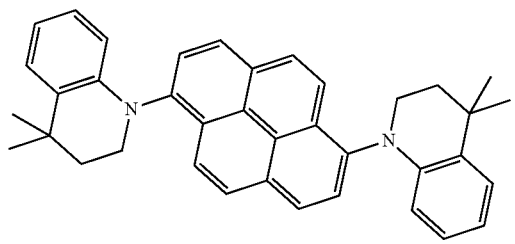
D-47
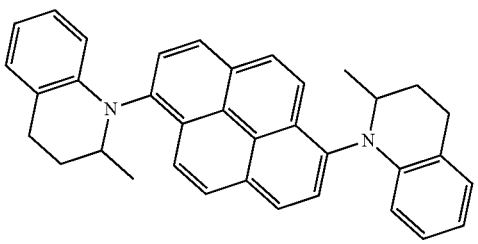
D-48
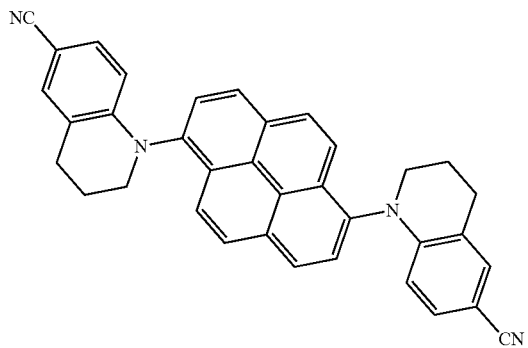
D-49
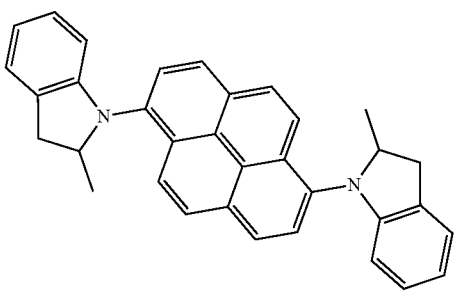

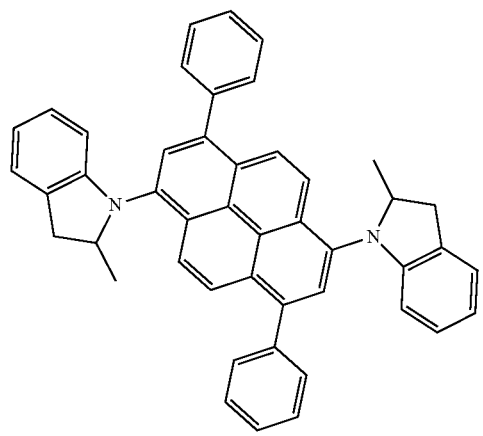
D-50
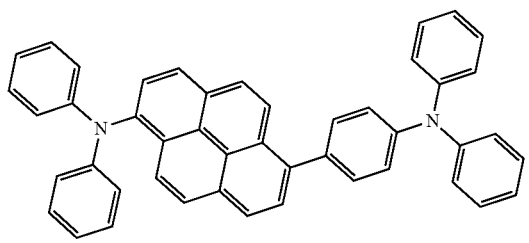
D-51
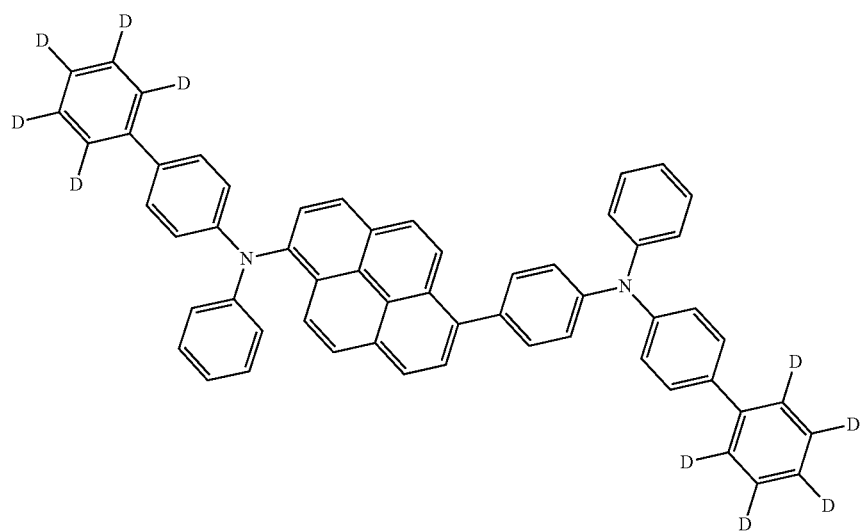
D-52
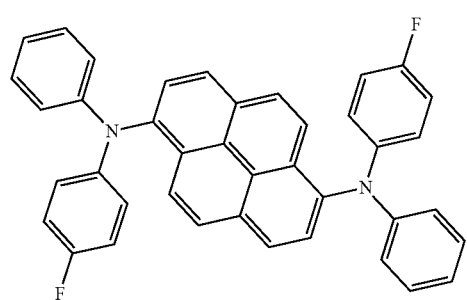
D-53
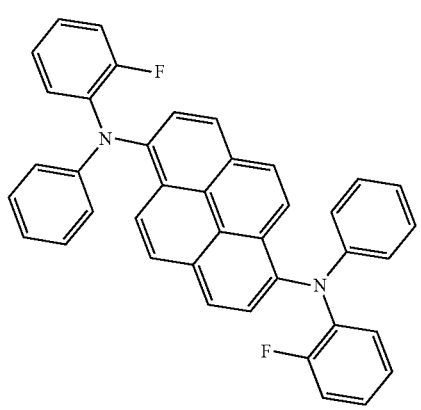
D-54

-continued
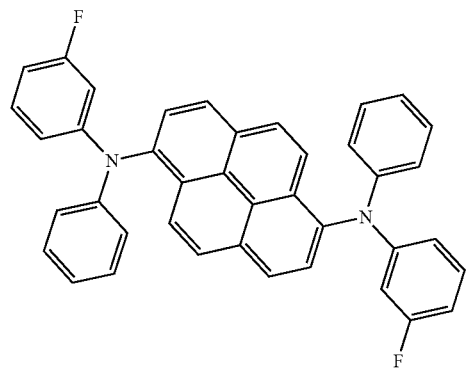
D-55
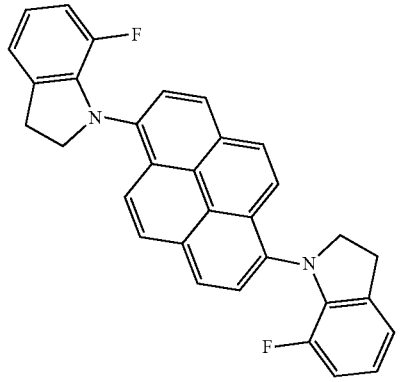
D-56
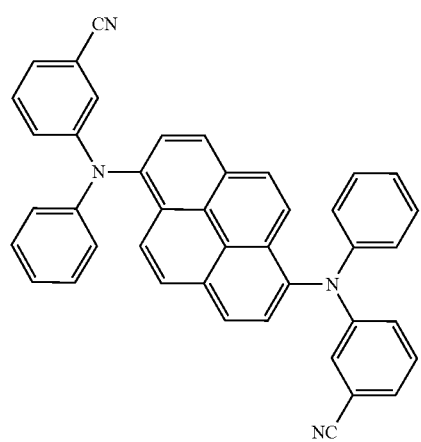
D-57
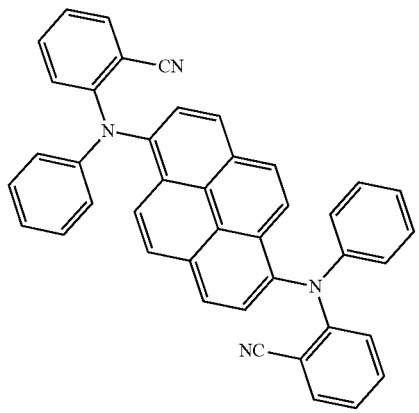
D-58
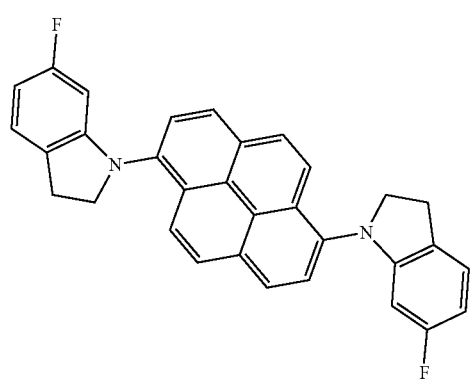
D-59
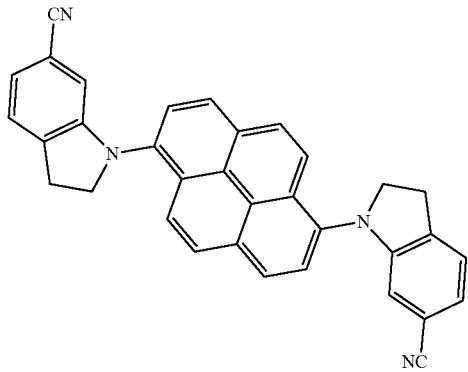
D-60
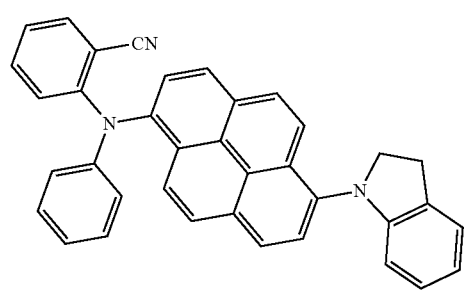
D-61
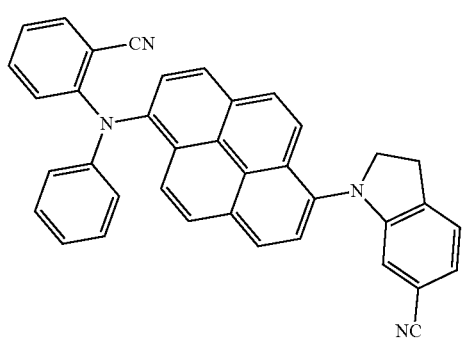
D-62

-continued
D-63
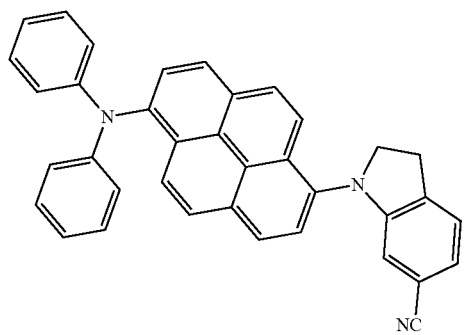
D-64
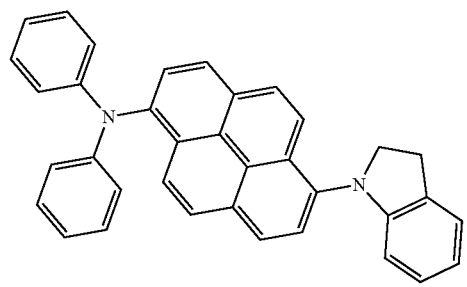
D-65
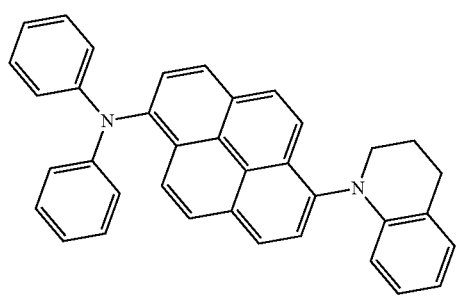
D-66
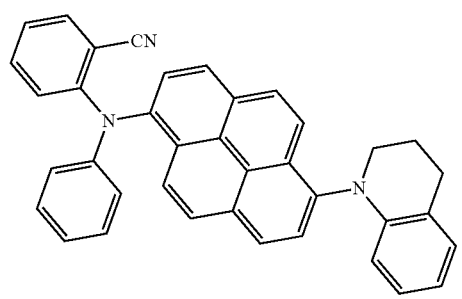
D-67
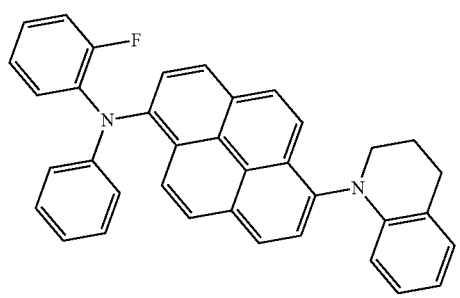
D-68
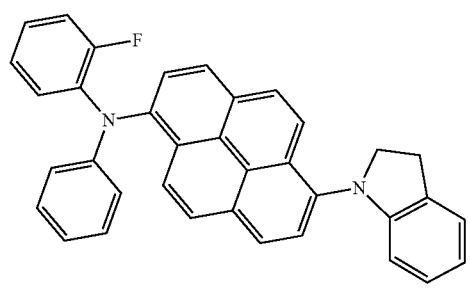
D-69
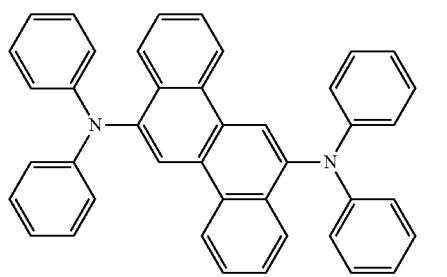
D-70
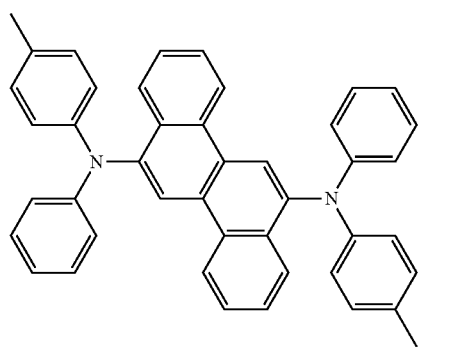
D-71
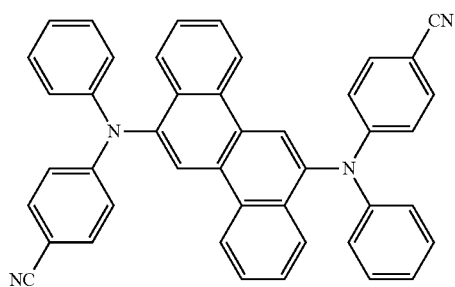
D-72
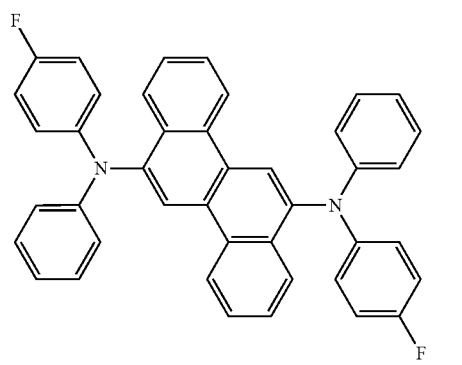

-continued
D-73
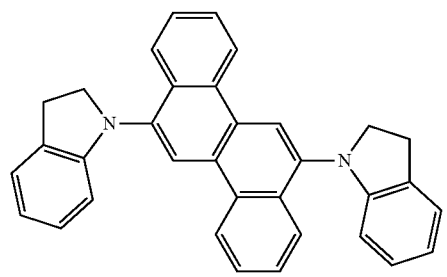
D-74
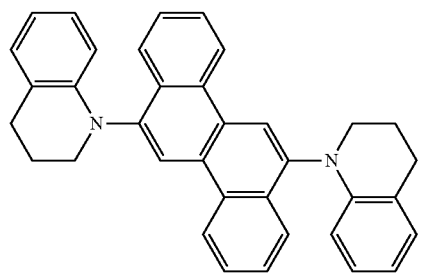
D-75
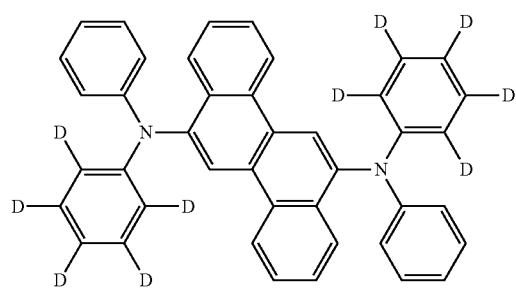
D-76
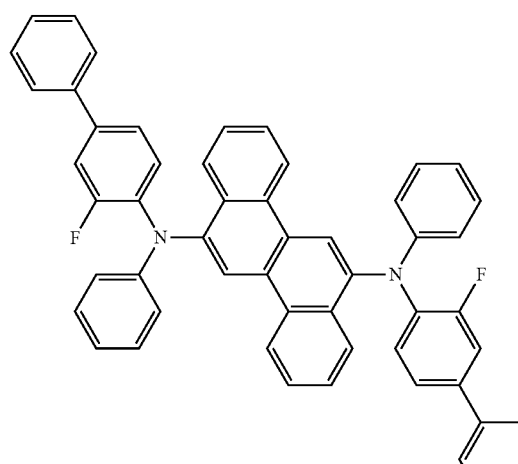
D-77
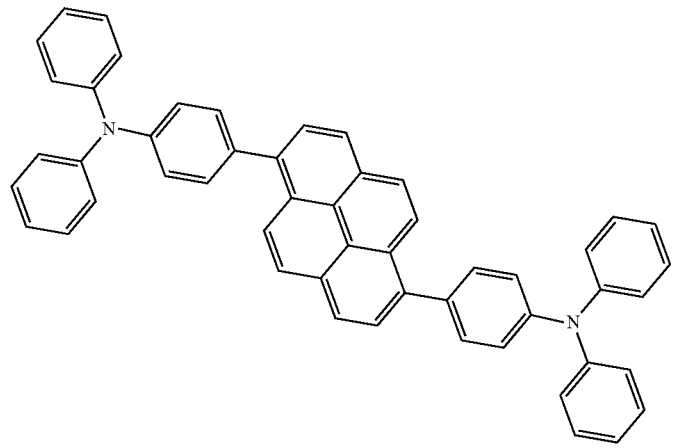
D-78
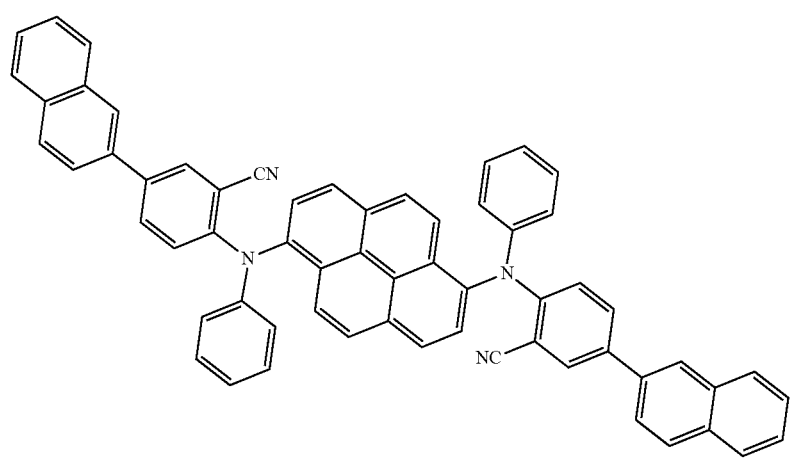

D-79
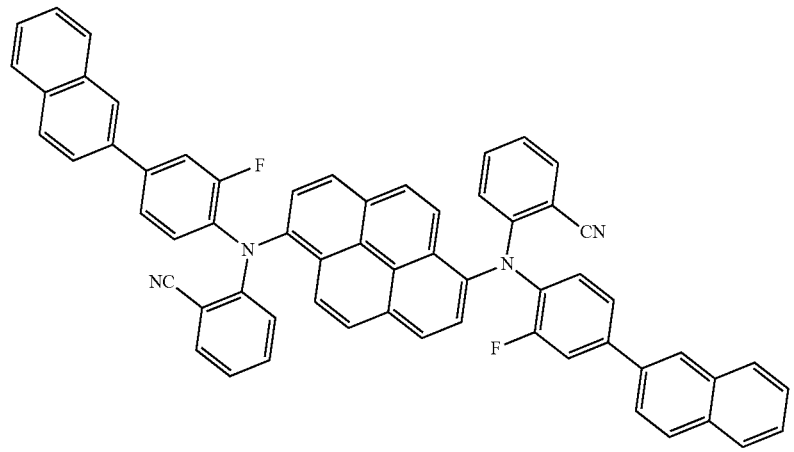
D-80
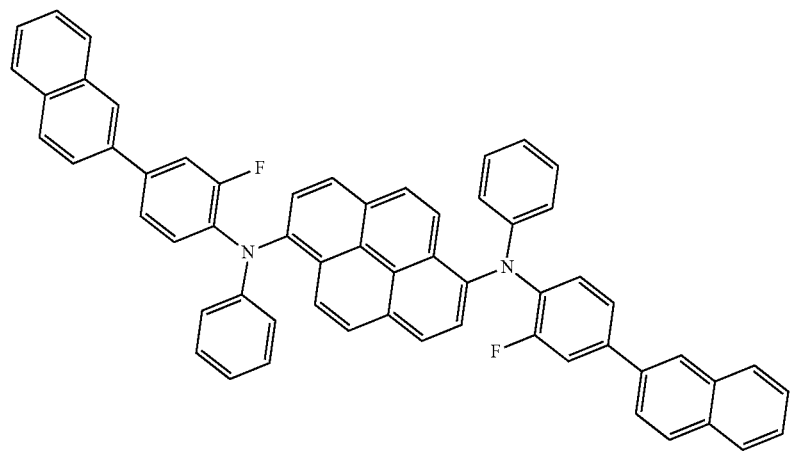
D-81
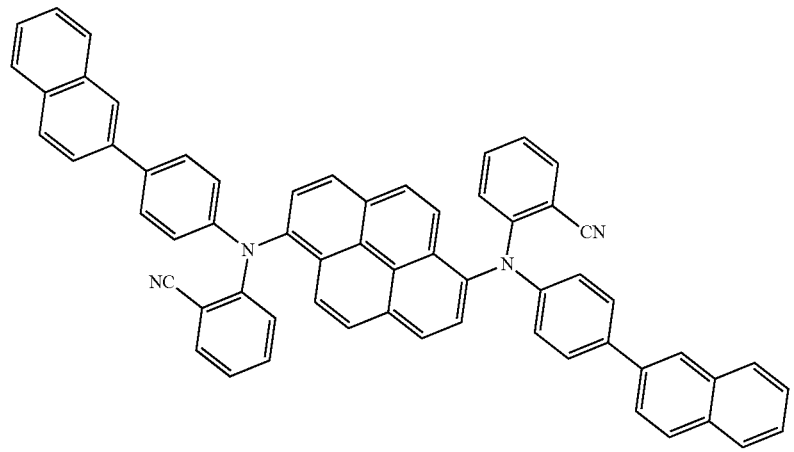
D-82
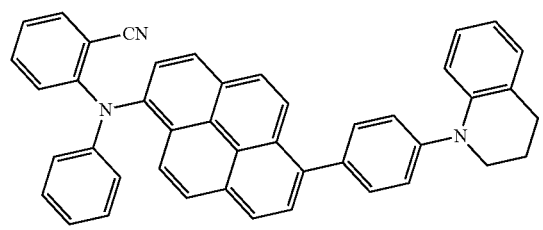
D-83
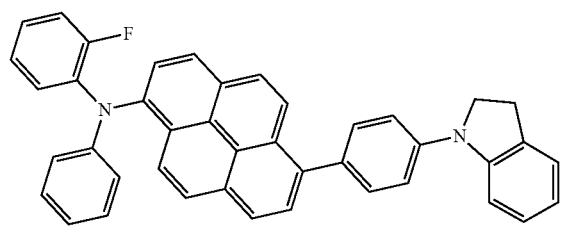

-continued
D-84
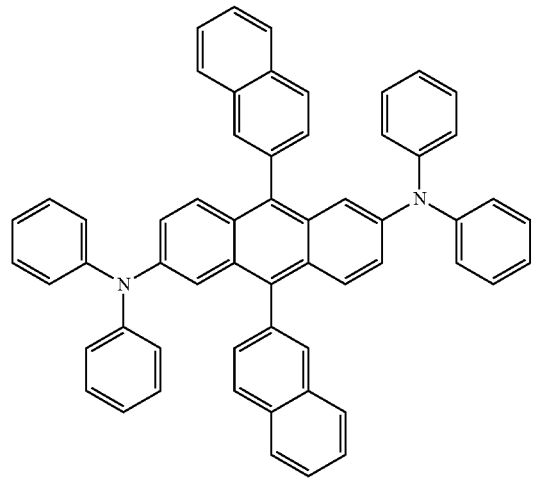
D-85
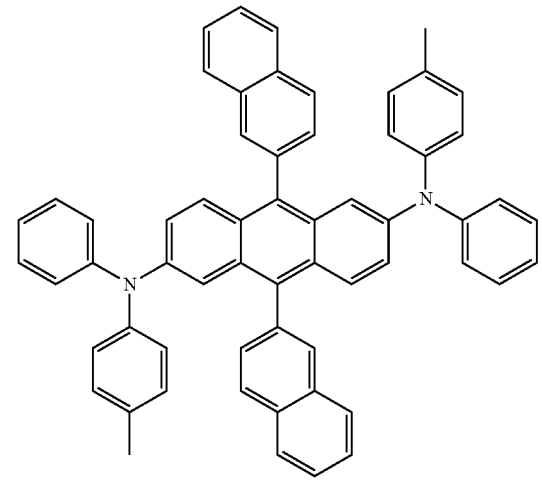
D-86
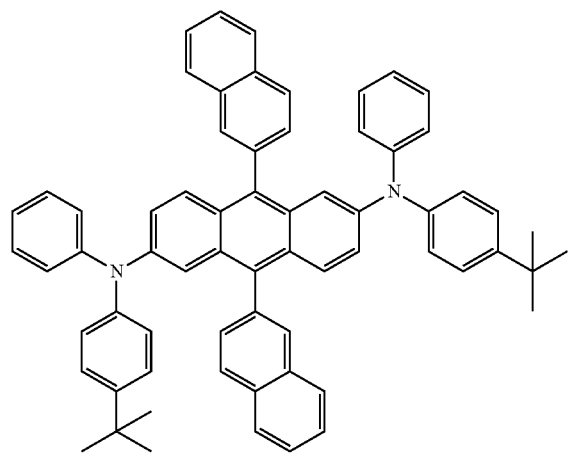
D-87
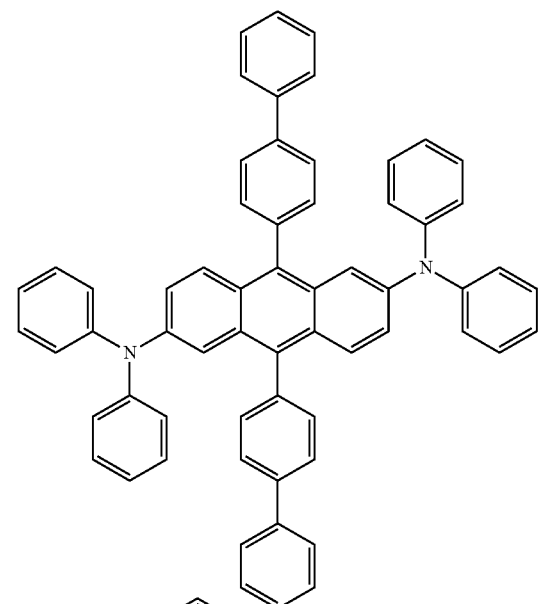
D-88
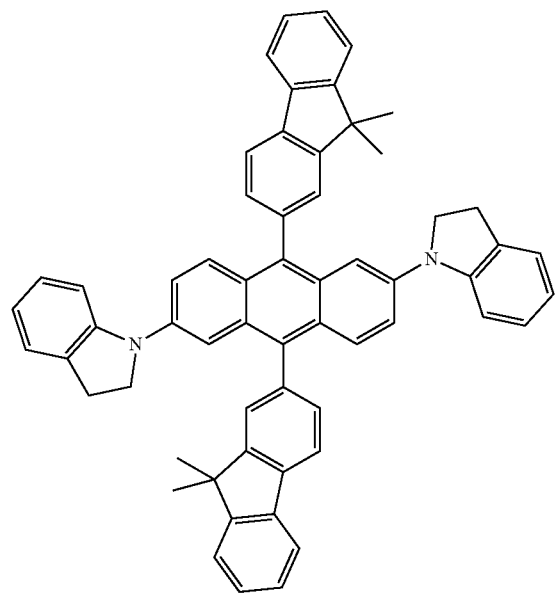
D-89
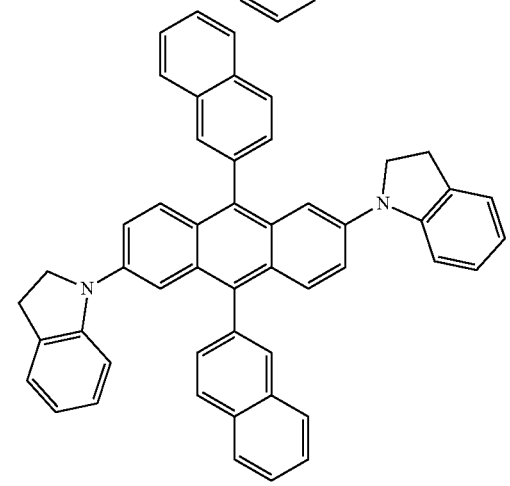

-continued
D-90
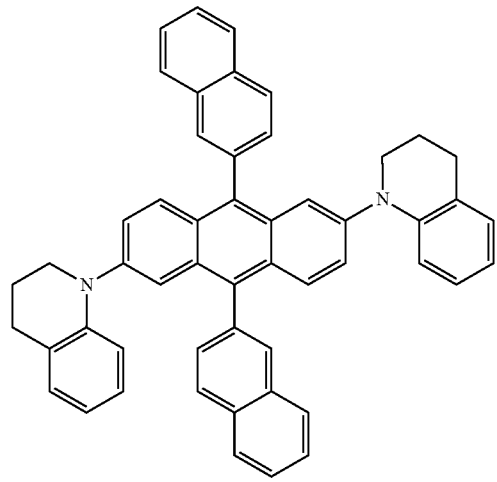
D-91
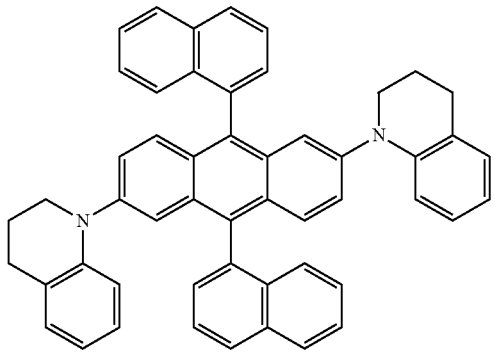
D-92
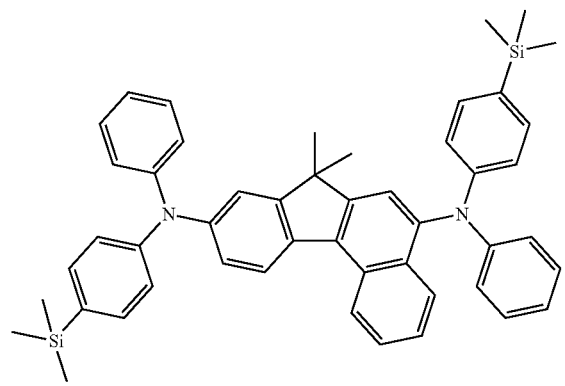
D-93
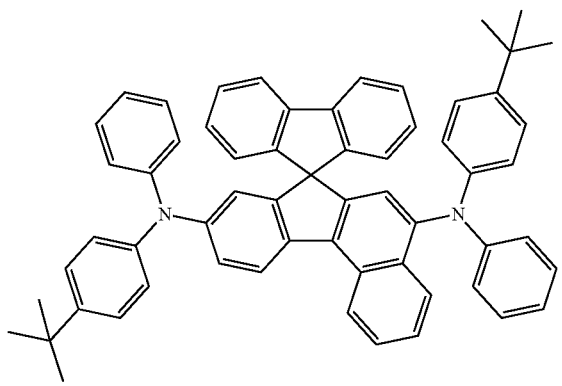
D-94
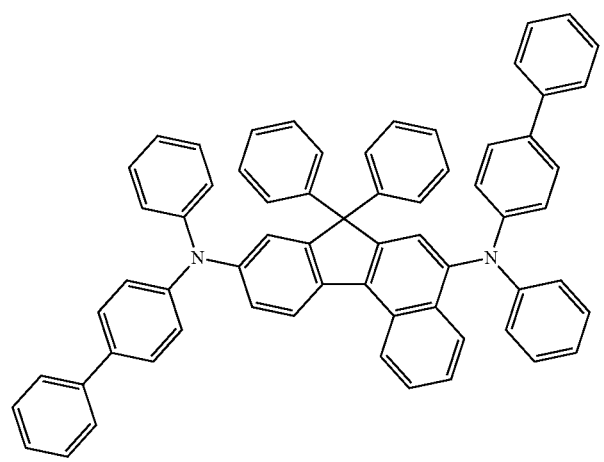

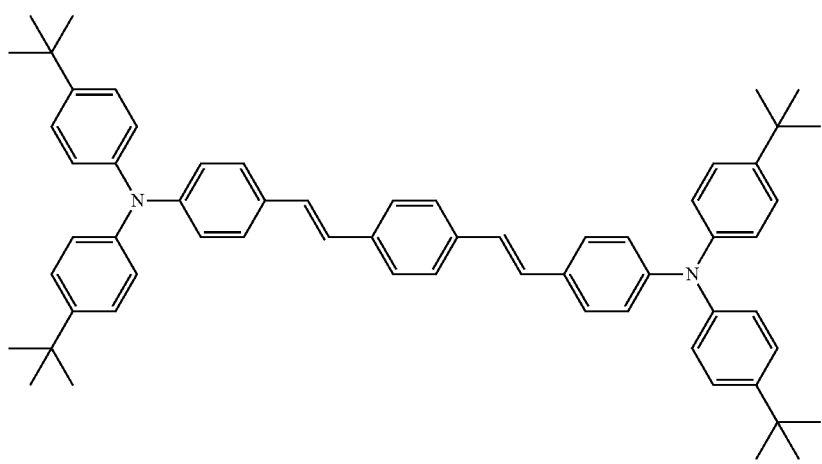
D-95
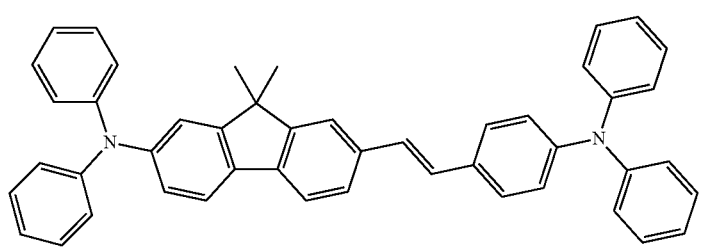
D-96
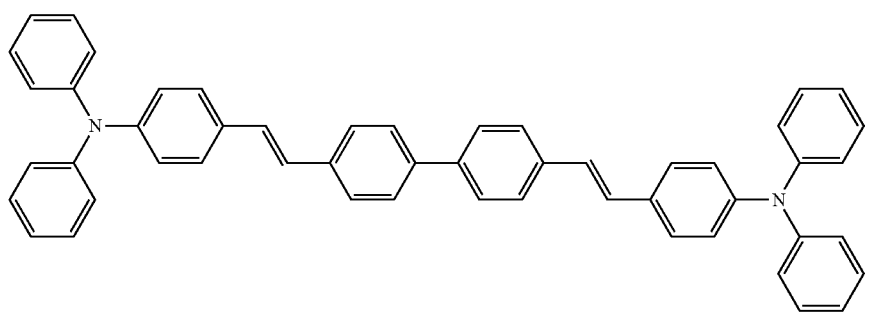
D-97
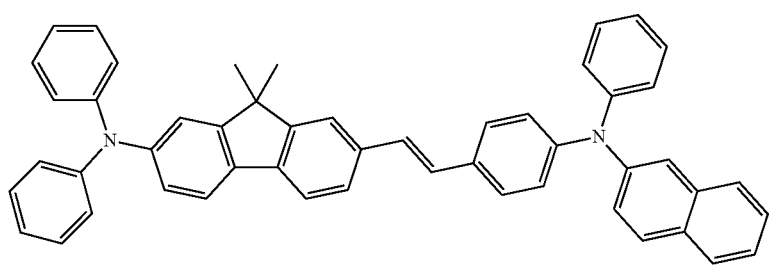
D-98
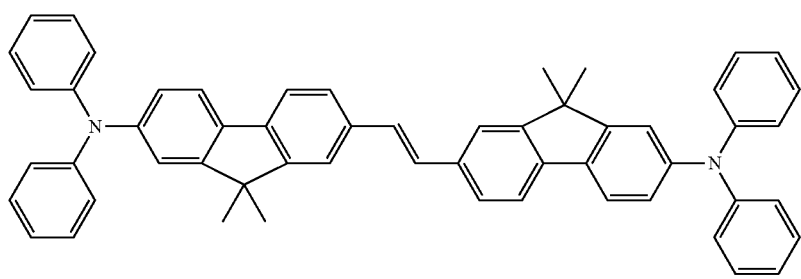
D-99

-continued

D-100
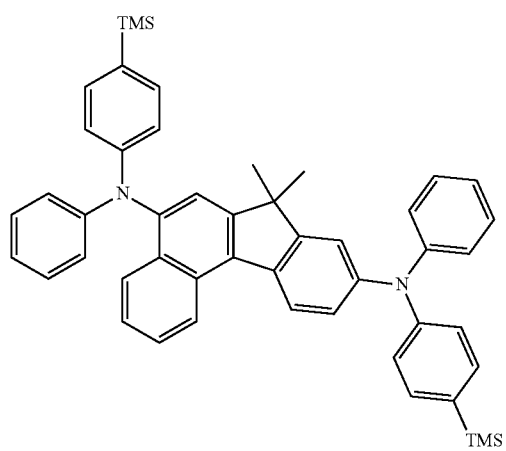

D-101
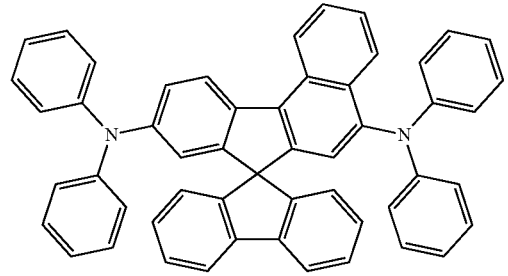

D-102

D-103
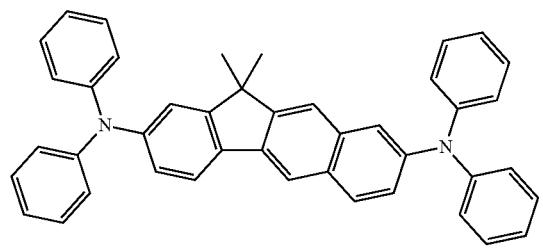

The dopant to be comprised in the organic electroluminescent device of the present disclosure is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

The compounds represented by the following formulae 100 to 102 may be used as the dopant to be comprised in the organic electroluminescent device of the present disclosure.

(100)

(101)
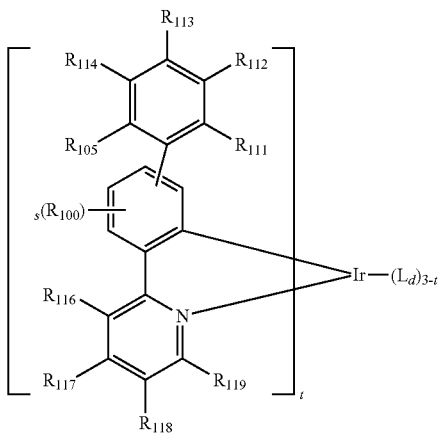

-continued (102)
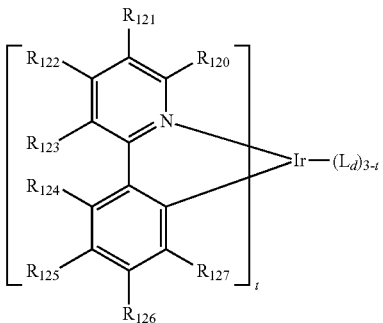

wherein $L_d$ is selected from the following structures:

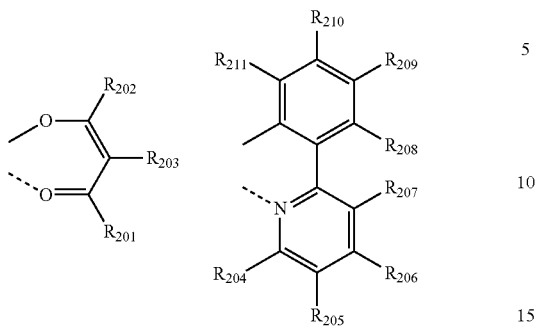

$R_{100}$ represents hydrogen, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a substituted or unsubstituted (C1-C30)alkyl, a substituted or unsubstituted (C3-C30)cycloalkyl, a cyano, or a substituted or unsubstituted (C1-C30)alkoxy; and $R_{120}$ to $R_{123}$, each independently, may be linked to an adjacent substituent(s) to form a fused ring, for example, a substituted or unsubstituted quinoline;

$R_{124}$ to $R_{127}$, each independently, represent hydrogen, deuterium, a halogen, a substituted or unsubstituted (C1-C30)alkyl, or a substituted or unsubstituted (C6-C30)aryl; $R_{124}$ to $R_{127}$, each independently, may be linked to an adjacent substituent(s) to form a fused ring, for example, a substituted or unsubstituted fluorene, a substituted or unsubstituted dibenzothiophene, or a substituted or unsubstituted dibenzofuran;

$R_{201}$ to $R_{211}$, each independently, represent hydrogen, deuterium, a halogen, a substituted or unsubstituted (C1-C30)alkyl, a substituted or unsubstituted (C3-C30)cycloalkyl, or a substituted or unsubstituted (C6-C30)aryl; $R_{201}$ to $R_{211}$, each independently, may be linked to an adjacent substituent(s) to form a fused ring, for example, a substituted or unsubstituted dibenzofuran, or a substituted or unsubstituted dibenzothiophene;

r and s, each independently, represent an integer of 1 to 3; where r or s is an integer of 2 or more, each of $R_{100}$ may be the same or different; and t represents an integer of 1 to 3.

Specifically, the phosphorescent dopant includes the following:

D-1

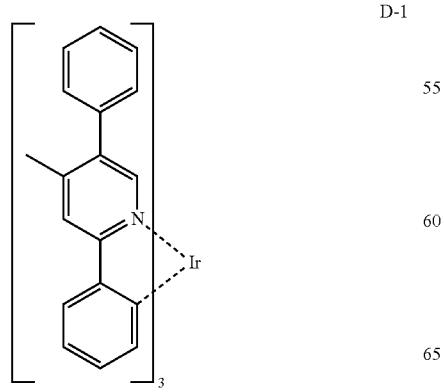

D-2

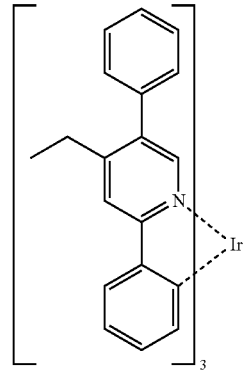

D-3

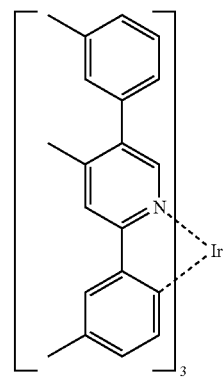

D-4

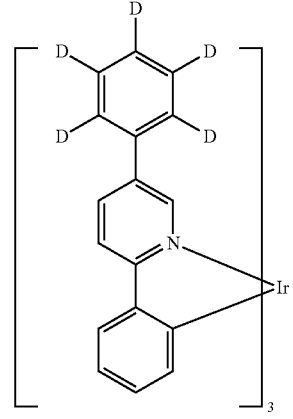

D-5

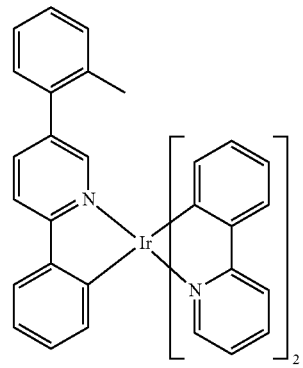

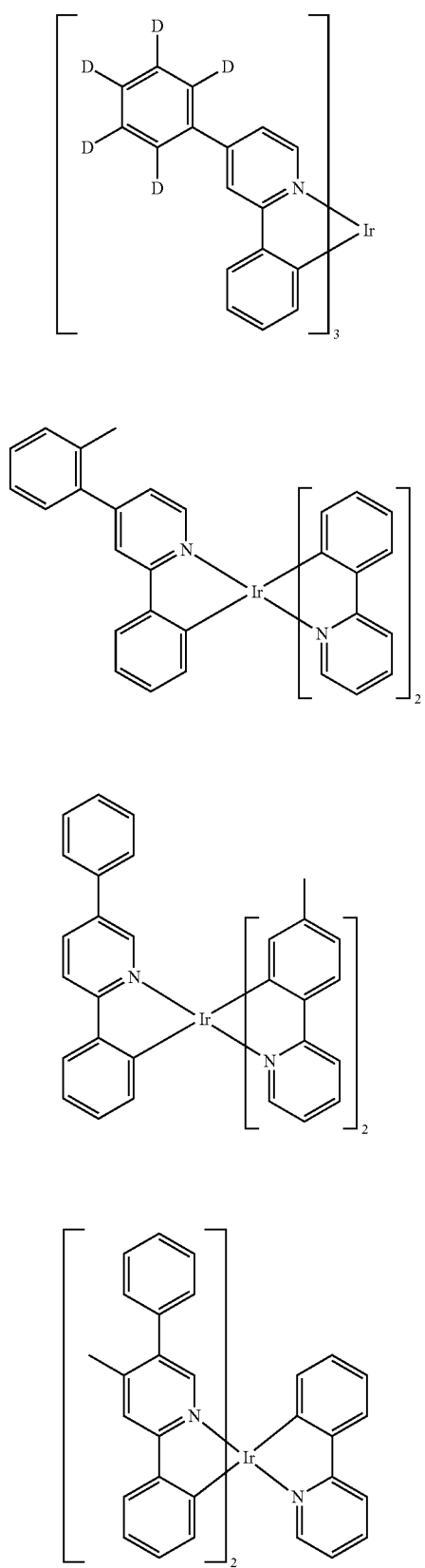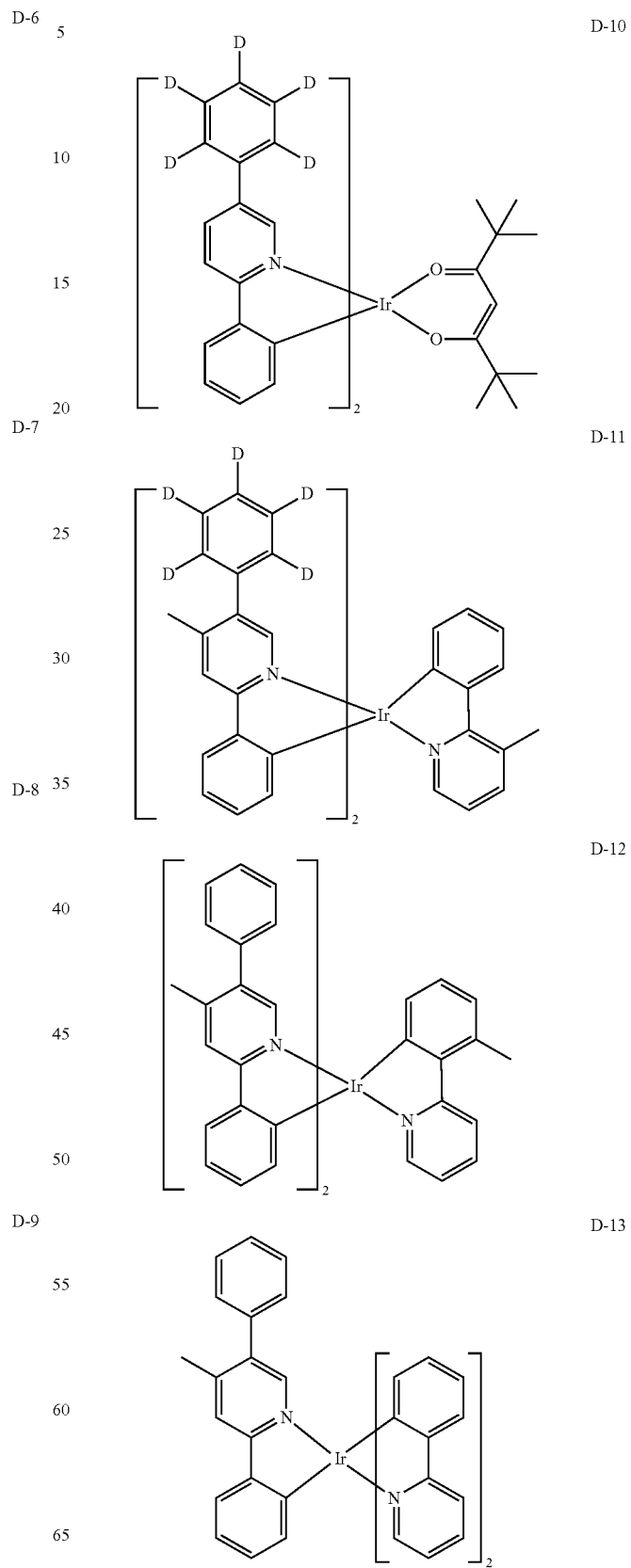

D-14
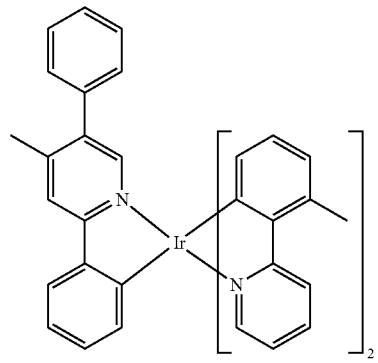
D-15
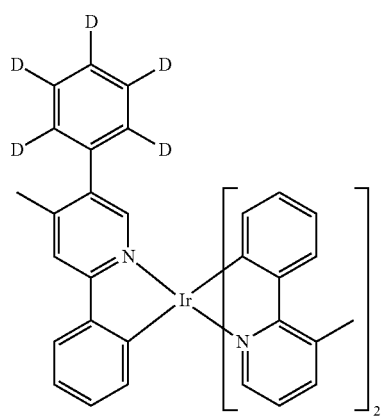
D-16
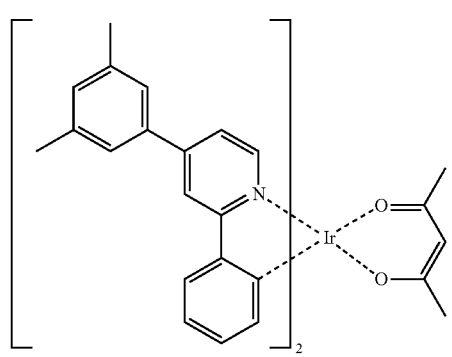
D-17
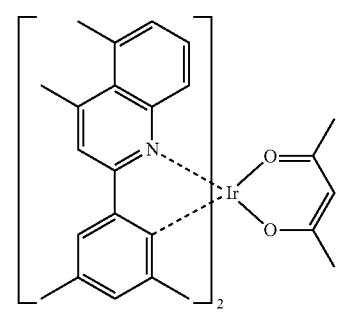
D-18
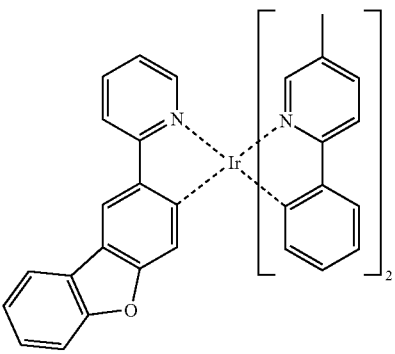
D-19
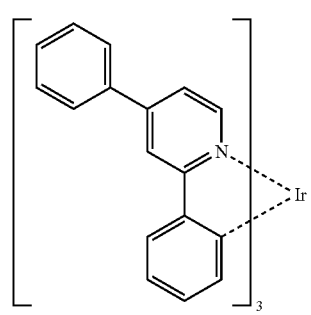
D-20
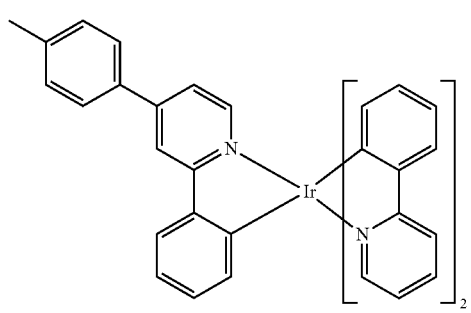
D-21
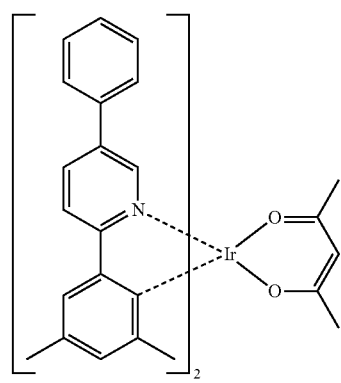

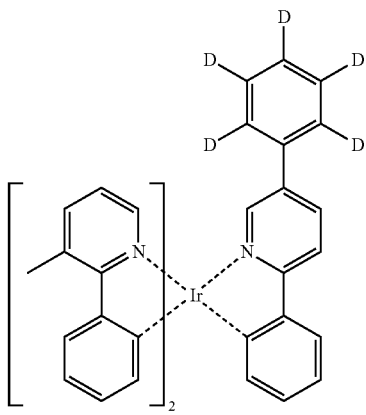 D-22
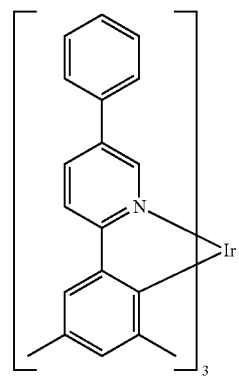 D-23
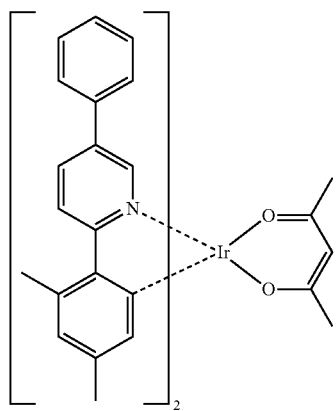 D-24
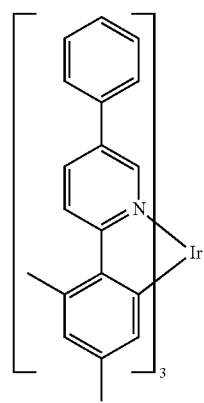 D-25
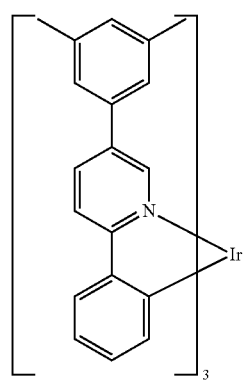 D-26
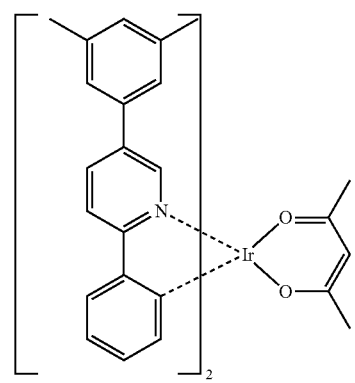 D-27
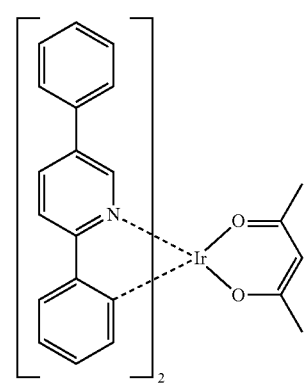 D-28
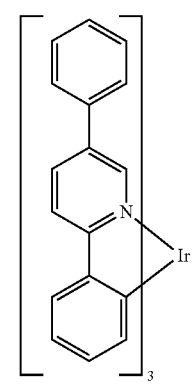 D-29

-continued
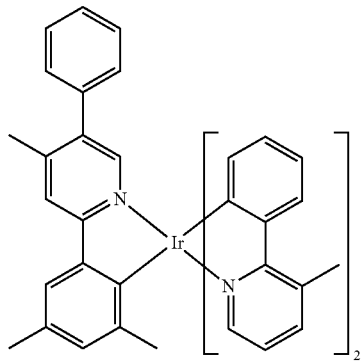
D-30
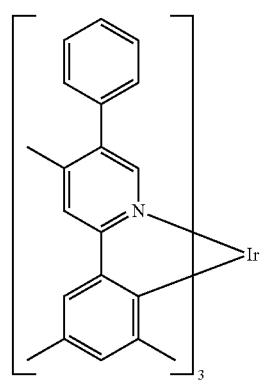
D-31
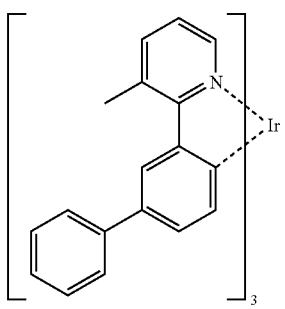
D-32
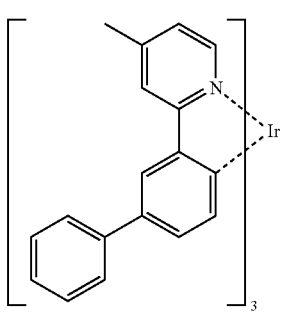
D-33
-continued
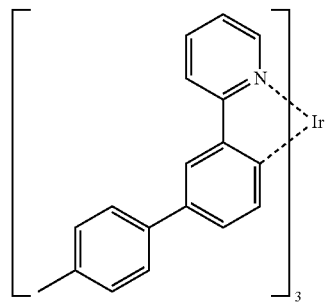
D-34
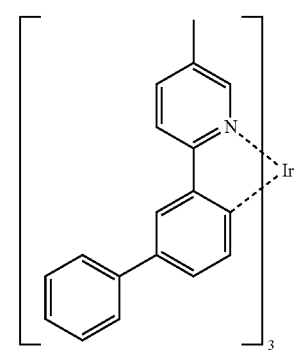
D-35
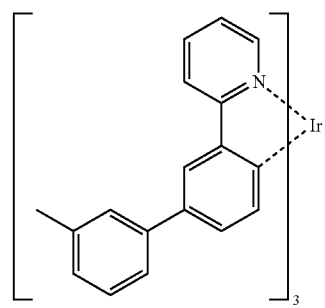
D-36
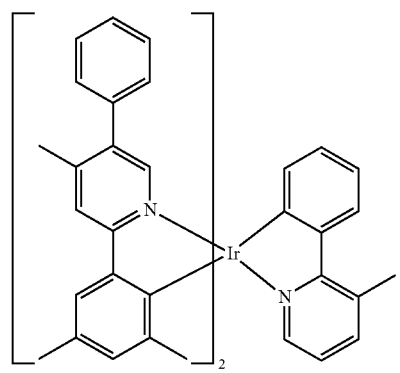
D-37

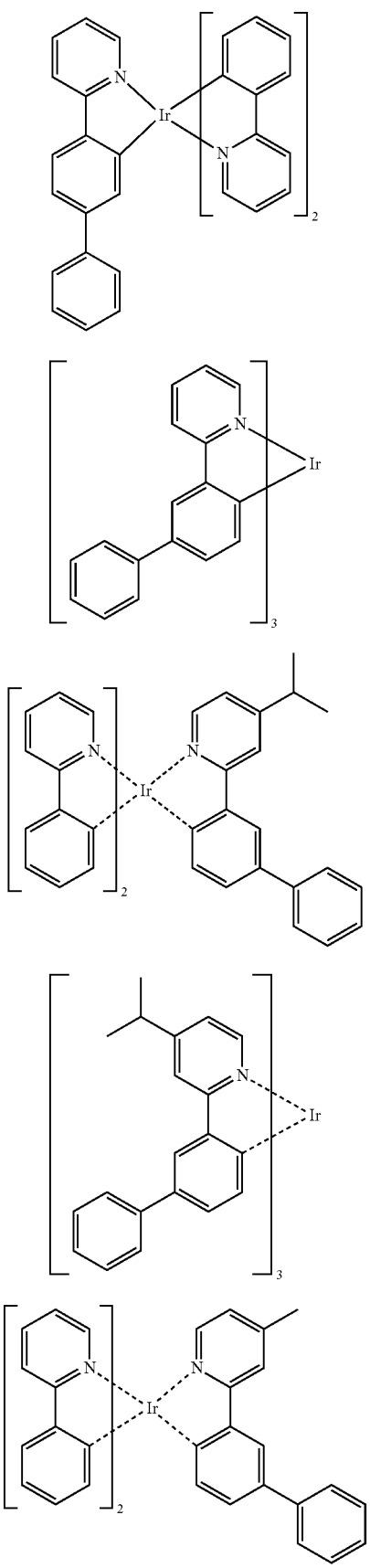

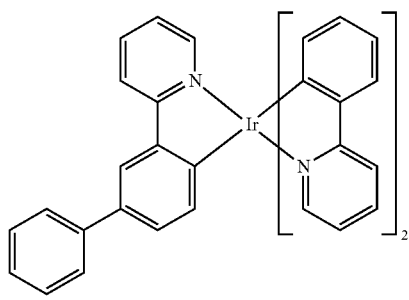
D-47
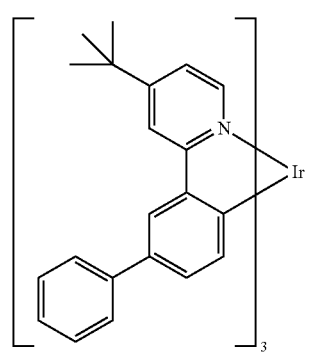
D-48
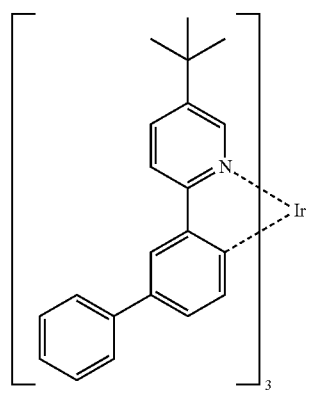
D-49
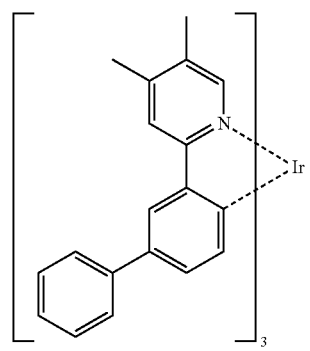
D-50
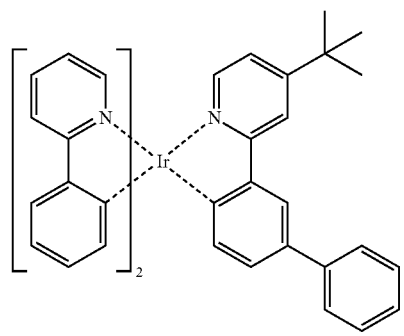
D-51
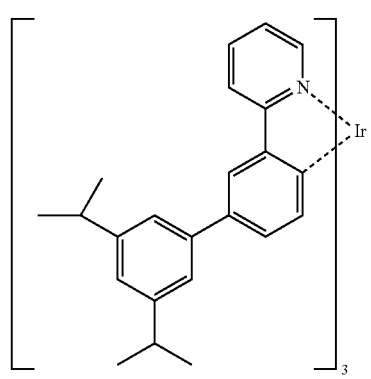
D-52
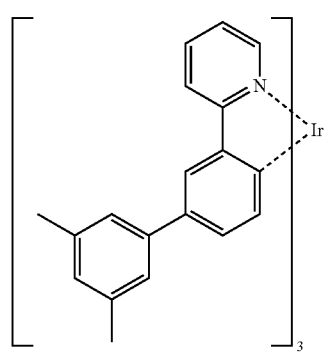
D-53
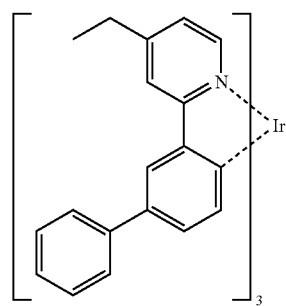
D-54

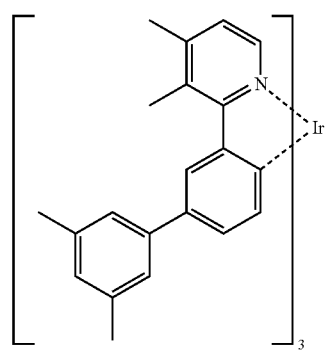 D-55
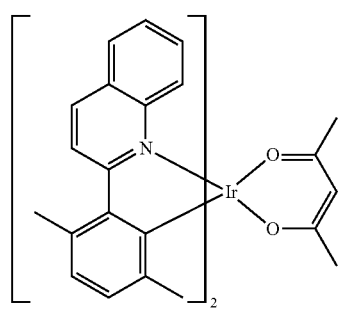 D-56
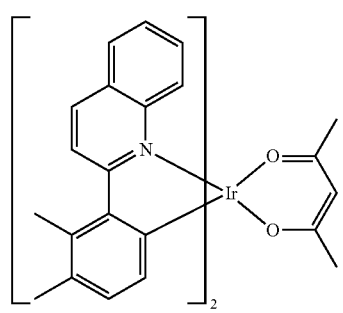 D-57
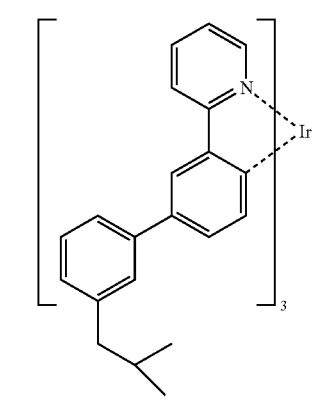 D-58
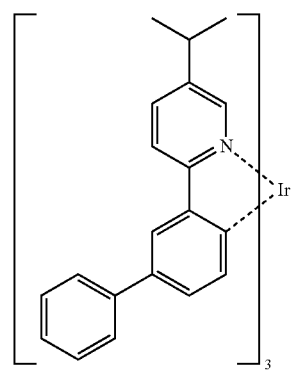 D-59
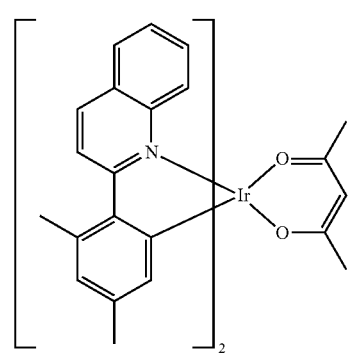 D-60
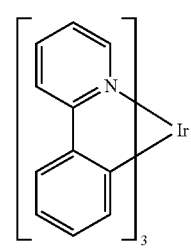 D-61
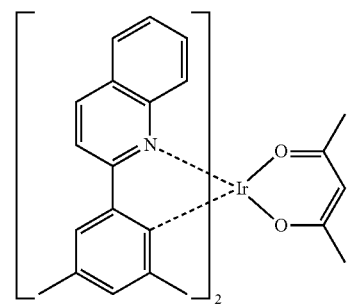 D-52

D-63
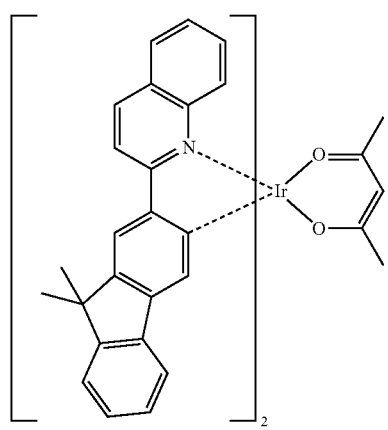
D-64
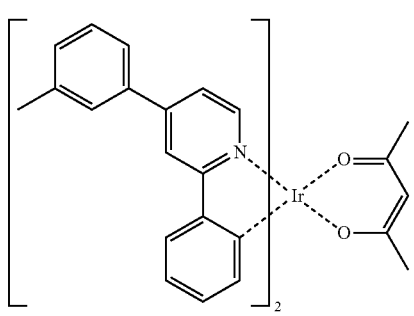
D-65
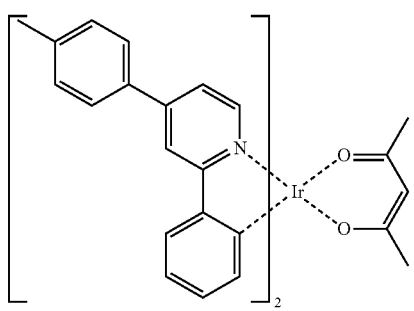
D-66
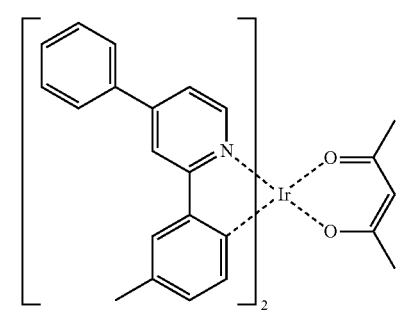
D-67
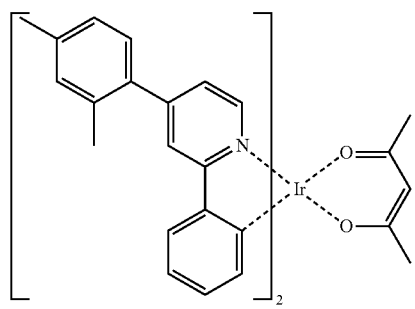
D-68
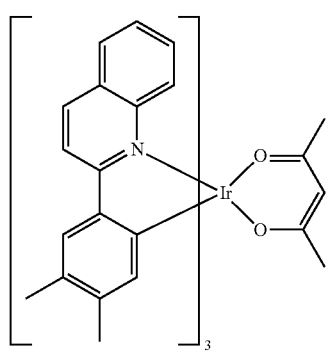
D-69
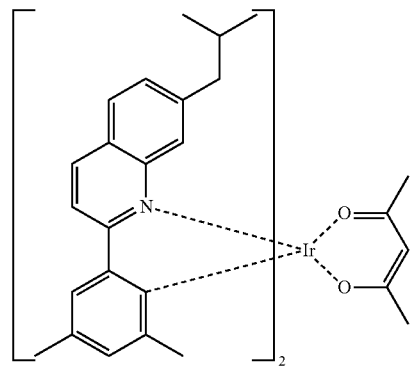
D-70
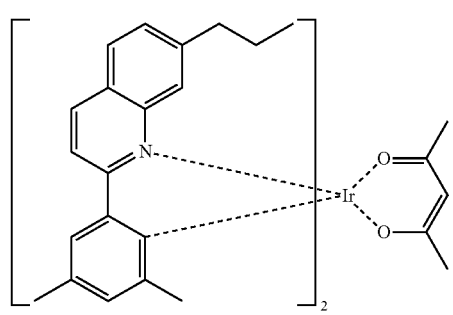

D-71
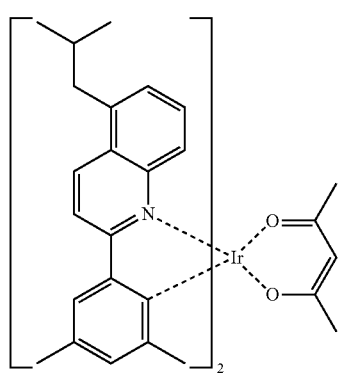
D-72
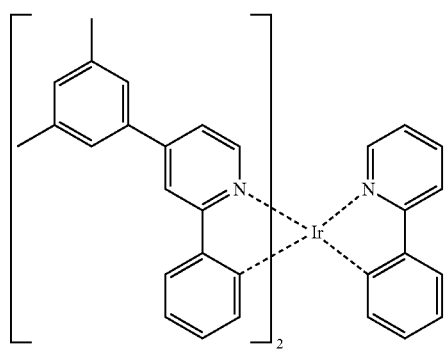
D-73
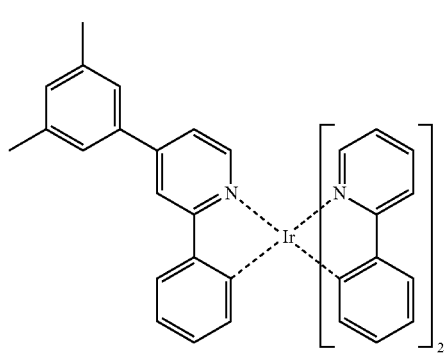
D-74
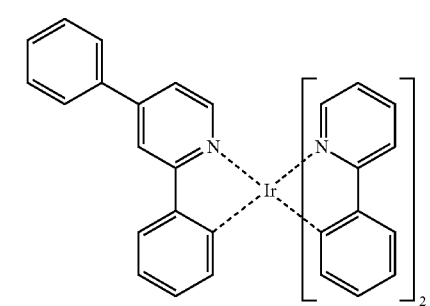
D-75
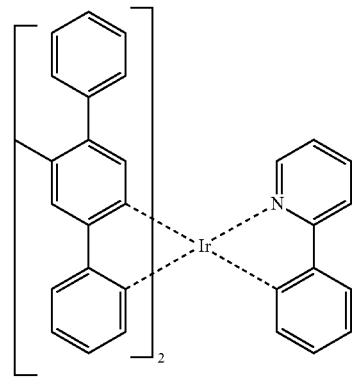
D-76
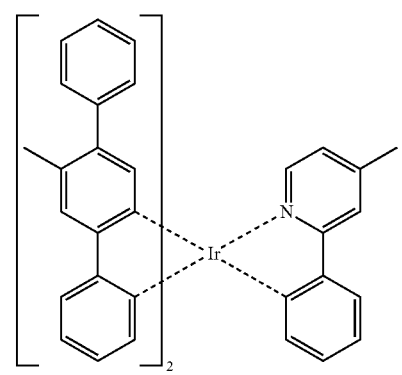
D-77
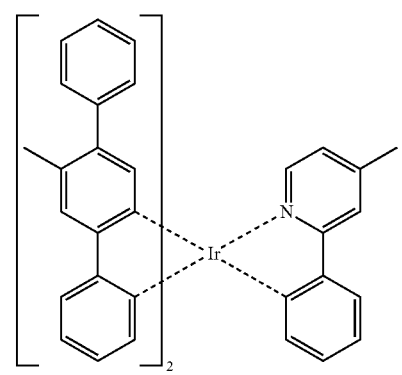
D-78
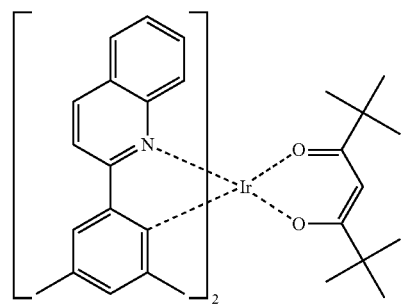

-continued
D-79
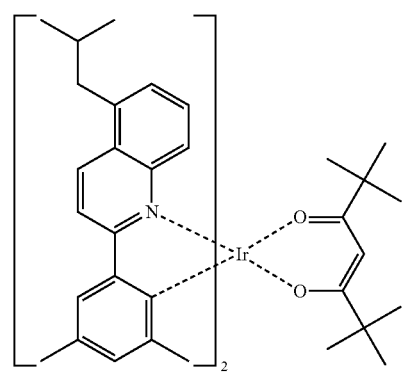
D-80
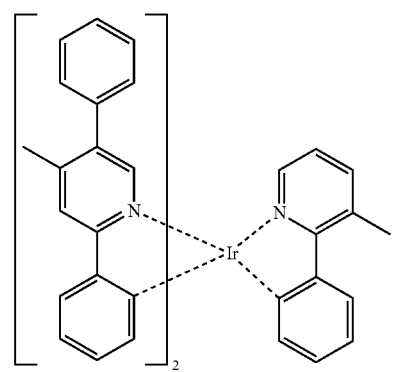
D-81
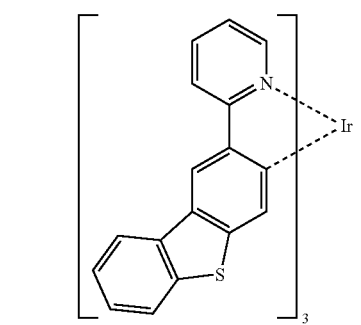
D-82
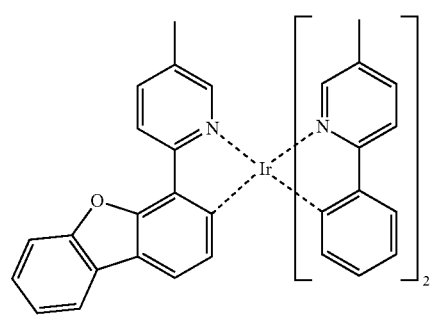
-continued
D-83
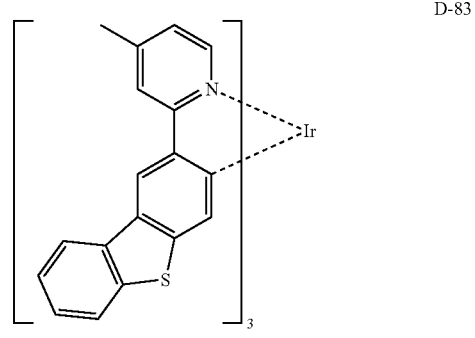
D-84
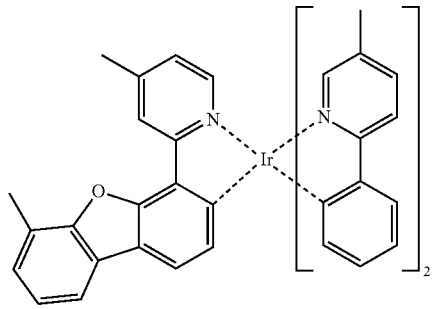
D-85
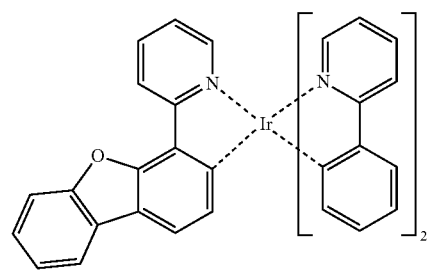
D-86
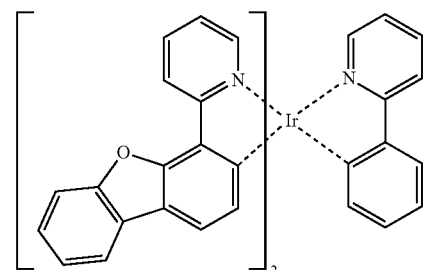
D-87
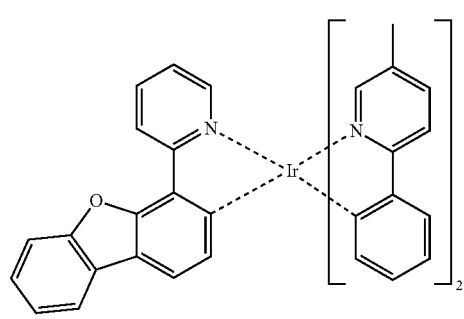

D-88
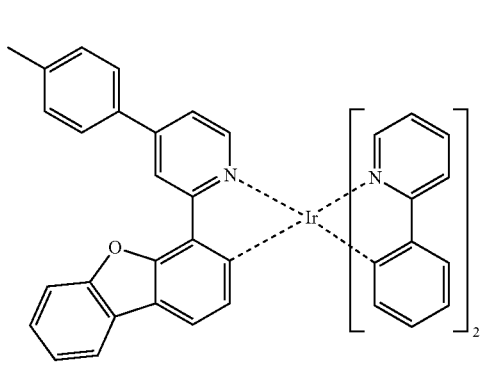
D-89
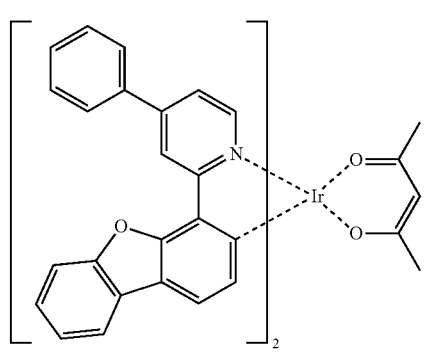
D-90
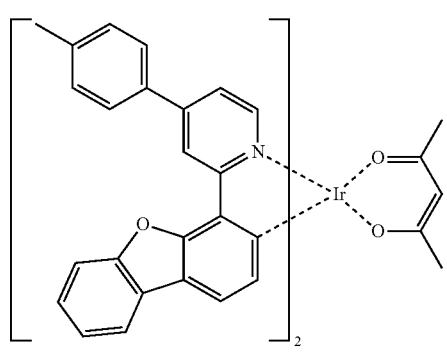
D-91
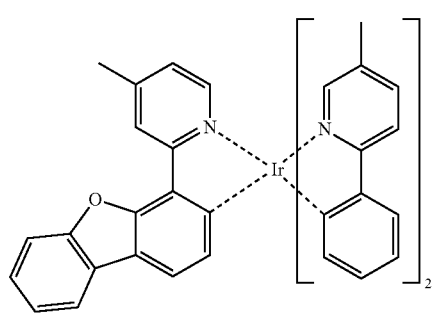
D-92
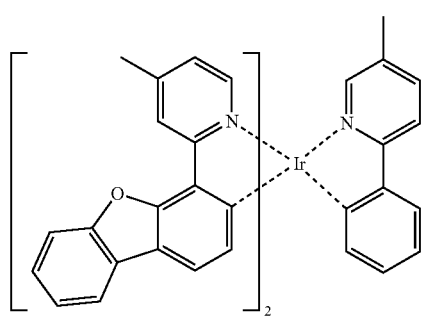
D-93
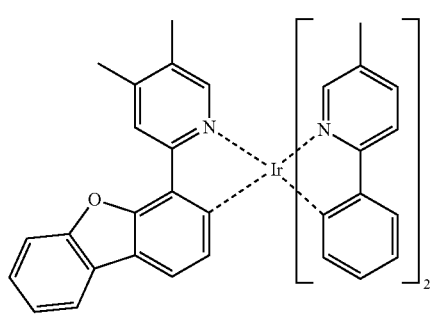
D-94
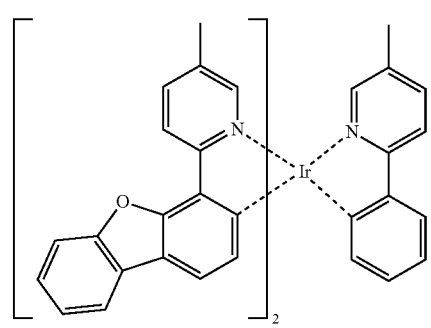
D-95
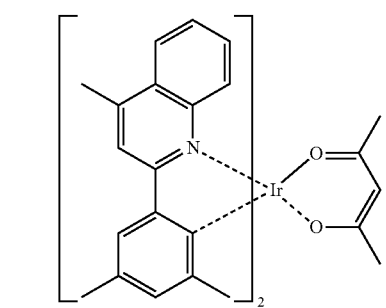
D-96
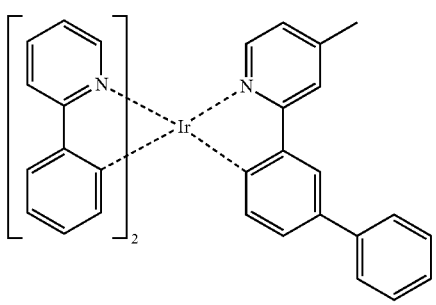

D-97
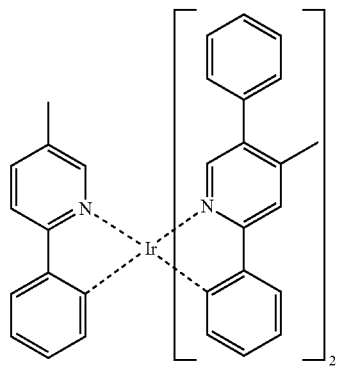
D-98
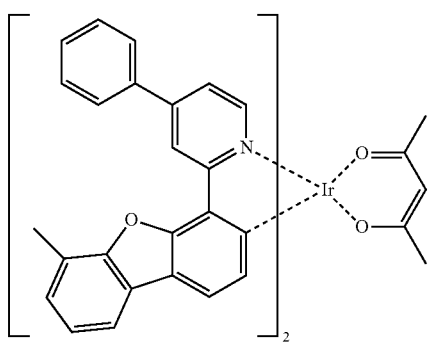
D-99
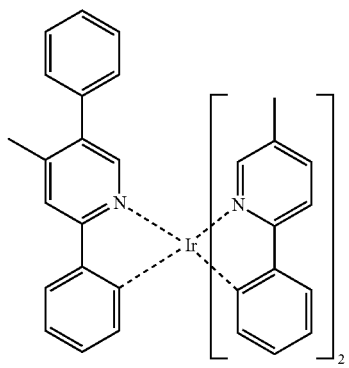
D-100
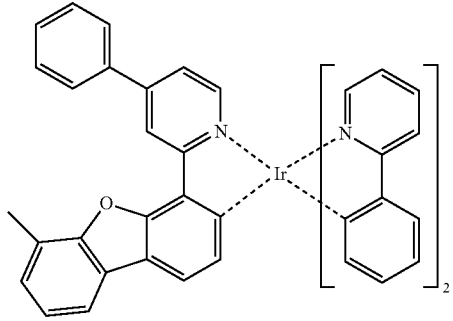
D-101
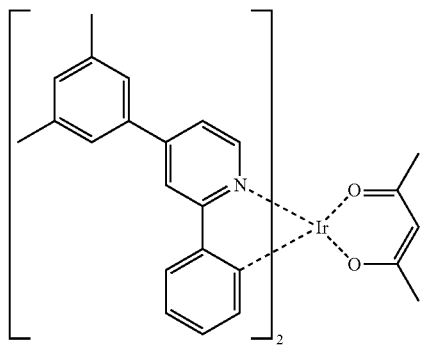
D-102
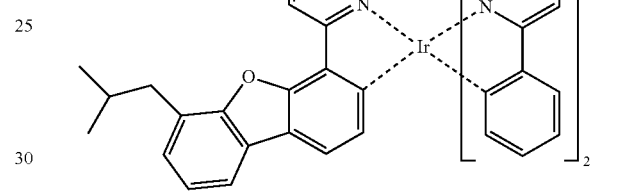
D-103
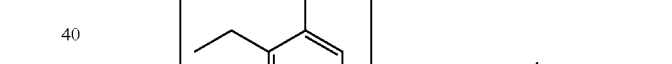
D-104
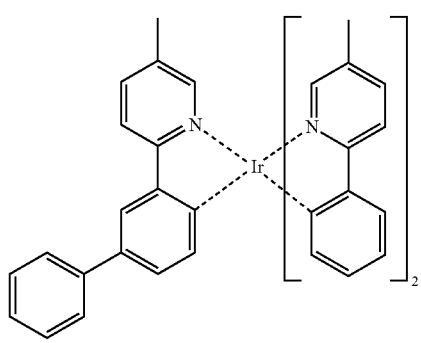

D-105
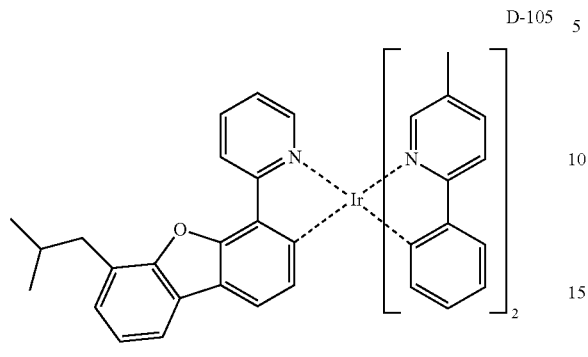
D-109
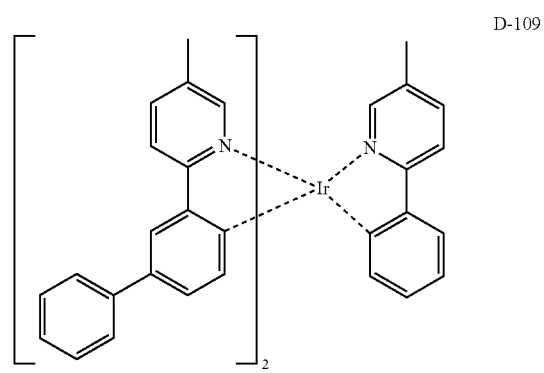
D-106
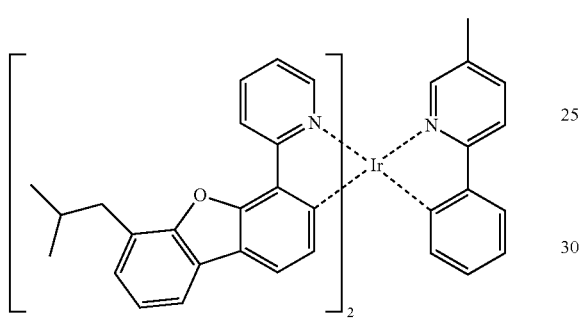
D-110
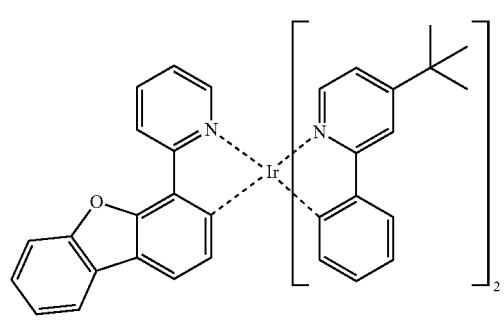
D-107
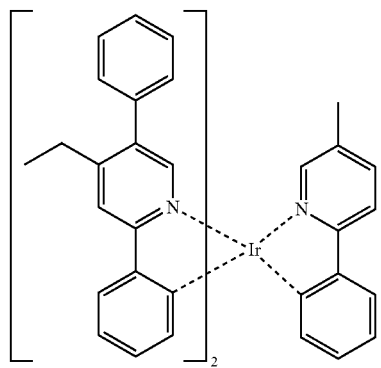
D-111
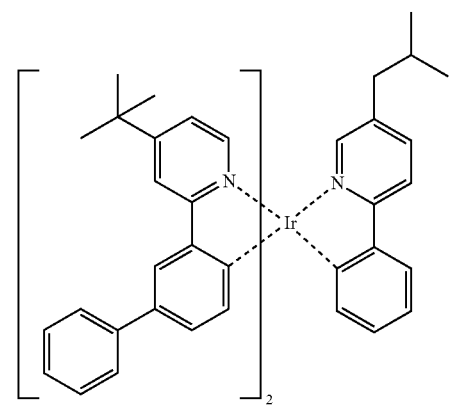
D-108
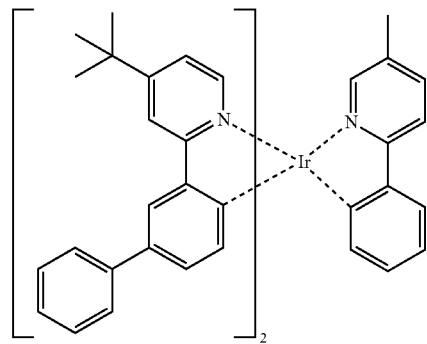
D-112
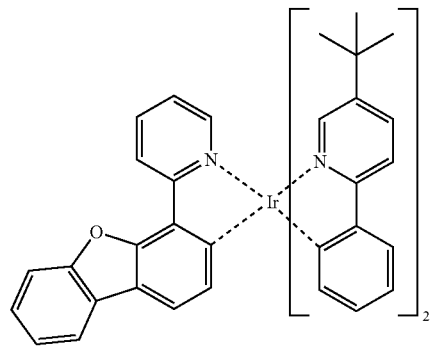

D-113
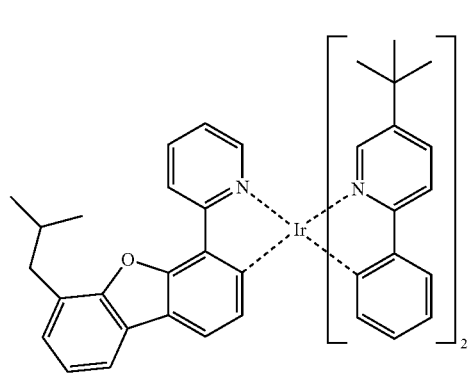
D-114
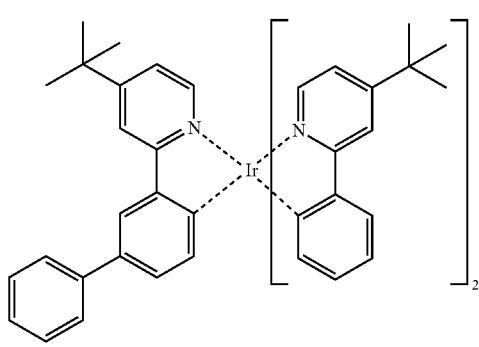
D-115
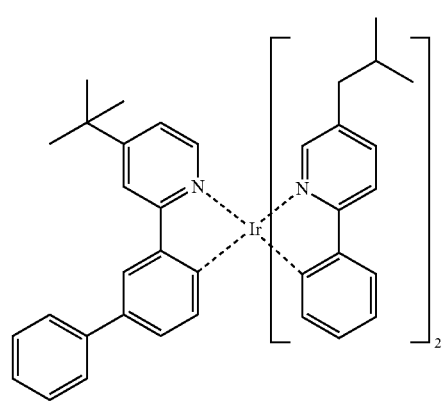
D-116
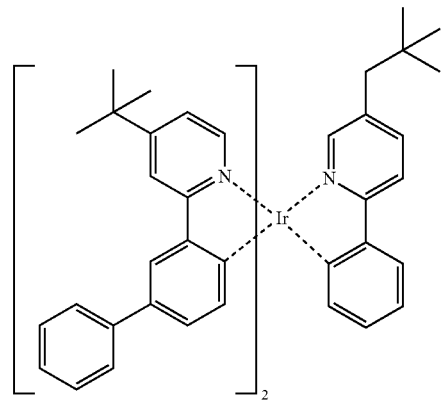
D-117
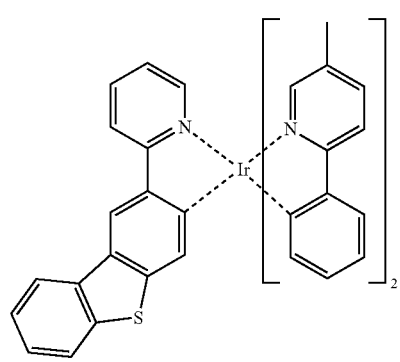
D-118
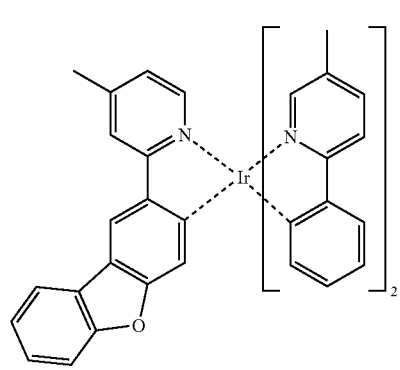
D-119
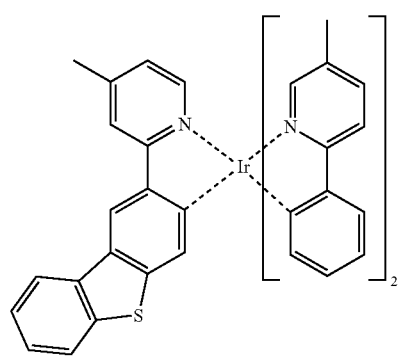
D-120
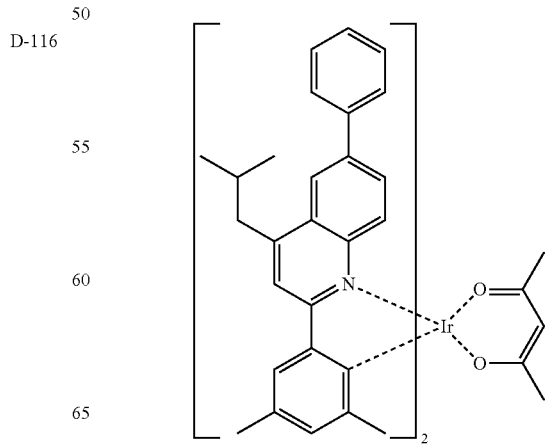

D-121
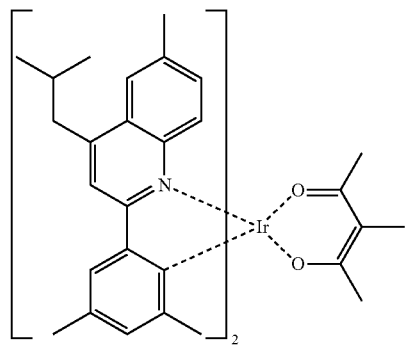
D-122
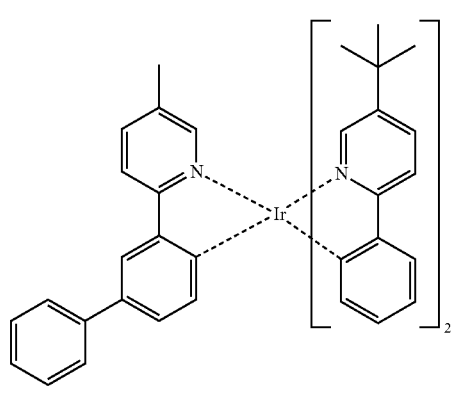
D-123
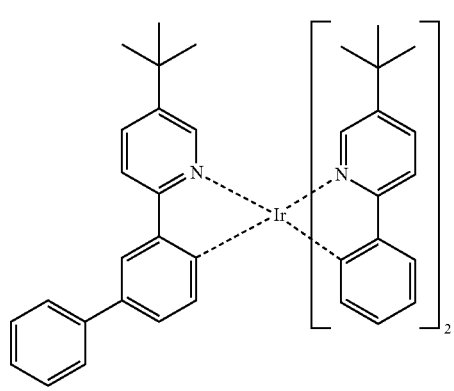
D-124
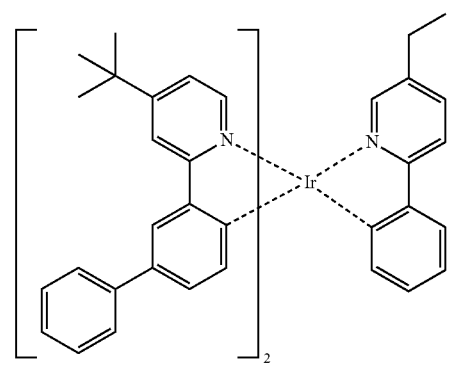
D-125
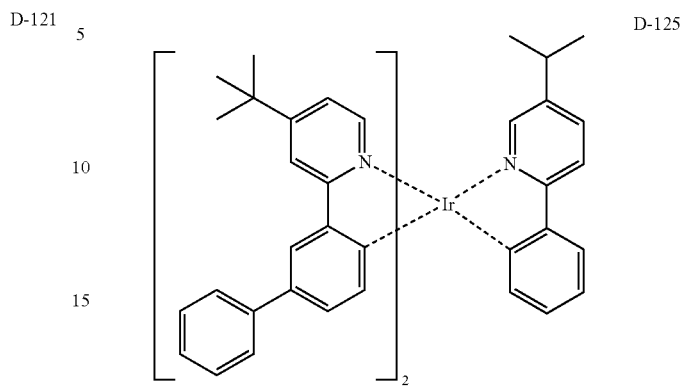
D-126
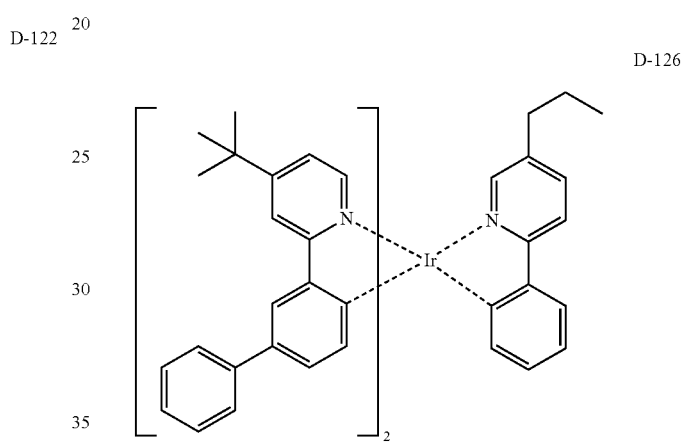
D-127
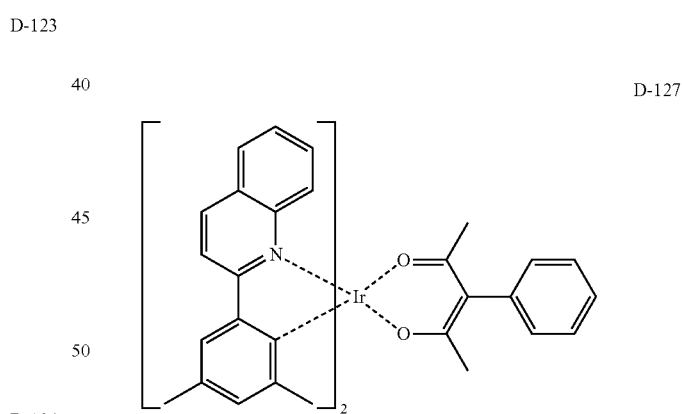
D-128
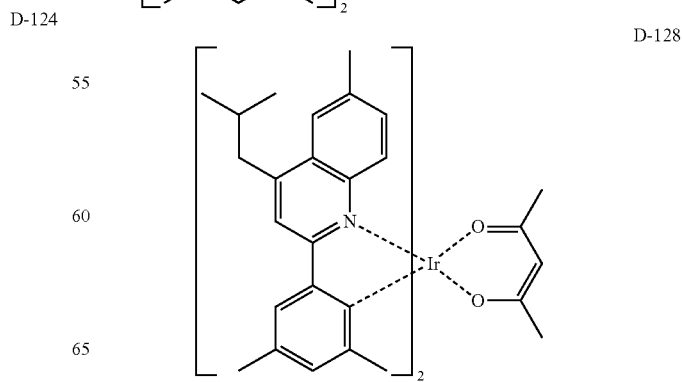

D-129
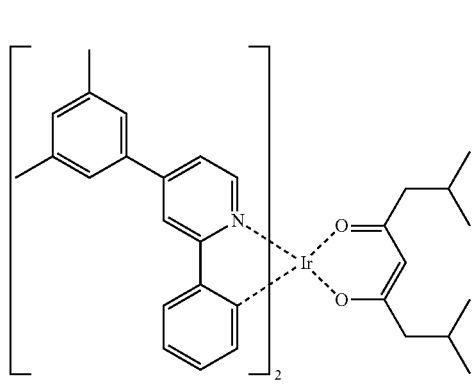
D-130
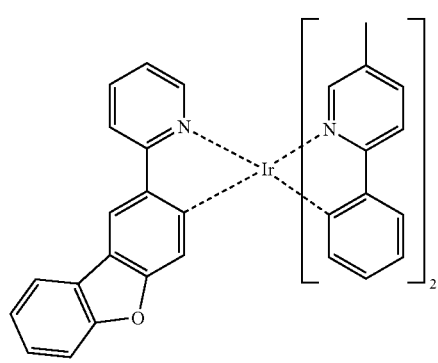
D-131
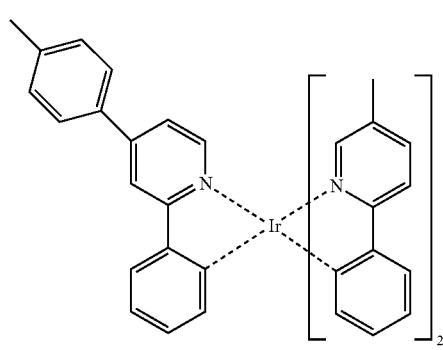
D-132
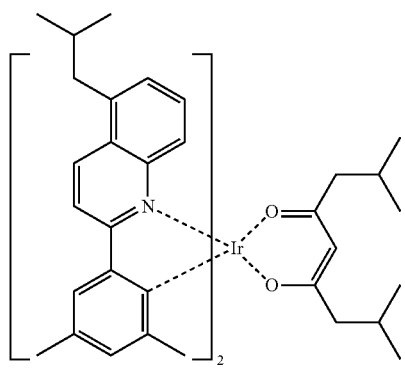
D-133
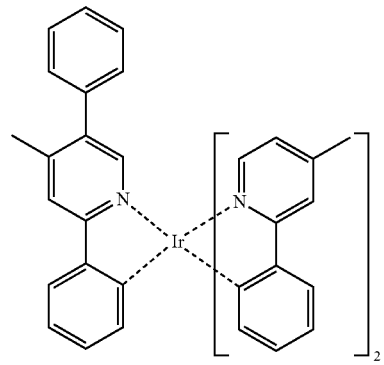
D-134
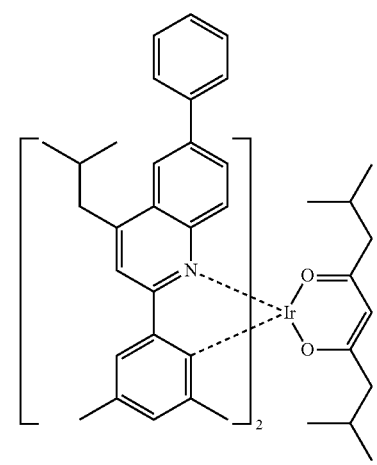
D-135
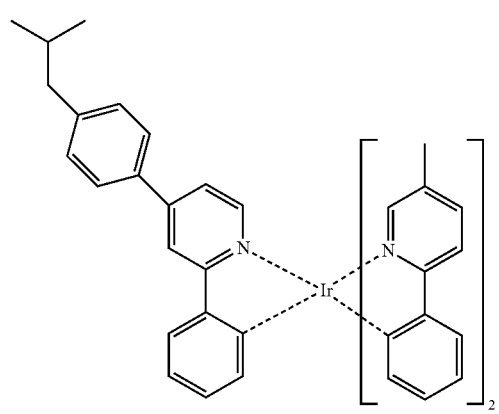
D-136
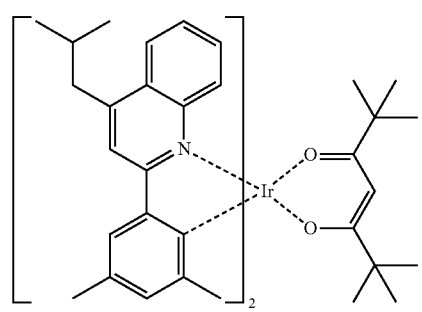

D-137 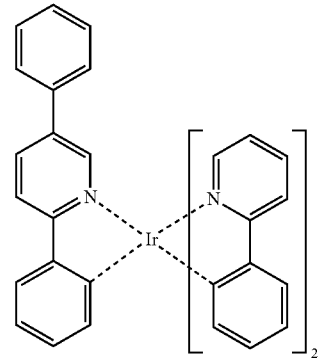
D-138 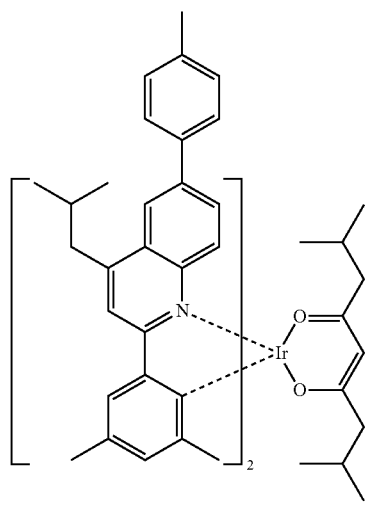
D-139 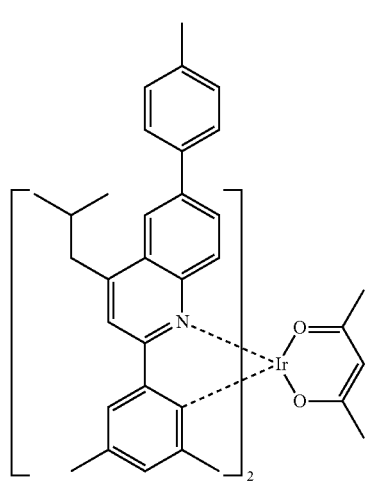
D-140 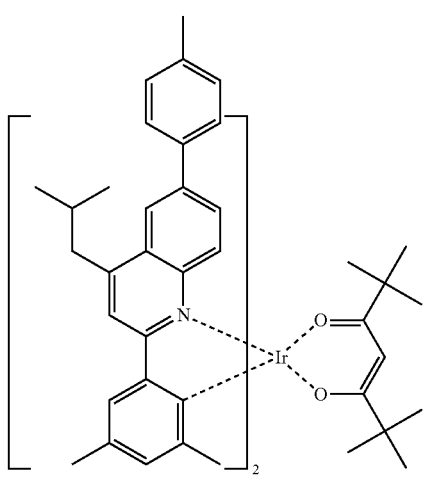
D-141 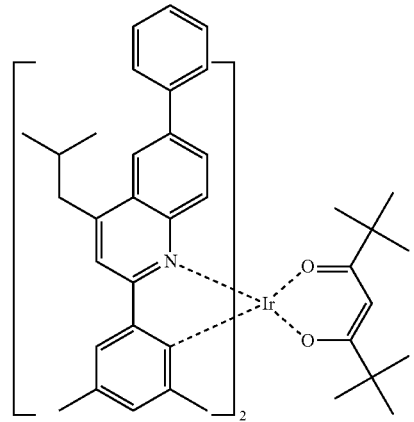
D-142 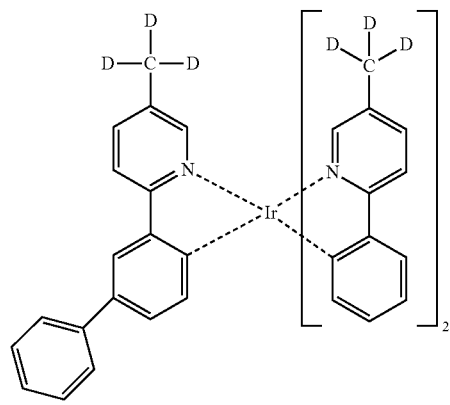
D-143 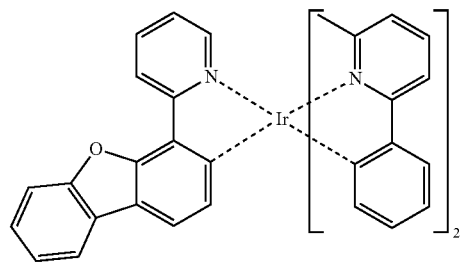

-continued

D-144
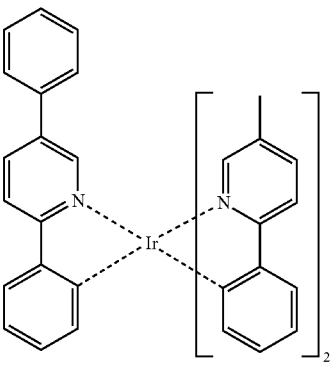

D-145
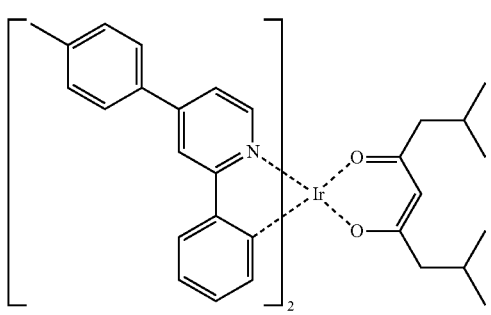

D-146
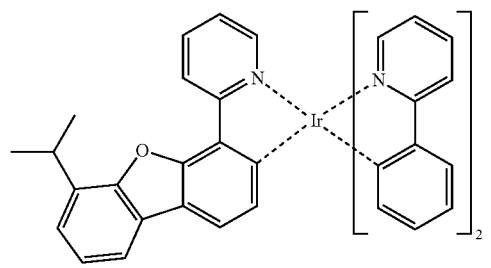

D-147
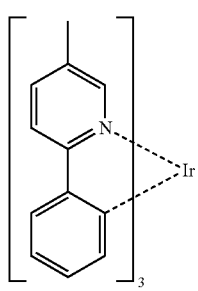

D-148
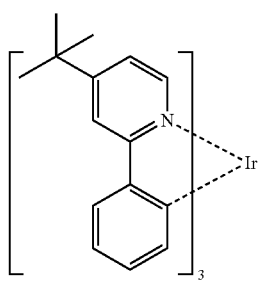

The OLED of the present disclosure comprises an organic electroluminescent compound of formula 1, and may further comprise at least one compound selected from the group consisting of arylamine-based compounds and styrylarylamine-based compounds.

In the OLED of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise a light-emitting layer and a charge generating layer.

In the OLED of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the OLED of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

Hereinafter, the organic electroluminescent compound of the present disclosure, the preparation method of the compound, and the luminescent properties of the OLED comprising the electron buffering material or the electron transport material comprising the compound of the present disclosure will be explained in detail with reference to the following examples.

[Example 1] Preparation of Compound C-24

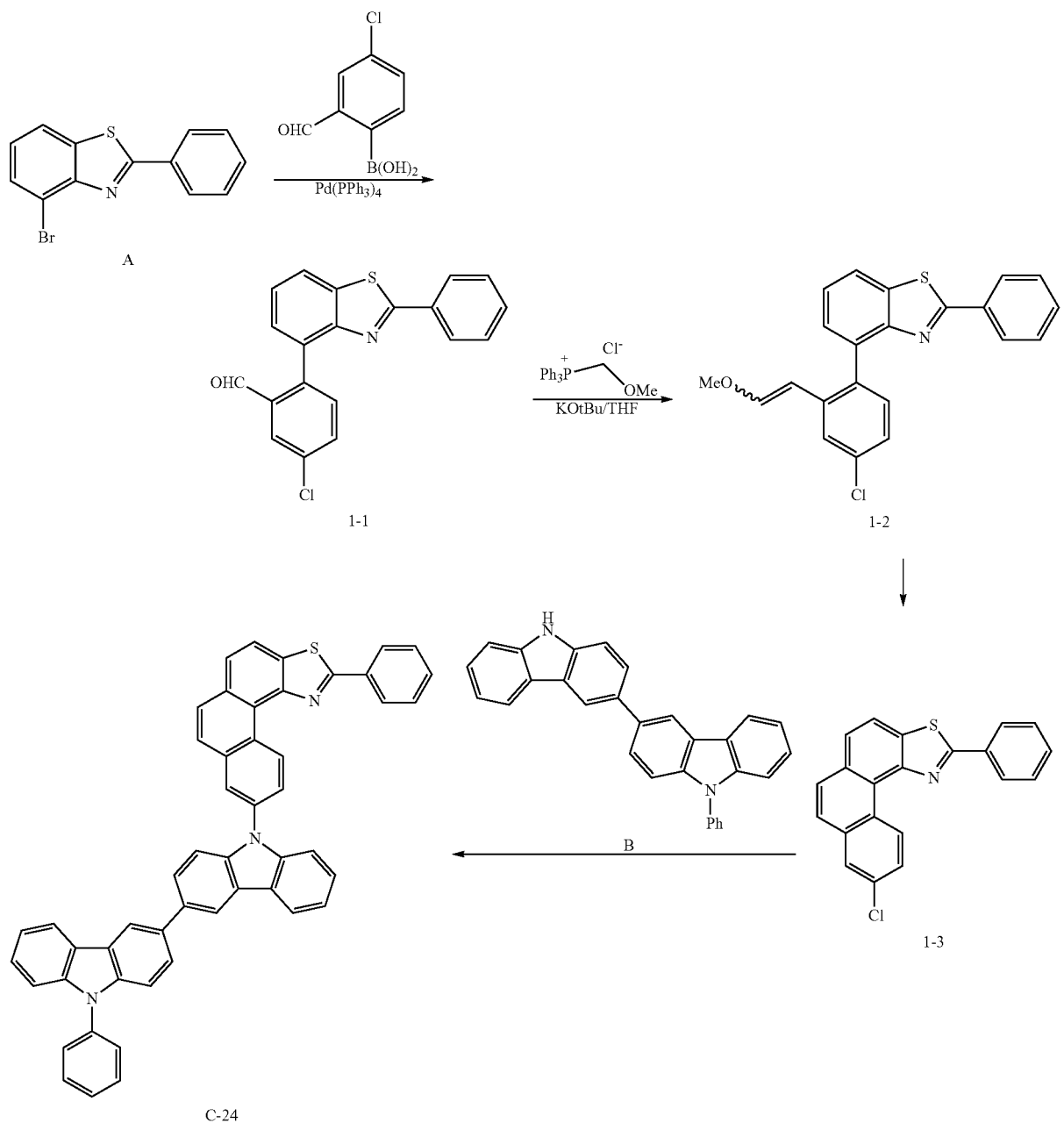

1) Preparation of Compound 1-1

After adding compound A (CAS: 1044146-16-8, 36 g, 124 mmol), 4-chloro-2-formylbenzene boronic acid (25.2 g, 136 mmol), tetrakis(triphenylphosphine)palladium (5.7 g, 5.0 mmol), sodium carbonate (33 g, 150 mmol), toluene (600 mL), EtOH (150 mL), and distilled water (150 mL) into a reaction vessel, the mixture was stirred at 140° C. for 3 hours. After completion of the reaction, the precipitated solid was washed with distilled water and MeOH. The obtained compound 1-1 was used in the next reaction without further purification.

2) Preparation of Compound 1-2

After introducing compound 1-1 (45.6 g, 130 mmol), (methoxymethyl)triphenylphosphonium chloride (74.3 g, 217 mmol), and tetrahydrofuran (1500 mL) into a reaction vessel, the reaction mixture was stirred for 5 minutes, and then potassium tert-butoxide (KOtBu) (1M in THF, 220 mL) was slowly added dropwise thereto at 0° C. The mixture was warmed slowly to room temperature, and then additionally stirred for 3 hours. The reaction was completed by the addition of distilled water to the reaction mixture, and the mixture was then extracted with ethyl acetate. After the extracted organic layer was dried with magnesium sulfate, the solvent was removed therefrom with a rotary evaporator.

The remaining product was purified by column chromatography to obtain compound 1-2 (48 g, yield: 97%).

3) Preparation of Compound 1-3

After introducing compound 1-2 (44.8 g, 119 mmol), Eaton's reagent (4.5 mL), and chlorobenzene (600 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 1-3 (36.3 g, yield: 89%).

4) Preparation of Compound C-24

After adding compound 1-3 (8 g, 23 mmol), compound B (CAS: 1060735-14-9, 9.5 g, 23 mmol), tris(dibenzylideneacetone)dipalladium ($Pd_2(dba)_3$) (1 g, 1.16 mmol), 2-dicyclohexylphosphino-2',6'-dimethoxybiphenyl(s-phos) (0.95 g, 2.31 mmol), sodium tert-butoxide (NaOtBu) (4.5 g, 46.3 mmol), and o-xylene (150 mL) into a reaction vessel, the mixture was stirred at 170° C. for 3 hours. After completion of the reaction, the mixture was added dropwise to MeOH, and then the resultant solid was filtered. The obtained solid was purified by column chromatography to obtain compound C-24 (8.7 g, yield: 68%).

[Example 2] Preparation of Compound C-1

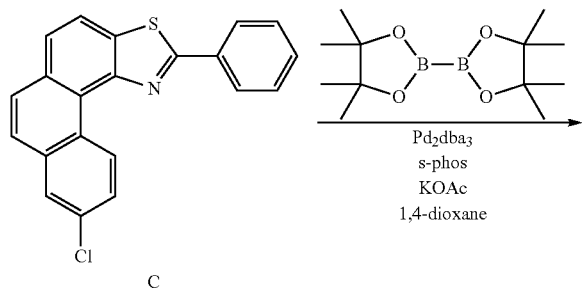

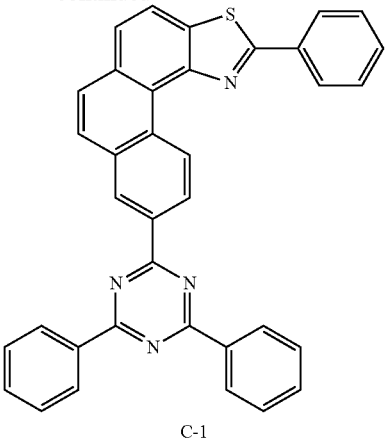

C-1

1) Preparation of Compound 2-1

After adding compound C (10 g, 29 mmol), bis(pinacolato)diborane (8.8 g, 34.8 mmol), tris(dibenzylideneacetone)dipalladium ($Pd_2(dba)_3$) (1.3 g, 1.45 mmol), 2-dicyclohexylphosphino-2',6'-dimethoxybiphenyl(s-phos) (1.2 g, 2.9 mmol), potassium acetate (KOAc) (8.5 g, 87 mmol), and 1,4-dioxane (150 mL) into a reaction vessel, the mixture was then stirred at 140° C. for 3 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 2-1 (10.4 g, yield: 82%).

2) Preparation of Compound C-1

After adding compound 2-1 (10 g, 23.8 mmol), 2-chloro-4,6-diphenyltriazine (CAS: 3842-55-5, 6.4 g, 23.8 mmol), tris(dibenzylideneacetone)dipalladium ($Pd_2(dba)_3$) (1 g, 1.16 mmol), 2-dicyclohexylphosphino-2',6'-dimethoxybiphenyl(s-phos) (1 g, 2.31 mmol), sodium tert-butoxide (NaOtBu) (4.5 g, 46.3 mmol), and o-xylene (150 mL) into a reaction vessel, the mixture was stirred at 170° C. for 3 hours. After completion of the reaction, the mixture was added dropwise to MeOH, and then the resultant solid was filtered. The obtained solid was purified by column chromatography to obtain compound C-1 (8.2 g, yield: 55%).

[Example 3] Preparation of Compound C-17

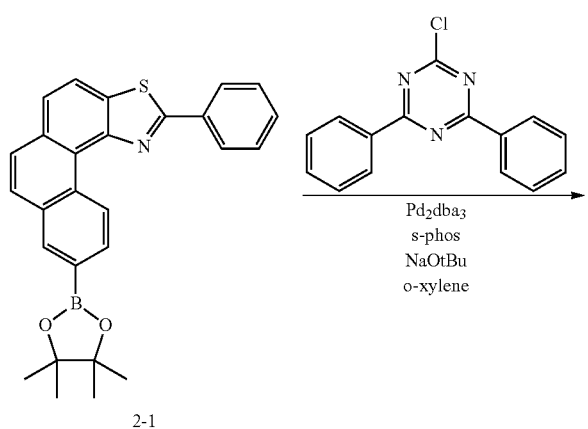

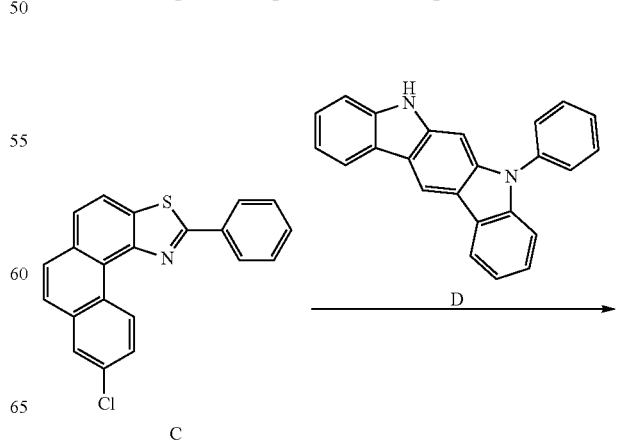

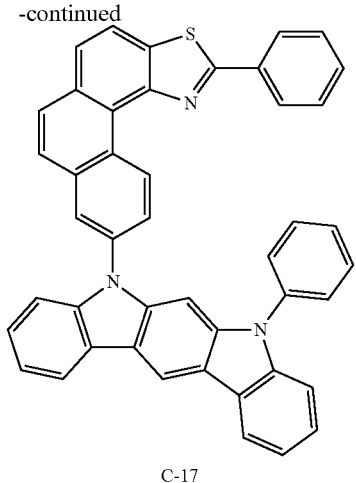

C-17

After adding compound C (8 g, 23.1 mmol), compound D (CAS: 1448296-00-1, 7.7 g, 23.1 mmol), tetrakis(triphenylphosphine)palladium (1.4 g, 1.19 mmol), $K_2CO_3$ (8.2 g, 60 mmol), toluene (90 mL), EtOH (30 mL), and distilled water (30 mL) into a reaction vessel, the mixture was stirred at 140° C. for 3 hours. After completion of the reaction, the precipitated solid was washed with distilled water and MeOH. The obtained compound was purified by column chromatography to obtain compound C-17 (8.7 g, yield: 77%).

[Example 4] Preparation of Compound C-39

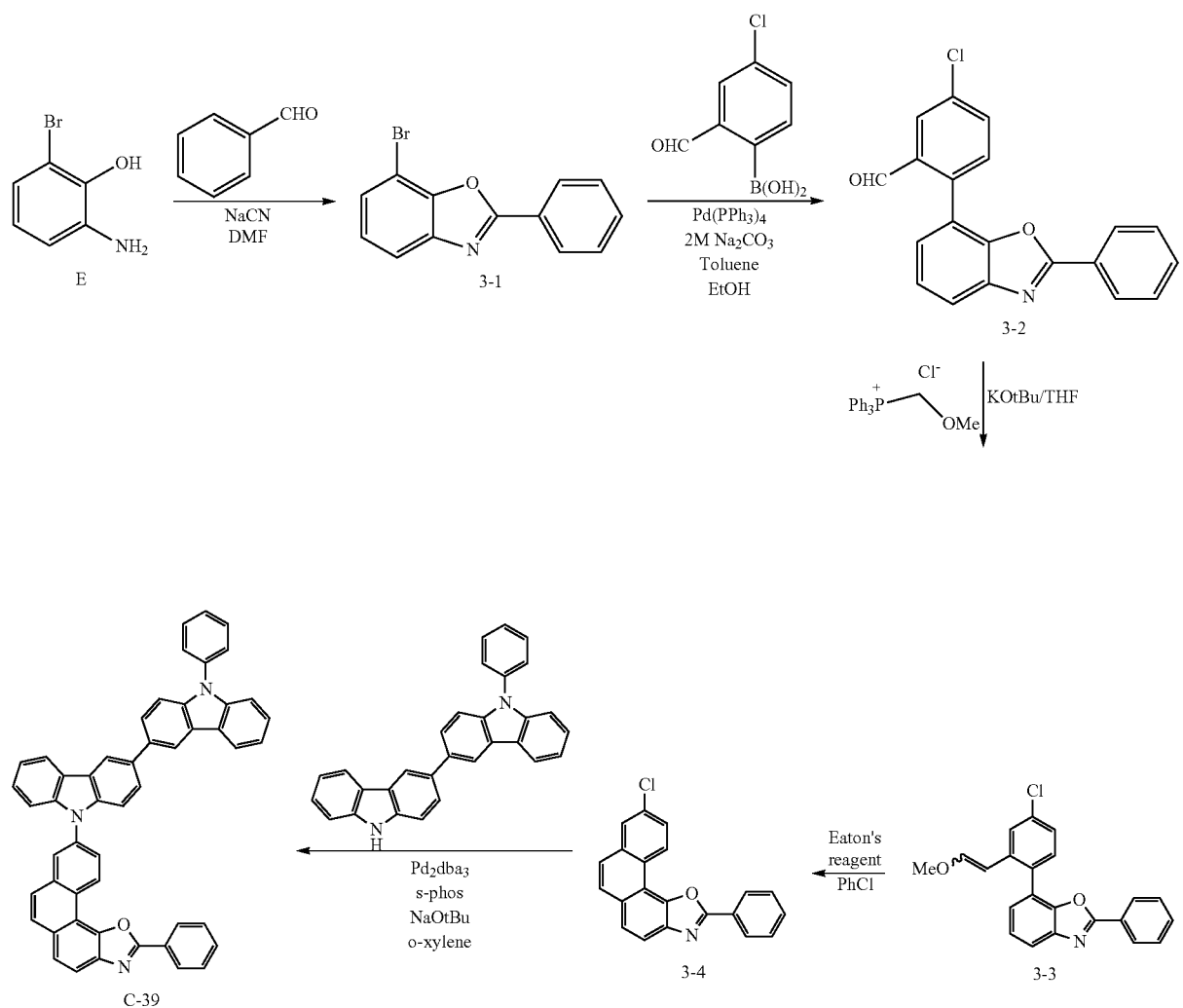

1) Preparation of Compound 3-1

After adding compound E (CAS: 913835-76-4, 40 g, 212.7 mmol), benzaldehyde (27 g, 255.29 mmol), sodium cyanide (10.4 g, 212.7 mmol), and N,N-dimethylformamide (DMF) (1000 mL) into a reaction vessel, the mixture was stirred at 100° C. for 3 hours. After the reaction solution was cooled to room temperature, the solution was extracted with ethyl acetate. The obtained compound 3-1 was used in the next reaction without further purification.

2) Preparation of Compound 3-2

After adding compound 3-1 (35 g, 128 mmol), 4-chloro-2-formylbenzene boronic acid (26 g, 141 mmol), tetrakis(triphenylphosphine)palladium (6 g, 5.1 mmol), sodium carbonate (34 g, 320 mmol), toluene (600 mL), EtOH (150 mL), and distilled water (150 mL) into a reaction vessel, the mixture was stirred at 140° C. for 3 hours. After completion of the reaction, the precipitated solid was washed with distilled water and MeOH. The obtained compound 3-2 was used in the next reaction without further purification.

3) Preparation of Compound 3-3

After introducing compound 3-2 (19 g, 56.9 mmol), (methoxymethyl)triphenylphosphonium chloride (29.3 g, 85.4 mmol), and tetrahydrofuran (500 mL) into a reaction vessel, the reaction mixture was stirred for 5 minutes, and then potassium tert-butoxide (KOtBu) (1M in THF, 85 mL) was slowly added dropwise thereto at 0° C. The mixture was warmed slowly to room temperature, and then additionally stirred for 3 hours. After distilled water was added to the reaction solution to stop the reaction, the solution was extracted with ethyl acetate. After the extracted organic layer was dried with magnesium sulfate, the solvent was removed therefrom with a rotary evaporator. The remaining product was purified by column chromatography to obtain compound 3-3 (16.4 g, yield: 80%).

4) Preparation of Compound 3-4

After introducing compound 3-3 (14.4 g, 39.8 mmol), Eaton's reagent (1.4 mL), and chlorobenzene (200 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 3-4 (11.1 g, yield: 79%).

5) Preparation of Compound C-39

After adding compound 3-4 (4 g, 12.1 mmol), compound B (CAS: 1060735-14-9, 4.9 g, 12.1 mmol), tris(dibenzylideneacetone)dipalladium (Pd$_2$(dba)$_3$) (0.5 g, 0.61 mmol), 2-dicyclohexylphosphino-2',6'-djimethoxybiphenyl(s-phos) (0.5 g, 1.21 mmol), sodium tert-butoxide (NaOtBu) (2.33 g, 24.3 mmol), and o-xylene (100 mL) into a reaction vessel, the mixture was stirred at 170° C. for 3 hours. After completion of the reaction, the mixture was added dropwise to MeOH, and then the resultant solid was filtered. The obtained solid was purified by column chromatography to obtain compound C-39 (8.7 g, yield: 47%).

[Example 5] Preparation of Compound C-49

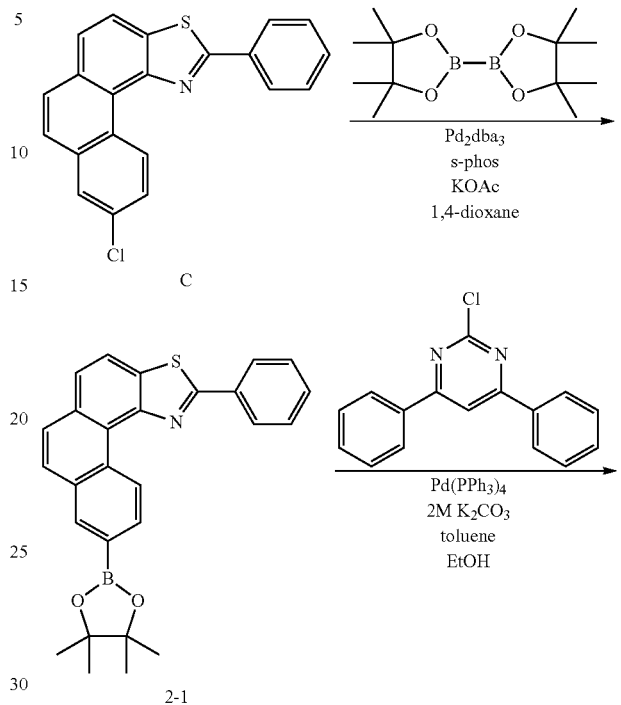

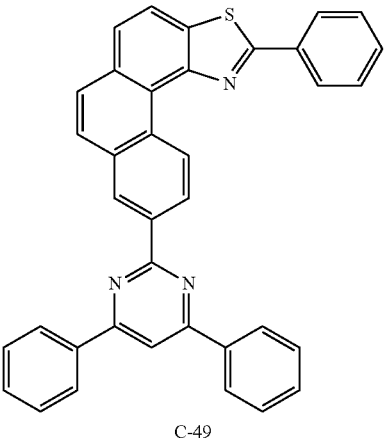

1) Preparation of Compound 2-1

Compound 2-1 was prepared in the same manner as in Example 2.

2) Preparation of Compound C-49

After adding compound 2-1 (4.5 g, 10 mmol), 2-chloro-4,6-diphenylpyrimidine (CAS: 2915-16-4, 2.7 g, 10 mmol), tetrakis(triphenylphosphine)palladium (0.47 g, 0.4 mmol), K$_2$CO$_3$ (3.6 g, 26 mmol), toluene (50 mL), EtOH (13 mL), and distilled water (13 mL) into a reaction vessel, the mixture was stirred at 120° C. for 4 hours. After completion of the reaction, the mixture was added dropwise to MeOH, and then the resultant solid was filtered. The obtained solid was purified by column chromatography to obtain compound C-49 (4.5 g, yield: 73%).

[Example 6] Preparation of Compound C-75

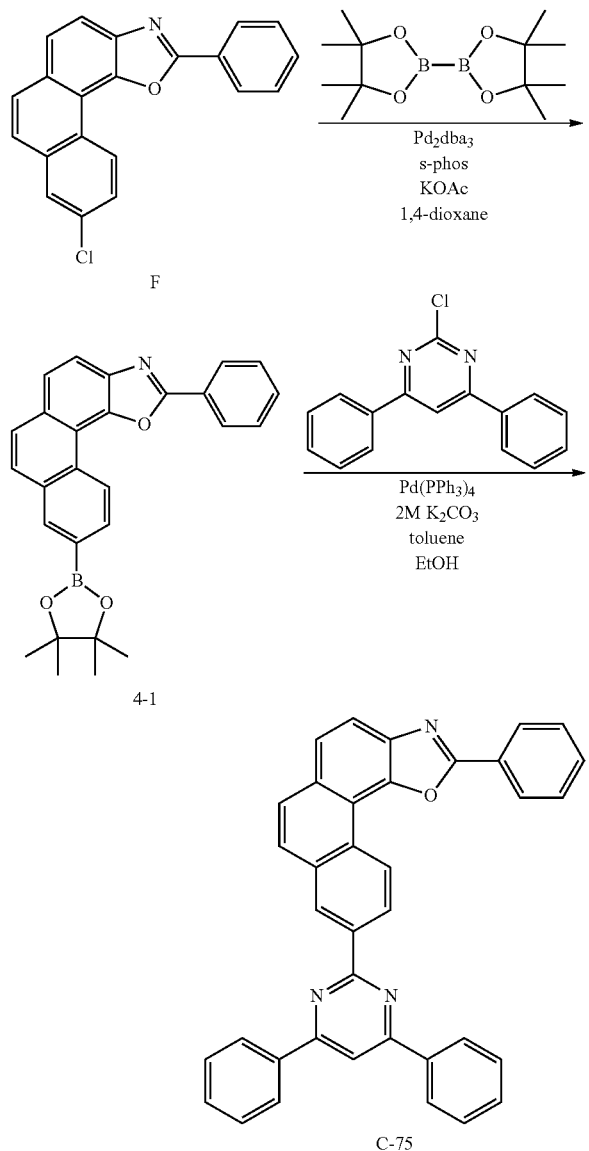

1) Preparation of Compound 4-1

After adding compound F (7.2 g, 21.8 mmol), bis(pinacolato)diborane (6.6 g, 26.2 mmol), tris(dibenzylideneacetone)dipalladium ($Pd_2(dba)_3$) (1.0 g, 1.1 mmol), 2-dicyclohexylphosphino-2',6'-dimethoxybiphenyl(s-phos) (0.89 g, 2.2 mmol), potassium acetate (KOAc) (6.4 g, 65 mmol), and 1,4-dioxane (150 mL) into a reaction vessel, the mixture was stirred at 140° C. for 3 hours. After completion of the reaction, the mixture was cooled to room temperature, and then the mixture was extracted with ethyl acetate. After the extracted organic layer was dried with magnesium sulfate, the solvent was removed therefrom with a rotary evaporator. The remaining product was purified by column chromatography to obtain compound 4-1 (5.2 g, yield: 57%).

2) Preparation of Compound C-75

After adding compound 4-1 (5.2 g, 12.3 mmol), 2-chloro-4,6-diphenylpyrimidine (CAS: 2915-16-4, 3.3 g, 12.3 mmol), tetrakis(triphenylphosphine)palladium (0.71 g, 0.62 mmol), $K_2CO_3$ (4.2 g, 30 mmol), toluene (60 mL), EtOH (20 mL), and distilled water (20 mL) into a reaction vessel, the mixture was stirred at 120° C. for 4 hours. After completion of the reaction, the mixture was added dropwise to MeOH, and then the resultant solid was filtered. The obtained solid was purified by column chromatography and recrystallization to obtain compound C-75 (5.3 g, yield: 82%).

[Example 7] Preparation of Compound C-140

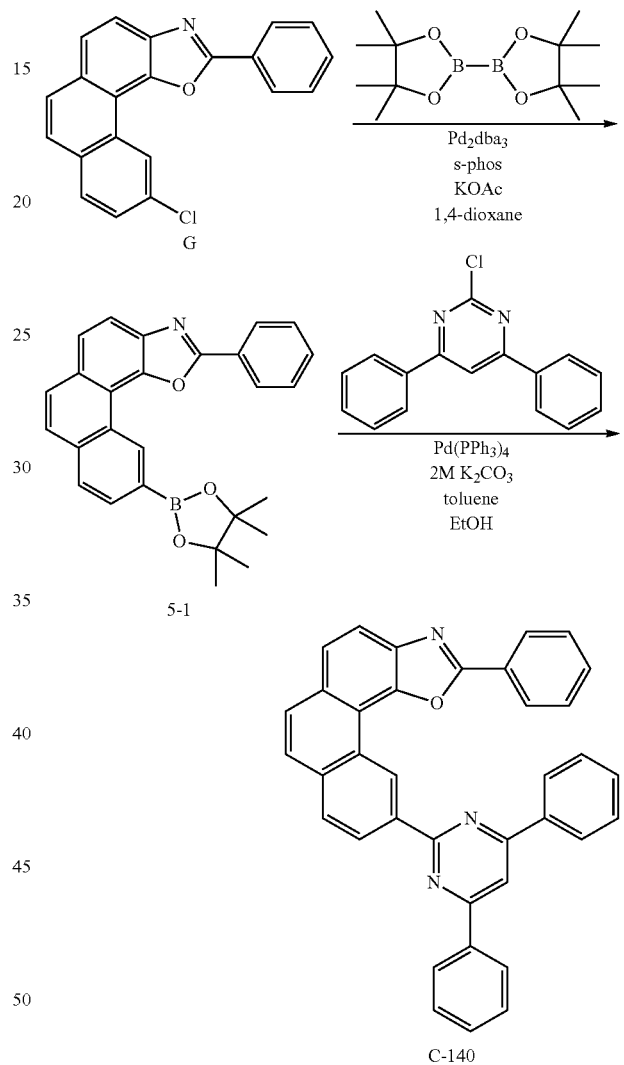

1) Preparation of Compound G

Compound G was prepared in the same manner as in the procedure for the preparation of compound 3-2 in Example 4, except that 4-chloro-2-formylbenzene boronic acid was replaced with 5-chloro-2-formyl boronic acid.

2) Preparation of Compound 5-1

After adding compound G (15 g, 45.5 mmol), bis(pinacolato)diborane (13.9 g, 54.6 mmol), tris(dibenzylideneacetone)dipalladium ($Pd_2(dba)_3$) (1.6 g, 1.8 mmol), 2-dicyclohexylphosphino-2',6'-dimethoxybiphenyl(s-phos) (0.9 g, 3.64 mmol), potassium acetate (KOAc) (13 g, 136 mmol), and 1,4-dioxane (350 mL) into a reaction vessel, the mixture was stirred at 140° C. for 3 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 5-1 (20 g, yield: 99%).

3) Preparation of Compound C-140

After adding compound 5-1 (10 g, 22.7 mmol), 2-chloro-4,6-diphenylpyrimidine (CAS: 2915-16-4, 5.5 g, 20.6 mmol), tetrakis(triphenylphosphine)palladium (1.2 g, 1.0 mmol), K₂CO₃ (7.1 g, 56 mmol), toluene (90 mL), EtOH (30 mL), and distilled water (30 mL) into a reaction vessel, the mixture was then stirred at 120° C. for 4 hours. After completion of the reaction, the mixture was added dropwise to MeOH, and then the resultant solid was filtered. The obtained solid was purified by column chromatography and recrystallization to obtain compound C-140 (5.5 g, yield: 51%).

[Example 8] Preparation of Compound C-100

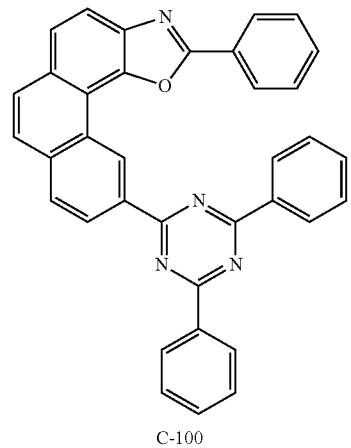

C-100

After adding compound 5-1 (10 g, 23.7 mmol), 2-chloro-4,6-diphenyltriazine (CAS: 3842-55-5, 5.8 g, 21.6 mmol), tetrakis(triphenylphosphine)palladium (1.2 g, 1.0 mmol), K₂CO₃ (7.5 g, 59 mmol), toluene (90 mL), EtOH (30 mL), and distilled water (30 mL) into a reaction vessel, the mixture was stirred at 120° C. for 4 hours. After completion of the reaction, the mixture was added dropwise to MeOH, and then the resultant solid was filtered. The obtained solid was purified by column chromatography and recrystallization to obtain compound C-100 (5.7 g, yield: 50%).

[Example 9] Preparation of Compound C-45

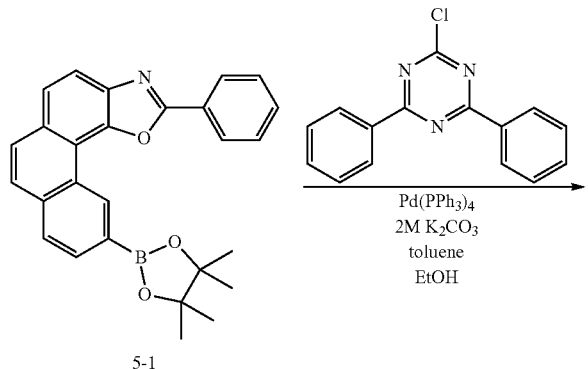

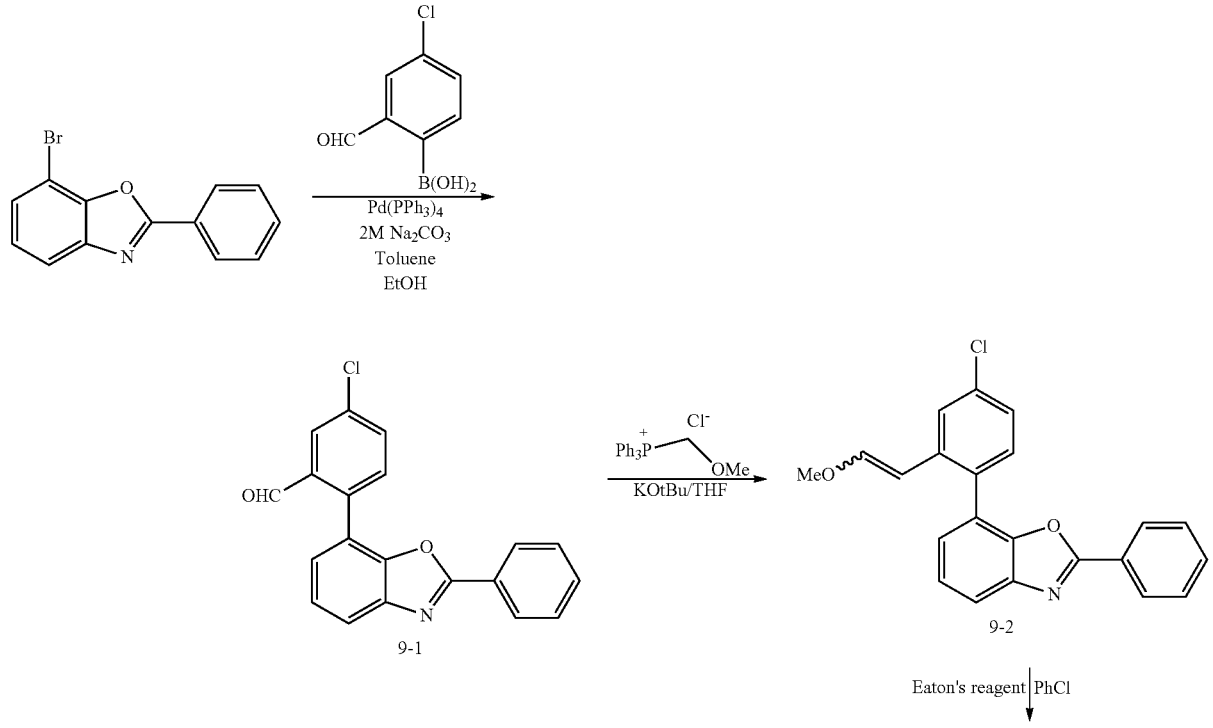

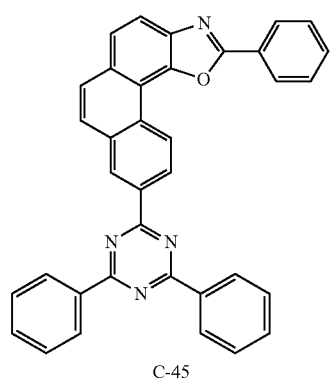
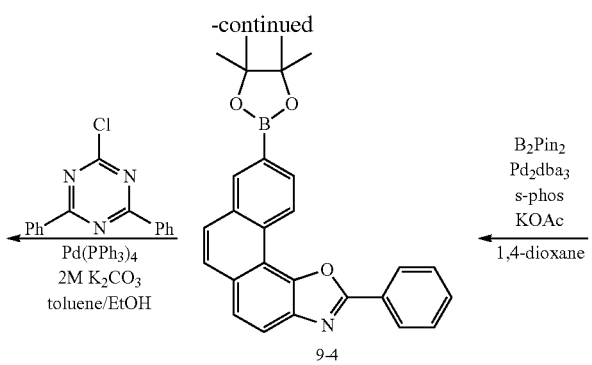

1) Preparation of Compound 9-1

After adding compound 7-bromo-2-phenyl-benzoxazole (37 g, 135 mmol), 4-chloro-2-formylbenzene boronic acid (25 g, 135 mmol), tetrakis(triphenylphosphine)palladium (7.8 g, 6.7 mmol), sodium carbonate (35 g, 338 mmol), toluene (680 mL), EtOH (170 mL), and distilled water (170 mL) into a reaction vessel, the mixture was stirred at 130° C. for 3 hours. After completion of the reaction, the precipitated solid was washed with distilled water and MeOH. The remaining product was purified by column chromatography to obtain compound 9-1 (26 g, yield: 60%).

2) Preparation of Compound 9-2

After introducing compound 9-1 (26 g, 80.2 mmol), (methoxymethyl)triphenylphosphonium chloride (41 g, 120 mmol), and tetrahydrofuran (800 mL) into a reaction vessel, the reaction mixture was stirred for 5 minutes, and then potassium tert-butoxide (KOtBu) (1M in THF, 120 mL) was slowly added dropwise thereto at 0° C. The mixture was warmed slowly to room temperature, and then additionally stirred for 3 hours. After distilled water was added to the reaction solution to stop the reaction, the solution was extracted with ethyl acetate. After the extracted organic layer was dried with magnesium sulfate, the solvent was removed therefrom with a rotary evaporator. The remaining product was purified by column chromatography to obtain compound 9-2 (25 g, yield: 87%).

3) Preparation of Compound 9-3

After introducing compound 9-2 (25 g, 70.2 mmol), Eaton's reagent (3 mL), and chlorobenzene (350 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 9-3 (13 g, yield: 56%).

4) Preparation of Compound 9-4

After adding compound 9-3 (13 g, 39 mmol), bis(pinacolato)diborane (12 g, 47 mmol), tris(dibenzylideneacetone)dipalladium (Pd$_2$(dba)$_3$) (1.8 g, 1.9 mmol), 2-dicyclohexylphosphino-2',6'-dimethoxybiphenyl(s-phos) (1.6 g, 3.9 mmol), potassium acetate (KOAc) (11 g, 118 mmol), and 1,4-dioxane (330 mL) into a reaction vessel, the mixture was stirred for at 130° C. for 4 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 9-4 (13 g, yield: 81%).

5) Preparation of Compound C-45

After adding compound 9-4 (13 g, 31 mmol), 2-chloro-4,6-diphenyltriazine (8 g, 30 mmol), tetrakis(triphenylphosphine)palladium (1.7 g, 1.5 mmol), K$_2$CO$_3$ (10 g, 75 mmol), toluene (140 mL), EtOH (35 mL), and distilled water (35 mL) into a reaction vessel, the mixture was stirred at 130° C. for 4 hours. After completion of the reaction, the precipitated solid was washed with distilled water and MeOH. The remaining product was purified by column chromatography to obtain compound C-45 (7.7 g, yield: 49%).

[Example 10] Preparation of Compound C-141

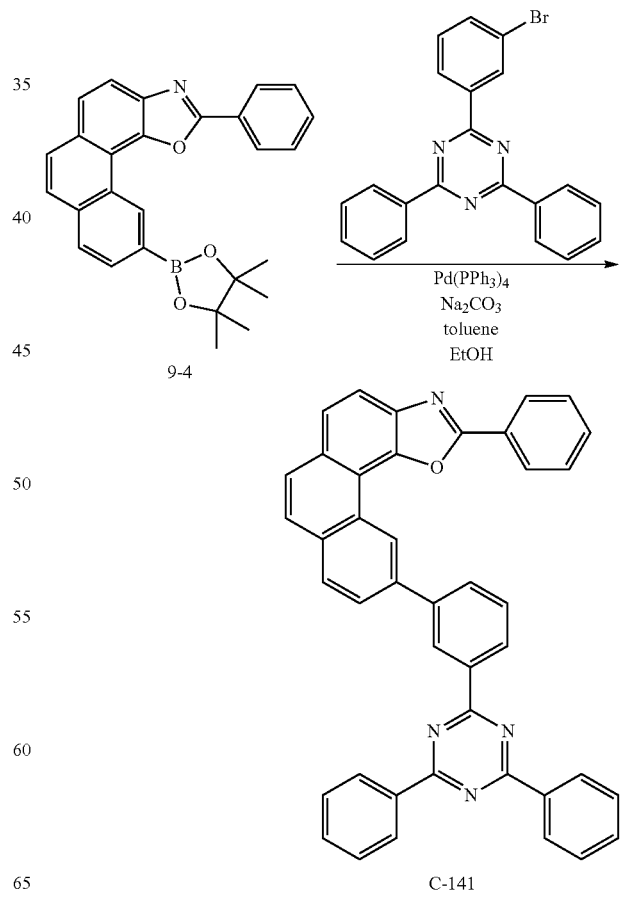

After adding compound 9-4 (3 g, 7.1 mmol), 2-(3-bromophenyl)-4,6-diphenyl-1,3,5-triazine (CAS: 864377-31-1, 3.04 g, 7.8 mmol), tetrakis(triphenylphosphine)palladium (0.41 g, 0.36 mmol), sodium carbonate (1.9 g, 17.8 mmol), toluene (24 mL), EtOH (6 mL), and distilled water (6 mL) into a reaction vessel, the mixture was stirred at 120° C. for 4 hours. After completion of the reaction, the mixture was added dropwise to MeOH, and then the resultant solid was filtered. The obtained solid was purified by column chromatography and recrystalization to obtain compound C-141 (2.3 g, yield: 54%).

[Example 11] Preparation of Compound C-142

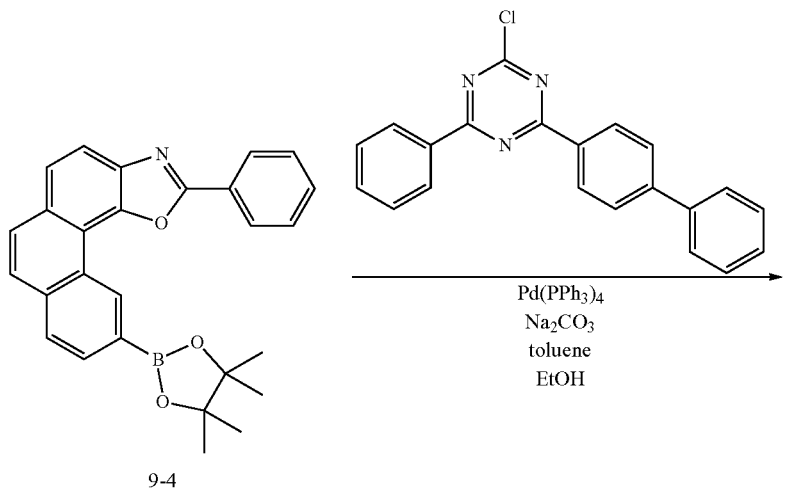

9-4

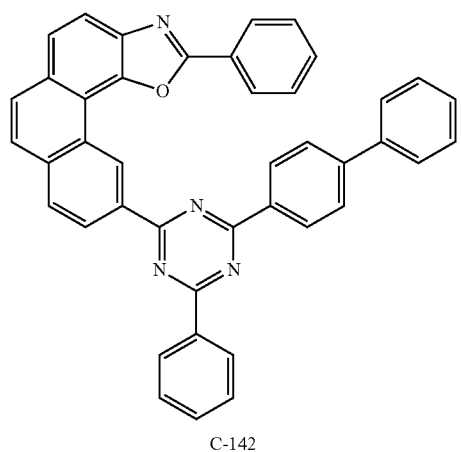

C-142

After adding compound 9-4 (3.48 g, 8.3 mmol), 2-([1,1'-biphenyl]-4-yl)-4-chloro-6-phenyl-1,3,5-triazine (CAS: 1472062-94-4, 3.53 g, 9.1 mmol), tetrakis(triphenylphosphine)palladium (0.48 g, 0.41 mmol), sodium carbonate (2.2 g, 20.7 mmol), toluene (28 mL), EtOH (7 mL), and distilled water (7 mL) into a reaction vessel, the mixture was stirred at 120° C. for 5 hours. After completion of the reaction, the mixture was added dropwise to MeOH, and then the resultant solid was filtered. The obtained solid was purified by column chromatography and recrystallization to obtain compound C-142 (3.7 g, yield: 74%).

[Example 12] Preparation of Compound C-101

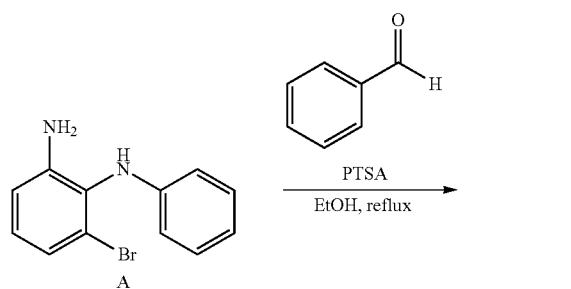

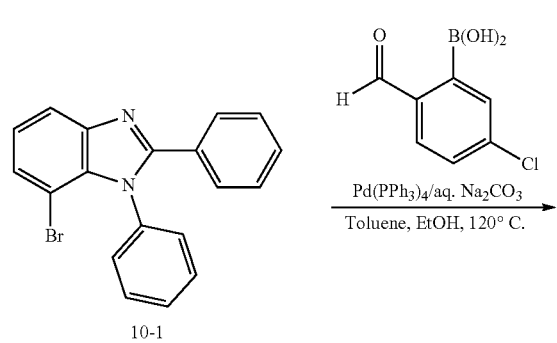

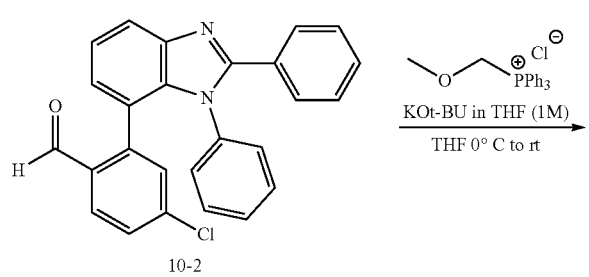

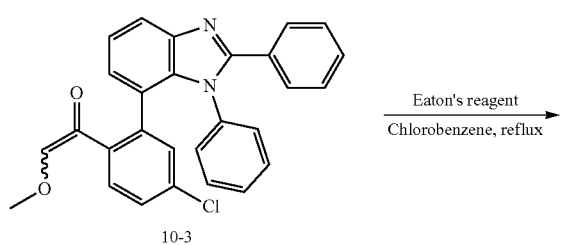

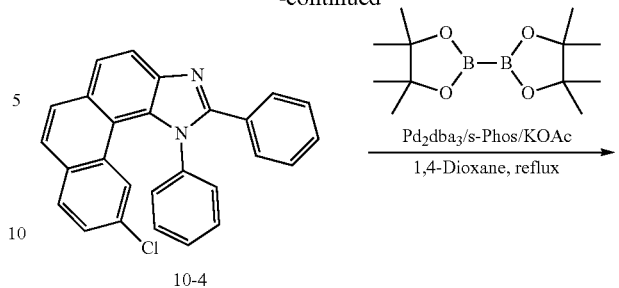

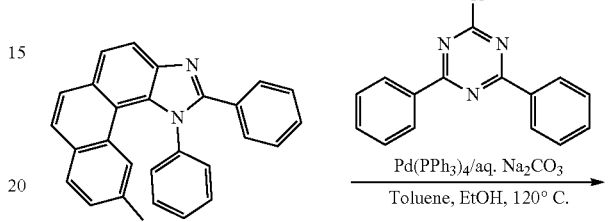

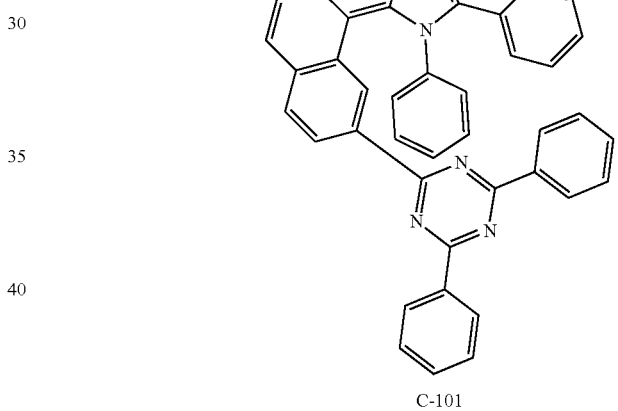

1) Preparation of Compound 10-1

After adding compound A (20 g, 76.0 mmol), benzaldehyde (8.1 g, 76.0 mmol), para-toluenesulfonic acid (1.5 g, 7.6 mmol), and EtOH (380 mL) into a reaction vessel, the mixture was stirred under reflux for 24 hours. After completion of the reaction, the precipitated solid was washed with distilled water and MeOH. The remaining product was purified by column chromatography to obtain compound 10-1 (20 g, yield: 75%).

2) Preparation of Compound 10-2

After adding compound 10-1 (20 g, 57.3 mmol), 4-chloro-2-formylbenzene boronic acid (10.6 g, 57.3 mmol), tetrakis(triphenylphosphine)palladium (2.0 g, 1.7 mmol), sodium carbonate (15.2 g, 143.3 mmol), toluene (300 mL), EtOH (100 mL), and distilled water (100 mL) into a reaction vessel, the mixture was stirred at 120° C. for 3 hours. After completion of the reaction, the precipitated solid was washed with distilled water and MeOH. The remaining product was purified by column chromatography to obtain compound 10-2 (16.5 g, yield: 70%).

3) Preparation of Compound 10-3

After introducing compound 10-2 (16.5 g, 40.4 mmol), (methoxymethyl)triphenyl phosphonium chloride (21 g, 61 mmol), and tetrahydrofuran (400 mL) into a reaction vessel, the reaction mixture was stirred for 5 minutes, and then potassium tert-butoxide (KOtBu) (1M in THF, 60 mL) was slowly added dropwise thereto at 0° C. The mixture was warmed slowly to room temperature, and then additionally stirred for 3 hours. After distilled water was added to the reaction solution to stop the reaction, the solution was extracted with ethyl acetate. After the extracted organic layer was dried with magnesium sulfate, the solvent was removed therefrom with a rotary evaporator. The remaining product was purified by column chromatography to obtain compound 10-3 (12 g, yield: 68%).

4) Preparation of Compound 10-4

After introducing compound 10-3 (12 g, 27.5 mmol), Eaton's reagent (1.2 mL), and chlorobenzene (140 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 10-4 (8 g, yield: 72%).

5) Preparation of Compound 10-5

After adding compound 10-4 (8 g, 19.8 mmol), bis(pinacolato)diborane (6 g, 23.7 mmol), tris(dibenzylideneacetone)dipalladium ($Pd_2(dba)_3$) (0.7 g, 0.8 mmol), 2-dicyclohexylphosphino-2',6'-dimethoxybiphenyl(s-phos) (0.7 g, 1.6 mmol), potassium acetate (KOAc) (5.8 g, 59.4 mmol), and 1,4-dioxane (100 mL) into a reaction vessel, the mixture was stirred at 130° C. for 4 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 10-5 (7 g, yield: 71%).

6) Preparation of Compound C-101

After adding compound 10-5 (5 g, 10.1 mmol), 2-chloro-4,6-diphenyltriazine (2.7 g, 30 mmol), tetrakis(triphenylphosphine)palladium (0.4 g, 0.3 mmol), sodium carbonate (3.5 g, 25.3 mmol), toluene (50 mL), EtOH (12 mL), and distilled water (12 mL) into a reaction vessel, the mixture was stirred at 120° C. for 4 hours. After completion of the reaction, the precipitated solid was washed with distilled water and MeOH. The remaining product was purified by column chromatography to obtain compound C-101 (4.1 g, yield: 67%).

Specific property data of the representative compounds are listed in the Table below:

| Compound | Yield (%) | UV spectrum (in toluene, nm) | PL spectrum (in toluene, nm) | MP (° C.) | MS/EIMS Found | MS/EIMS Calculated |
|---|---|---|---|---|---|---|
| C-24 | 68 | 306 | 418 | 240 | 718.1 | 717.22 |
| C-1 | 55 | 306 | 426 | 276 | 543.2 | 542.16 |
| C-17 | 77 | 306 | 426 | 276 | 642.0 | 641.19 |
| C-39 | 47 | 304 | 400 | 230 | 702.1 | 701.25 |
| C-49 | 73 | 362 | 420 | 279 | 542.0 | 541.66 |
| C-75 | 82 | 260 | 392 | 300 | 526.1 | 525.18 |
| C-140 | 51 | 296 | 402 | 278 | 526.1 | 525.18 |
| C-100 | 50 | 290 | 427 | 291 | 527.1 | 526.18 |
| C-45 | 49 | 345 | 426 | 309 | 526.6 | 526.18 |
| C-141 | 54 | 358 | 401 | 298 | 602.7 | 602.21 |
| C-142 | 74 | 324 | 429 | 299 | 602.7 | 602.21 |
| C-101 | 67 | 324 | 499 | | 601.7 | |

Hereinafter, the luminescent properties of the OLED comprising the organic electroluminescent compound of the present disclosure will be explained for detailed understanding of the present disclosure.

[Comparative Example 1] Preparation of a Blue-Emitting OLED in which an Electron Buffering Layer is not Comprised An OLED was produced using the organic electroluminescent compound of the present disclosure as follows. A transparent electrode indium tin oxide (ITO) thin film (10 Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. $N^4,N^{4'}$-diphenyl-$N^4,N^{4'}$-bis(9-phenyl-9H-carbazol-3-yl)-[1,1'-biphenyl]-4,4'-diamine (compound HI-1) was introduced into a cell of the vacuum vapor depositing apparatus, and then the pressure in the chamber of said apparatus was controlled to $10^{-7}$ torr. Thereafter, an electric current was applied to the cell to evaporate the above introduced material, thereby forming a first hole injection layer having a thickness of 60 nm on the ITO substrate. 1,4,5,8,9,11-hexaazetriphenylene-hexacarbonitrile (HAT-CN) (compound HI-2) was then introduced into another cell of the vacuum vapor depositing apparatus, and was evaporated by applying an electric current to the cell, thereby forming a second hole injection layer having a thickness of 5 nm on the first hole injection layer. N-([1,1*-biphenyl]-4-yl)-9,9-dimethyl-N-(4-(9-phenyl-9H-carbazol-3-yl)phenyl)-9H-fluoren-2-amine (HT-1) was then introduced into another cell of the vacuum vapor depositing apparatus, and was evaporated by applying an electric current to the cell, thereby forming a first hole transport layer having a thickness of 20 nm on the second hole injection layer. Thereafter, 9-(naphthalen-2-yl)-3-(4-(9-phenyl-9H-carbazol-3-yl)phenyl)-9H-carbazole (compound HT-2) was introduced into another cell of the vacuum vapor depositing apparatus, and was evaporated by applying an electric current to the cell, thereby forming a second hole transport layer having a thickness of 5 nm on the first hole transport layer. After forming the hole injection layer and the hole transport layer, a light-emitting layer was deposited thereon as follows. Thereafter, compound BH-1 was introduced into one cell of the vacuum vapor depositing apparatus, as a host material, and compound BD-1 was introduced into another cell as a dopant. The two materials were evaporated at different rates, so that the dopant was deposited in a doping amount of 2 wt % based on the total amount of the host and dopant to form a light-emitting layer having a thickness of 20 nm on the hole transport layer. 2-(3-(phenanthren-9-yl)-S-(pyridin-3-yl)phenyl)-4,6-diphenyl-1,3,5-triazine (compound EIL-1) was then introduced into one cell, and lithium quinolate (compound EIL-1) was introduced into another cell. The two materials were evaporated at the same rate, so that they were respectively deposited in a doping amount of 50 wt % to form an electron transport layer having a thickness of 35 nm on the light-emitting layer. After depositing lithium quinolate (compound EIL-1) as an electron injection layer having a thickness of 2 nm on the electron transport layer, an Al cathode having a thickness of 80 nm was then deposited by another vacuum vapor deposition apparatus on the electron injection layer. Thus, an OLED was produced. All the material used for producing the OLED device were those purified by vacuum sublimation at $10^{-6}$ torr.

The driving voltage based on a luminance of 1,000 nits, luminous efficiency, CIE color coordinate, external quantum efficiency, and a luminance (%) at 10 hours based on a luminance of 2,000 nits were evaluated for the prepared OLED and are shown in Table 1 below.

The Compound Used in the Comparative Example and the Example

Hole injection layer/
Hole transport layer

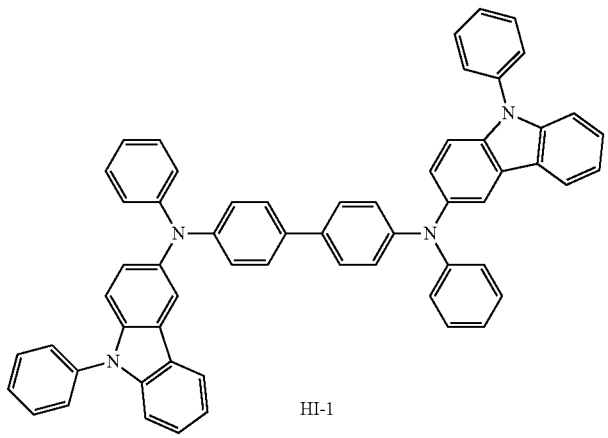 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1 ; [I-]]

HI-1

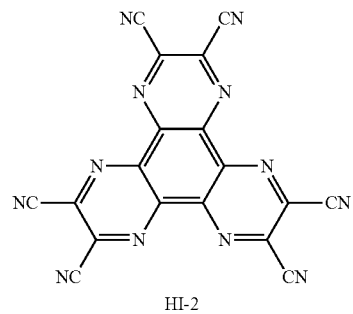

HI-2

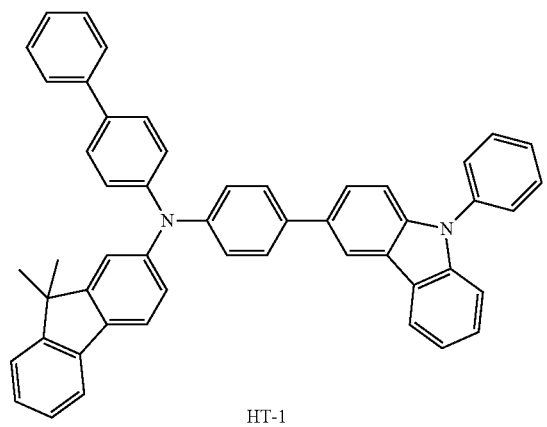

HT-1

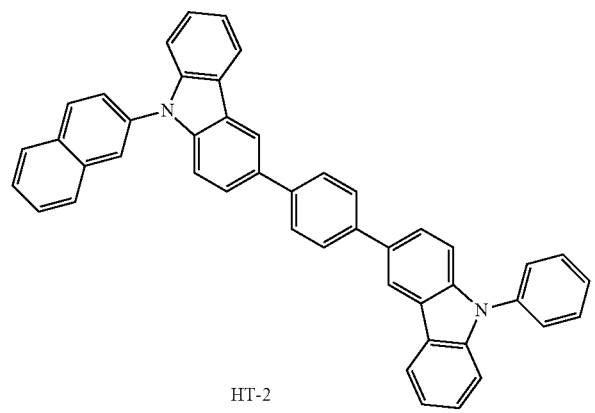
HT-2
Light-emitting layer
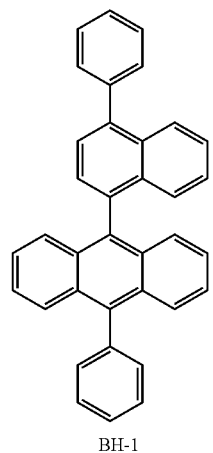
BH-1
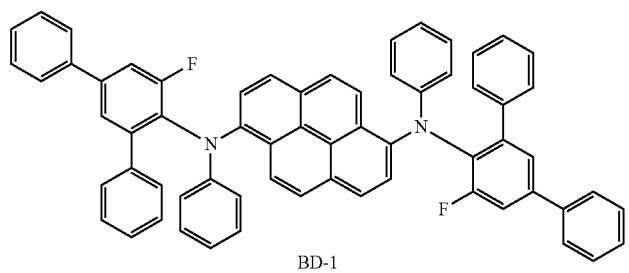 [SMILES: Fc1cc(-c2ccccc2)cc(-c2ccccc2)c1N(c1ccccc1)c1ccc2ccc3c(N(c4ccccc4)c4c(F)cc(-c5ccccc5)cc4-c4ccccc4)ccc4ccc1c2c43 ; "BD-1"]
BD-1
Electron buffering layer
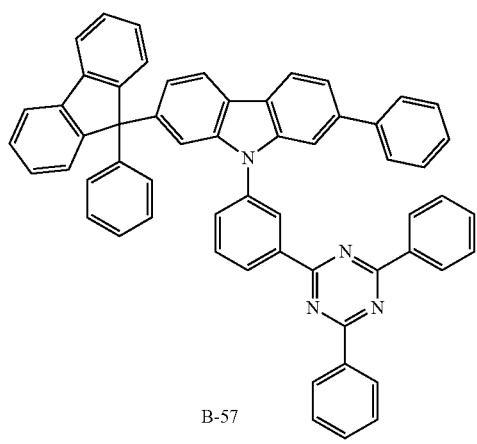
B-57

Electron transport layer/
Electron injection
layer

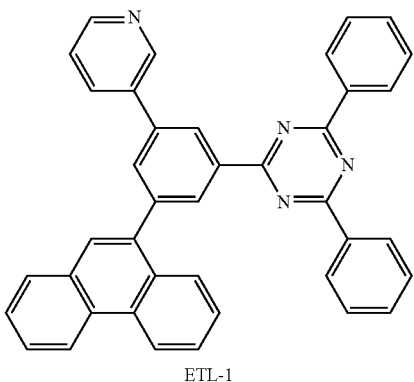 [SMILES: c1ccc(-c2nc(-c3ccccc3)nc(-c3cc(-c4cccnc4)cc(-c4cc5ccccc5c5ccccc45)c3)n2)cc1]

ETL-1

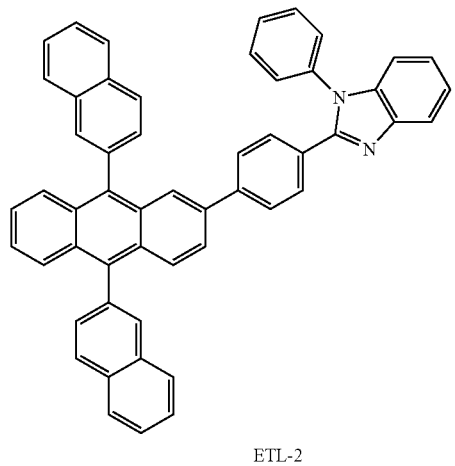 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

ETL-2

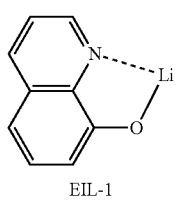

EIL-1

[Examples 1 to 3] Preparation of a Blue-Emitting OLED Comprising an Electron Buffering Material of the Present Disclosure In Examples 1 to 3, OLEDs were produced and evaluated in the same manner as in Comparative Example 1, except that the thickness of the electron transport layer was 25 nm, and an electron buffering layer (comprising compound C-49, C-75 or C-100) having a thickness of 5 nm was interposed between the light-emitting layer and the electron transport layer. Evaluation results of the devices prepared in Examples 1 to 3 are shown in Table 1 below.

TABLE 1

|  | Electron buffering material | Voltage (V) | Current Efficiency (cd/A) | Color coordinate (x) | Color coordinate (y) | External quantum efficiency (%) | Lifespan (10 hr) (%) |
|---|---|---|---|---|---|---|---|
| Comparative Example 1 | — | 4.3 | 6.0 | 139 | 88 | 8.7 | 95.1 |
| Example 1 | C-49 | 4.1 | 6.7 | 139 | 88 | 9.6 | 95.1 |

TABLE 1-continued

| | Electron buffering material | Voltage (V) | Current Efficiency (cd/A) | Color coordinate (x) | Color coordinate (y) | External quantum efficiency (%) | Lifespan (10 hr) (%) |
|---|---|---|---|---|---|---|---|
| Example 2 | C-75 | 4.2 | 6.2 | 139 | 87 | 8.6 | 96.5 |
| Example 3 | C-100 | 4.0 | 6.6 | 139 | 90 | 9.2 | 95.7 |

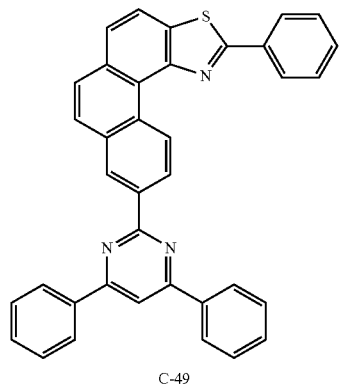

C-49

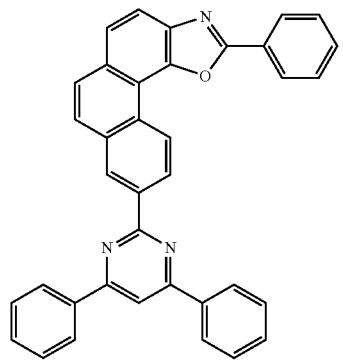

C-75

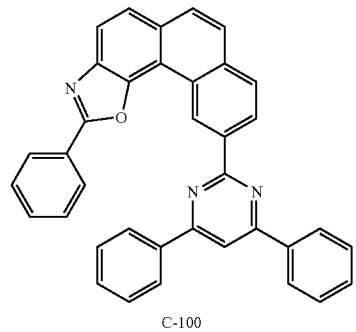

C-100

From Table 1 above, it is recognized that due to rapidness of electron current by the electron buffering material of the present disclosure, the devices of Examples 1 to 3 show higher efficiencies and longer lifespan than those of Comparative Example 1 in which an electron buffering layer is not comprised.

[Comparative Example 2] Preparation of a Blue-Emitting OLED Comprising an Electron Buffering Layer of a Conventional Electron Transport Material In Comparative Example 2, an OLED was produced in the same manner as in Comparative Example 1, except that an electron transport layer and an electron injection layer were changed below: Compound ETL-2 was introduced into one cell of the vacuum vapor depositing apparatus, as an electron transport material and was evaporated to form an electron transport layer having a thickness of 33 nm, and then depositing lithium quinolate (compound EIL-1) as an electron injection layer having a thickness of 4 nm.

Evaluation results of driving voltage based on a luminance of 1,000 nits, luminous efficiency, CIE color coordinate and external quantum efficiency of the device prepared in Example 2 are shown in Table 2 below.

[Examples 4 to 7] Preparation of a Blue-Emitting OLED Comprising an Electron Transport Material of the Present Disclosure In Examples 4 to 7, OLEDs were produced in the same manner as in Comparative Example 2, except that an electron transport material was changed as shown in Table 2 below. Evaluation results of the devices prepared in Examples 4 to 7 are shown in Table 2 below.

TABLE 2

| Electron buffering material | Voltage (V) | Current Efficiency (cd/A) | Color coordinate (x) | Color coordinate (y) | External quantum efficiency (%) |
|---|---|---|---|---|---|
| Comparative Example 2 | ETL-2 | 4.6 | 4.6 | 144 | 115 | 4.8 |
| Example 4 | C-49 | 3.8 | 6.6 | 139 | 89 | 9.1 |
| Example 5 | C-75 | 4.3 | 6.1 | 139 | 88 | 8.6 |
| Example 6 | C-24 | 4.7 | 6.7 | 139 | 90 | 9.2 |
| Example 7 | C-1 | 4.3 | 5.7 | 139 | 92 | 7.3 |

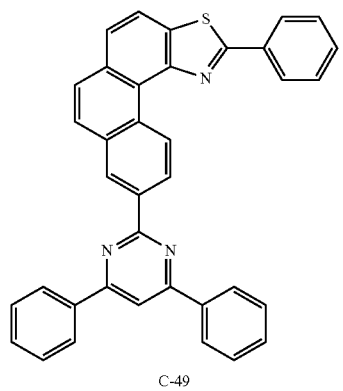

C-49

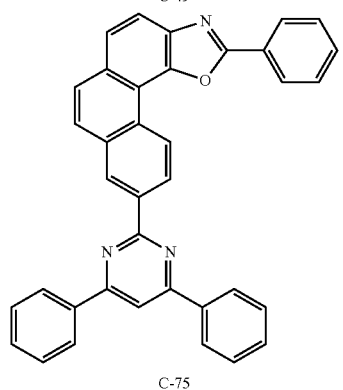

C-75

TABLE 2-continued

| Electron buffering material | Voltage (V) | Current Efficiency (cd/A) | Color coordinate (x) | Color coordinate (y) | External quantum efficiency (%) |
|---|---|---|---|---|---|

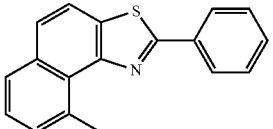

C-24

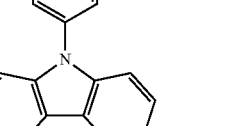

C-1

From Examples 4 to 7, it is recognized that due to rapid electron injection characteristic by the electron transport material of the present disclosure, the devices of Examples 4 to 7 show higher efficiencies than that of Comparative Example 2.

[Comparative Example 3] Preparation of a Blue-Emitting OLED Comprising a Conventional Electron Transport Material In Comparative Example 3, an OLED was produced in the same manner as in Comparative Example 1, except that an electron transport layer and an electron injection layer were changed below: Compound 2-(4-(9,10-di(naphthalen-2-yl)anthracen-2-yl)phenyl)-1-phenyl-1H-benzo[d]imidazole (compound ETL-2) was introduced into one cell of the vacuum vapor depositing apparatus, as an electron transport material and lithium quinolate (compound EIL-1) was introduced into another cell, respectively. The two materials were evaporated at the same rate, so that they were respectively deposited in a doping amount of 50 wt % to form an electron transport layer having a thickness of 35 nm. Thereafter, lithium quinolate (compound EIL-1) was deposited as an electron injection layer having a thickness of 2 nm.

Evaluation results of driving voltage based on a luminance of 1,000 nits, luminous efficiency, CIE color coordinate, and external quantum efficiency of the device prepared in Comparative Example 3 are shown in Table 3 below.

[Examples 8 to 10] Preparation of a Blue-Emitting OLED Comprising an Electron Transport Material of the Present Disclosure In Example 8 to 10, OLEDs were produced in the same manner as in Comparative Example 3, except that an electron transport material was changed as shown in Table 3 below. Evaluation results of the devices prepared in Examples 8 to 10 are shown in Table 3 below.

Evaluation results of driving voltage based on a luminance of 1,000 nits, luminous efficiency, CIE color coordinate, and external quantum efficiency of the device prepared in Example 11 are shown in Table 4 below.

[Examples 12 and 13] Preparation of a Blue-Emitting OLED Comprising an Electron Transport Material of the Present Disclosure and Comprising an Electron Buffering Layer In Examples 12 and 13, OLEDs were produced in the same manner as in Example 11, except that an electron buffering material was changed as shown in Table 4 below. Evaluation results of the devices prepared in Examples 12 and 13 are shown in Table 4 below.

TABLE 4

|  | Electron buffering material | Electron transport material | Voltage (V) | Current Efficiency (cd/A) | Color coordinate (x) | Color coordinate (y) | External quantum efficiency (%) |
| --- | --- | --- | --- | --- | --- | --- | --- |
| Example 11 | — | C-49:EIL-1 (7:3) | 3.8 | 6.5 | 139 | 92 | 8.6 |
| Example 12 | B-57 | C-49:EIL-1 (7:3) | 4.1 | 6.9 | 139 | 93 | 9.5 |
| Example 13 | C-49 | C-49:EIL-1 (7:3) | 3.9 | 6.7 | 138 | 94 | 8.9 |

TABLE 3

|  | Electron transport material | Voltage (V) | Current Efficiency (cd/A) | Color coordinate (x) | Color coordinate (y) | External quantum efficiency (%) |
| --- | --- | --- | --- | --- | --- | --- |
| Comparative Example 3 | ETL-2:EIL-1 (5:5) | 4.2 | 5.5 | 140 | 92 | 7.6 |
| Example 8 | C-49:EIL-1 (5:5) | 4.0 | 6.6 | 139 | 88 | 8.5 |
| Example 9 | C-75:EIL-1 (5:5) | 4.2 | 6.6 | 140 | 87 | 9.4 |
| Example 10 | C-1:EIL-1 (5:5) | 4.4 | 6.2 | 139 | 87 | 8.9 |

From Example 8 to 10, it is recognized that due to rapid electron injection characteristic by the electron transport material of the present disclosure, the devices of Examples 8 to 10 show higher efficiencies than that of Comparative Example 3.

[Example 11] Preparation of a Blue-Emitting OLED Comprising an Electron Transport Material of the Present Disclosure and Non-Comprising an Electron Buffering Layer In Example 11, an OLED was produced in the same manner as in Comparative Example 3, except that an electron transport material was changed to compound C-49 and a doping weight ratio with compound EIL-1 was changed to 70:30 wt %

In Examples 12 and 13, OLED characteristics were evaluated for the devices that in-variably have compounds C-49: EIL-1(7:3) as an electron transport material, but have different electron buffering material, respectively. From Table 4, it is recognized that OLEDs (Example 12 and 13) comprising the compounds of the present disclosure as an electron transport material and further comprising an electron buffering material show improved current efficiency than OLED (Example 11) comprising the compounds of the present disclosure as an electron transport material, but not comprising an electron buffering material. Specific examination on the differences in the current efficiency and the performance due to variation of the HOMO orbital characteristics of the electron buffering material shows that both the OLED that comprises diphenylfluorene as an electron buffering material and benzophenanthrothiophene as an electron transport material (Example 12) and the OLED that comprises only benzophenanthrothiophene as both an electron buffering material and an electron transport material (Example 13) have higher current efficiencies characteristic than the OLED of Example 11.

[Example 14] Preparation of a Blue-Emitting OLED Comprising an Electron Transport Material of the Present Disclosure and not Comprising an Electron Buffering Layer In Example 14, an OLED was produced in the same manner as in Comparative Example 3, except that an electron transport material was changed to compound C-75 and a doping weight ratio with compound EIL-1 was changed to 60:40 wt %.

Evaluation results of driving voltage based on a luminance of 1,000 nits, luminous efficiency, CIE color coordinate and external quantum efficiency, and lifespan time for luminance reduction from 100% to 90% of the device prepared in Example 14 are shown in Table 5 below.

[Examples 15 and 16] Preparation of a Blue-Emitting OLED Comprising an Electron Transport Material of the Present Disclosure and Comprising an Electron Buffering Layer In Examples 15 and 16, OLEDs were produced and evaluated in the same manner as in Example 14, except that an electron buffering material was changed as shown in Table 5 below. Evaluation results of the devices prepared in Examples 15 and 16 are shown in Table 5 below.

TABLE 5

| | Electron buffering material | Electron transport material | Voltage (V) | Current Efficiency (cd/A) | Color coordinate (x) | Color coordinate (y) | External quantum efficiency (%) | Lifespan T90 (hr) |
|---|---|---|---|---|---|---|---|---|
| Ex. 14 | — | C-75:EIL-1 (6:4) | 4.1 | 6.7 | 139 | 88 | 9.7 | 26.1 |
| Ex. 15 | B-57 | C-75:EIL-1 (6:4) | 4.2 | 6.7 | 139 | 88 | 9.6 | 36.9 |
| Ex. 16 | C-75 | C-75:EIL-1 (6:4) | 4.1 | 6.6 | 139 | 88 | 9.6 | 35.3 |

In Examples 15 and 16, OLED characteristics were evaluated for the devices that in-variably comprise compounds C-75:EIL-1(6:4) as an electron transport material, but comprise different electron buffering material, respectively. From Table 5 above, it is recognized that OLEDs (Examples 15 and 16) comprising the compounds of the present disclosure as an electron transport material and further comprising an electron buffering material show improved lifespan than the OLED (Example 14) comprising the compounds of the present disclosure as an electron transport material, but not comprising an electron buffering material.

From Tables 4 and 5, it is recognized that the compounds of the present disclosure can enhance the current efficiency and lifespan characteristics of an OLED when they are used alone as an electron transport material or together with an electron buffering material of the present disclosure or conventional electron buffering material.

The invention claimed is:
1. An electron buffering material comprising compound represented by the following formula 1:

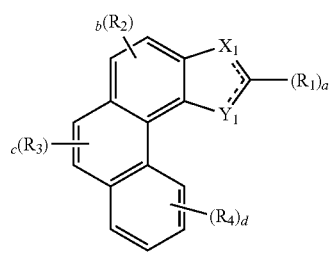

(1)

wherein,
$X_1$ represents —N=, —O— or —S—;
$Y_1$ represents —N=, —NR$_8$—, —O— or —S—;
where $X_1$ is —N=, $Y_1$ is —NR$_8$—, —O— or —S—;
where $X_1$ is —NR$_7$—, $Y_1$ is —N=; the case that both of $X_1$ and $Y_1$ are —O— or —S—, and the case that one of $X_1$ and $Y_1$ is —O—, and the other is —S— are excluded;
$R_1$ represents an (C6-C30)aryl, unsubstituted or mono-substituted with a triazine wherein the triazine is substituted with a (C6-30)aryl, a dibenzofurayl, or a dibenzothiophenyl, or a (3 to 30-membered)heteroaryl unsubstituted or substituted with a (C6-C30)aryl;
$R_2$ represents hydrogen, deuterium, a halogen, a cyano, a substituted or unsubstituted (C1-C30)alkyl, a substituted or unsubstituted (C6-C30)aryl, a substituted or unsubstituted (3 to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C6-C30)arylamino;
$R_3$ and $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3 to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6- C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino, or may be linked to an adjacent substituent(s) to form a substituted or unsubstituted (C3-C30), mono- or polycyclic, alicyclic or aromatic ring, whose carbon atom(s) may be replaced with at least one heteroatom selected from nitrogen, oxygen, and sulfur;
$R_7$ and $R_8$, each independently, represent hydrogen, deuterium, a halogen, a cyano, a substituted or unsubstituted (C1-C30)alkyl, an unsubstituted (C6-C30)aryl, a substituted or unsubstituted (3 to 30-membered)heteroaryl, a substituted or unsubstituted (C3-C30)cycloalkyl, a substituted or unsubstituted (C1-C30) alkoxy, a substituted or unsubstituted tri(C1-C30) alkylsilyl, a substituted or unsubstituted di(C1-C30) alkyl (C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

a represents an integer of 1; b and c, each independently, represent an integer of 1 or 2; d represents an integer of 1 to 4; and the heteroaryl contains at least one heteroatom selected from B, N, O, S, Si and P.

2. The electron buffering material according to claim 1, wherein formula 1 is represented by the following formulae 2 to 4:

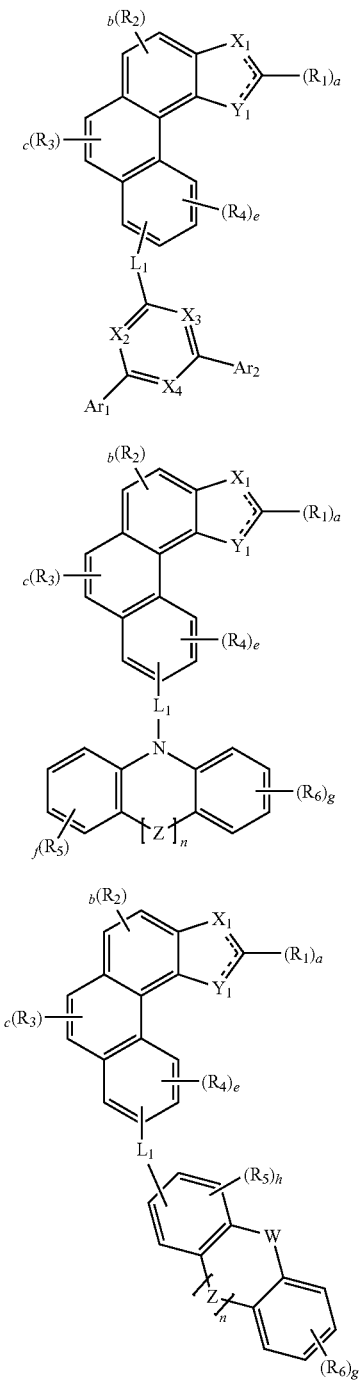

wherein $L_1$ represents a single bond, a substituted or unsubstituted (C6-C30)arylene, or a substituted or unsubstituted (3- to 30-membered)heteroarylene;

$X_2$ to $X_4$, each independently, represent —N— or —$CR_9$—;

$Ar_1$ and $Ar_2$, each independently, represent a substituted or unsubstituted (C6-C30)aryl, or a substituted or unsubstituted (3- to 30-membered)heteroaryl;

$R_9$ has the same definition as $R_3$ and $R_4$;

Z represents a single bond, or a substituted or unsubstituted (C1-C6)alkylene,

W represents —$NR_{10}$—, —O—, —S— or —$CR_{11}R_{12}$—, $R_{10}$ represents a substituted or unsubstituted (C6-C30) aryl, or a substituted or unsubstituted (3- to 30-membered)heteroaryl, $R_{11}$ and $R_{12}$, each independently, represent a substituted or unsubstituted (C1-C30)alkyl, a substituted or unsubstituted (C6-C30)aryl, or a substituted or unsubstituted (3- to 30-membered)heteroaryl, $R_5$ and $R_6$ are as defined for $R_3$ and $R_4$, n represents 0 or 1, e and h, each independently, represent an integer of 1 to 3, f and g, each independently, represent an integer of 1 to 4, and X1, Y1, R1 to R4, and a to c are as defined in claim 1.

3. The electron buffering material according to claim 1, wherein the compound of formula 1 is selected from the group consisting of:

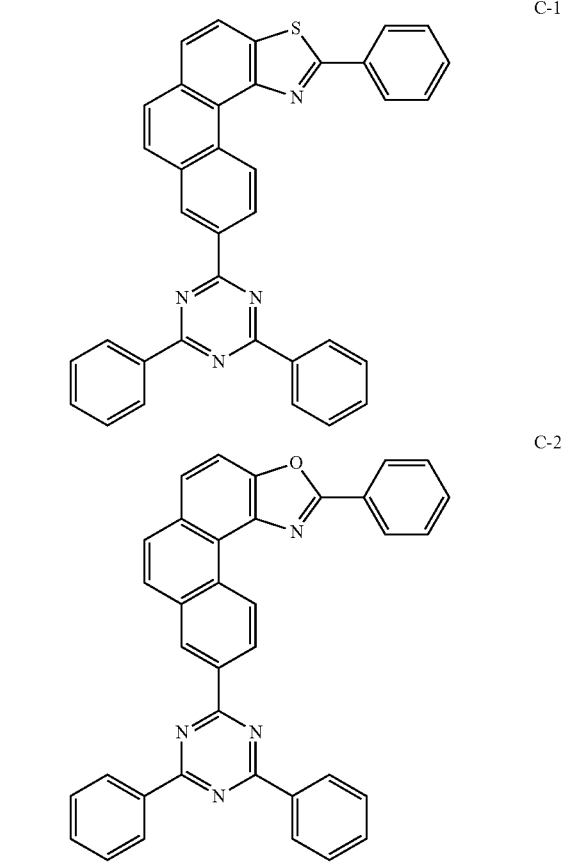

225
-continued
226
-continued
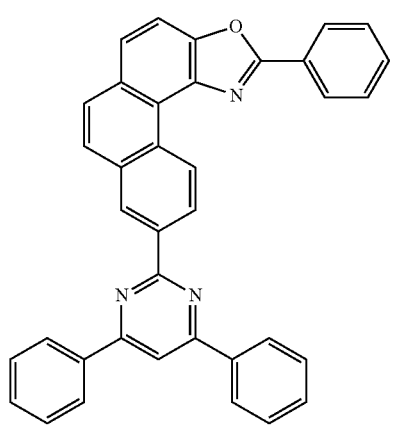
C-3
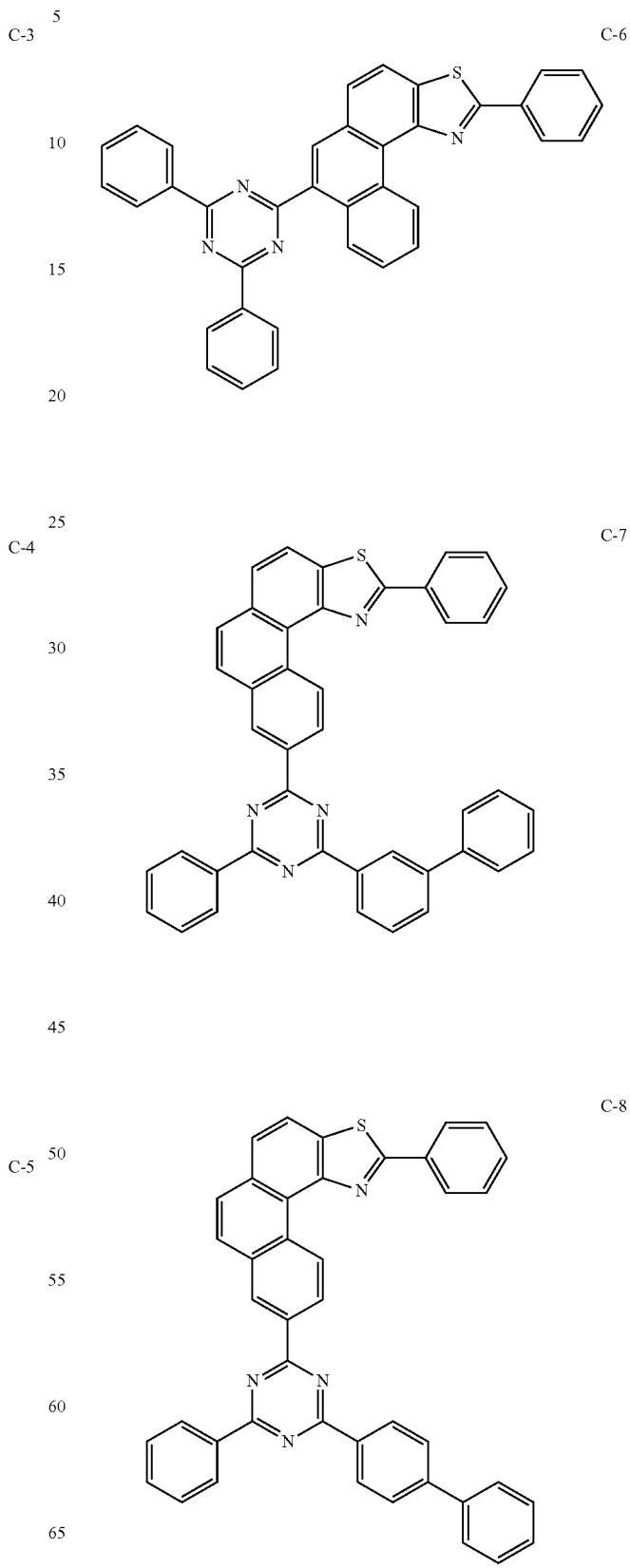
C-6
C-4
C-7
C-5
C-8

C-9
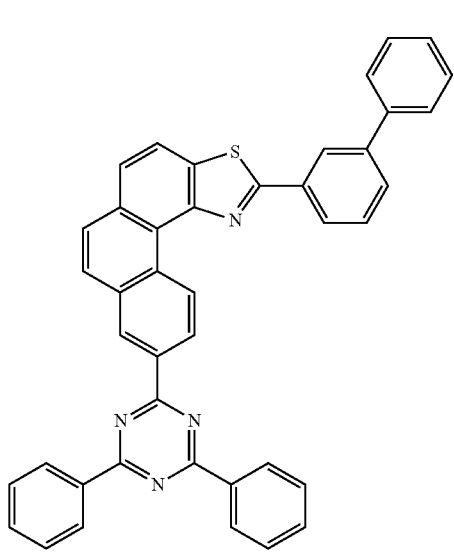
C-10
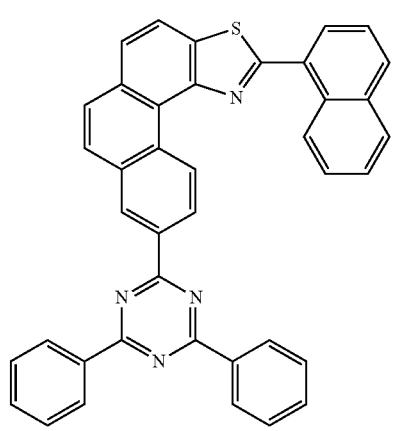
C-11
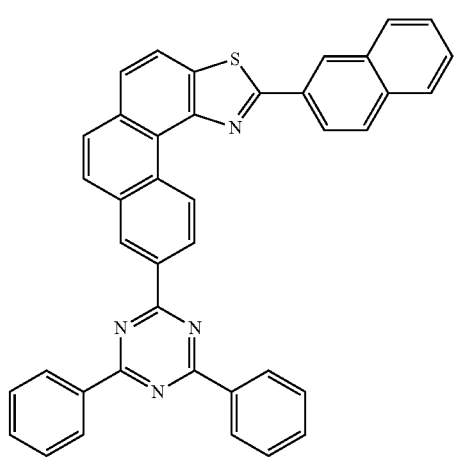
C-12
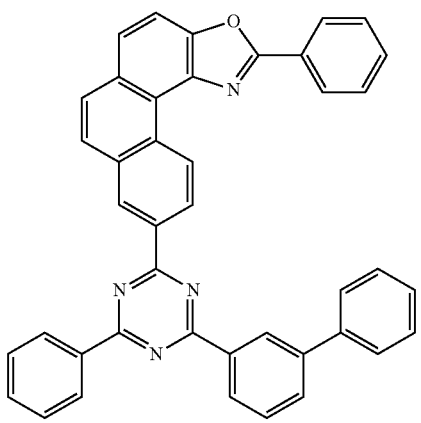
C-13
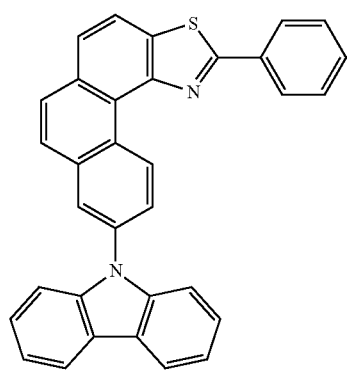
C-14
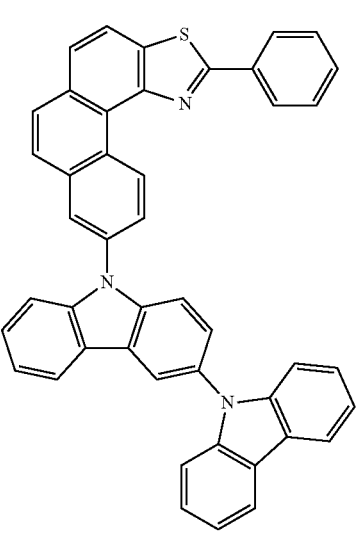

-continued
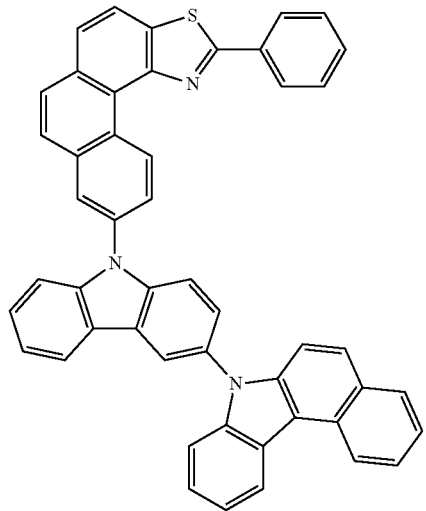
C-15
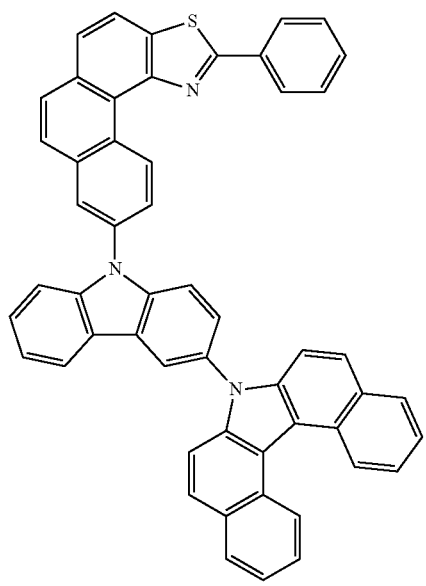
C-16
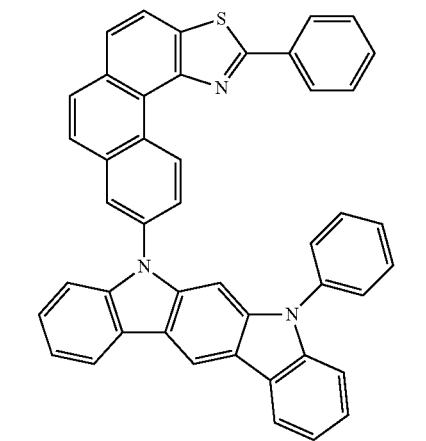
C-17
-continued
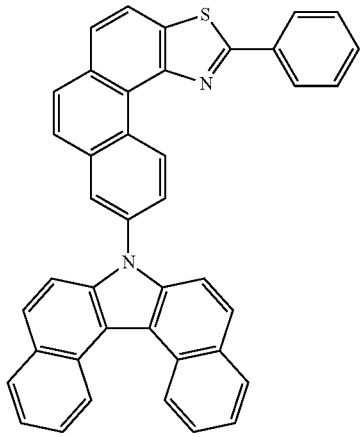
C-18
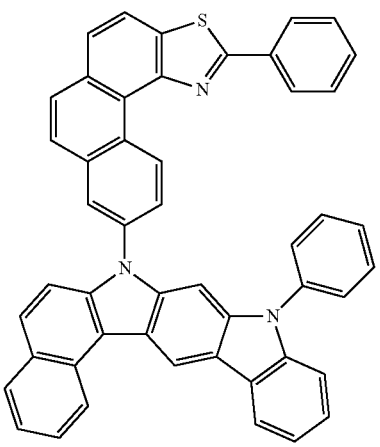
C-19
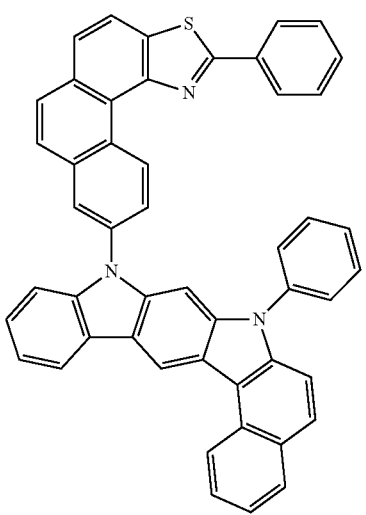
C-20

231
-continued
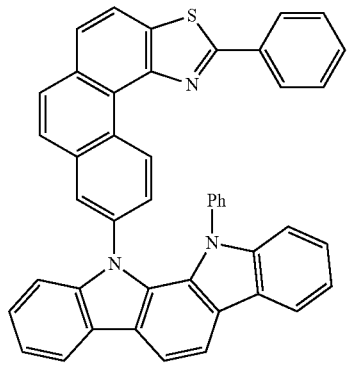
C-21
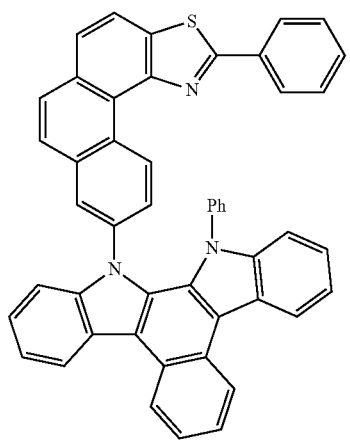
C-22
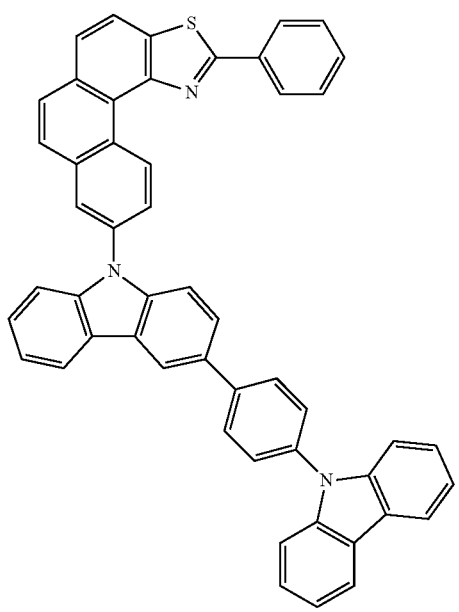
C-23
232
-continued
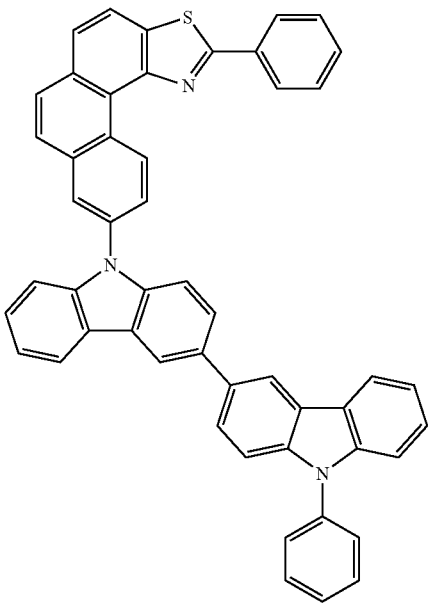
C-24
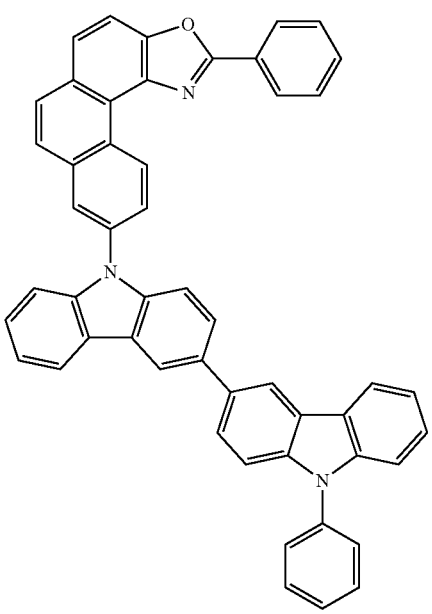
C-25

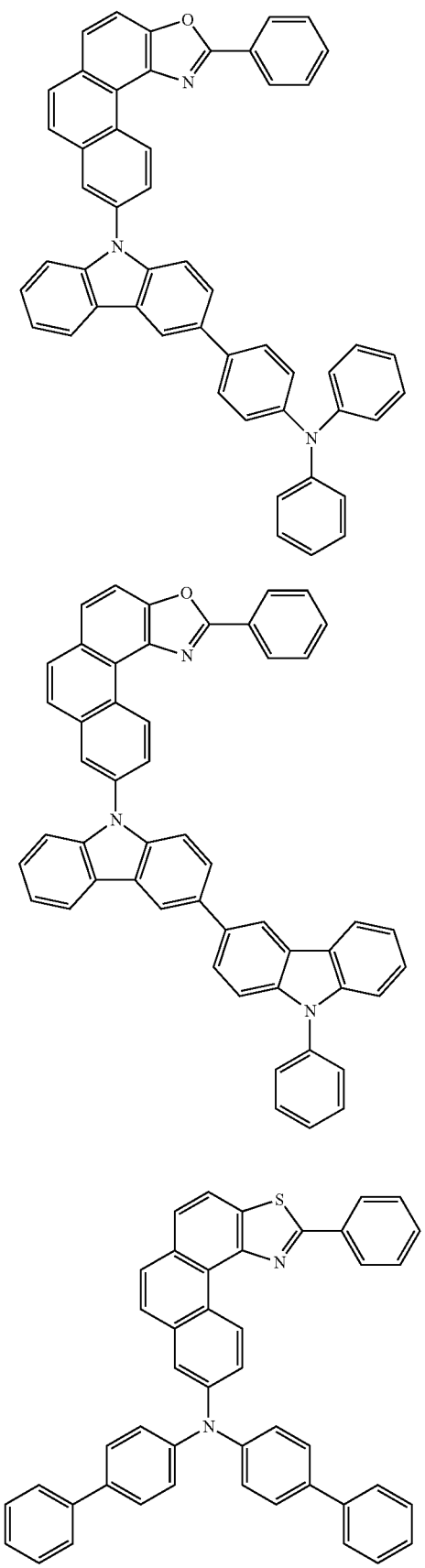

-continued
C-32
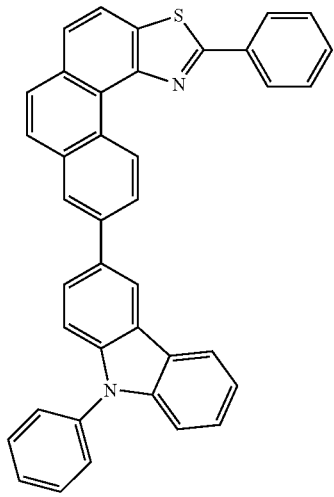
C-33
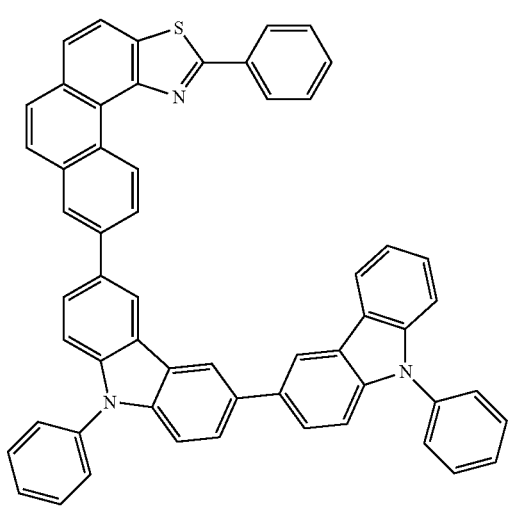
C-34
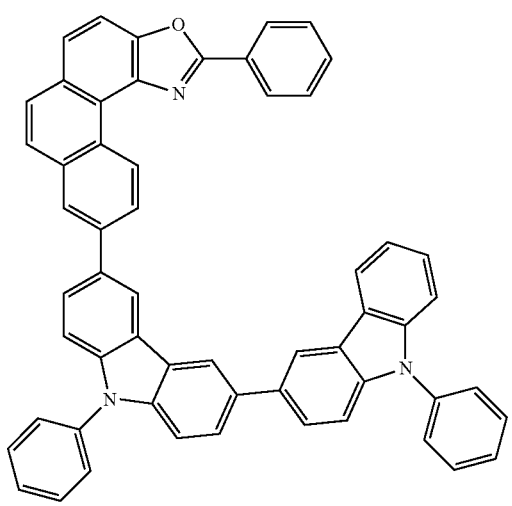
-continued
C-35
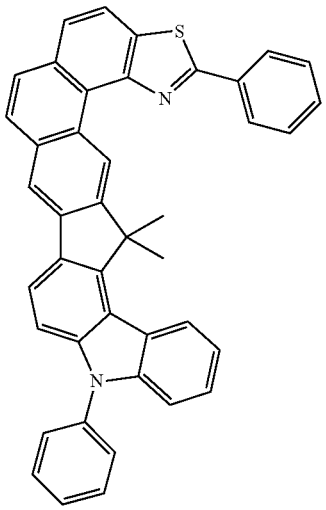
C-36
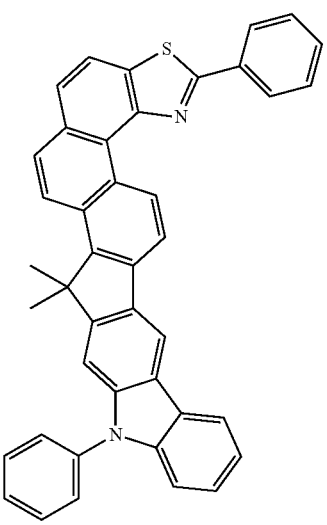
C-37
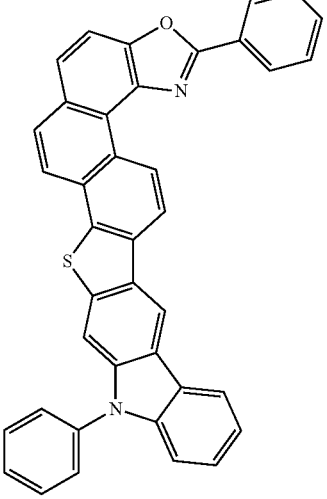

-continued
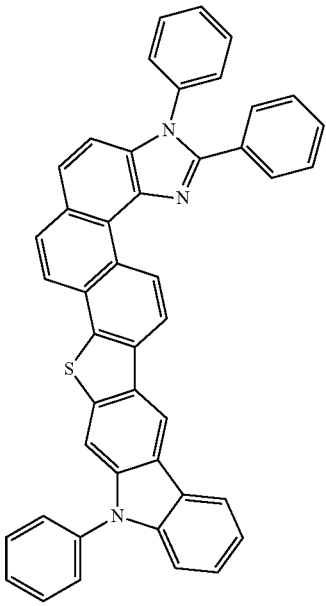
C-38
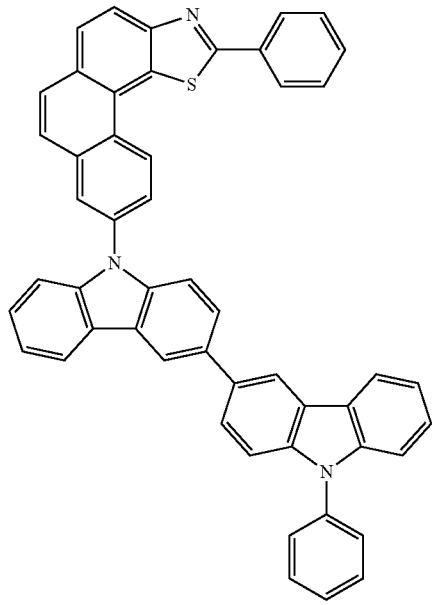
C-40
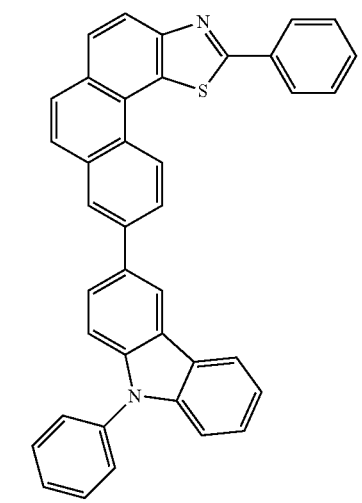
C-41
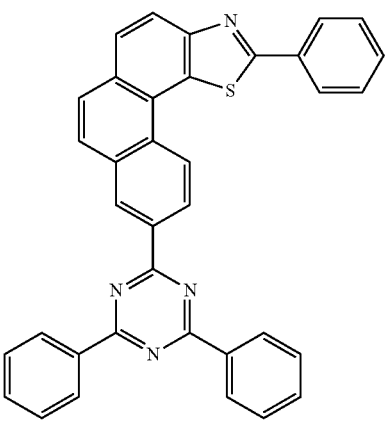
C-42
C-39

239
-continued
C-43
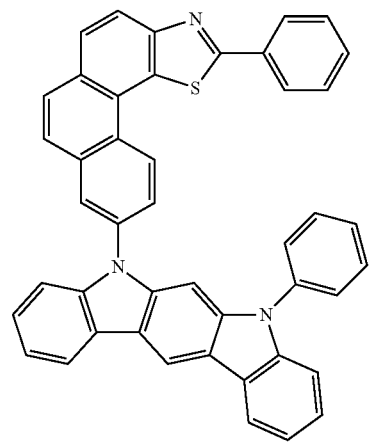
C-44
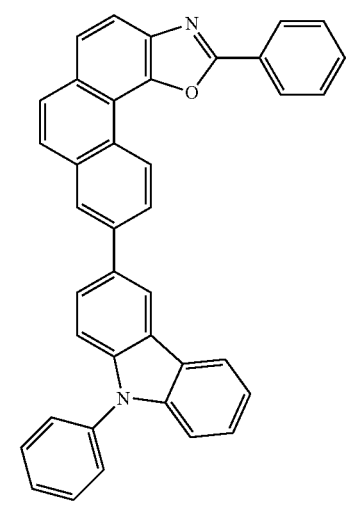
C-45
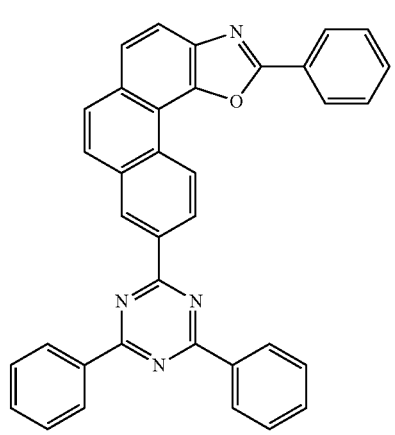
240
-continued
C-46
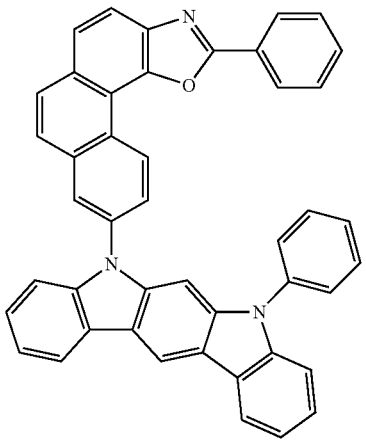
C-47
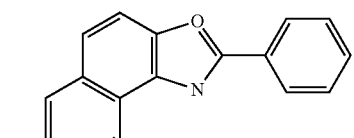
C-48
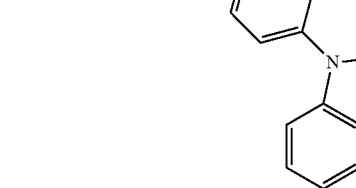

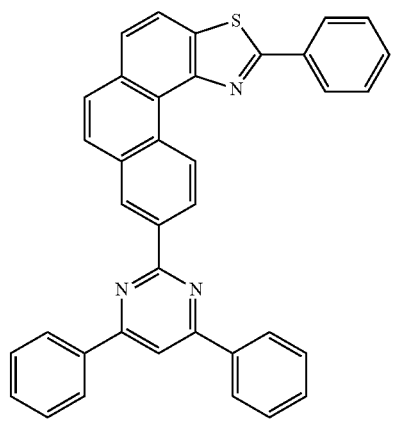
C-49
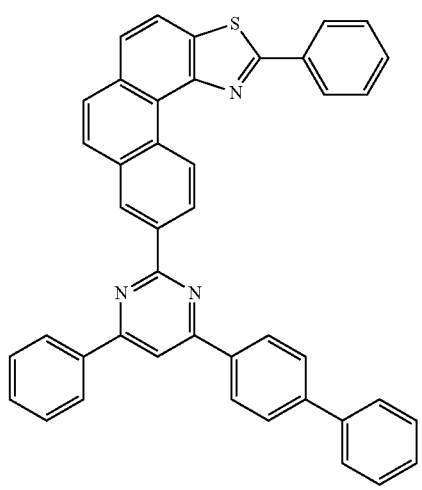
C-50
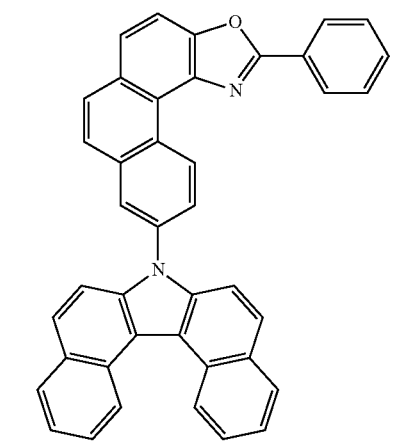
C-51
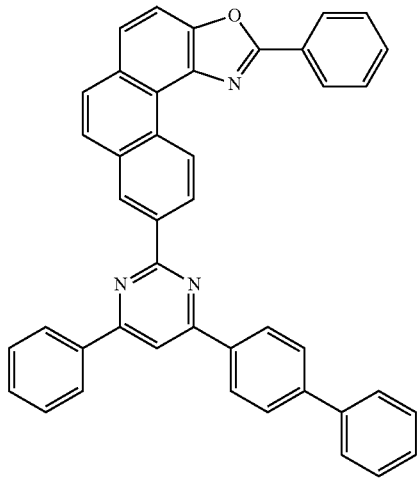
C-52
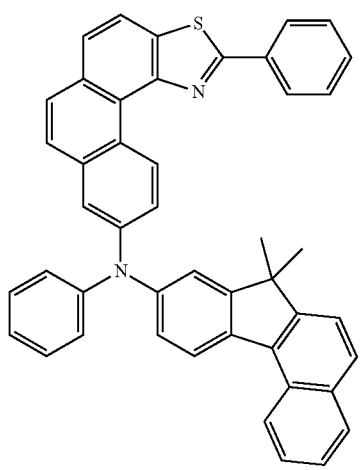
C-53
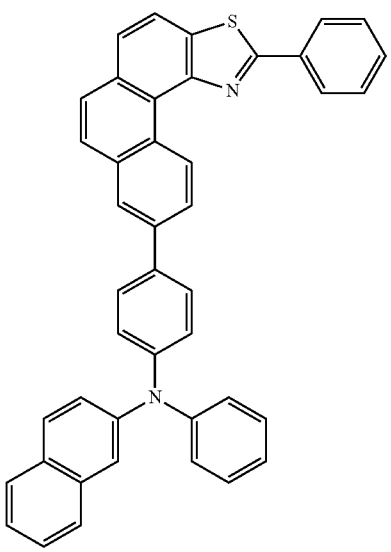
C-54

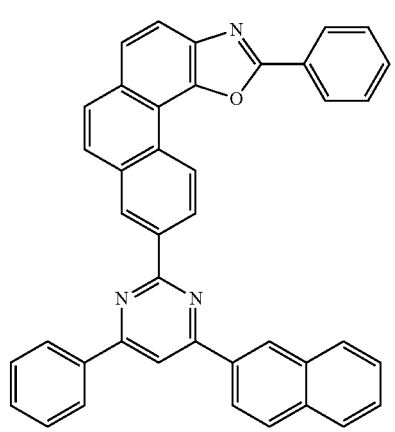
C-55
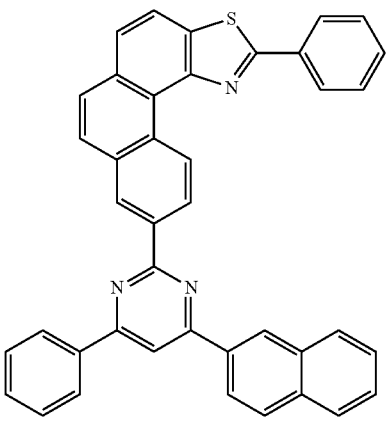
C-58
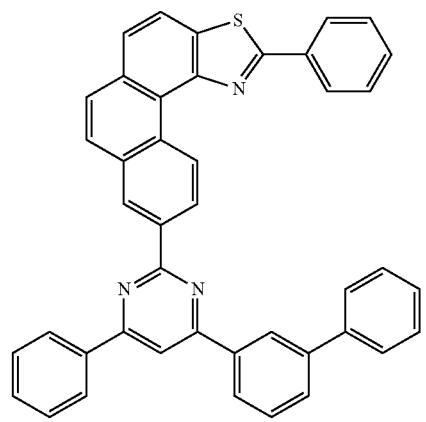
C-56
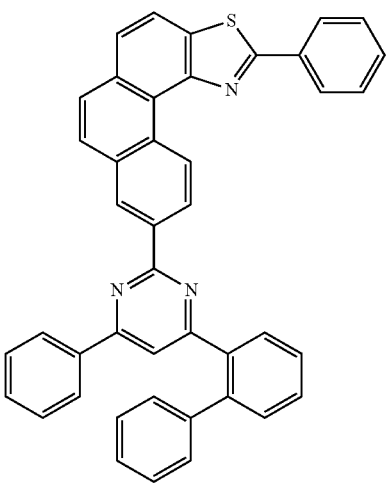
C-59
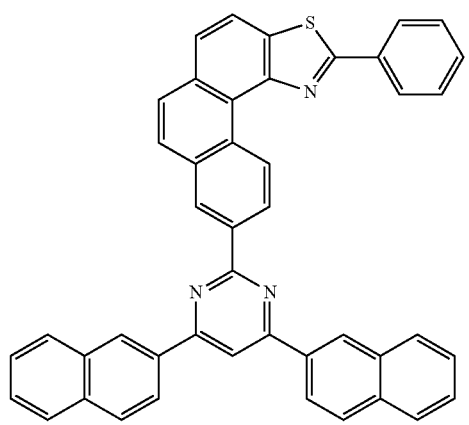
C-57
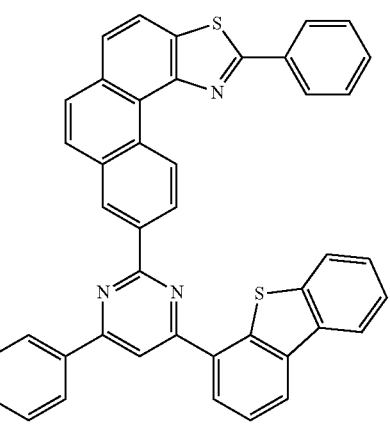
C-60

C-61
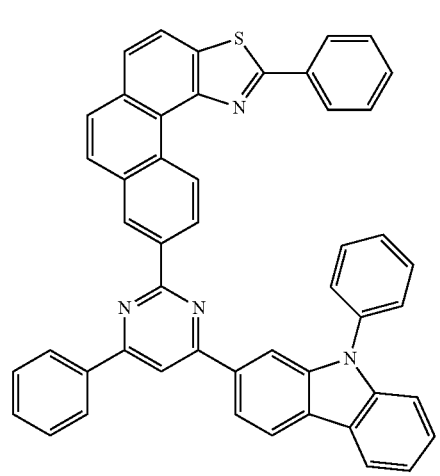
C-64
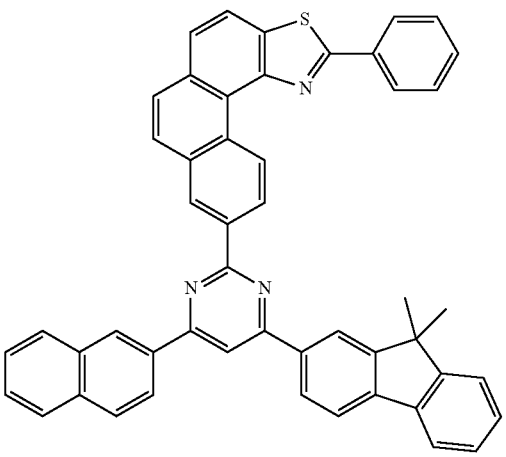
C-62
C-65
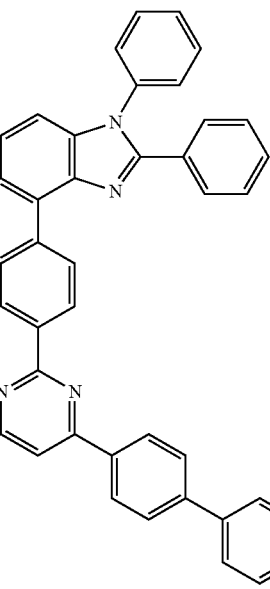
C-63
C-66
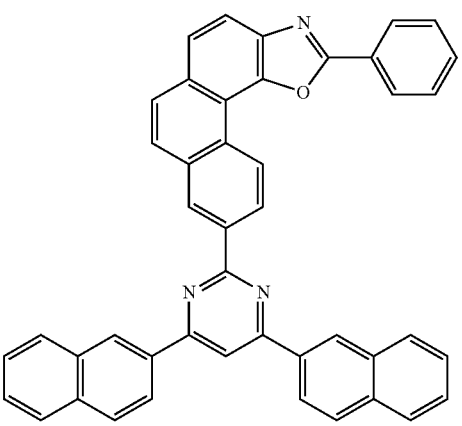

C-67
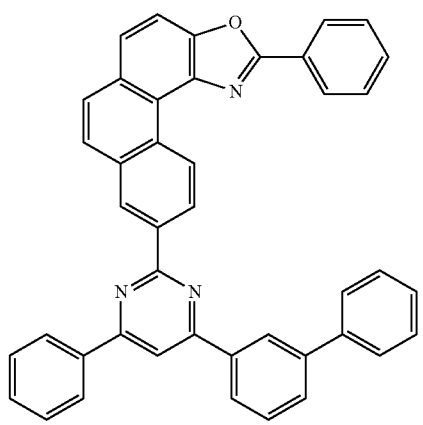
C-68
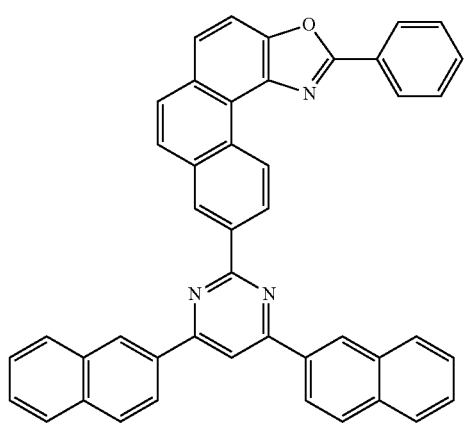
C-69
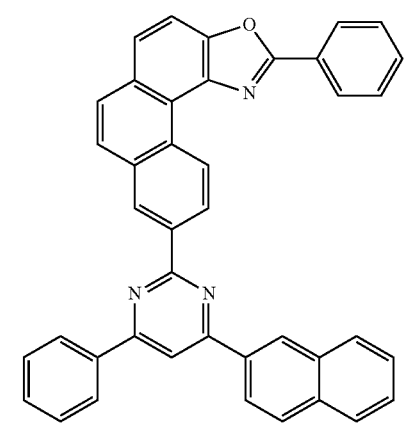
C-70
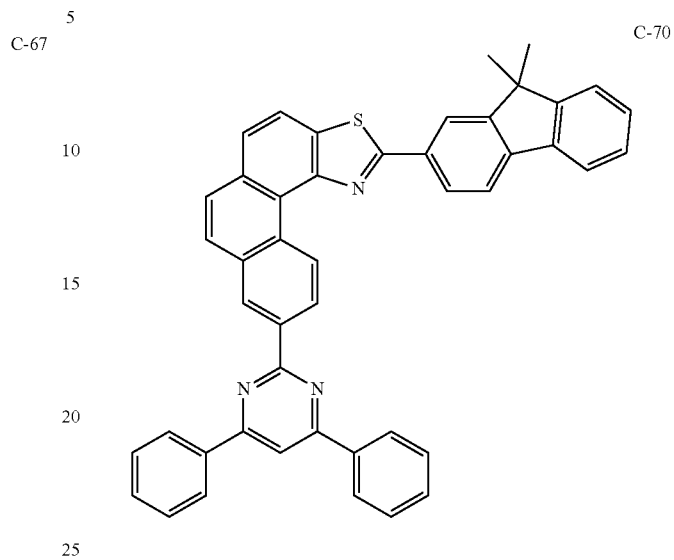
C-71
C-72

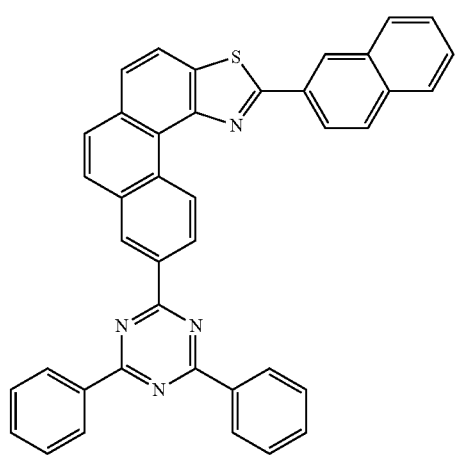
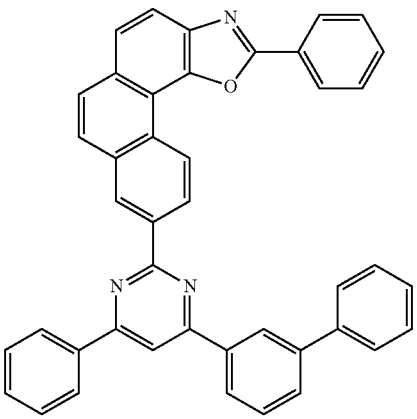

-continued
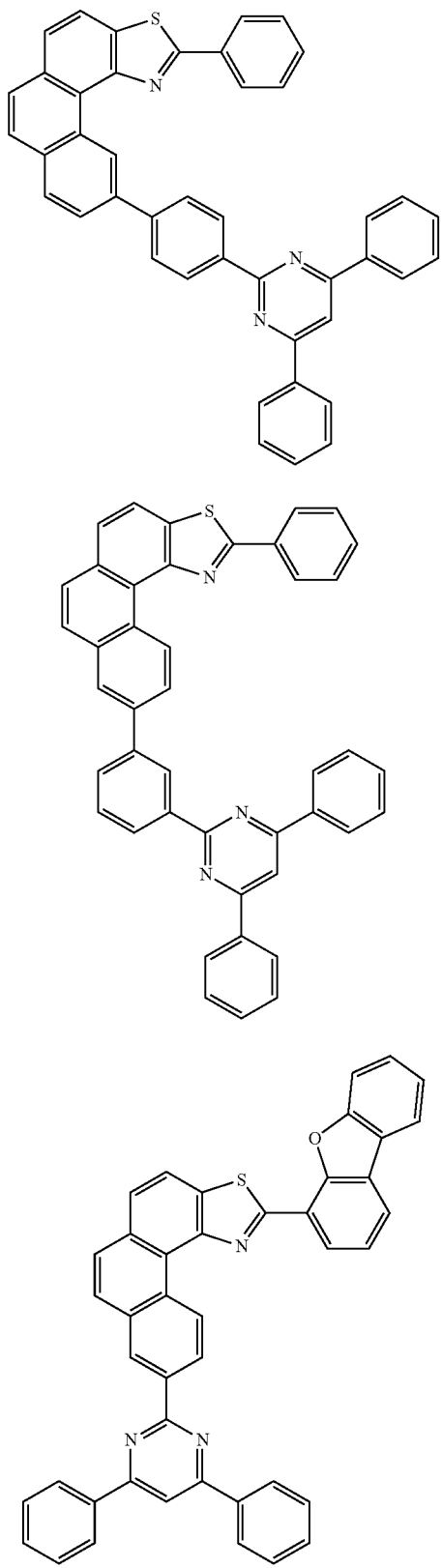
C-79
C-80
C-81
-continued
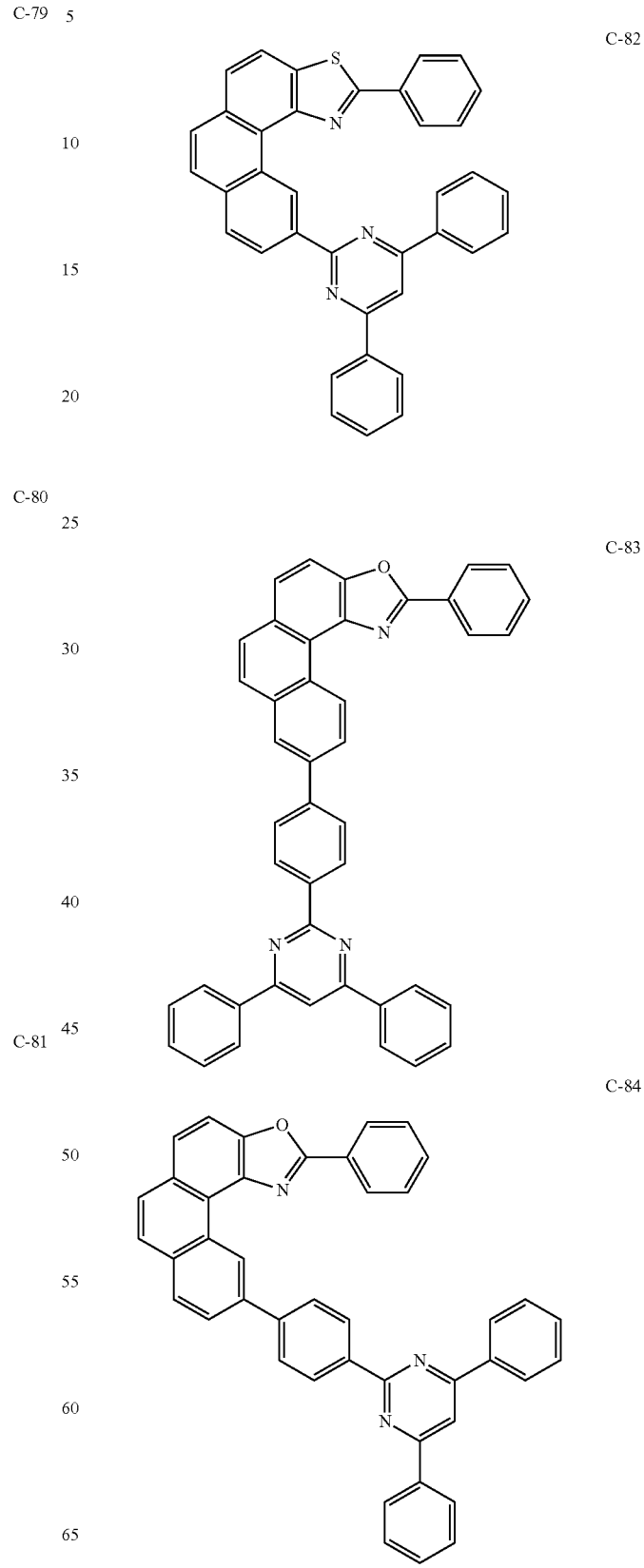
C-82
C-83
C-84

C-85
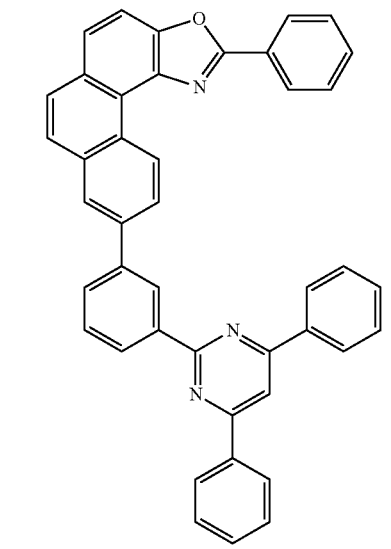
C-86
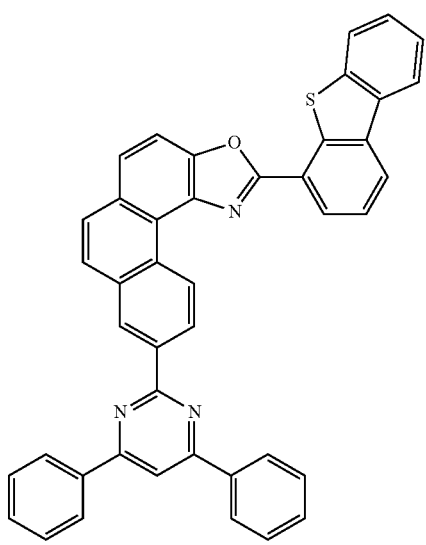
C-87
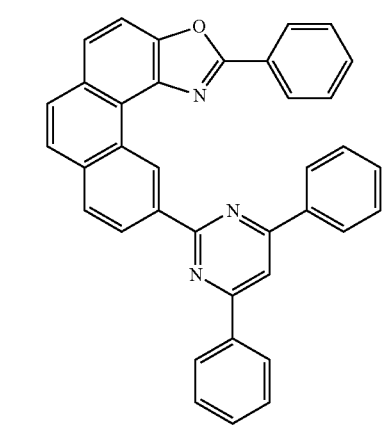
C-88
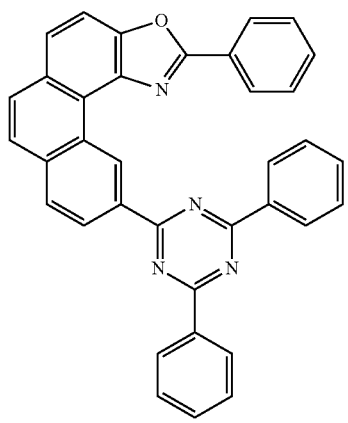
C-89
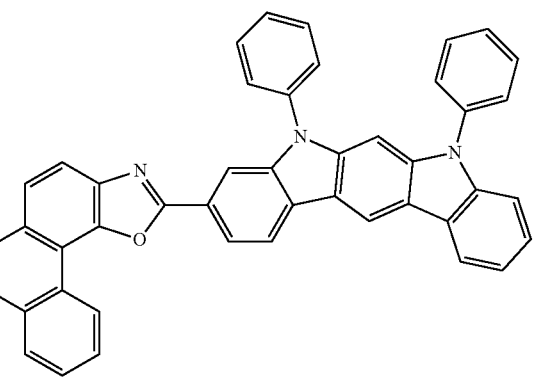
C-90
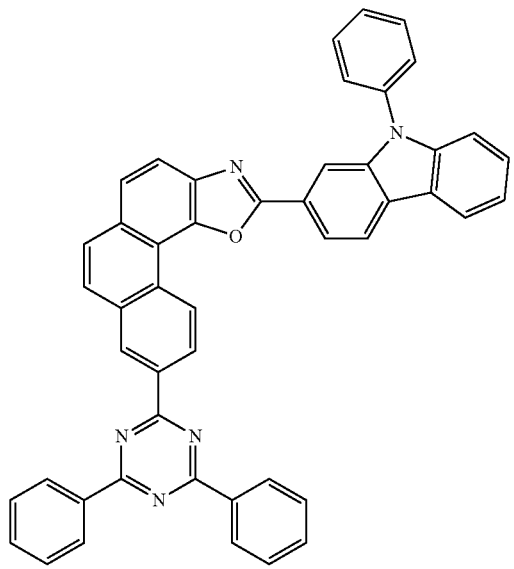

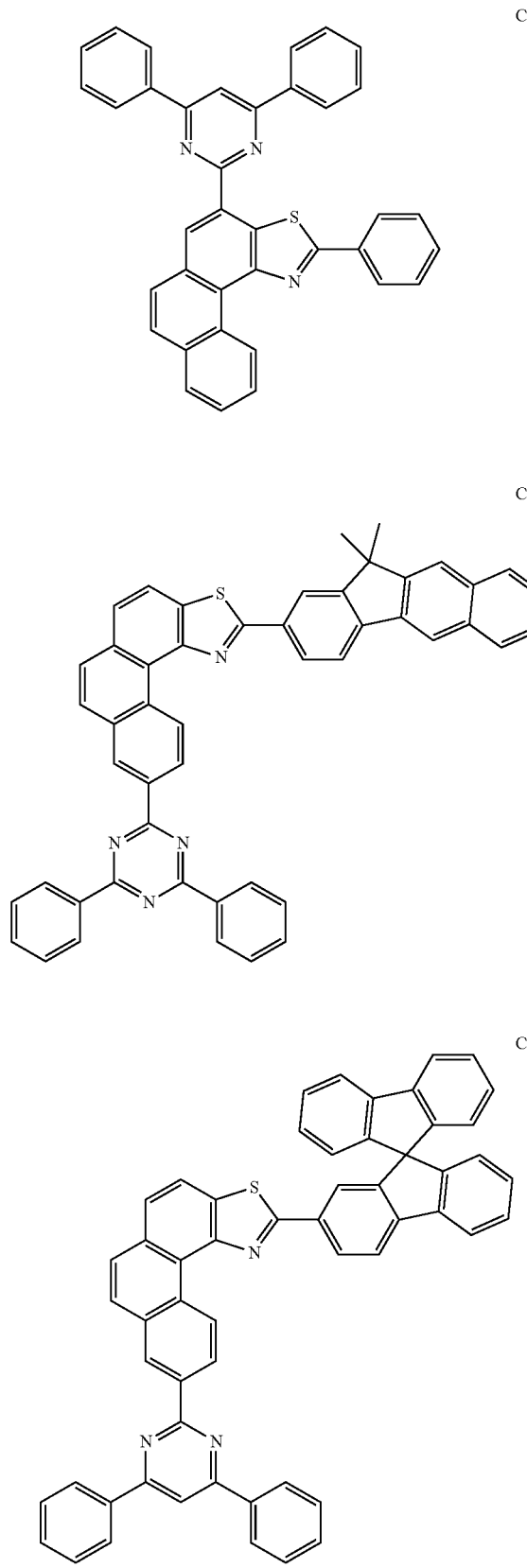
C-91
C-92
C-93
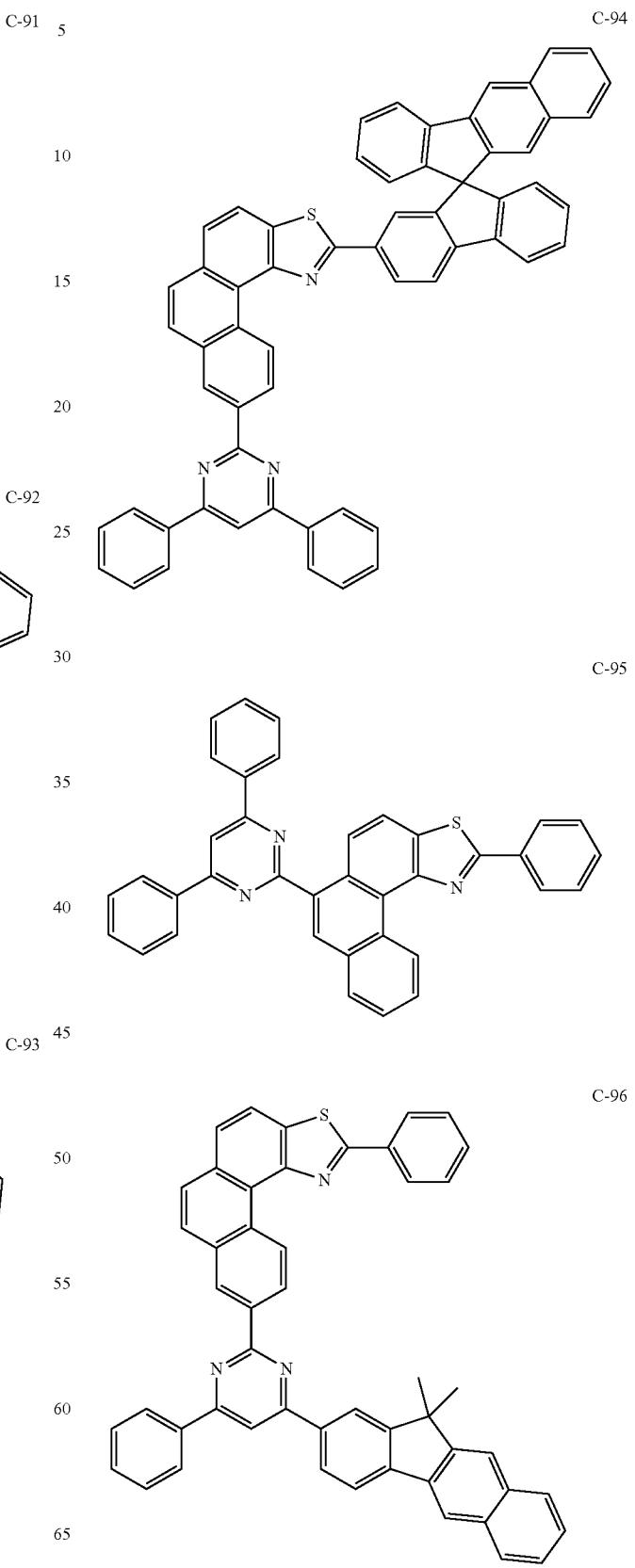
C-94
C-95
C-96

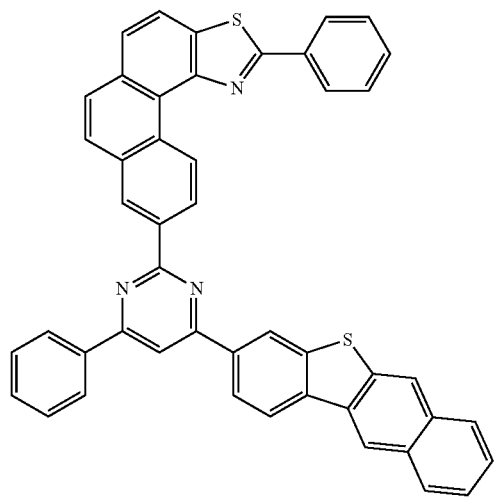
C-97
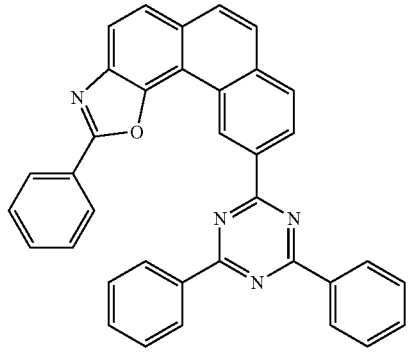
C-100
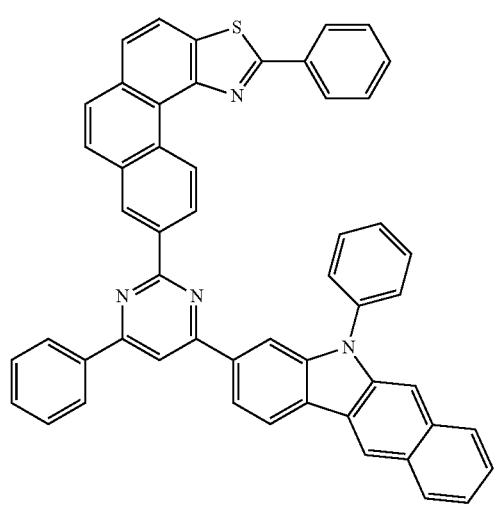
C-98
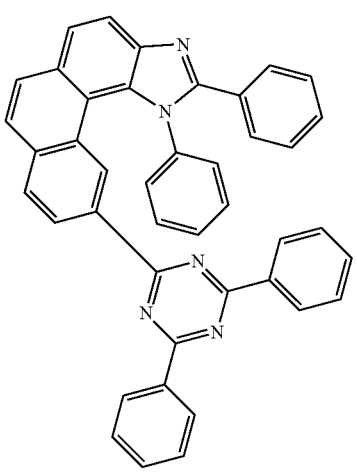
C-101
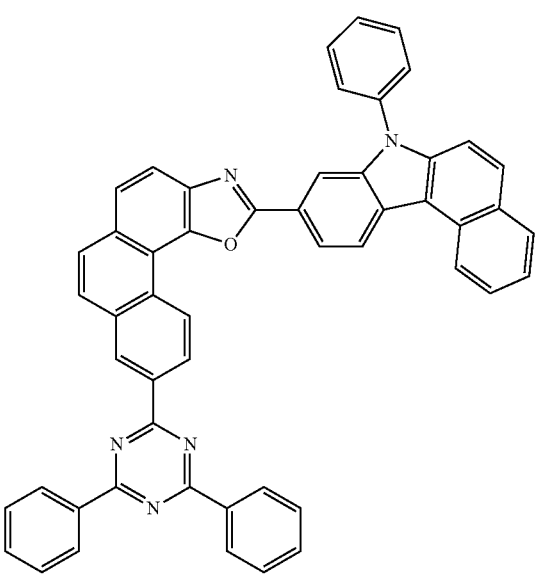
C-99
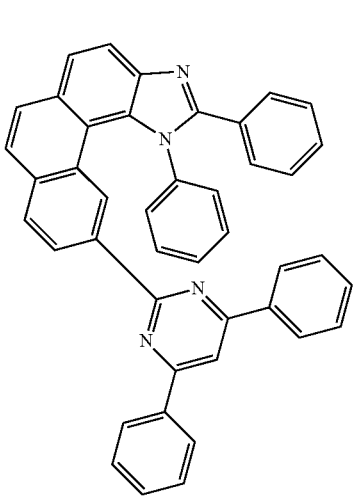
C-102

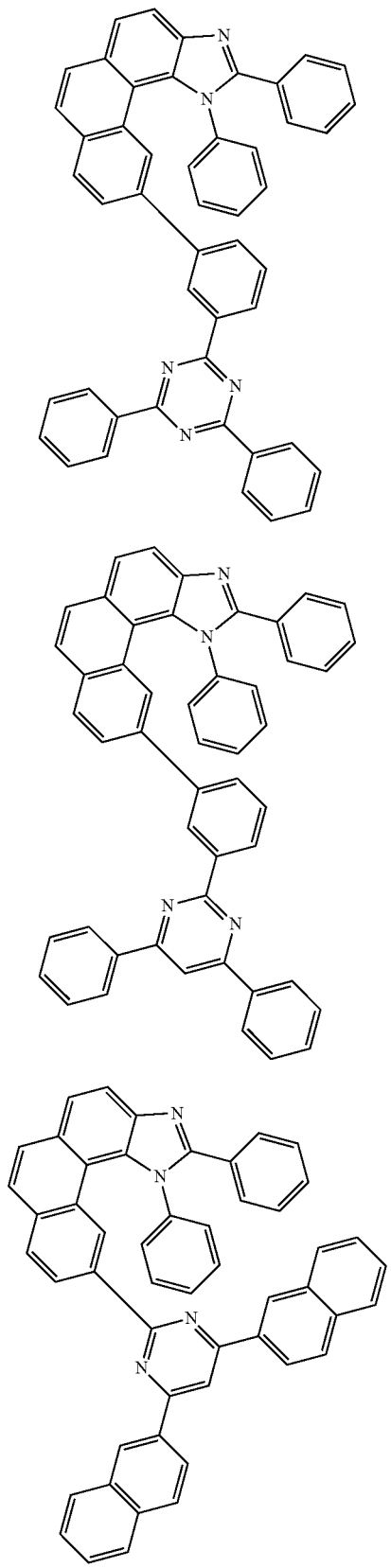
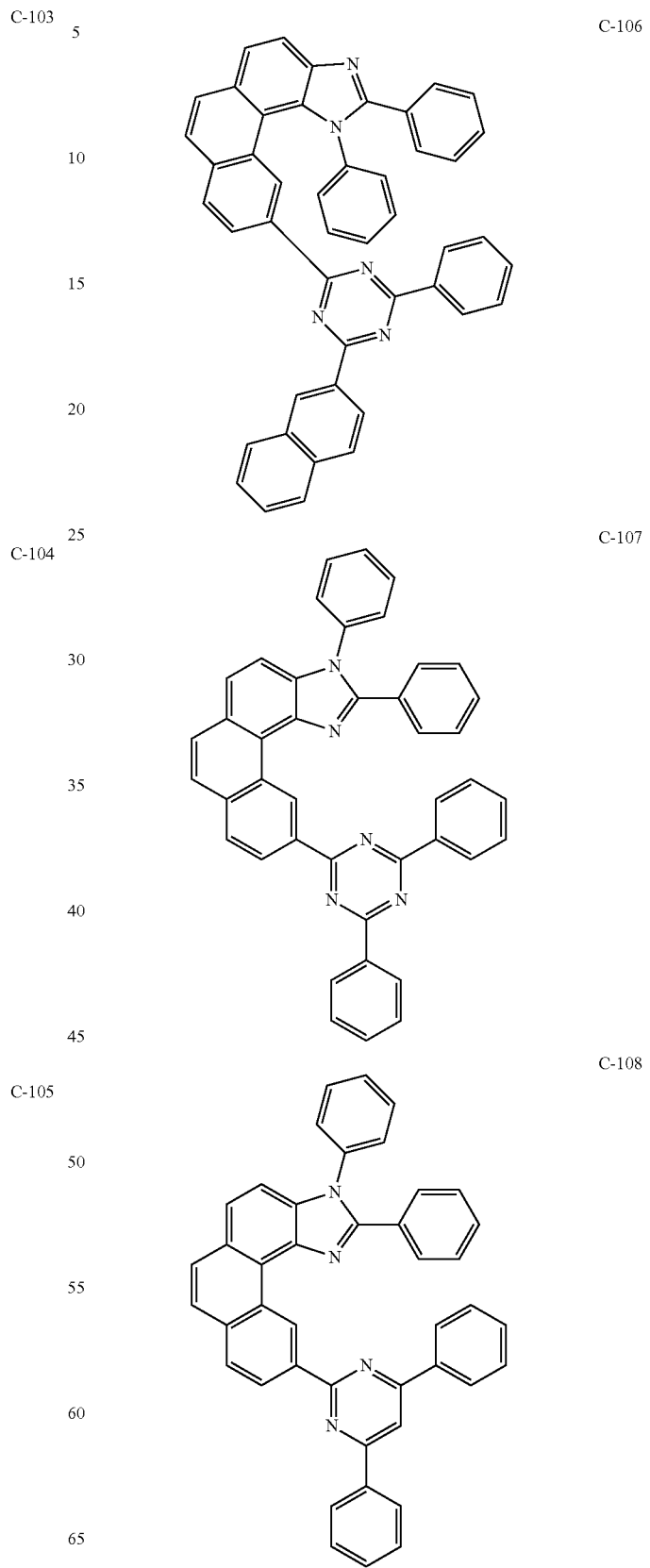

C-109
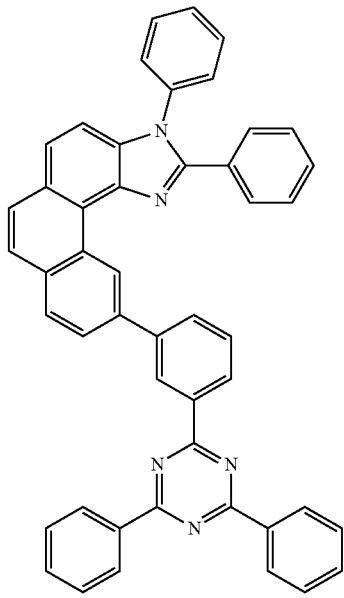
C-110
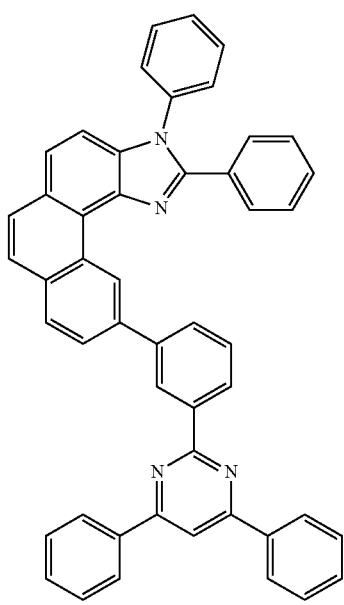
C-111
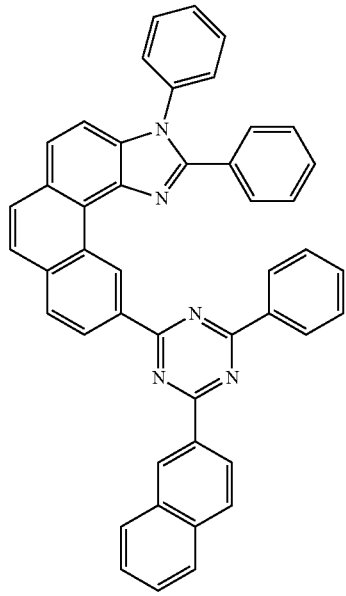
C-112
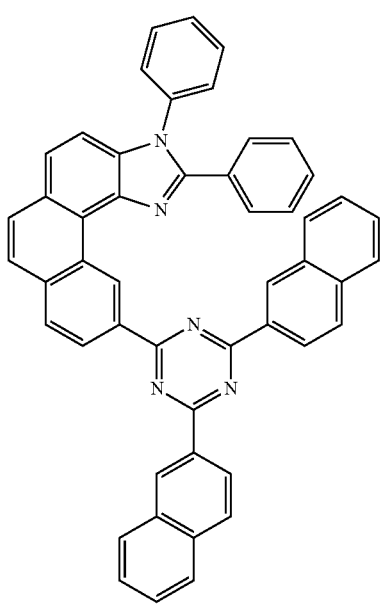
C-113
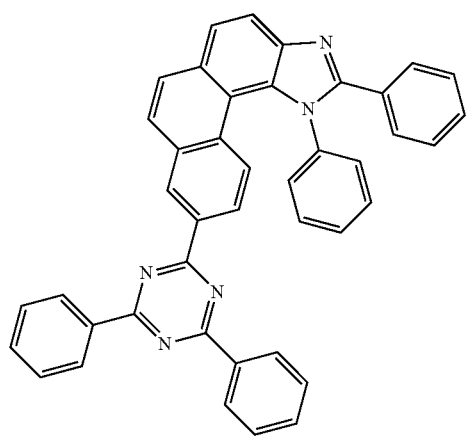

C-114
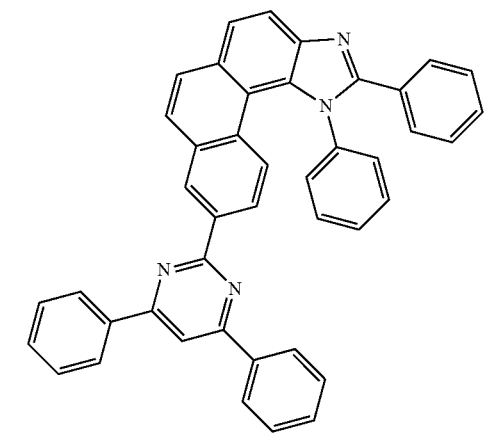
C-115
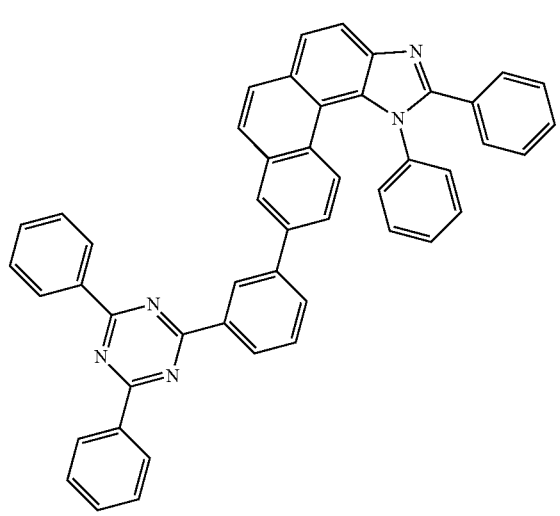
C-116
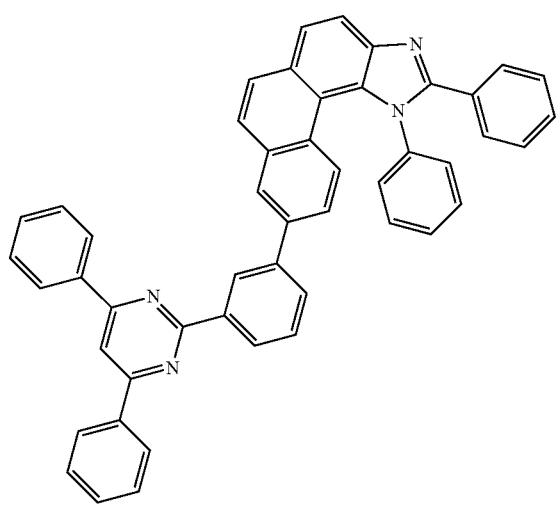
C-117
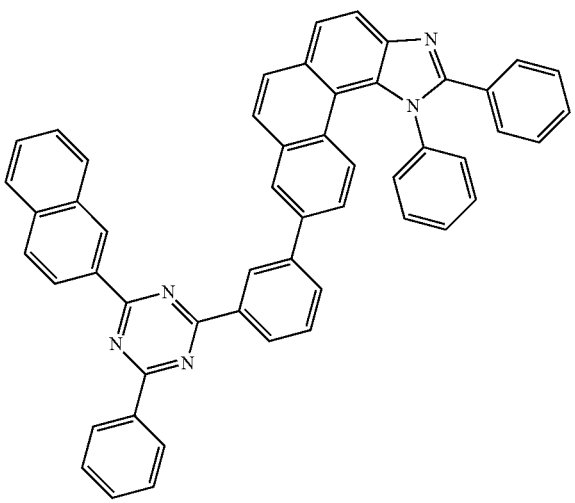
C-118
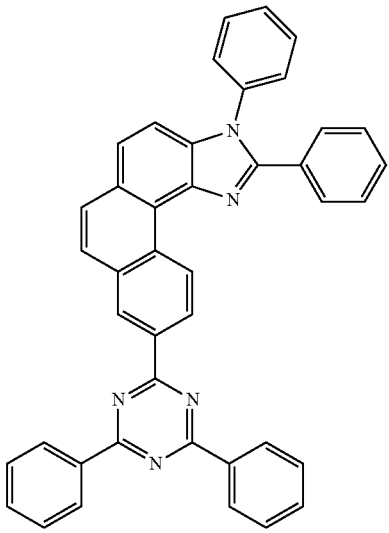
C-119

C-120
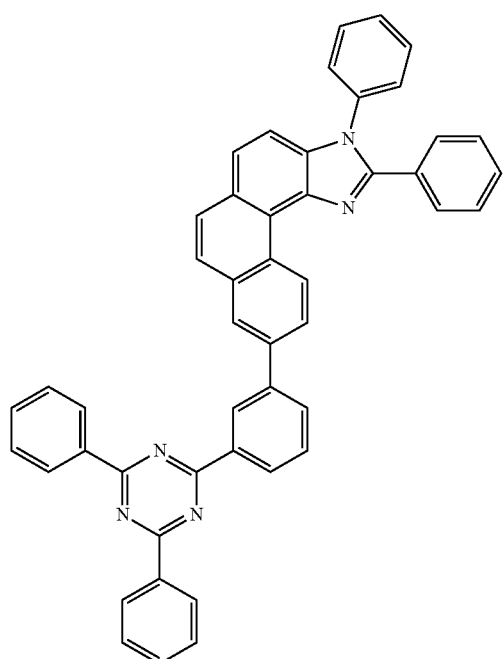
C-121
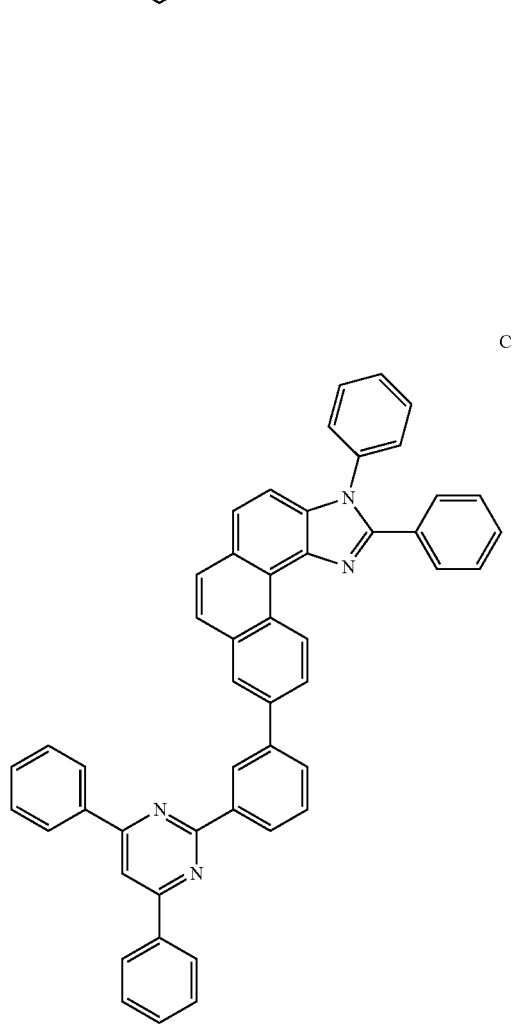
C-122
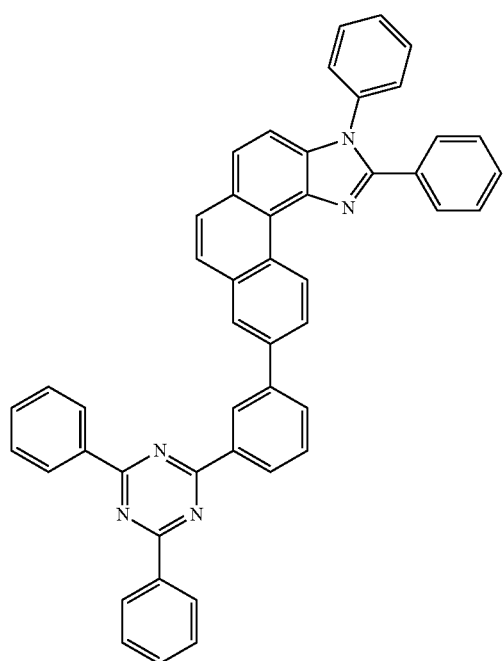
C-123
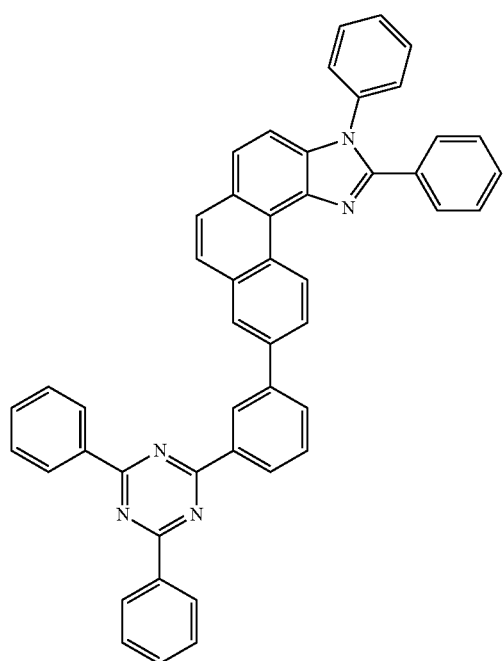
C-124
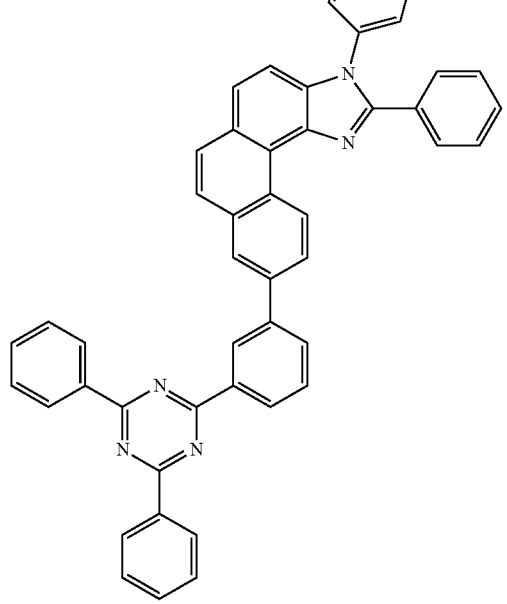

C-125
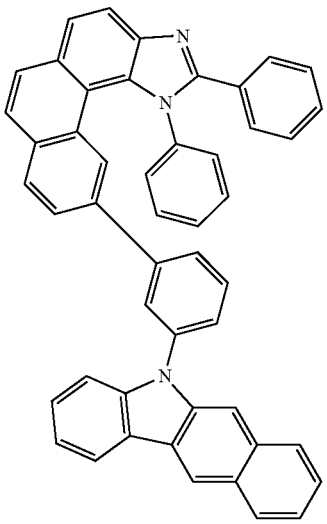
C-126
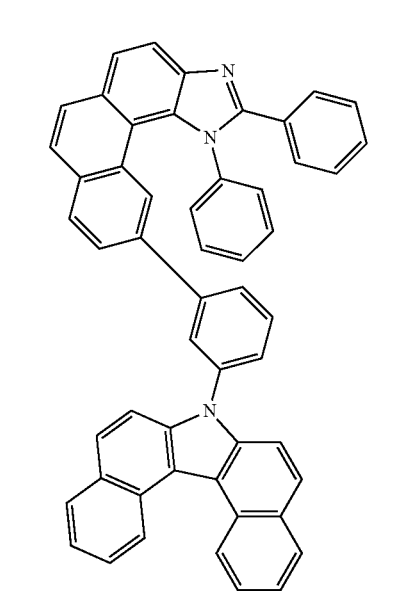
C-127
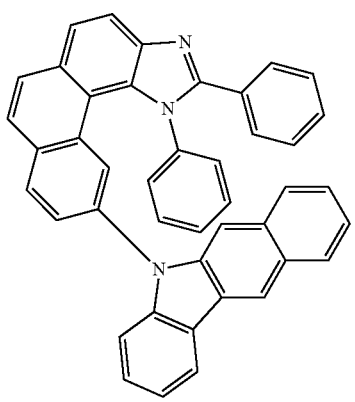
C-128
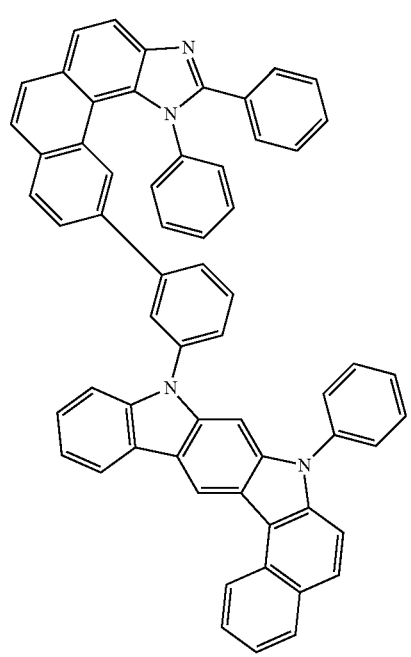
C-129
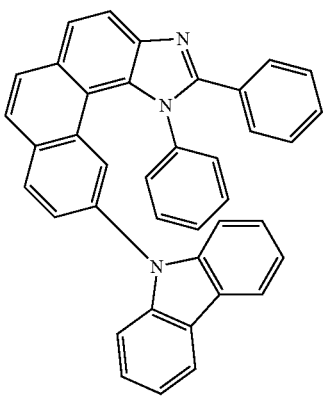

C-130
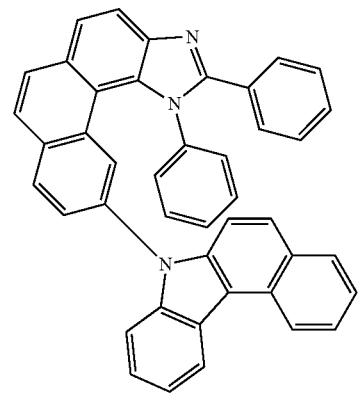
C-131
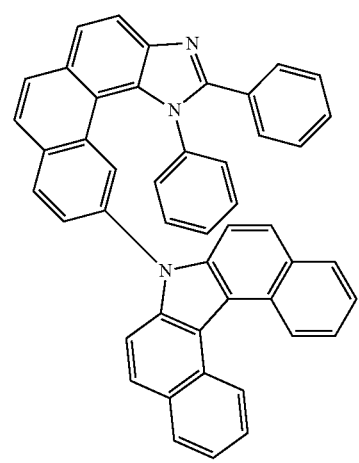
C-132
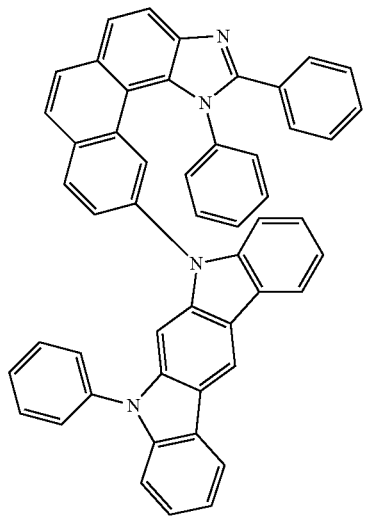
C-133
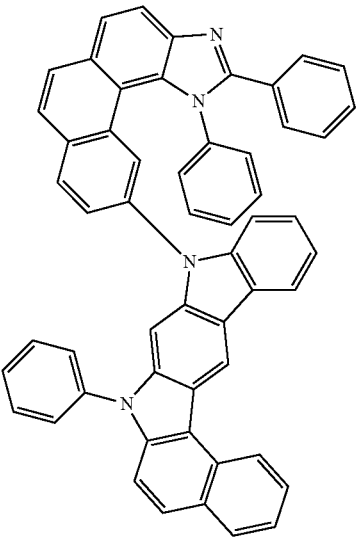
C-134
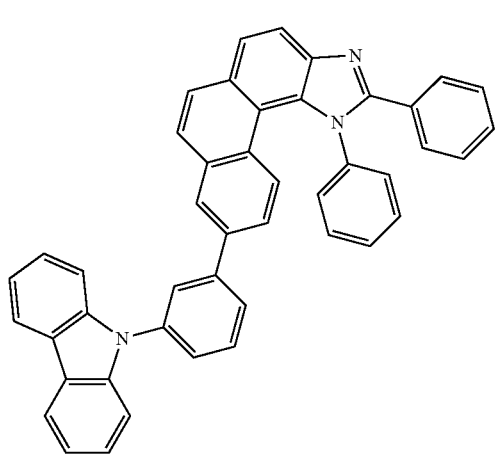
C-135
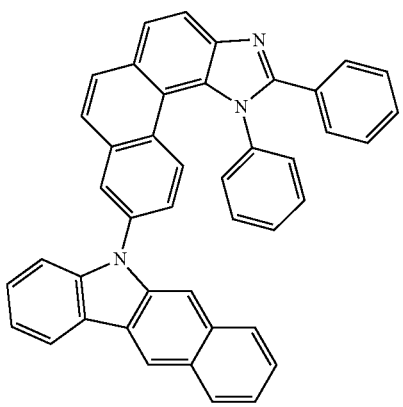

-continued
C-136
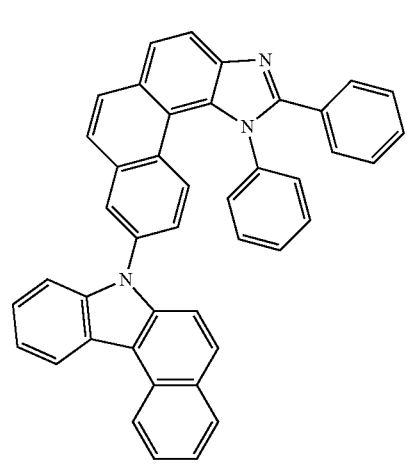
C-137
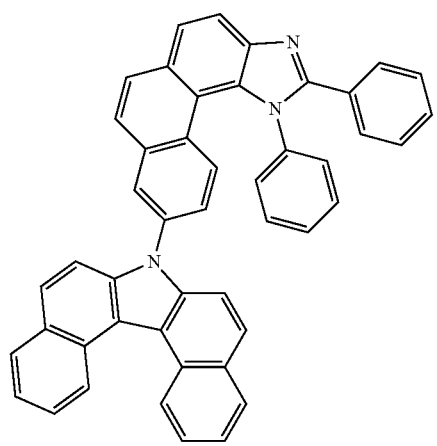
C-138
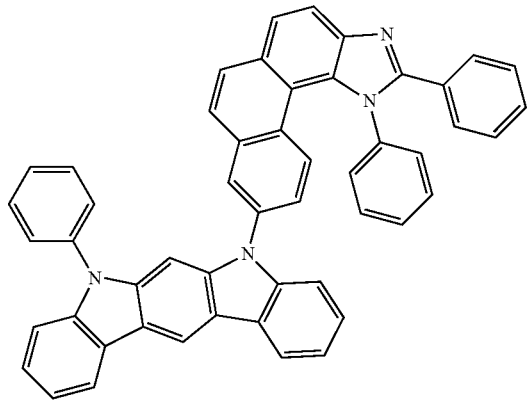
-continued
C-139
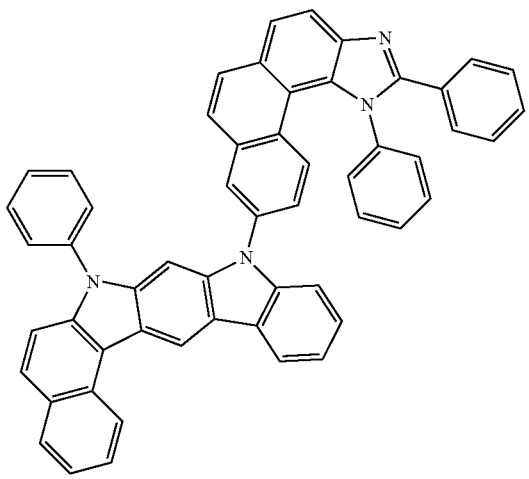
C-140
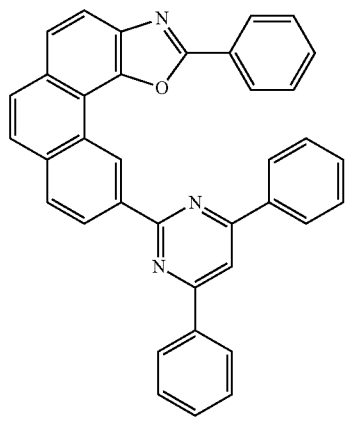
C-141
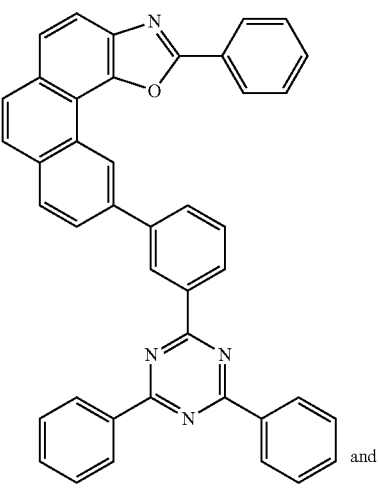
and

C-142

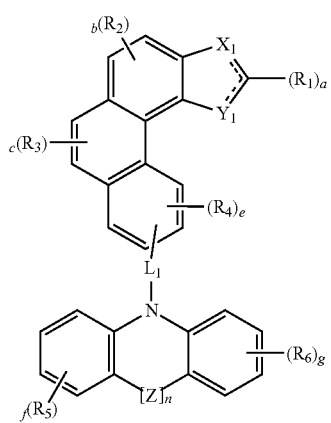

4. An electron transport material comprising a compound represented by the following formula 1:

(1)

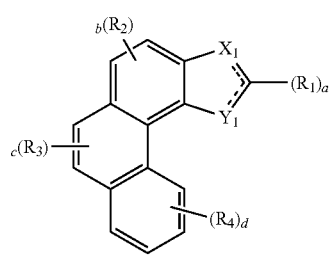

wherein, $X_1$, $Y_1$, $R_1$ to $R_4$, and a to d are as defined in claim 1.

5. The electron transport material according to claim 4, wherein formula 1 is represented by any of the following formulae 2 to 4:

(2)

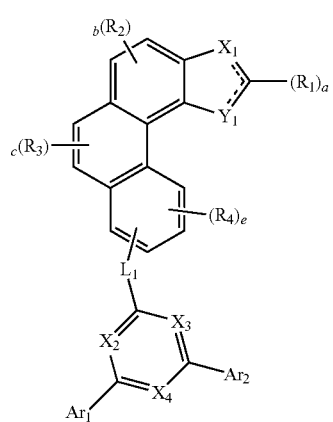

(3)

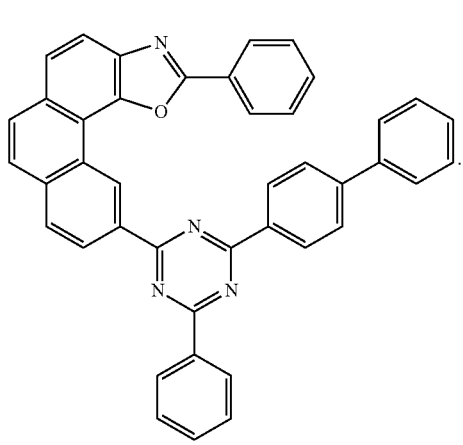

(4)

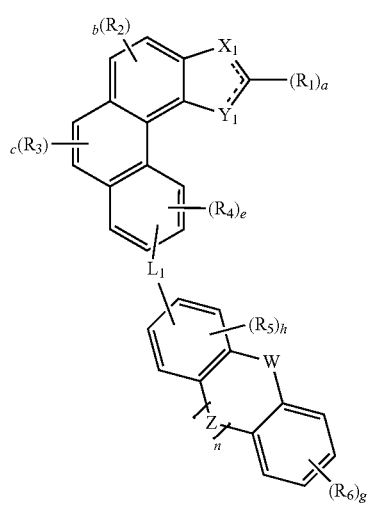

wherein, $X_1$ to $X_4$, $Y_1$, $R_1$ to $R_6$, $L_1$, $Ar_1$, $Ar_2$, Z, a to c, e to g and n are as defined in claim 2.

6. The electron transport material according to claim 4, wherein the compound of formula 1 is selected from the group consisting of:

C-1

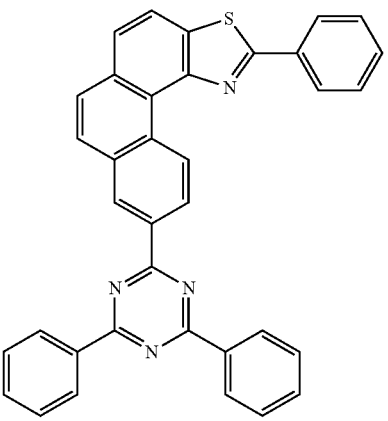

275
-continued
C-2
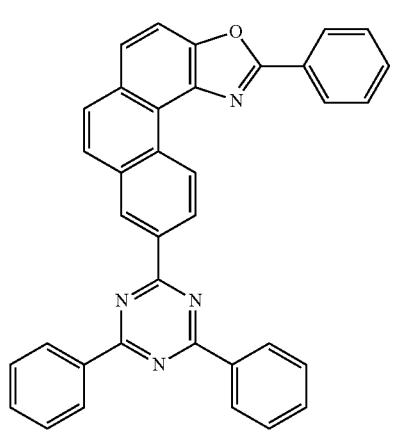
C-3
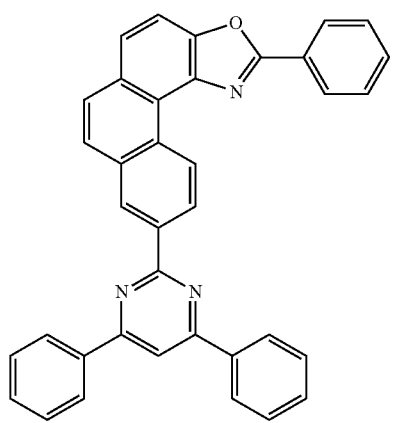
C-4
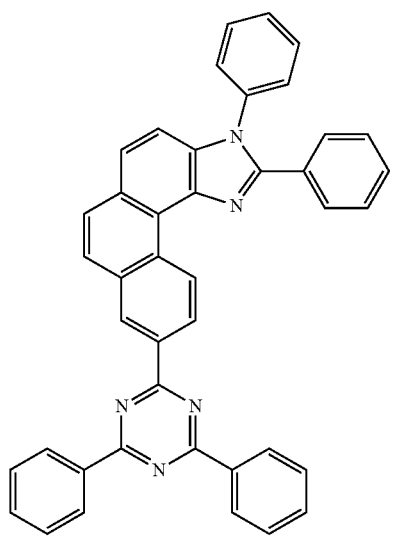
276
-continued
C-5
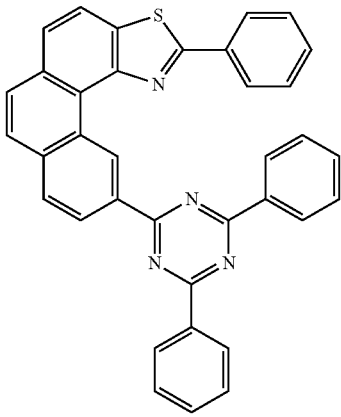
C-6, C-7
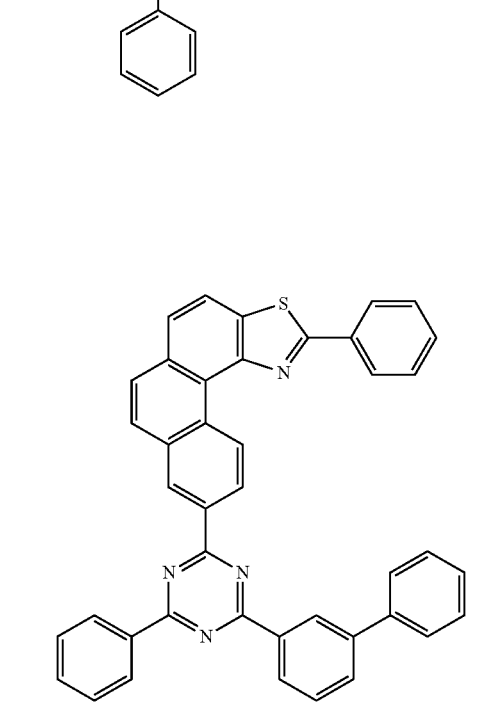

-continued
C-8
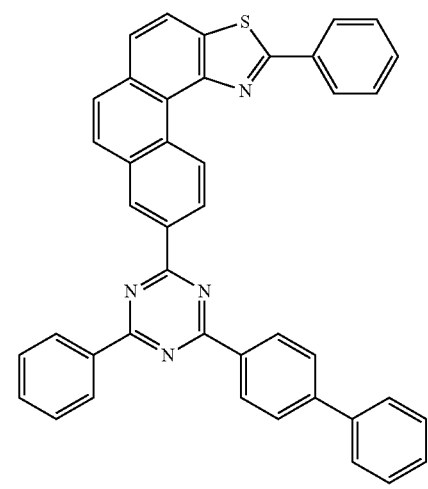
C-9
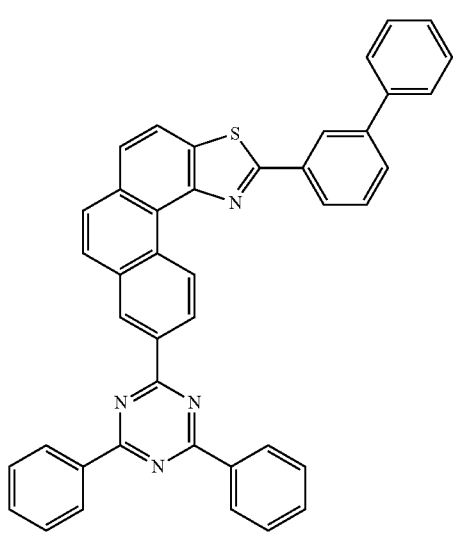
C-10
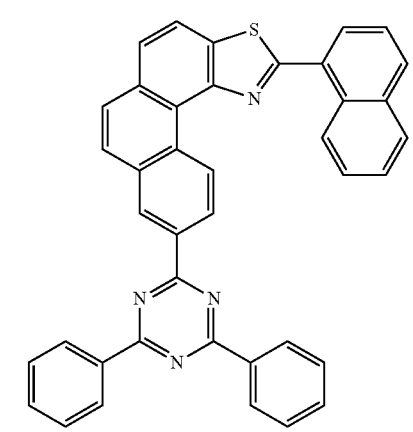
-continued
C-11
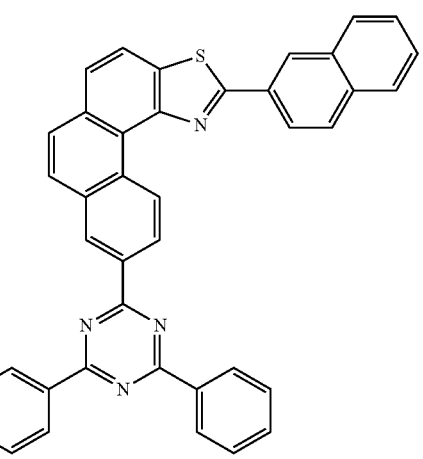
C-12
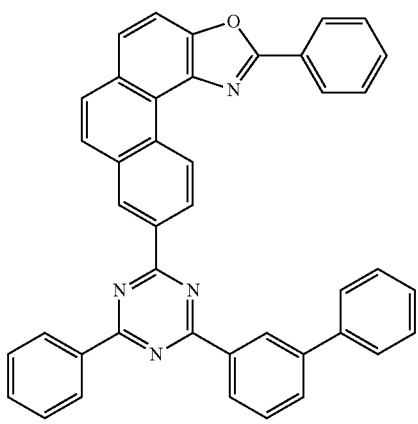
C-13
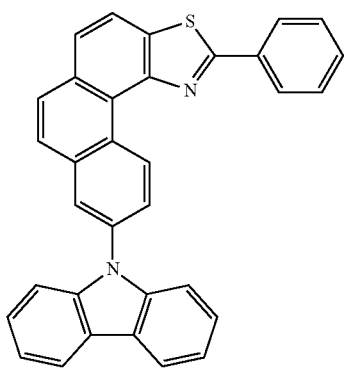

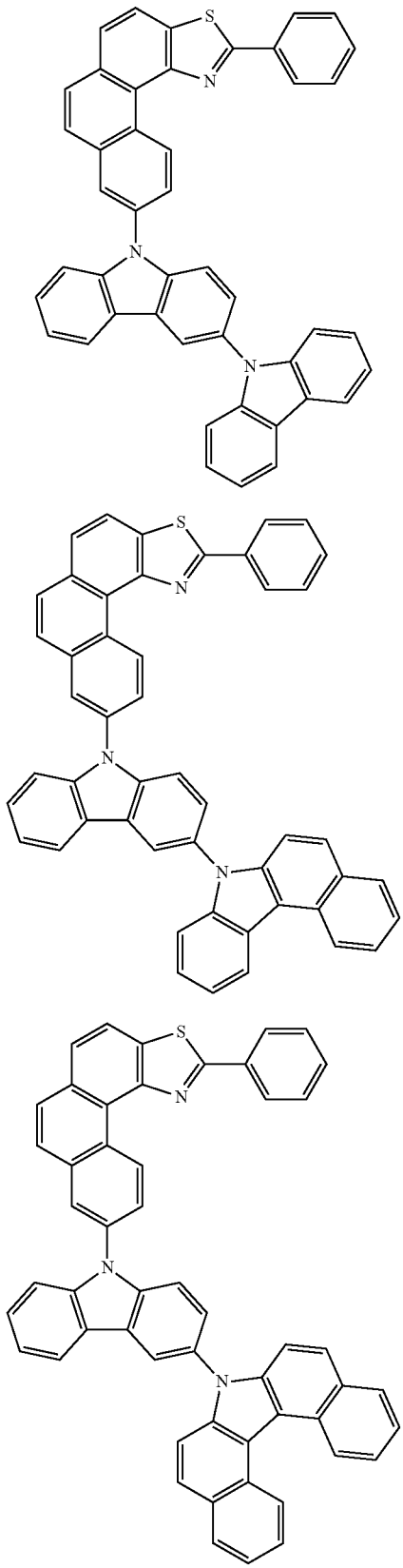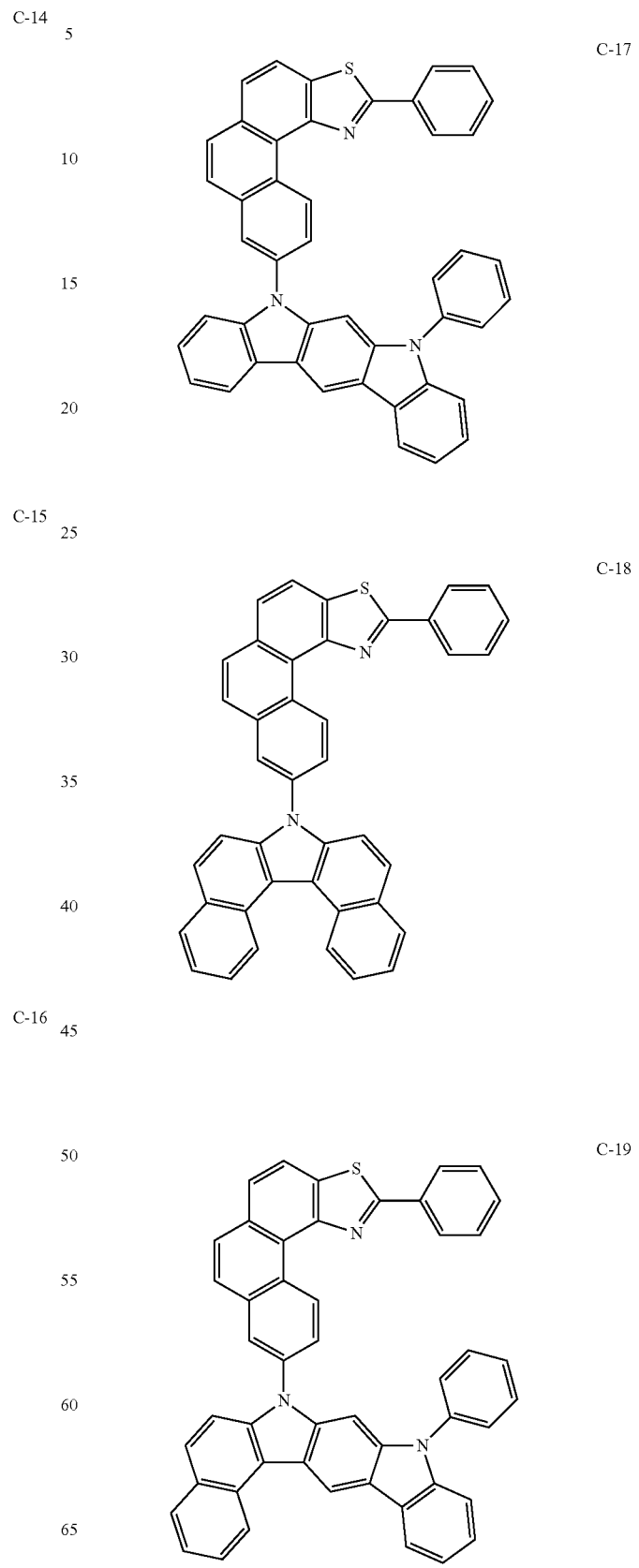

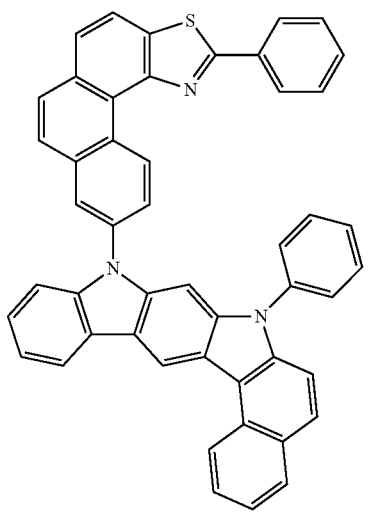
C-20
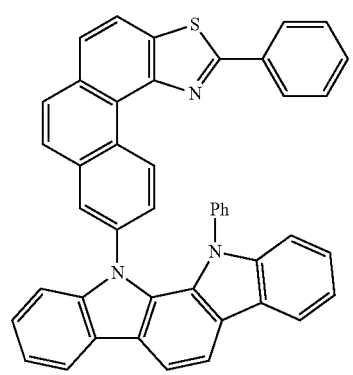
C-21
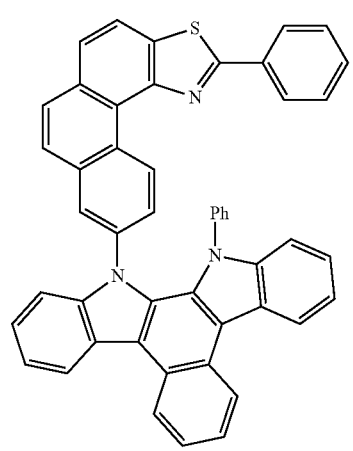
C-22
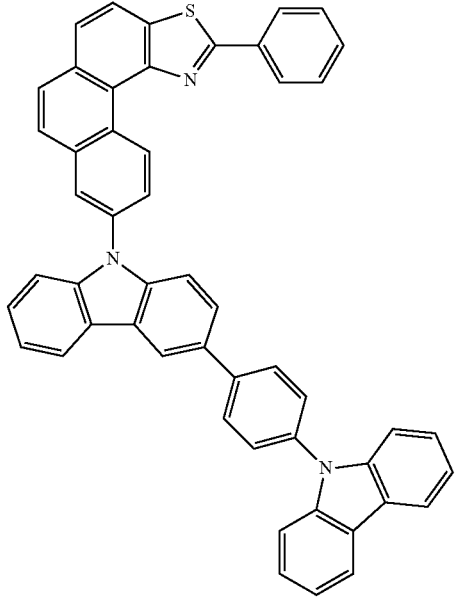
C-23
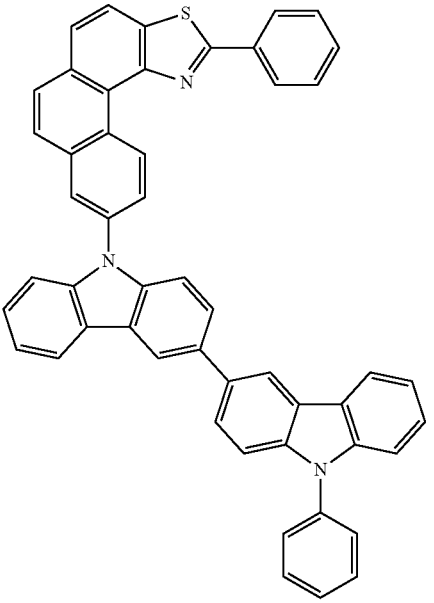
C-24

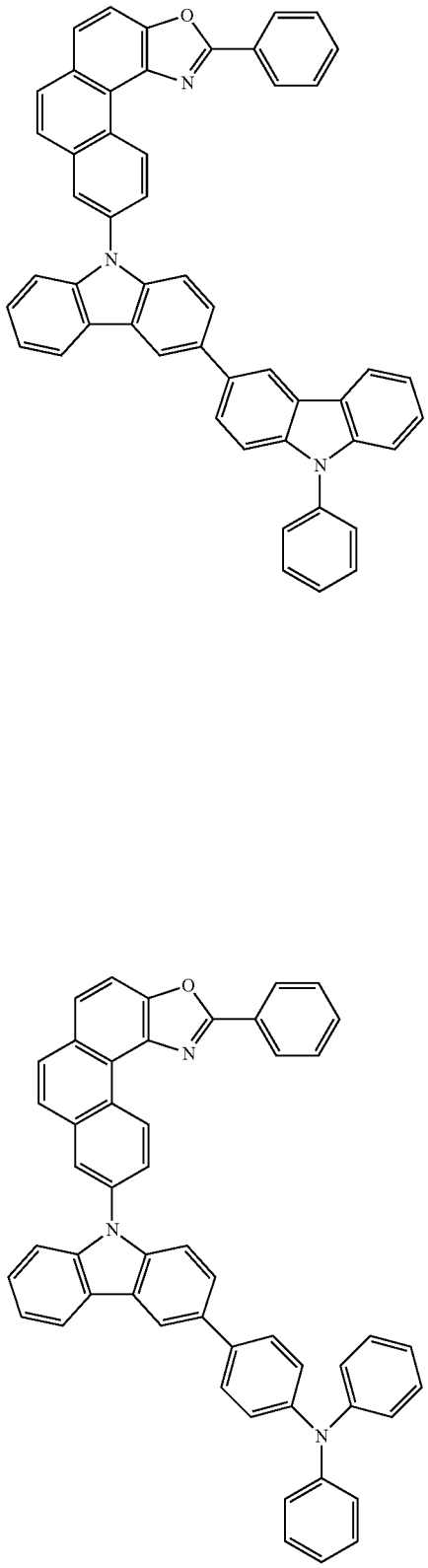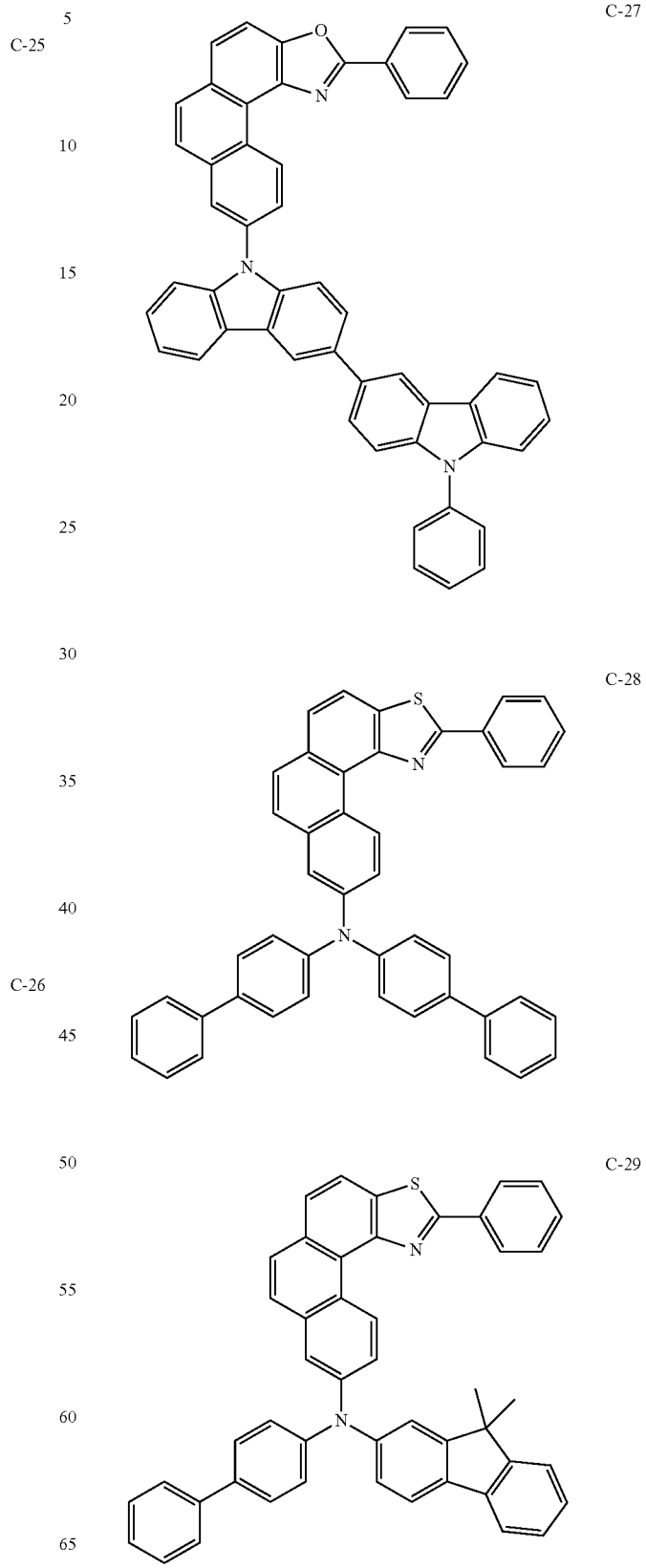

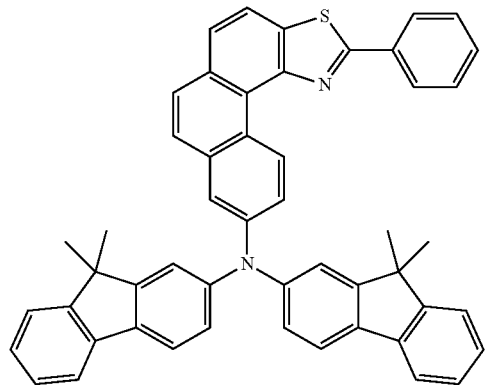
C-30
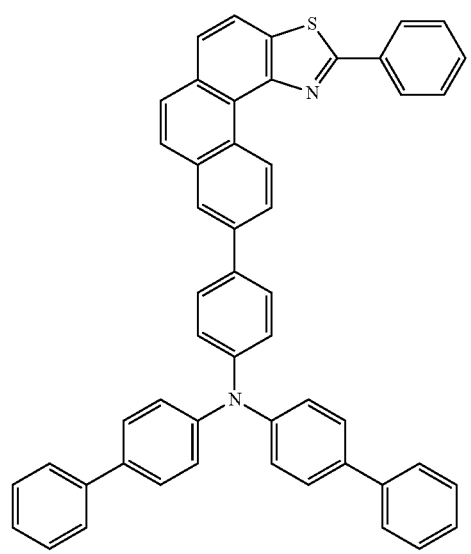
C-31
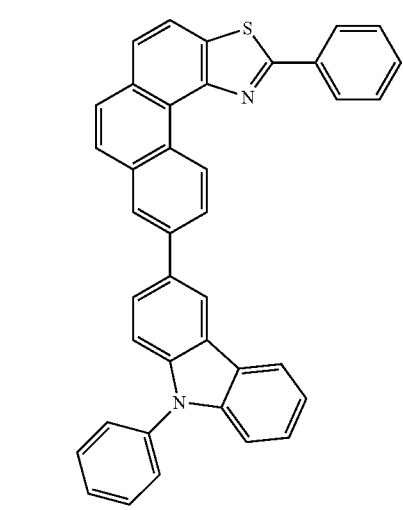
C-32
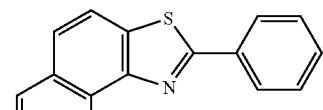
C-33
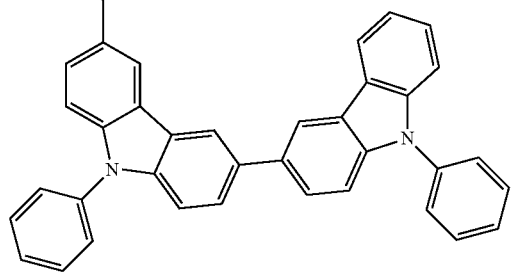
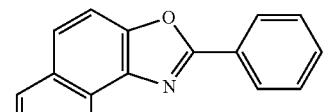
C-34
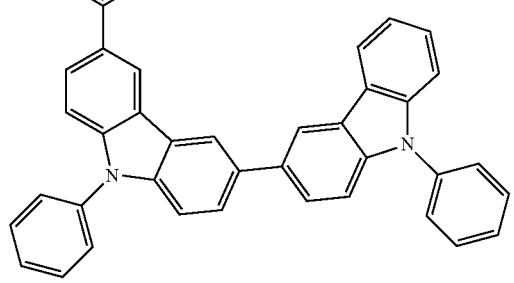
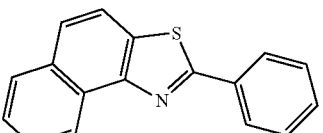
C-35
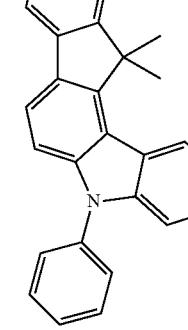

C-36
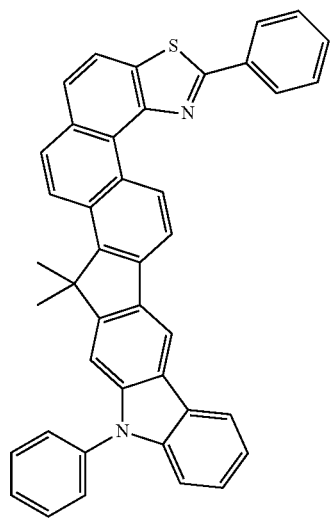
C-37
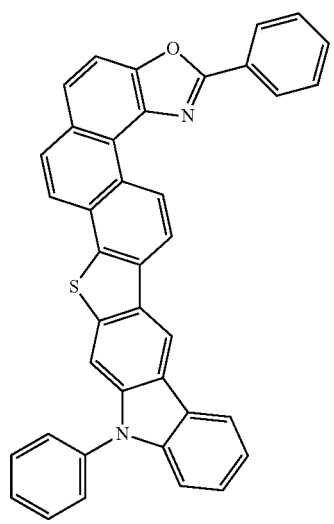
C-38
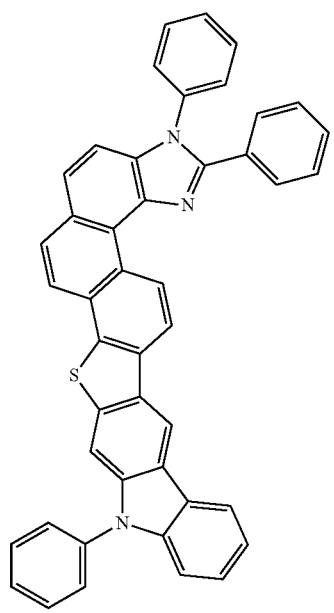
C-39
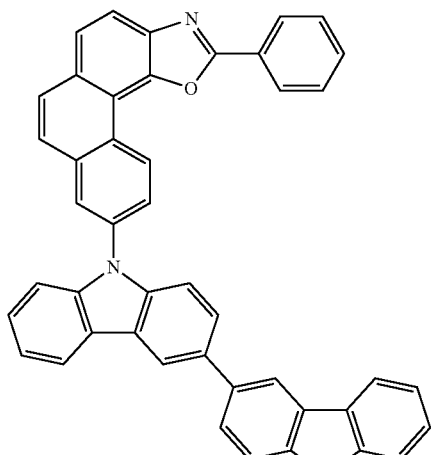
C-40
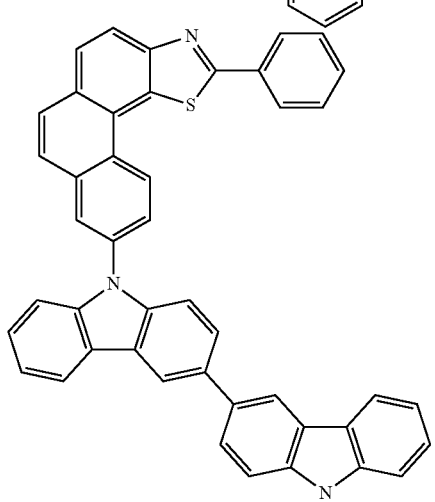
C-41
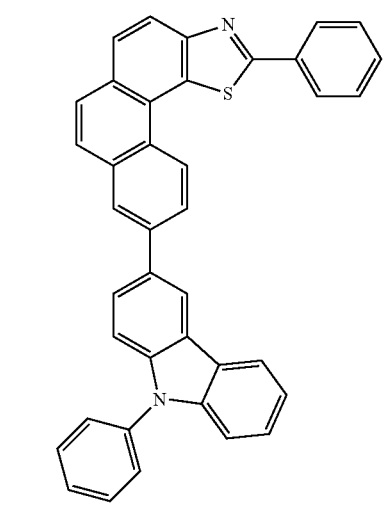

C-42 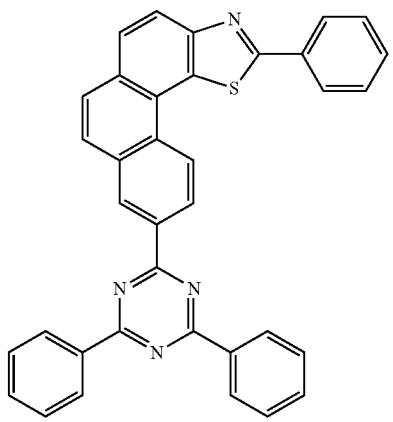
C-45 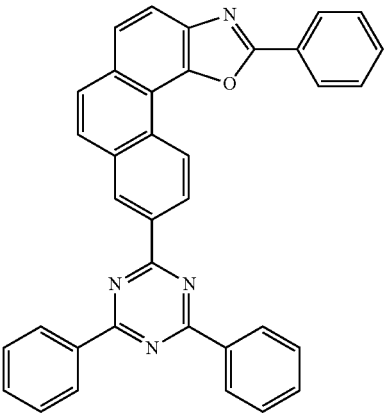
C-43 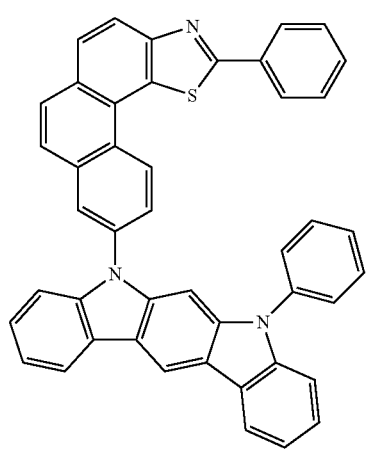
C-46 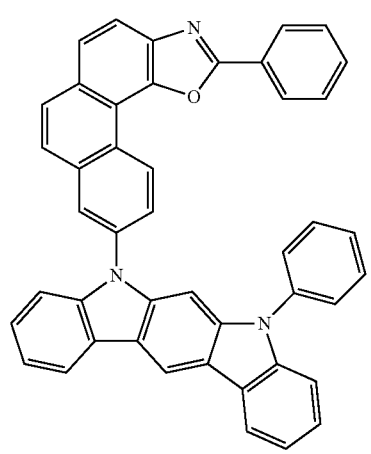
C-44 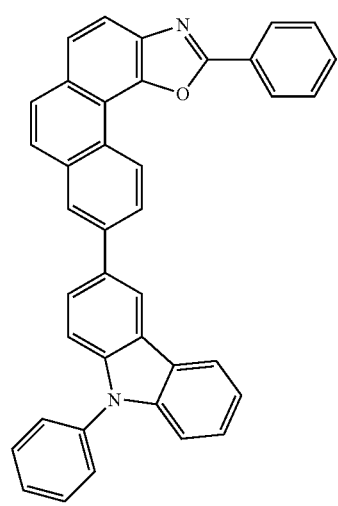
C-47 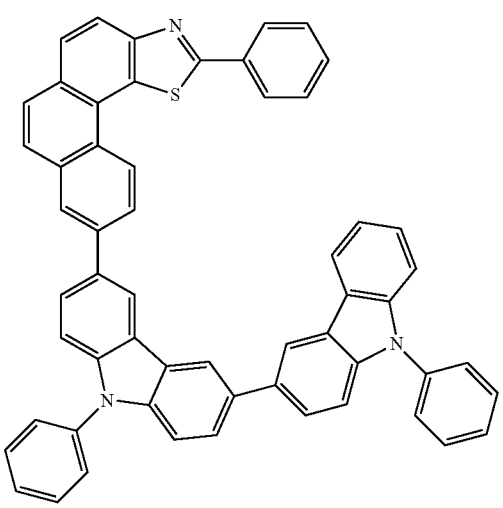

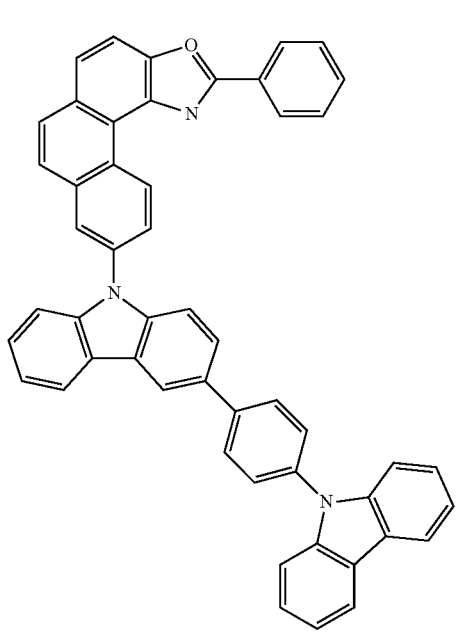
C-48
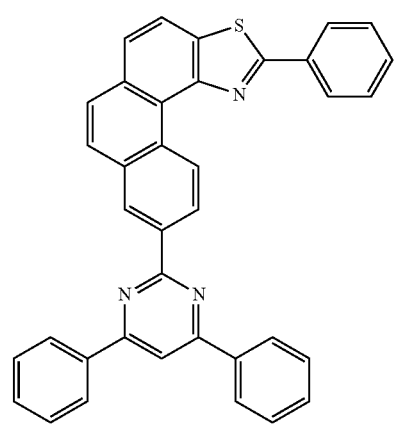
C-49
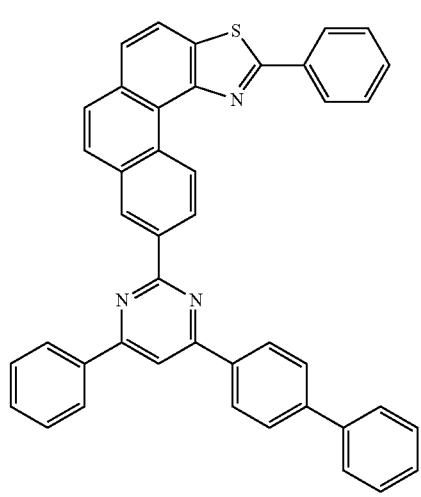
C-50
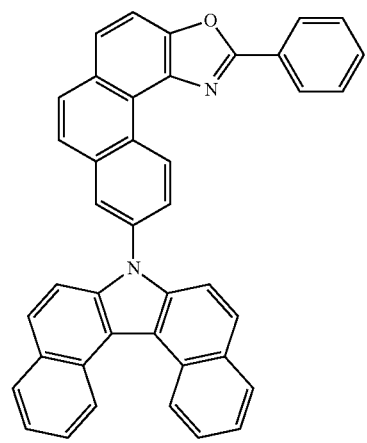
C-51
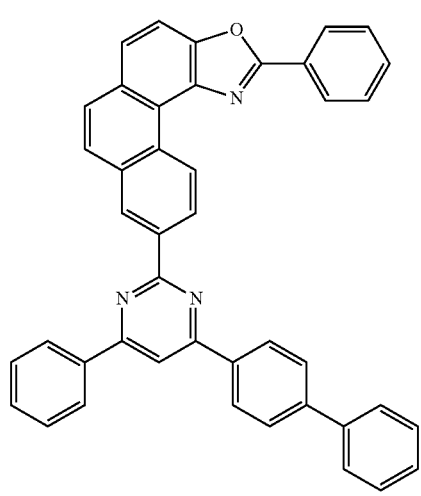
C-52
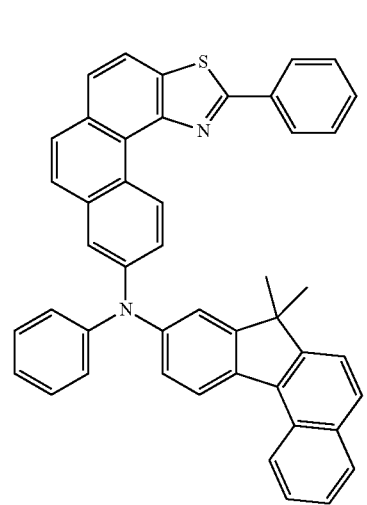
C-53

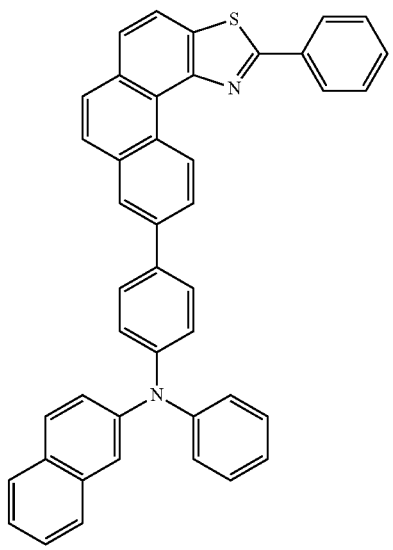
C-54
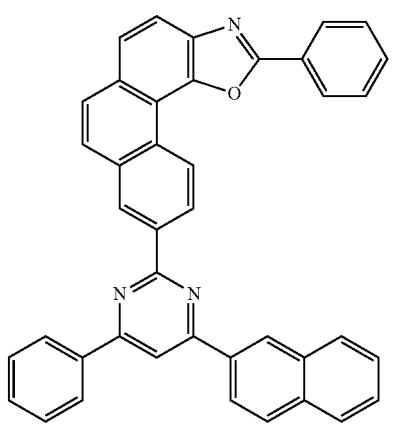
C-55
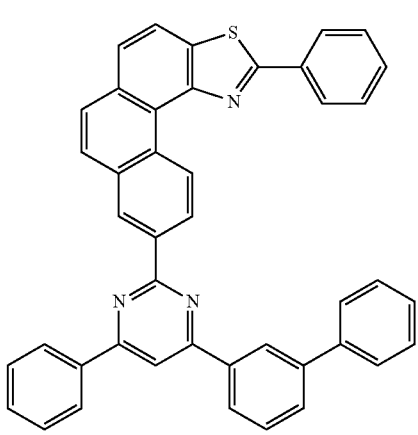
C-56
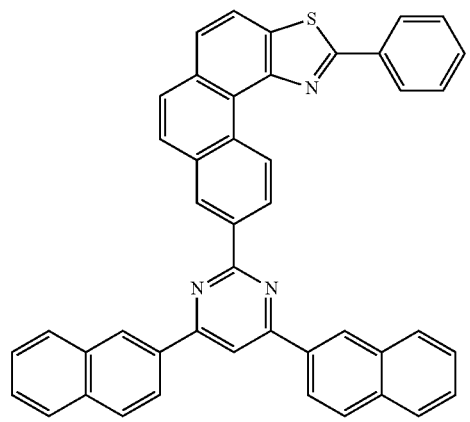
C-57
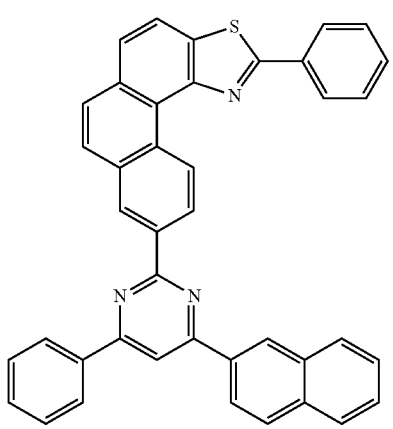
C-58
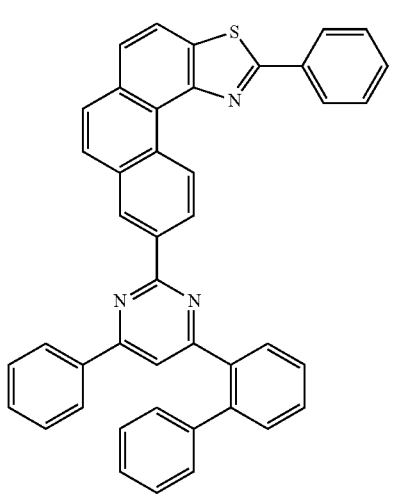
C-59

-continued
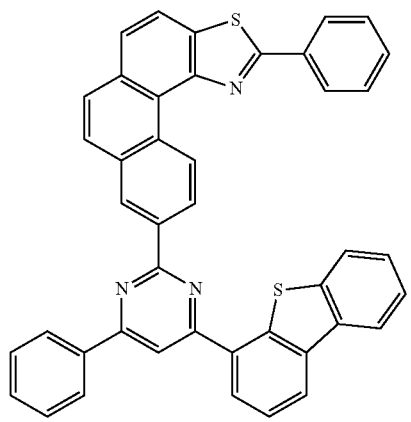
C-60
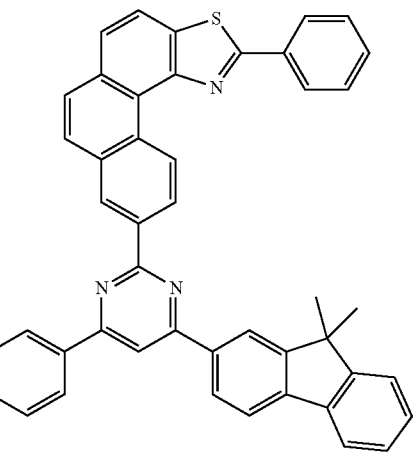
C-63
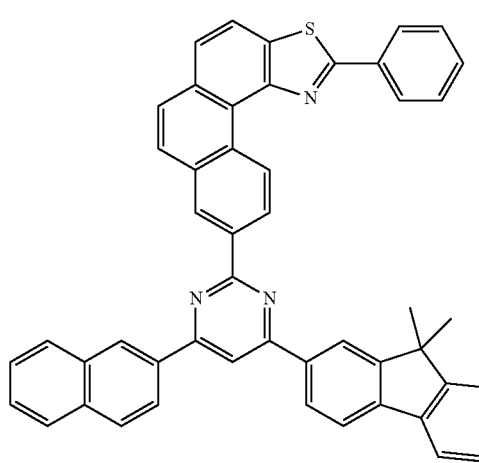
C-61
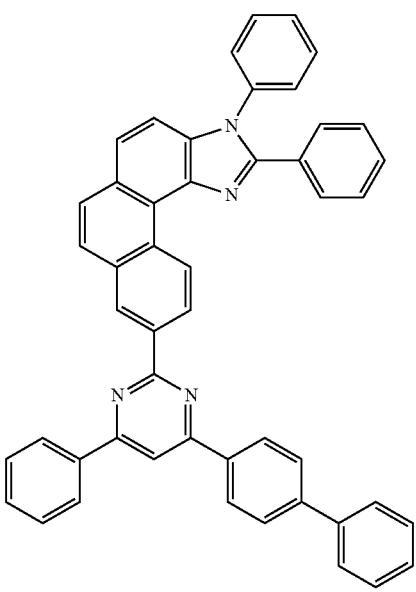
C-64
C-62
C-65

C-66
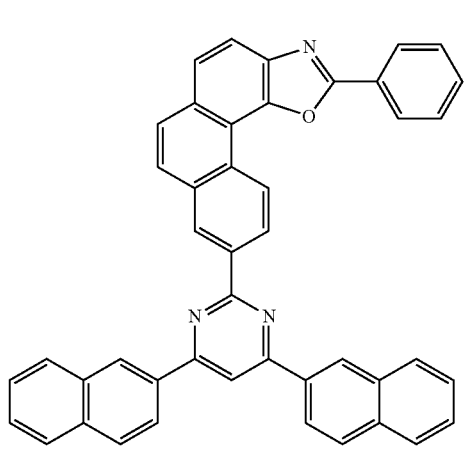
C-67
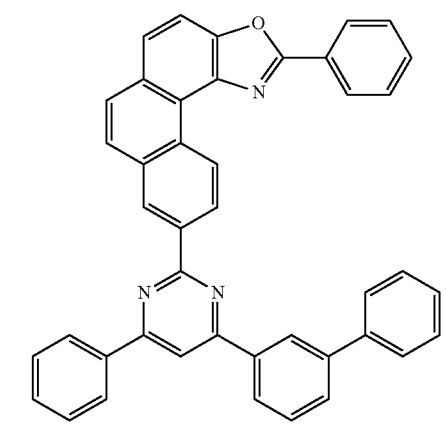
C-68
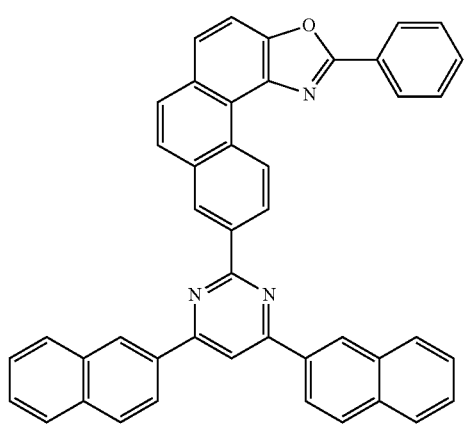
C-69
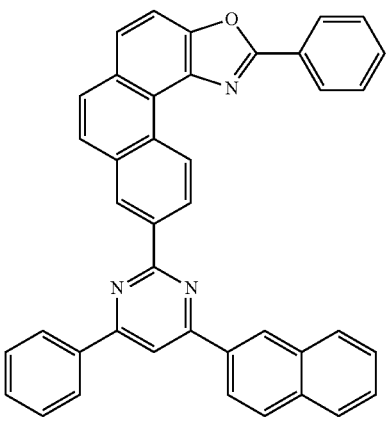
C-70
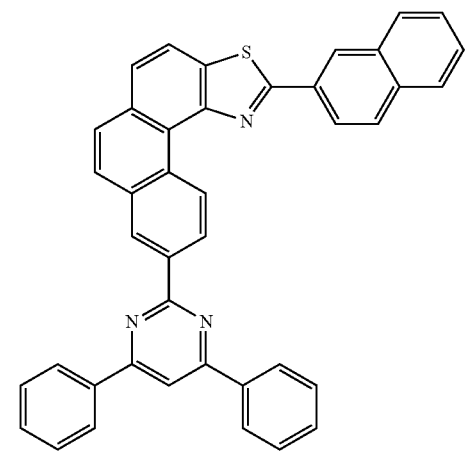
C-71
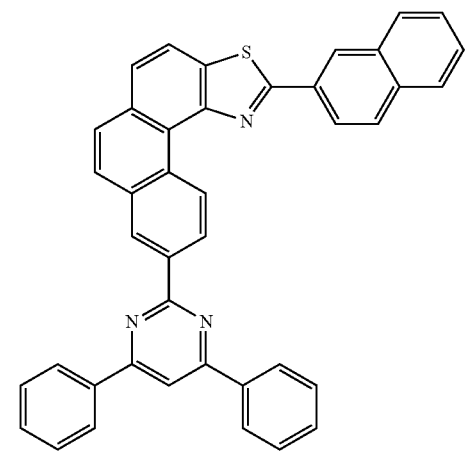

-continued
C-72
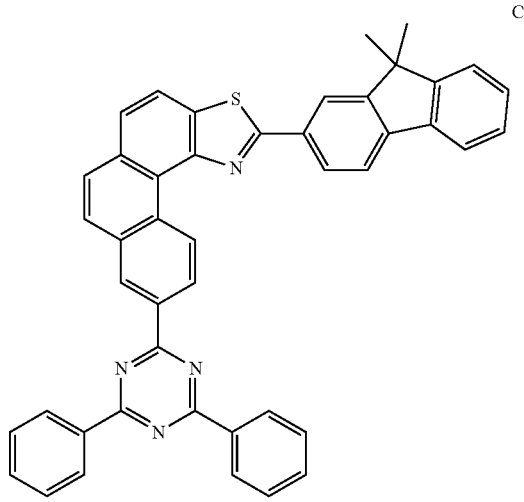
C-73
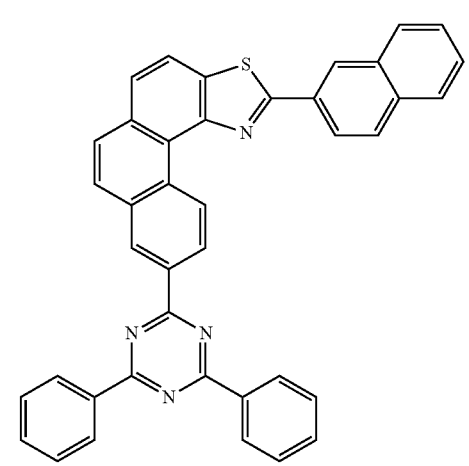
C-74
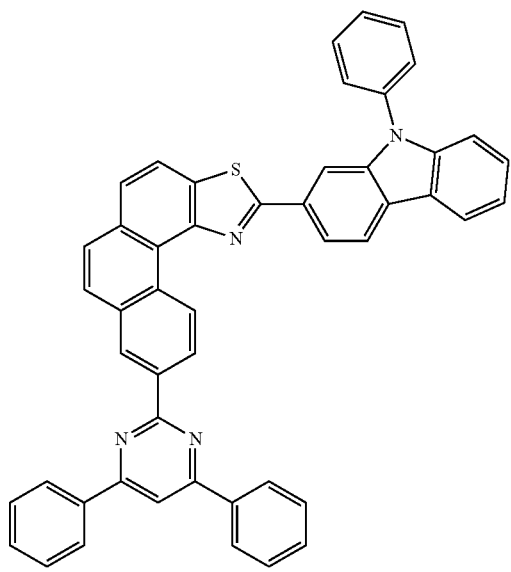
-continued
C-75
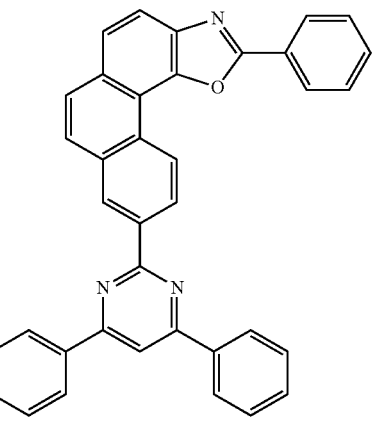
C-76
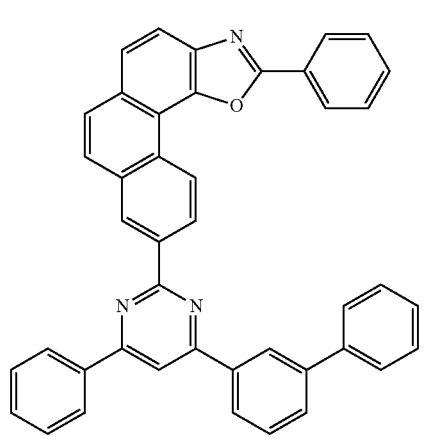
C-77
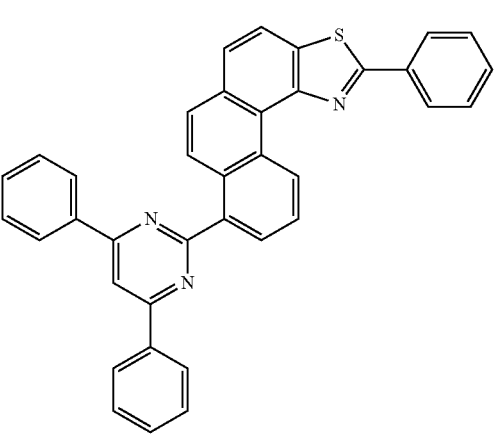

C-78
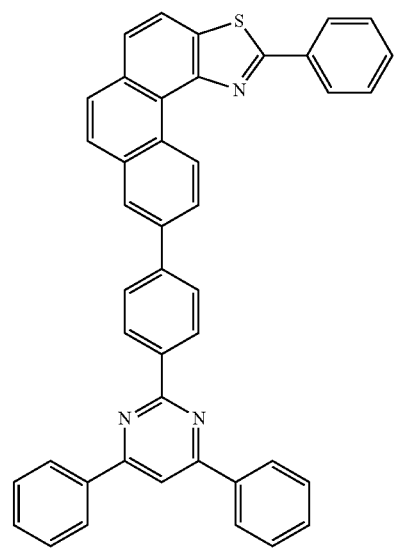
C-79
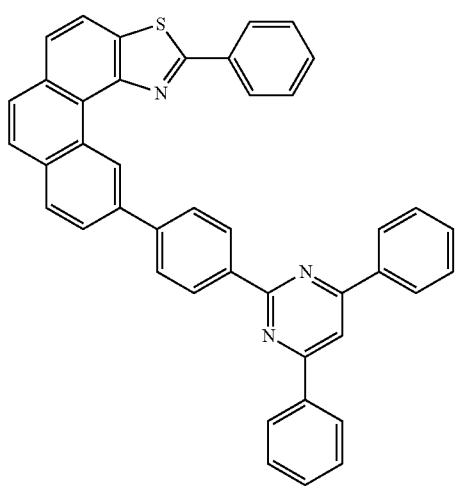
C-80
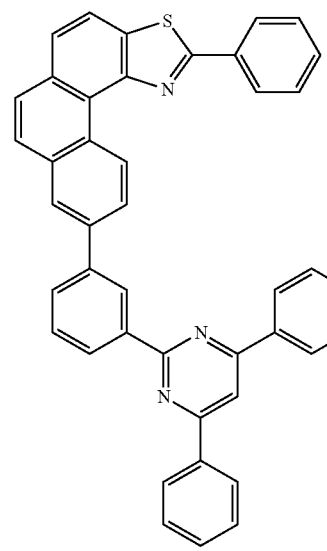
C-81
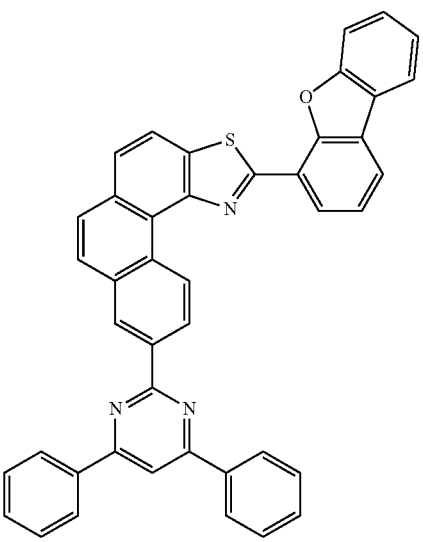
C-82
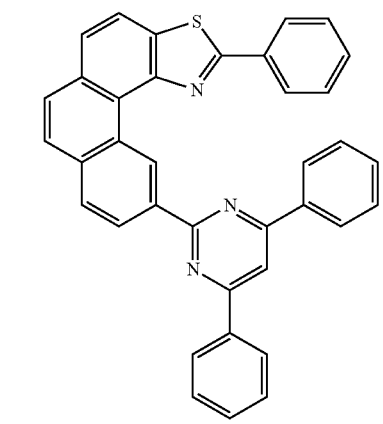
C-83
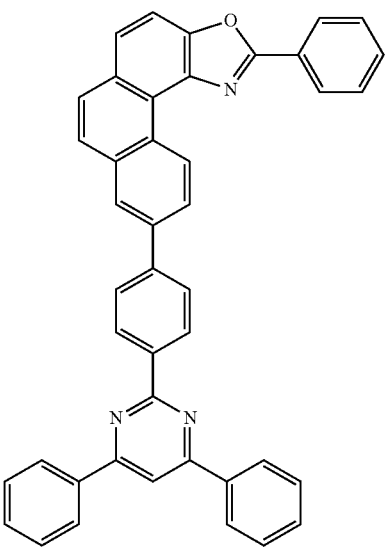

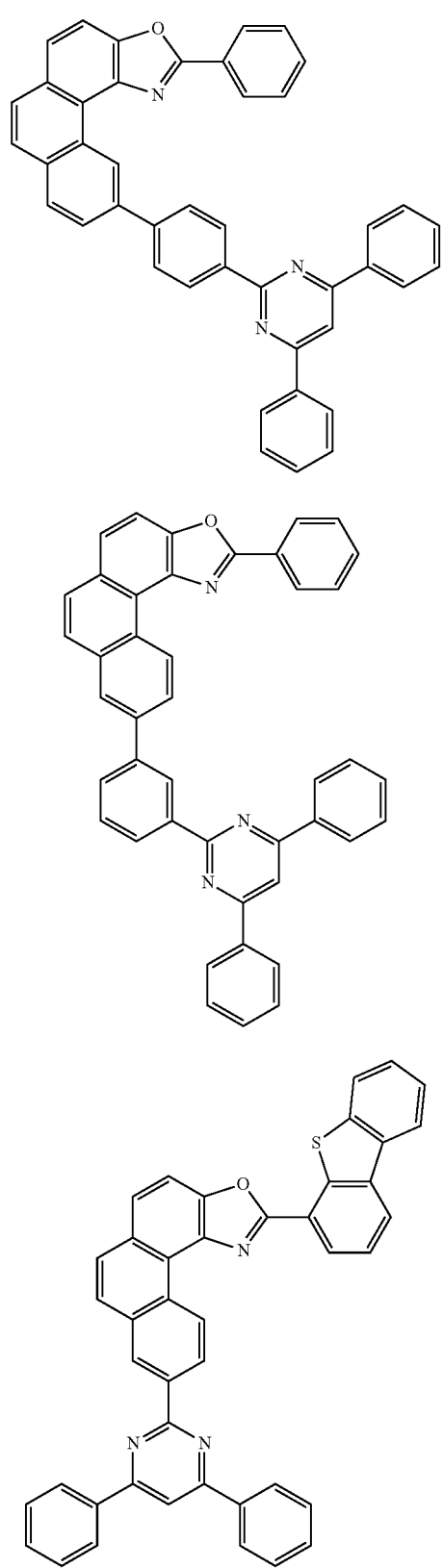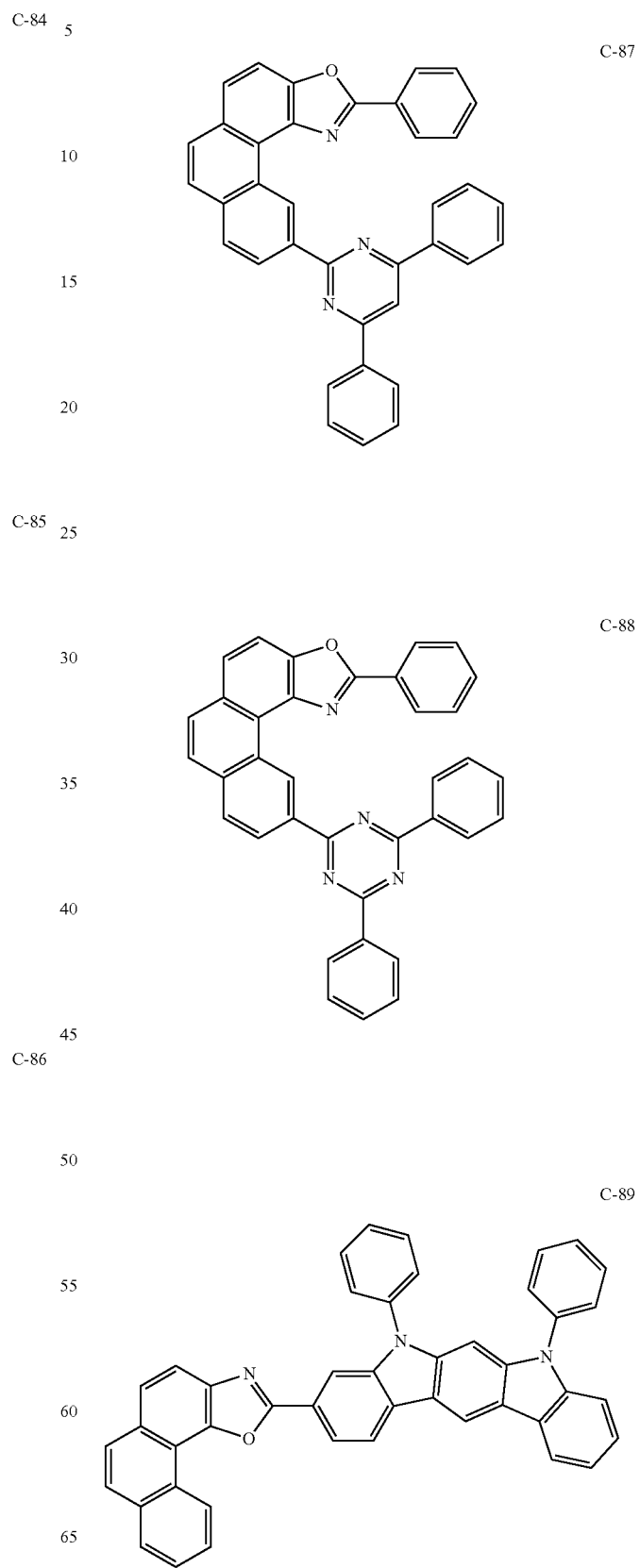

305
-continued
306
-continued
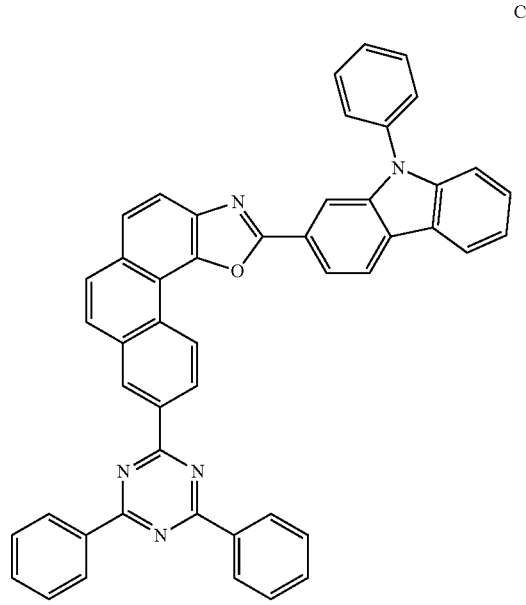
C-90
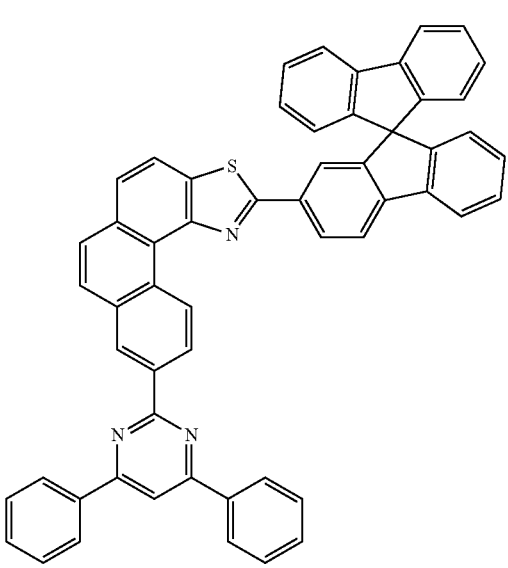
C-93
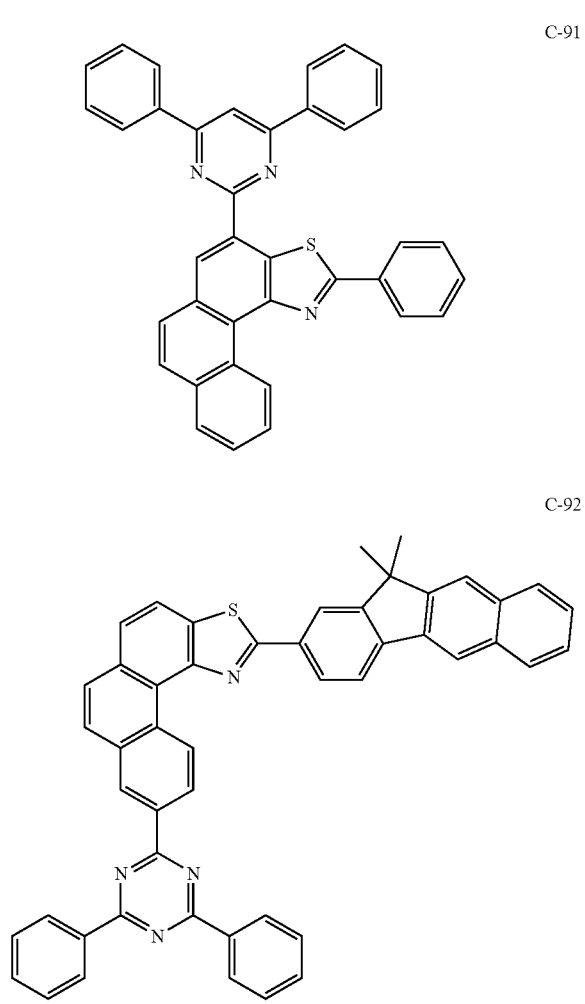
C-91
C-92
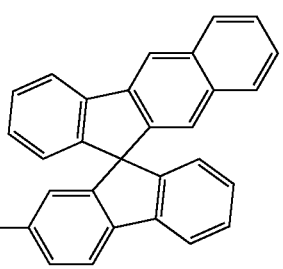
C-94
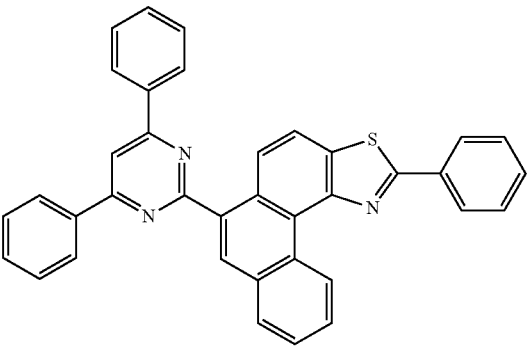
C-95

-continued
C-96
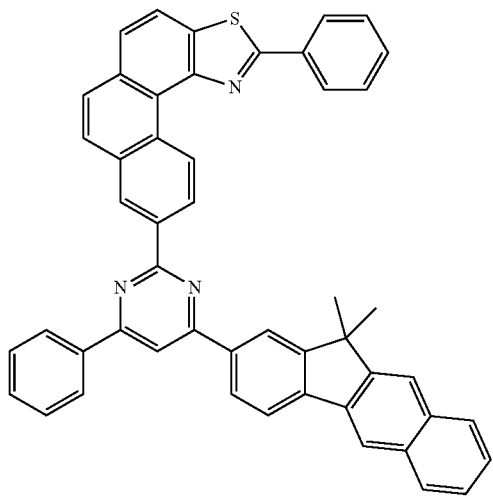
C-97
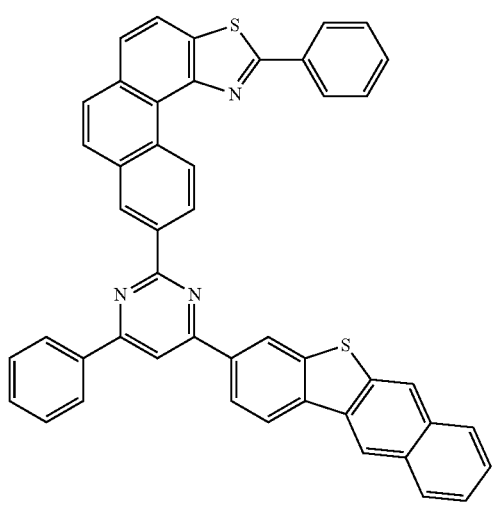
C-98
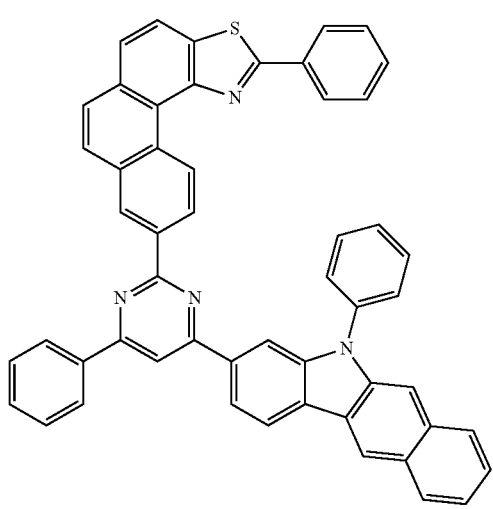
-continued
C-99
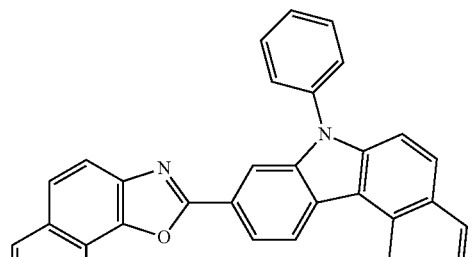
C-100
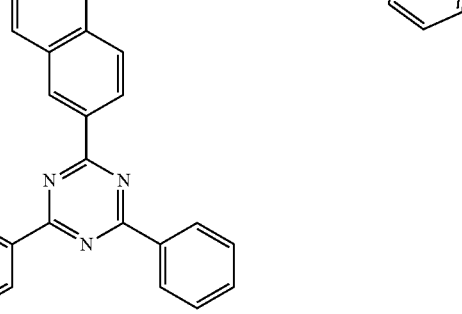
C-101
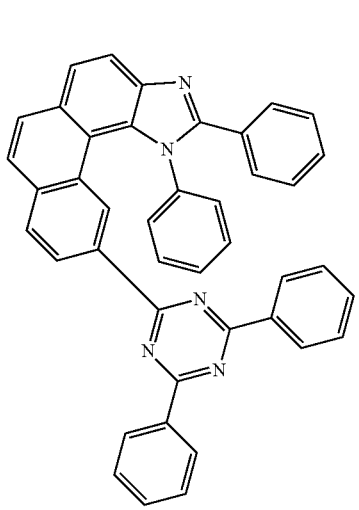

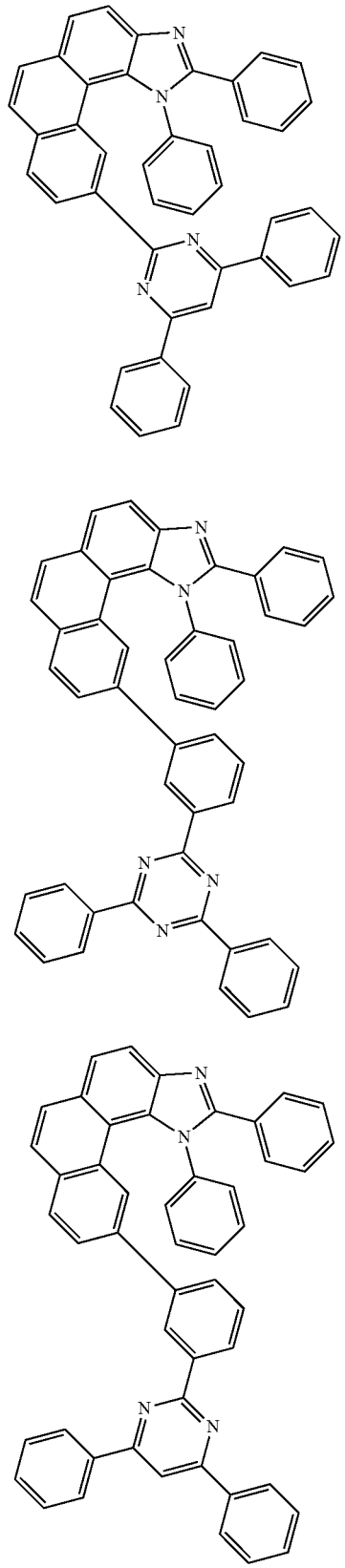
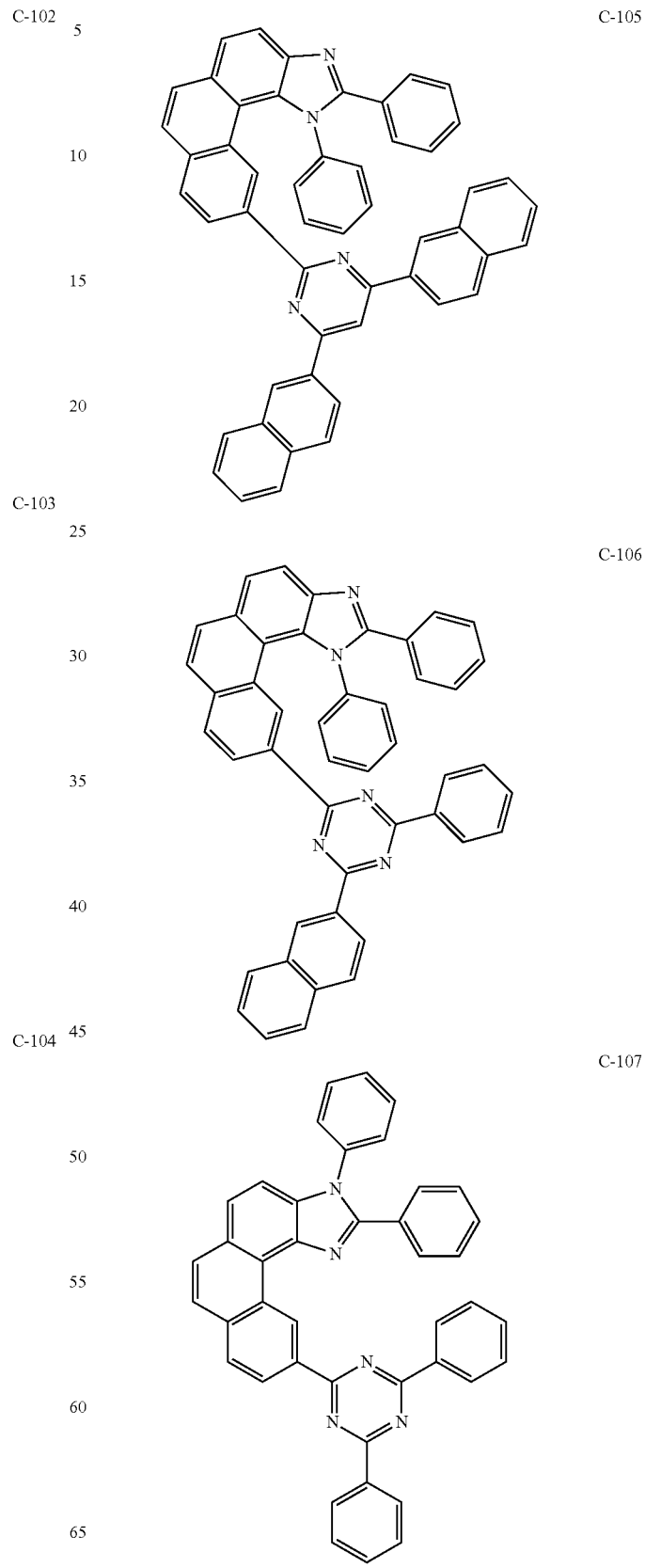

-continued
C-108
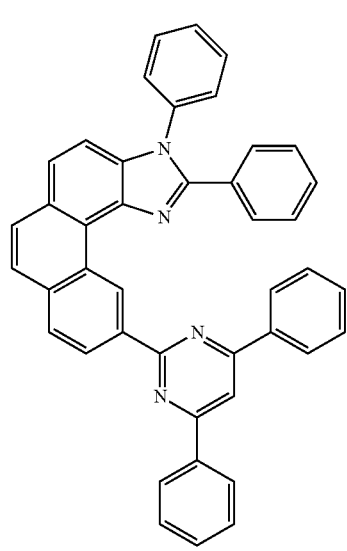
C-109
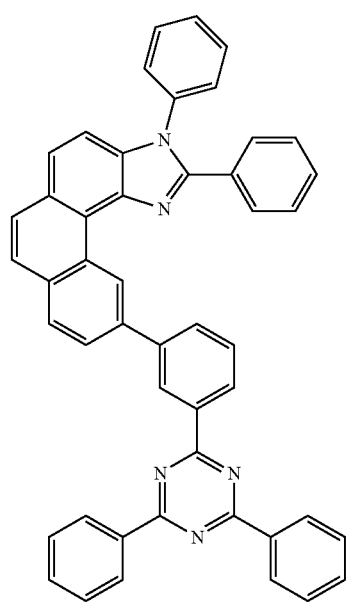
C-110
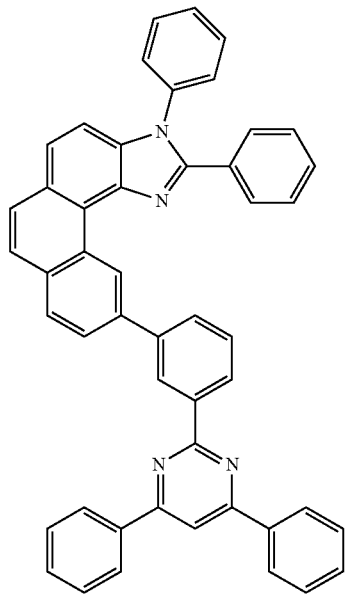
C-111
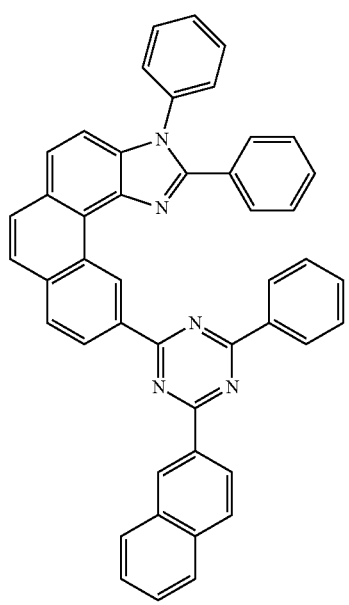

-continued
C-112
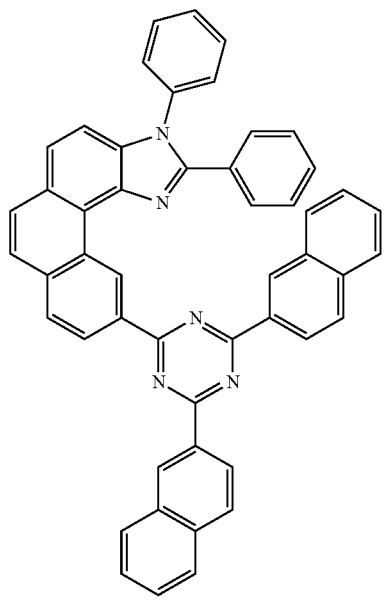
C-113
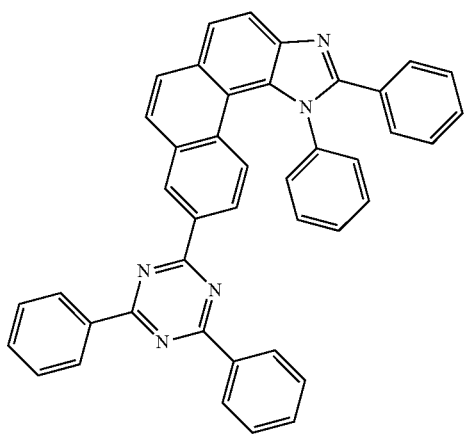
C-114
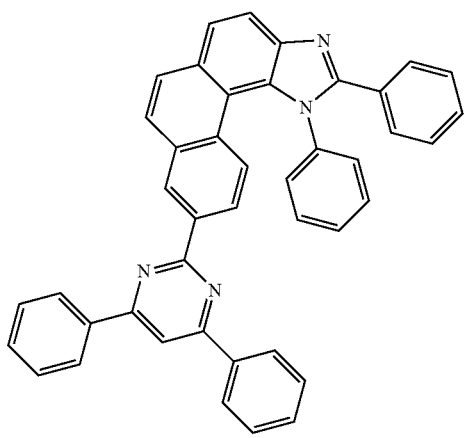
-continued
C-115
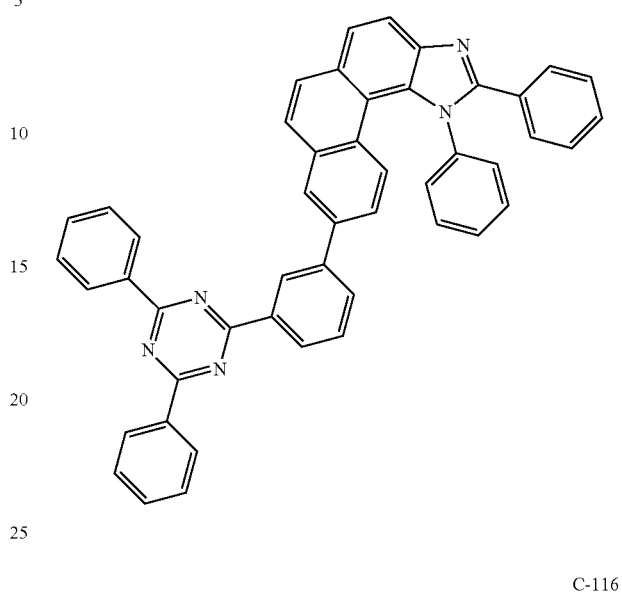
C-116
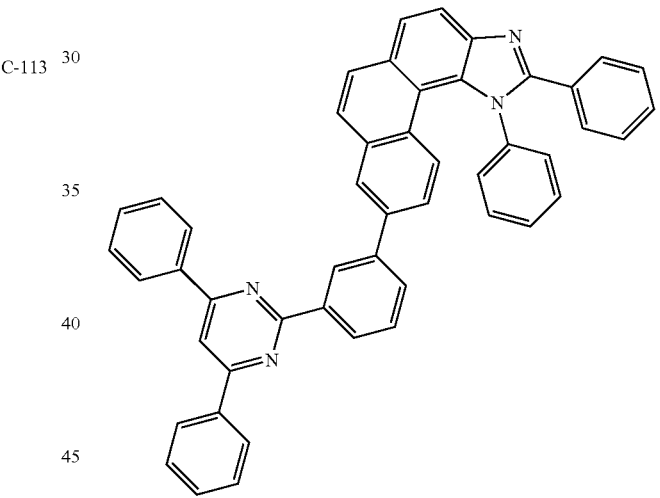
C-117
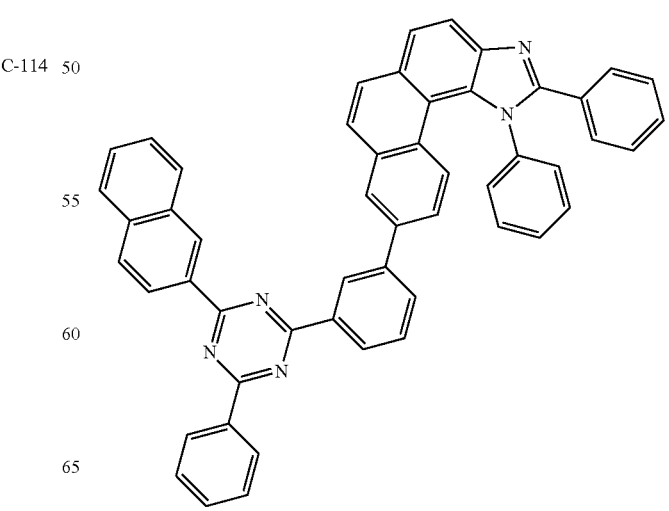

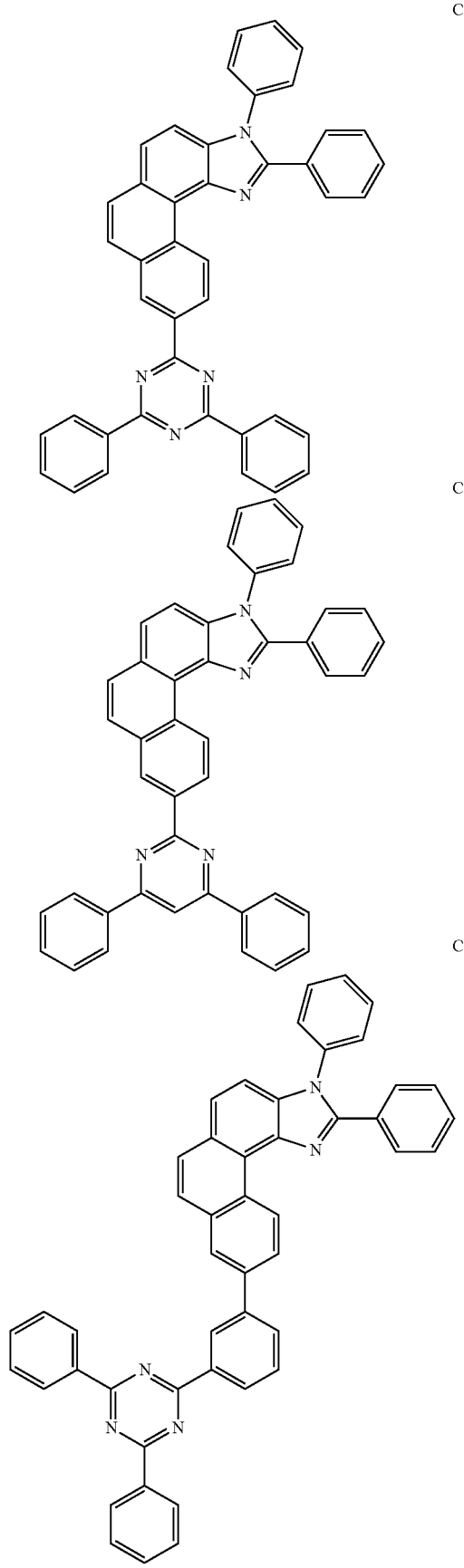
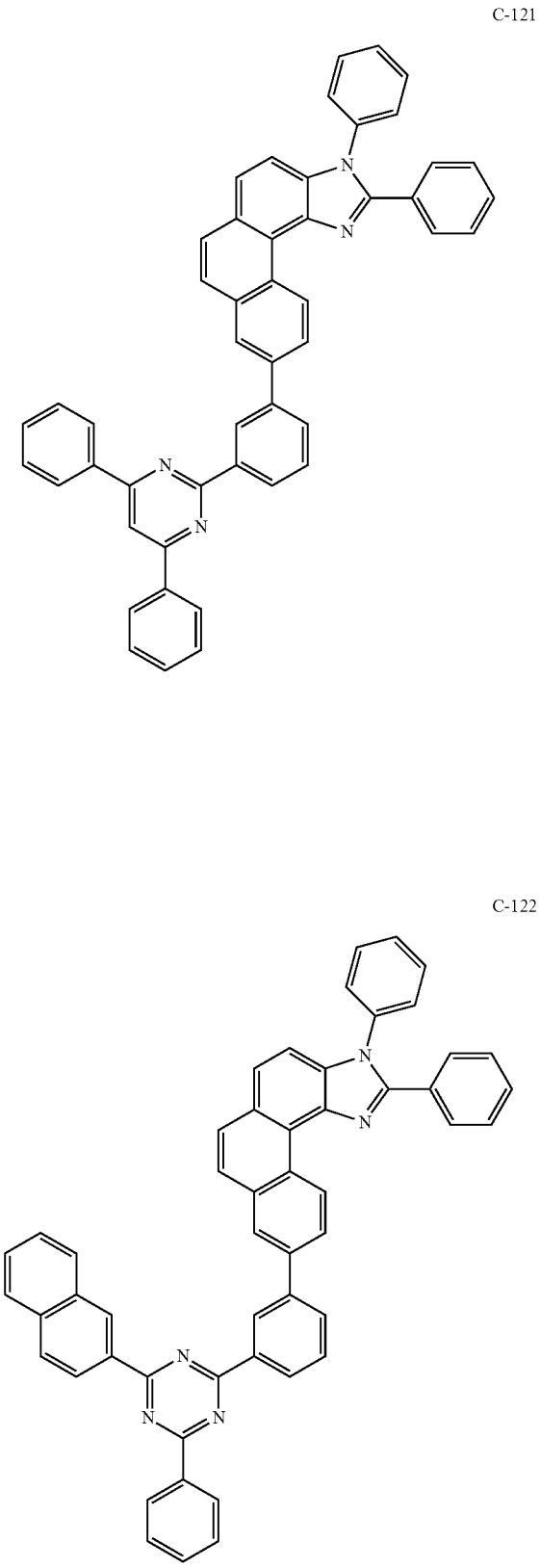

-continued
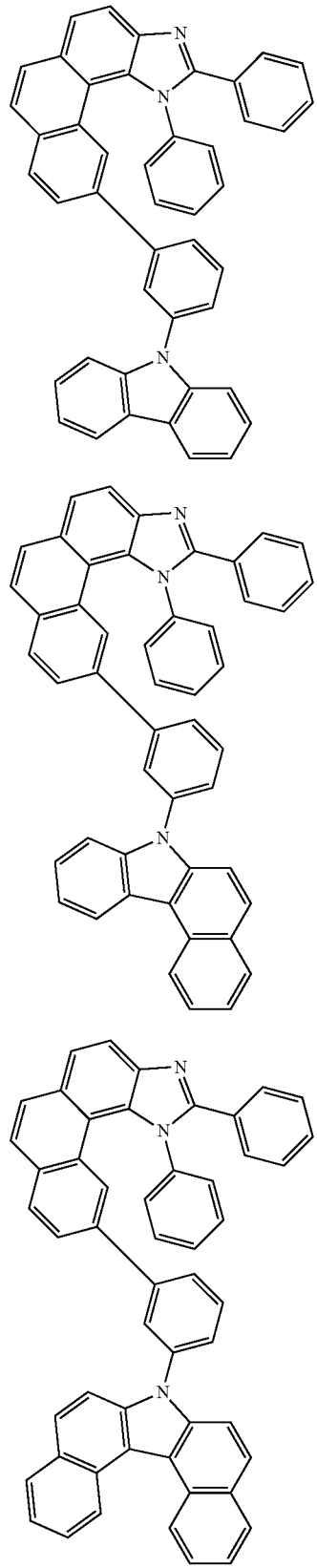
C-123
C-124
C-125
-continued
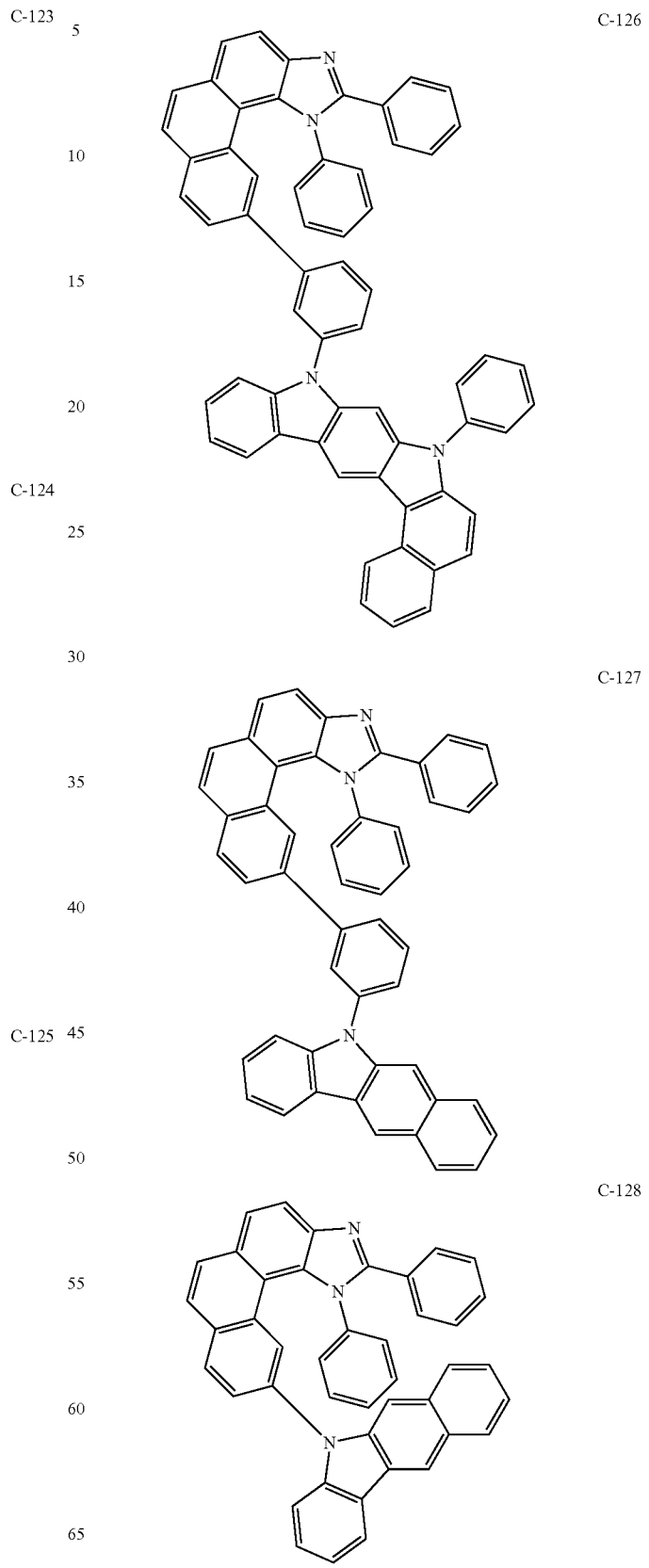
C-126
C-127
C-128

C-129
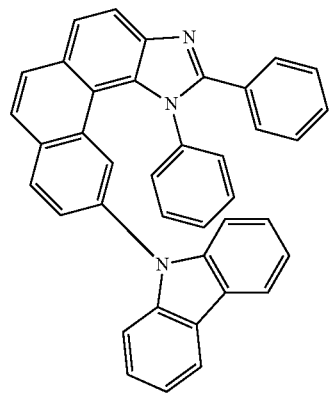
C-130
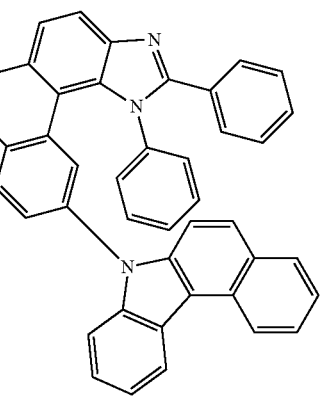
C-131
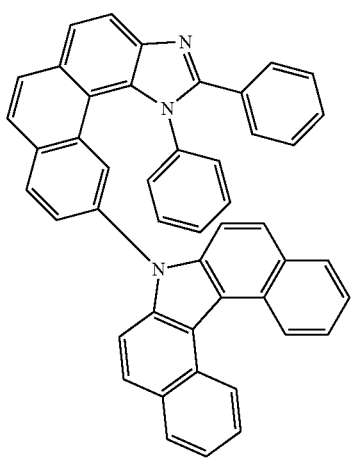
C-132
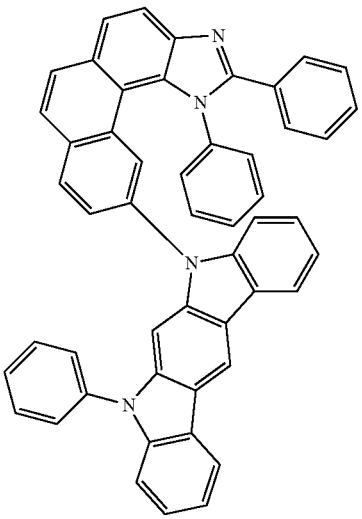
C-133
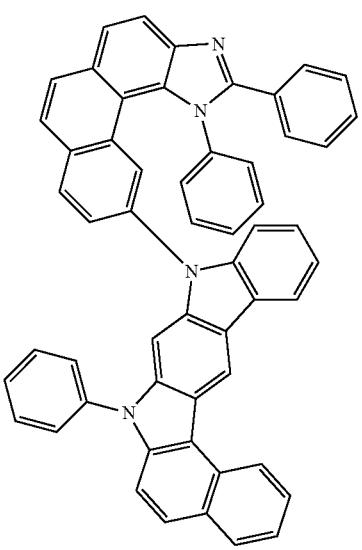
C-134
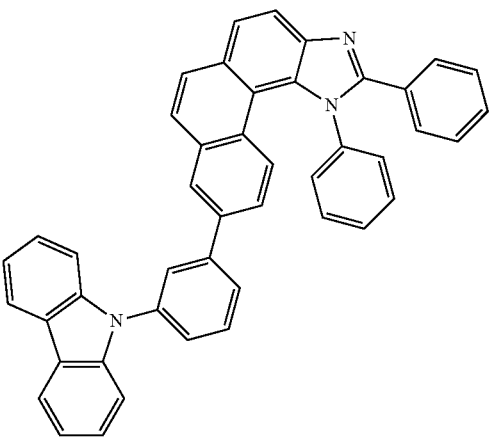

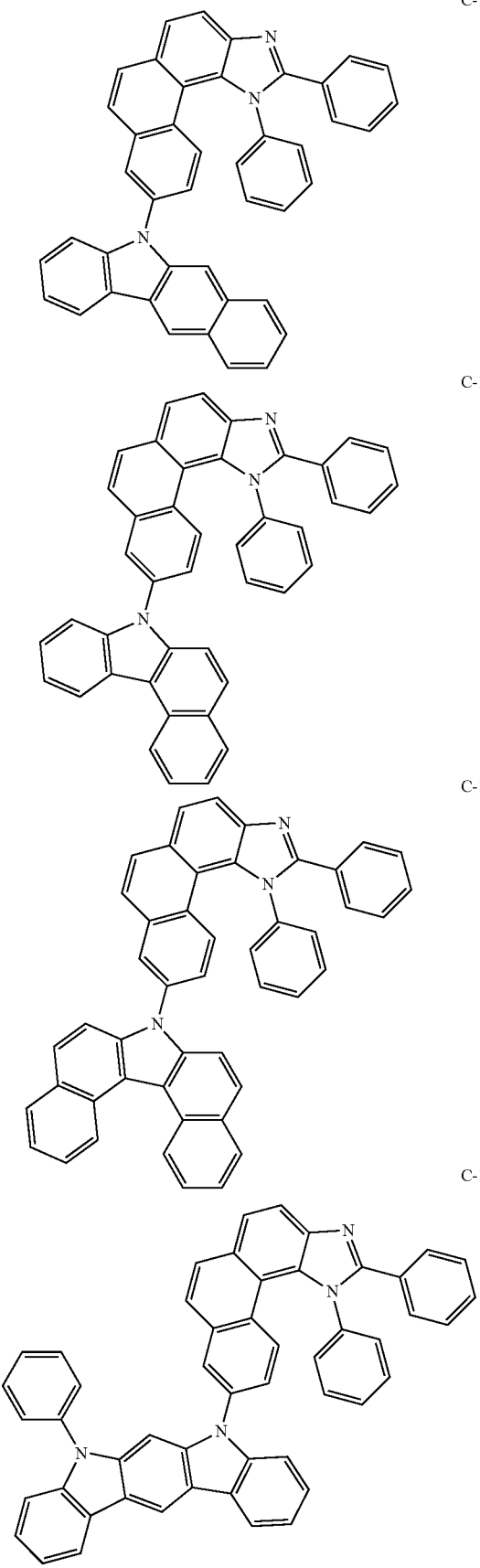
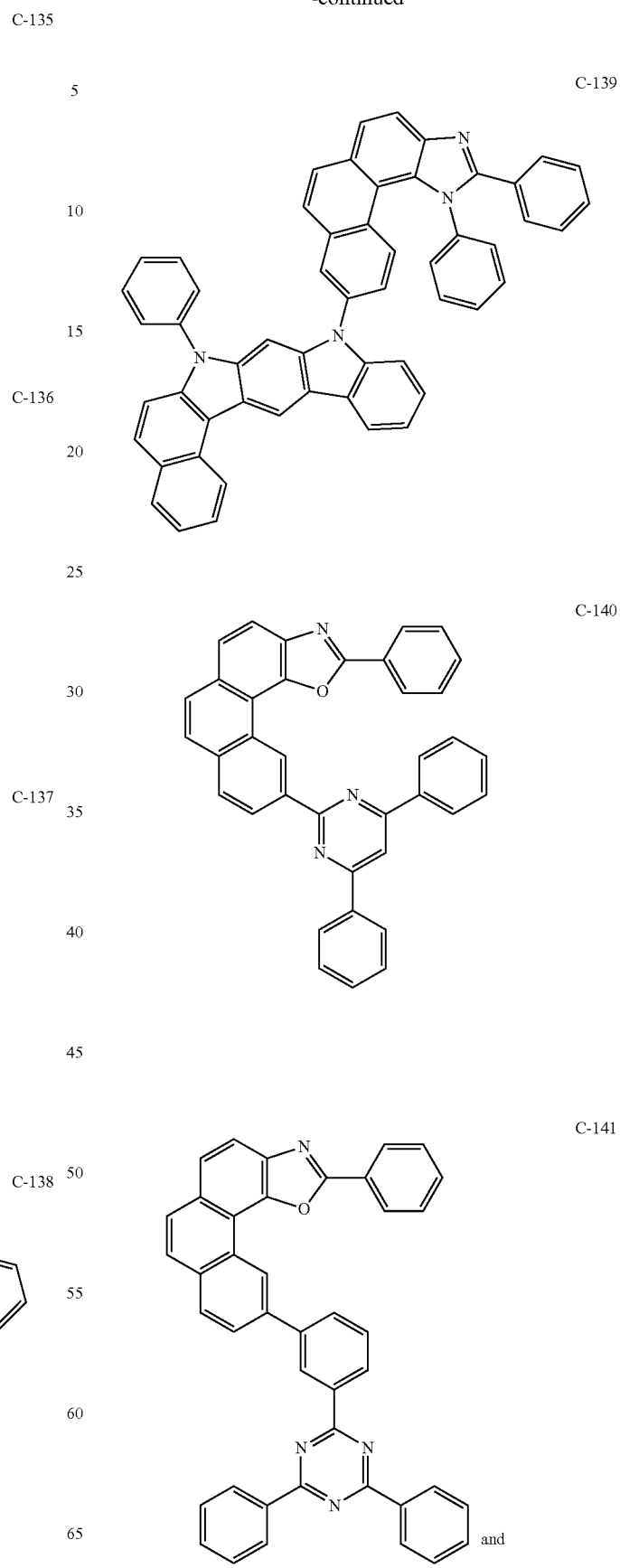

-continued

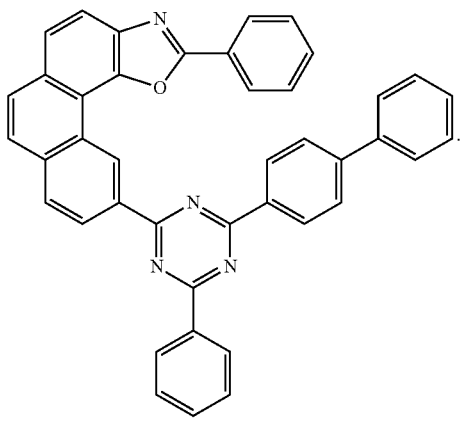

C-142

7. An organic electroluminescent device comprising a first electrode, a second electrode facing the first electrode, a light-emitting layer between the first electrode and the second electrode, and an electron transport zone between the light-emitting layer and the second electrode, wherein the electron transport zone comprises the electron transport material according to claim 4.

8. An organic electroluminescent device comprising a first electrode, a second electrode facing the first electrode, a light-emitting layer between the first electrode and the second electrode, and an electron transport zone and an electron buffering layer between the light-emitting layer and the second electrode, wherein the electron buffering layer comprises the electron buffering material according to claim 1.

9. The organic electroluminescent device according to claim 8, wherein the electron transport zone comprises the electron transport material according to claim 4.

10. The organic electroluminescent device according to claim 7, wherein the electron transport zone further comprises a reductive dopant.

11. The organic electroluminescent device according to claim 9, wherein the electron transport zone further comprises a reductive dopant.

* * * * *